United States Patent
Springer et al.

(10) Patent No.: US 10,266,513 B2
(45) Date of Patent: Apr. 23, 2019

(54) BRUTON'S TYROSINE KINASE INHIBITORS

(71) Applicant: Pfizer Inc., New York, NY (US)

(72) Inventors: John Robert Springer, Wentzville, MO (US); Balekudru Devadas, Chesterfield, MO (US); Danny James Garland, House Springs, MO (US); Margaret Lanahan Grapperhaus, Troy, IL (US); Seungil Han, Mystic, CT (US); Susan Landis Hockerman, Kirkwood, MO (US); Robert Owen Hughes, Newtown, CT (US); Eddine Saiah, Brookline, MA (US); Mark Edward Schnute, Acton, MA (US); Shaun Raj Selness, Chesterfield, MO (US); Daniel Patrick Walker, Augusta, MO (US); Zhao-Kui Wan, Lexington, MA (US); Li Xing, Lexington, MA (US); Christoph Wolfgang Zapf, Marlborough, MA (US); Michelle Ann Schmidt, Millstadt, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/624,969

(22) Filed: Jun. 16, 2017

(65) Prior Publication Data
US 2017/0283393 A1    Oct. 5, 2017

Related U.S. Application Data

(63) Continuation of application No. 14/439,478, filed as application No. PCT/IB2013/059846 on Nov. 1, 2013, now abandoned.

(60) Provisional application No. 61/772,028, filed on Mar. 4, 2013, provisional application No. 61/721,920, filed on Nov. 2, 2012.

(51) Int. Cl.
C07D 403/04    (2006.01)
C07D 401/04    (2006.01)

(52) U.S. Cl.
CPC .................. C07D 401/04 (2013.01)

(58) Field of Classification Search
CPC .................................................... C07D 403/04
USPC ........................................ 548/364.1; 514/406
See application file for complete search history.

(56) References Cited

U.S. PATENT DOCUMENTS

| | | | |
|---|---|---|---|
| 5,033,252 A | 7/1991 | Carter | |
| 5,052,558 A | 10/1991 | Carter | |
| 5,323,907 A | 6/1994 | Kalvelage | |
| 6,326,469 B1 | 12/2001 | Ullrich et al. | |
| 9,926,299 B2 * | 3/2018 | Han | C07D 231/38 |

| | | | |
|---|---|---|---|
| 2009/0291984 A1 | 11/2009 | Bjergarde et al. | |
| 2012/0252822 A1 | 10/2012 | Honigberh et al. | |
| 2014/0249215 A1 | 9/2014 | Pimont-Garro et al. | |

FOREIGN PATENT DOCUMENTS

| | | |
|---|---|---|
| WO | 2007/117692 A2 | 10/2007 |
| WO | 2008/039218 A2 | 4/2008 |
| WO | 2009/011880 A2 | 1/2009 |
| WO | 2010/009342 A2 | 1/2010 |
| WO | 2010/010154 A1 | 1/2010 |
| WO | 2011/029046 A1 | 3/2011 |
| WO | 2011/159857 A1 | 12/2011 |
| WO | 2014/025976 A1 | 2/2014 |
| WO | 2014/082598 A1 | 6/2014 |

OTHER PUBLICATIONS

Fedorek et al, "A novel colon-specific steroid prodrug enhances sodium chloride absorption in rat colitis", American Journal of Physiology—Gastrointestinal and Liver Physiology 269(2):G210-G218 (1995).

Hochhaus et al, "A Selective HPLC/RIA for Dexamethasone and its Prodrug Dexamethasone-21-sulphobenzoate Sodium in Biological Fluids", Biomedical Chromatography 6:283-286 (1992).

Larsen et al, "Prodrug forms for the sulfonamide group. I. Evaluation of N-acyl derivatives, N-sulfonylamidines, N-sulfonylsulfilimines and sulfonylureas as possible prodrug derivatives", International Journal of Pharmaceutics 37:87-95 (1987).

(Continued)

*Primary Examiner* — Patricia L Morris
(74) *Attorney, Agent, or Firm* — James T. Wasicak

(57) ABSTRACT

Disclosed herein are compounds that form covalent bonds with Bruton's tyrosine kinase (BTK). Methods for the preparation of the compounds are disclosed. Also disclosed are pharmaceutical compositions that include the compounds. Methods of using the BTK inhibitors are disclosed, alone or in combination with other therapeutic agents, for the treatment of autoimmune diseeases or conditions, heteroimmune diseases or conditions, cancer, including lymphoma, and inflammatory diseases or conditions.

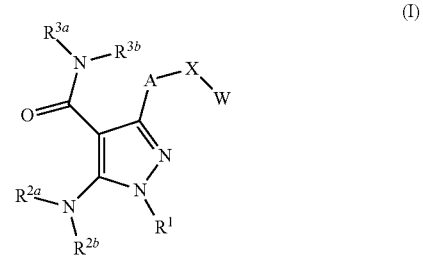

(I)

6 Claims, No Drawings

(56) References Cited

OTHER PUBLICATIONS

Larsen et al, "Prodrug forms for the sulfonamide group. II. Water-soluble amino acid derivatives of N-methylsulfonamides as possible prodrugs", International Journal of Pharmaceutics 47:103-110 (1988).
Mcleod et al, "A Glucocorticoid Prodrug Facilitates Normal Mucosal Function in Rat Colitis Without Adrenal Suppression", Gastroenterology 106:405-413 (1994).
Nandakumar et al, "Collagen Type II-Specific Monoclonal Antibody-Induced Arthritis in Mice", American Journal of Pathology 163(5):1827-1837).
Nisitani et al, "In situ detection of activitated Bruton's tyrosine kinase in the lg signaling complex by phosphopeptide-specific monoclonal antibodies", Proc. Natl. Acad. Sci. USA 96:2771-2726 (1999).
Pagel et al, "Induction of Apoptosis Using Inhibitors of Lysophosphatidic Acid Acyltransferase-β and Anti-CD20 Monoclonal Antibodies for Treatment of Human Non-Hodgkin's Lymphomas", Clinical Cancer Research 11(13):4857-4866 (2005).
Saulnier et al, "An Efficient Method for the Synthesis of Guanidino Prodrugs", Bioorganic & Medicinal Chemistry Letters 4(16):1985-1990 (1994).
Sinkula et al, "Rationale for Design of Biologically Reversible Drug Derivatives: Prodrugs", Journal of Pharmaceutical Sciences 64(2):181-210 (1975).
Afar et al, "Regulation of Btk by Src Family Tyrosine Kinases", Molecular and Cellular Biology 16(7):3465-3471(1996).

\* cited by examiner

BRUTON'S TYROSINE KINASE INHIBITORS

BACKGROUND

Signaling through the B-cell receptor (BCR) can lead to a range of biological outputs depending upon, in part, the developmental stage of the B-cell. Faulty signaling through the BCR can cause disregulation of the B-cell function and/or the formation of auto-antibodies which may lead to the auto-immune and/or inflammatory diseases. Therapeutics, such as Rituxan, which deplete B-cells are effective in the treatment of inflammatory diseases such as rheumatiod arthritis. Bruton's Tyrosine Kinase (BTK) is a member of the TEC family of kinases and is a regulator of B-cell development, activation, signaling and survival. BTK is downstream of the BCR. In humans, mutation of BTK causes X-linked agammaglobuliaemia results in a compromised immune system, impaired maturation of B-cells, decreased peripheral B-cell levels and reduced calcium mobilization following stimulation through the BCR. Further evidence for the role of BTK in autoimmune and inflammatory diseases has been established utilizing both BTK knock-out mouse models and pharmacological inhibitors. In addition to to B-cells, BTK is expressed on several other cell types that may contribute to disease, for example: mast cells, basophils, neutrophils, monocytes and osteoclasts. From this prespective it is clear that BTK inhibitors should provided substantial therapeutic benefit for patients afflicted with, for example: multiple sclerosis, type I diabetes, rheumatoid arthritis, SLE, idiopathic thrombocytopenic purpura, myasthenia gravis, allergic rhinitis, Sjögren's syndrome, B-cell lymphoma and leukemia.

SUMMARY

Described herein are inhibitors of Bruton's tyrosine kinase (BTK). Also described herein are methods for synthesizing such inhibitors, methods for using such inhibitors in the treatment of diseases, including diseases wherein inhibition of BTK provides therapeutic benefit to a patient having the disease. Further described are pharmaceutical formulations that include an inhibitor of BTK.

Compounds described herein include those that have a structure of Formula (I) and pharmaceutically acceptable salts, solvates, esters, acids and prodrugs thereof. In particular, one aspect of the invention relates to compounds represented by Formula (I):

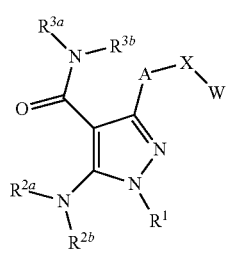

(I)

or a pharmaceutically acceptable salt, pharmaceutically active metabolite, pharmaceutically acceptable prodrug, or pharmaceutically acceptable solvate therof, wherein A is arylene, 5-membered heteroarylene or 6-membered heteroarylene, optionally substituted with one, two, three or four $R^6$ independently selected from the group consisting of $(C_1-C_4)$alkyl, halo$(C_1-C_4)$alkyl, halo, hydroxy and $(C_1-C_4)$alkoxy;

X is O, S, C(=O), CH(OR$^4$) or C(R$^{5a}$)(R$^{5b}$);

W is aryl, 5-membered heteroaryl or 6-membered heteroaryl, optionally substituted with one, two, three, four or five $R^7$ independently selected from the group consisting of $(C_1-C_4)$alkyl, halo$(C_1-C_4)$alkyl, $(C_3-C_6)$cycloalkyl, 4-6 membered saturated heterocycle, halo, hydroxy, hydroxy $(C_1-C_4)$alkyl, $(C_1-C_4)$alkoxy, hydroxy$(C_2-C_4)$alkoxy, and halo$(C_1-C_4)$alkoxy;

$R^1$ is a 4-8 membered nitrogen-containing heterocyclyl substituted on said nitrogen with R and optionally further substituted with one, two, three, four or five substituents independently selected from the group consisting of $(C_1-C_4)$alkyl, halo$(C_1-C_4)$alkyl, halo, hydroxyl and $(C_1-C_4)$alkoxy;

R is cyano, cyano$(C_1-C_3)$alkyl,

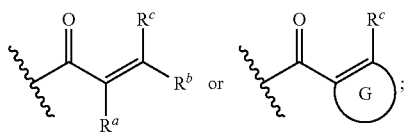

$R^{2a}$, $R^{2b}$, $R^{3a}$ and $R^4$ are independently selected from the group consisting of hydrogen or $(C_1-C_3)$alkyl;

$R^{5a}$ and $R^{5b}$ are independently selected from the group consisting of hydrogen, halo and $(C_1-C_3)$alkyl;

$R^a$ is hydrogen, halo, cyano, $(C_1-C_6)$alkoxy, halo$(C_1-C_6)$alkoxy, $(C_1-C_4)$alkylthio, $(C_1-C_4)$alkylsulfonyl, or $(C_1-C_6)$alkyl optionally substituted by halo, hydroxyl, $(C_1-C_6)$alkoxy or halo$(C_1-C_6)$alkoxy;

$R^b$ and $R^c$ are independently selected from the group consisting of hydrogen, halo, cyano, $(C_1-C_6)$alkoxy, halo$(C_1-C_6)$alkoxy, $(C_3-C_6)$cycloalkyl, C(=O)R$^d$ and $(C_1-C_6)$alkyl optionally substituted with one, two or three $R^f$ Independently selected from the group consisting of halo, hydroxyl, N(R$^e$)$_2$, $(C_1-C_6)$alkoxy, halo$(C_1-C_6)$alkoxy and aryl; or $R^b$ and $R^c$ taken together with the carbon to which they are bound form a 4-7 membered carbocycyl or heterocycyl optionally substituted with one, two or three $R^f$ independently selected from the group consisting of halo, hydroxyl, N(R$^e$)$_2$, $(C_1-C_6)$alkoxy; halo$(C_1-C_6)$alkoxy and aryl;

$R^d$ is $(C_1-C_6)$alkyl, $(C_1-C_6)$alkoxy, N(R$^e$)$_2$ or aryl;

$R^e$ is independently selected for each occurrence from the group consisting of hydrogen and $(C_1-C_4)$ alkyl, or both $R^e$ taken together with the nitrogen atom to which they are bound form a 4-7 membered heterocycyl; and G is a 5-7 membered carbocycyl or heterocycyl optionally substituted with one, two or three $R^f$ independently selected from the group consisting of halo, hydroxyl, N(R$^e$)$_2$, $(C_1-C_6)$alkoxy; halo$(C_1-C_6)$alkoxy and aryl.

In a further aspect are provided pharmaceutical compositions, which include a therapeutically effective amount of compound(s) of the Invention, or a pharmaceutically acceptable salt, pharmaceutically active metabolite, pharmaceutically acceptable prodrug, or pharmaceutically acceptable solvate therof. In certain embodiments, compositions provided herein further include a pharmaceutically acceptable diluent, excipient and/or binder.

Another aspect of the invention provides a method of treating a subject suffering from a medical disorder. The method comprises administering to the subject a therapeutically effective amount of a compound(s) of the invention, or a pharmaceutically acceptable salt, pharmaceutically active metabolite, pharmaceutically acceptable prodrug, or pharmaceutically acceptable solvate therof. A large number of disorders can be treated using the compounds described herein. For example, the compounds described herein can be used to treat a cancer, an immune disorder or Inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, sceroderma, ulcerative colitis, asthma, epidermal hyperplasia, and other medical disorders described herein.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description.

DETAILED DESCRIPTION

The invention provides compounds, pharmaceutical compositions, methods of inhibiting BTK activity and therapeutic uses of said compounds and pharmaceutical compositions. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Various aspects of the invention are set forth below in sections; however, aspects of the Invention described in one particular section are not to be limited to any particular section. Further, when a variable is not accompanied by a definition, the previous definition of the variable controls.

Definitions

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not Intended to limit the scope of the methods and compositions described herein, which will be limited only by the appended claims.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP.sub.—000052).

The term "Bruton's tyrosine kinase homolog," as used herein, refers to orthologs of Bruton's tyrosine kinase, e.g., the orthologs from mouse (GenBank Acession No. AAB47246), dog (GenBank Acession No. XP.sub.—549139.), rat (GenBank Acession No. NP.sub.—001007799), chicken (GenBank Acession No. NP.sub.—989564), or zebra fish (GenBank Acession No. XP.sub.—698117), and fusion proteins of any of the foregoing that exhibit kinase activity towards one or more substrates of Bruton's tyrosine kinase.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. Other examples of kinases having homologous cysteines are shown in FIG. 1 of U.S. Patent Application Publication No. 2012/252822, which is hereby incorporated by reference. See also the sequence alignments of tyrosine kinases (TK) published on the world wide web at kinase.com/human/kinome/phylogeny.html.

The term "BTK inhibitor," as used herein, refers to an inhibitor of BTK that can form a covalent bond with an amino acid residue of BTK. In one embodiment, the inhibitor of BTK can form a covalent bond with a Cys residue of BTK.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an Increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "alkyl" refers to a linear or branched-chain saturated hydrocarbyl substituent (i.e., a substituent obtained from a hydrocarbon by removal of a hydrogen) containing from one to twelve carbon atoms. Examples of such substituents include methyl, ethyl, propyl (including n-propyl and isopropyl), butyl (including n-butyl, Isobutyl, sec-butyl and tert-butyl), pentyl, isoamyl, hexyl and the like. The terms "haloalkyl" and "haloalkoxy" include alkyl, and alkoxy structures, respectively, in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, $-CF_3$, $-CH_2CF_3$, $-CF_2CF_3$, $-CH_2CH_2CF_3$ and the like.

The term "cycloalkyl" refers to a carbocyclic substituent obtained by removing a hydrogen from a saturated carbocyclic molecule and having three to ten carbon atoms. In one embodiment, a cycloalkyl substituent has three to ten carbon atoms. Cycloalkyl may be a single ring, which typically contains from 3 to 6 ring atoms. Examples of cycloalkyl include cyclopropyl, cyclobutyl, cyclopentyl and cyclohexyl. Alternatively, cycloalkyl may be 2 or 3 rings fused together, such as bicyclo[4.2.0]octane and decalinyl and may also be referred to as "bicycloalkyl".

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_{4-10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one more substituents, the one or more substitutents, unless otherwise specified, are each bound to an aromatic carbon of the fused aryl group. The fused $C_{4-10}$ carbocyclic or 4- to 10-membered heterocyclic ring may be optionally substituted with halogen, $C_{1-6}$alkyl, $C_{3-10}$cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

The term "arylene" refers to a bivalent radical formed by removing a hydrogen atom from an aryl, as described above.

In some instances, the number of atoms in a cyclic substituent containing one or more heteroatoms (i.e., heteroaryl or heterocycloalkyl) is indicated by the prefix "A-B membered", wherein A is the minimum and B is the maximum number of atoms forming the cyclic moiety of the substituent. Thus, for example, 5-8 membered heterocycloalkyl refers to a heterocycloalkyl containing from 5 to 8 atoms, including one or more heteroatoms, in the cyclic moiety of the heterocycloalkyl.

The term "hydroxy" or "hydroxyl" refers to OH.

The term "cyano" (also referred to as "nitrile") means CN.

The terms "halogen" and "halo" refer to fluorine (which may be depicted as F), chlorine (which may be depicted as Cl), bromine (which may be depicted as Br), or iodine (which may be depicted as I). In one embodiment, the halogen is chlorine. In another embodiment, the halogen is fluorine. In another embodiment, the halogen is bromine.

The terms "heterocycloalkyl" and "heterocyclyl" are used interchangeably and refer to a substituent obtained by removing a hydrogen from a saturated or partially saturated ring structure containing a total of 4 to 14 ring atoms, wherein at least one of the ring atoms is a heteroatom selected from oxygen, nitrogen, or sulfur. For example, as used herein, the term "4- to 10-membered heterocycloalkyl" means the substituent is a single ring with 4 to 10 total members. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be one of the heteroatoms, or it may be a ring carbon atom, where the ring carbon atom may be in the same ring as the heteroatom(s) or where the ring carbon atom may be in a different ring from the heteroatom(s). Similarly, if the heterocycloalkyl substituent is in turn substituted with a group or substituent, the group or substituent may be bound to the heteroatom(s), or it may be bound to a ring carbon atom, where the ring carbon atom may be in the same ring as the at least one heteroatom or where the ring carbon atom may be in a different ring from the heteroatom(s).

The term "heteroaryl" refers to a substituent obtained by removing a hydrogen from an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include but are not limited to: 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the heteroatom, or it may be bound to a ring carbon atom, where the ring carbon atom may be in the same ring as the heteroatom(s) or where the ring carbon atom may be in a different ring from the heteroatom(s). The term "heteroaryl" also includes pyridyl N-oxides and groups containing a pyridine N-oxide ring.

The term "heteroarylene" refers to a bivalent radical formed by removing a hydrogen atom from a heteroaryl, as described above.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described such that it "may be substituted" or as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a ($C_1$-$C_6$) prefix on ($C_1$-$C_6$)alkylcycloalkyl means that the alkyl moiety of the alkylcycloalkyl contains from 1 to 6 carbon atoms; the ($C_1$-$C_6$)-prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution only occurs on the alkyl moiety, the substituent would be described as "alkoxyhaloalkyl." If the halogen substitution occurs on both the alkyl moiety and the alkoxy moiety, the substituent would be described as "haloalkoxyhaloalkyl."

As used herein the term "Formula (I) and Formula (II)" may be referred to as a "compound(s) of the invention." Such terms are also defined to include all forms of the compounds of Formula (I) and Formula (II) including hydrates, solvates, isomers, crystalline and non-crystalline forms, isomorphs, polymorphs, and metabolites thereof. For example, the compounds of Formula (I) and Formula (II), and pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel sovates and hygroscopic compounds, the water/solvent content will be dependent on humidity and drying conditions. In such cases, non-stoichiometry will be the norm.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, inc., San Diego, pages 352-401, Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, int. J. Pharmaceutics, 37, 87 (1987); J. Larsen et al., int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

The compounds of the invention may have asymmetric carbon atoms. The carbon-carbon bonds of the compounds of the invention may be depicted herein using a solid line, a solid wedge or a dotted wedge. The use of a solid line to depict bonds to asymmetric carbon atoms is meant to indicate that all possible stereolsomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compounds of the invention and the use of a solid or dotted wedge to depict bonds to other asymmetric carbon atoms in the same compound is meant to indicate that a mixture of diastereomers is present.

Stereoisomers of compounds of the invention include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes isotopically-labeled compounds, which are identical to those recited in Formulae (I) and (II) herein, but for the fact that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl. Certain isotopically-labeled compounds of Formula (I) and Formula (II), for example those into which radioactive isotopes such as $^3$H and $^{14}$O are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds the invention may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compounds of Formula (I) and Formula (II) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or Inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluene-sulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cydopentanepropionate, dodecylsulfate, glycoheptanoate, glycerophosphate, heptanoate, hexanoate, nicotinate, 2-naphthalesulfonate, oxalate, palmoate, pectinate, 3-phenylproplonate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Compounds

In the following description of BTK compounds suitable for use in the methods described herein. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for BTK (e.g., human BTK) are known in the art as disclosed in, e.g., U.S. Pat. No. 6,326,469.

In certain embodiments, the compounds of the invention described herein are selective for BTK and kinases having a cysteine residue in an amino acid sequence position of the tyrosine kinase that is homologous to the amino acid sequence position of cysteine 481 in BTK.

Generally, an Inhibitor compound of BTK used in the methods described herein is identified or characterized in an in vitro assay, e.g., an acellular biochemical assay or a cellular functional assay. Such assays are useful to determine an in vitro $IC_{50}$ for said compounds.

In some embodiments, the BTK inhibitor compound used for the methods described herein inhibits BTK or a BTK homolog kinase activity with an in vitro $IC_{50}$ of less than 10 μM. (e.g., less than 1 μM, less than 0.5 μM, less than 0.4 μM, less than 0.3 μM, less than 0.1, less than 0.08 μM, less than 0.06 μM, less than 0.05 μM, less than 0.04 μM, less than 0.03 μM, less than less than 0.02 μM, less than 0.01, less than 0.008 μM, less than 0.006 μM, less than 0.005 μM, less than 0.004 μM, less than 0.003 μM, less than less than 0.002 μM, less than 0.001, less than 0.00099 μM, less than 0.00098 μM, less than 0.00097 μM, less than 0.00096 μM, less than 0.00095 μM, less than 0.00094 μM, less than 0.00093 μM, less than 0.00092, or less than 0.00090 μM).

Described herein are compounds of Formula (I), including those of Formula (II). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by Formula (I) or Formula (II), are also provided.

In one embodiment are compounds of Formula (I):

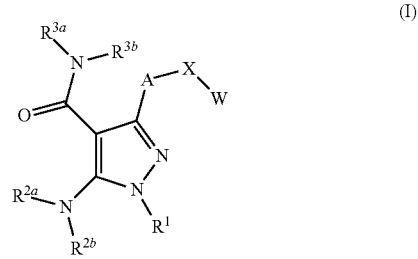

(I)

or pharmaceutically acceptable salts, pharmaceutically active metabolites, pharmaceutically acceptable prodrugs, or pharmaceutically acceptable solvates thereof, as described in the Summary above.

In certain embodiments, the present invention relates to any of the aforementioned compounds, wherein A is arylene optionally substituted with one, two, three or four $R^e$ Independently selected from the group consisting of ($C_1$-$C_4$) alkyl, halo($C_1$-$C_4$)alkyl, halo, hydroxy and ($C_1$-$C_4$)alkoxy.

In certain embodiments, the present invention relates to any of the aforementioned compounds, wherein A is

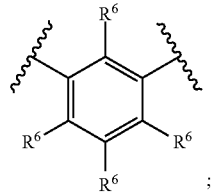

;

and $R^e$ is independently selected for each occurrence from the group consisting of hydrogen, ($C_1$-$C_4$)alkyl, halo($C_1$-$C_3$) alkyl and halo. In certain embodiments, the present invention relates to any of the aforementioned compounds, wherein A is

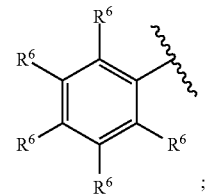

;

and $R^6$ is independently selected for each occurrence from the group consisting of hydrogen, $(C_1$-$C_4)$alkyl, halo$(C_1$-$C_3)$alkyl and halo. In certain embodiments, the present invention relates to any of the aforementioned compounds, wherein $R^6$ is hydrogen.

In certain embodiments, the present invention relates to any of the aforementioned compounds, wherein A is 5-membered heteroarylene optionally substituted with one, two, three or four $R^e$ independently selected from the group consisting of $(C_1$-$C_4)$alkyl, halo$(C_1$-$C_4)$alkyl, halo, hydroxy and $(C_1$-$C_4)$alkoxy. In certain embodiments, the present invention relates to any of the aforementioned compounds, wherein A is 6-membered heteroarylene, optionally substituted with one, two, three or four $R^e$ independently selected from the group consisting of $(C_1$-$C_4)$alkyl, halo$(C_1$-$C_4)$alkyl, halo, hydroxy and $(C_1$-$C_4)$alkoxy.

In certain embodiments, the present invention relates to any of the aforementioned compounds, wherein X is O, $CH_2$ or C(=O). In certain embodiments, the present invention relates to any of the aforementioned compounds, wherein X is S. In certain embodiments, the present invention relates to any of the aforementioned compounds, wherein X is O. In certain embodiments, the present invention relates to any of the aforementioned compounds, wherein X is C(=O). In certain embodiments, the present invention relates to any of the aforementioned compounds, wherein X is CH(OR$^4$). In certain embodiments, the present invention relates to any of the aforementioned compounds, wherein X is C(R$^{5a}$)(R$^{5b}$). In certain embodiments, the present invention relates to any of the aforementioned compounds, wherein X is $CH_2$.

In certain embodiments, the present invention relates to any of the aforementioned compounds, wherein W is aryl optionally substituted with one, two, three, four or five $R^7$ independently selected from the group consisting of $(C_1$-$C_4)$alkyl, halo$(C_1$-$C_4)$alkyl, $(C_3$-$C_6)$cycloalkyl, 4-6 membered saturated heterocycle, halo, hydroxy, hydroxy$(C_1$-$C_4)$alkyl, $(C_1$-$C_4)$alkoxy, hydroxy$(C_2$-$C_4)$alkoxy, and halo$(C_1$-$C_4)$alkoxy. In certain embodiments, the present invention relates to any of the aforementioned compounds, wherein W is phenyl optionally substituted with one, two, three, four or five $R^7$ independently selected for each occurrence from the group consisting of $(C_1$-$C_4)$alkyl, halo$(C_1$-$C_3)$alkyl, $(C_1$-$C_4)$alkoxy and halo. In certain embodiments, the present invention relates to any of the aforementioned compounds, wherein W is

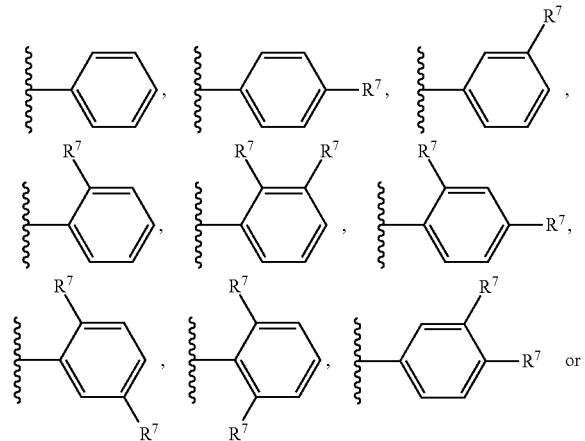

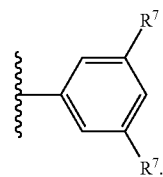

In certain embodiments, the present invention relates to any of the aforementioned compounds, wherein W is

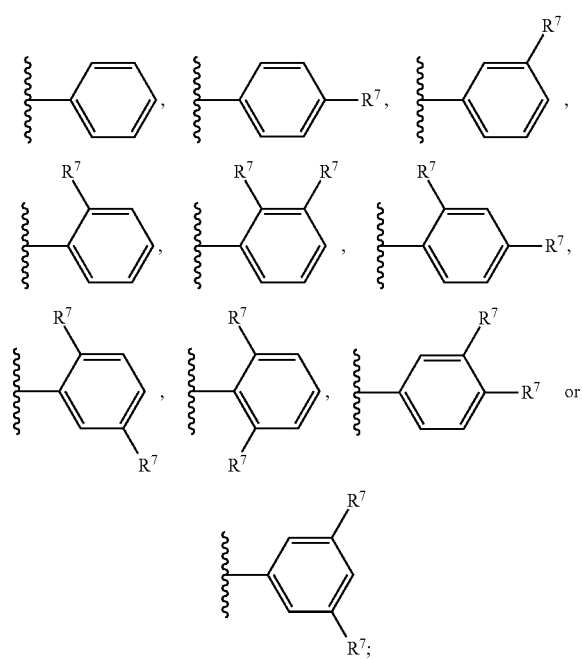

and $R^7$ is independently selected from the group consisting of F, Cl, methoxy and methyl. In certain embodiments, the present invention relates to any of the aforementioned compounds, wherein W is

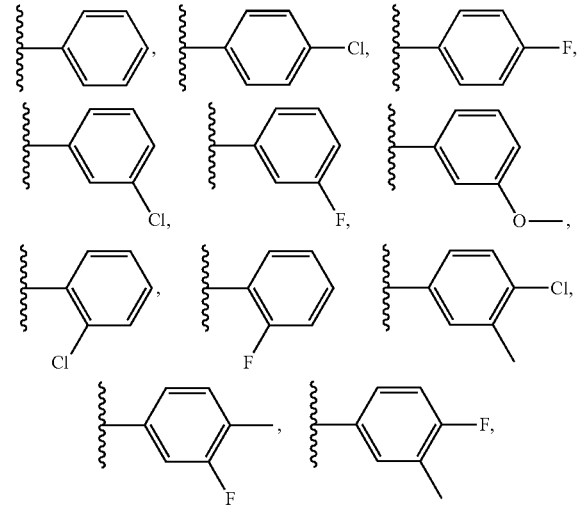

-continued

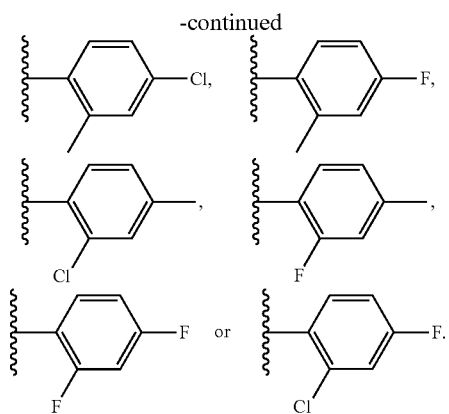

In certain embodiments, the present invention relates to any of the aforementioned compounds, wherein W is 5-membered heteroaryl optionally substituted with one, two, three, four or five $R^7$ Independently selected from the group consisting of $(C_1-C_4)$alkyl, halo$(C_1-C_4)$alkyl, $(C_3-C_6)$cycloalkyl, 4-6 membered saturated heterocycle, halo, hydroxy, hydroxy$(C_1-C_4)$alkyl, $(C_1-C_4)$alkoxy, hydroxy$(C_2-C_4)$alkoxy, and halo$(C_1-C_4)$alkoxy. In certain embodiments, the present invention relates to any of the aforementioned compounds, wherein W is 6-membered heteroaryl, optionally substituted with one, two, three, four or five $R^7$ independently selected from the group consisting of $(C_1-C_4)$alkyl, halo$(C_1-C_4)$alkyl, $(C_3-C_6)$cycloalkyl, 4-6 membered saturated heterocycle, halo, hydroxy, hydroxy$(C_1-C_4)$alkyl, $(C_1-C_4)$alkoxy, hydroxy$(C_2-C_4)$alkoxy, and halo$(C_1-C_4)$alkoxy. In certain embodiments, the present invention relates to any of the aforementioned compounds, wherein W is pyridine optionally substituted with one, two, three, or four $R^7$ independently selected from the group consisting of $(C_1-C_4)$alkyl, halo$(C_1-C_4)$alkyl, halo, hydroxy, hydroxy$(C_1-C_4)$alkyl, $(C_1-C_4)$alkoxy, and halo$(C_1-C_4)$alkoxy. In certain embodiments, the present invention relates to any of the aforementioned compounds, wherein W is,

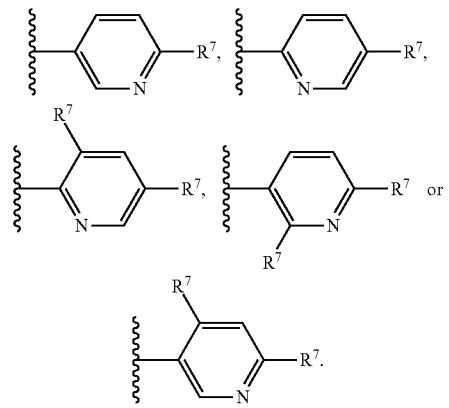

In certain embodiments, the present invention relates to any of the aforementioned compounds, wherein W is

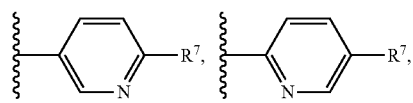

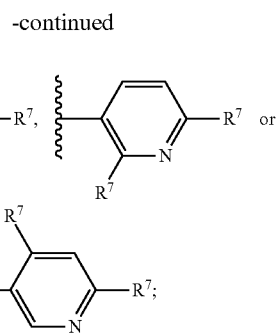

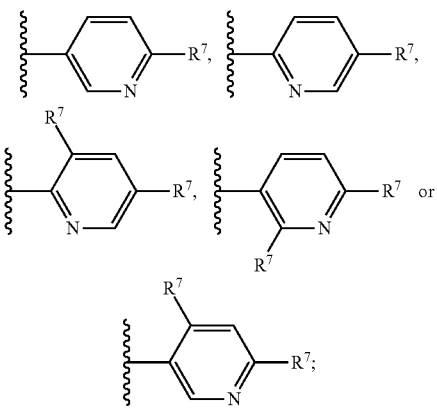

and $R^7$ is independently selected for each occurrence from the group consisting of $(C_1-C_4)$alkyl, $(C_1-C_3)$haloalkyl, $(C_1-C_4)$alkoxy, and halo. In certain embodiments, the present invention relates to any of the aforementioned compounds, wherein W is and $R^7$ is F, Cl or $CF_3$. In certain embodiments, the present invention relates to any of the aforementioned compounds, wherein W is

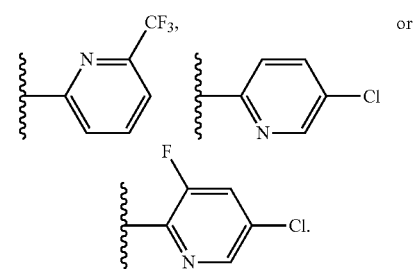

In certain embodiments, the present invention relates to any of the aforementioned compounds, wherein $R^1$ is a 4-membered nitrogen-containing heterocyclyl substituted on said nitrogen with R and optionally further substituted with one, two, three, four or five substituents independently selected from the group consisting of $(C_1-C_4)$alkyl, halo$(C_1-C_4)$alkyl, halo, hydroxyl and $(C_1-C_4)$alkoxy; and R is cyano. In certain embodiments, the present invention relates to any of the aforementioned compounds, wherein $R^1$ is a 5-membered nitrogen-containing heterocyclyl substituted on said nitrogen with R and optionally further substituted with one, two, three, four or five substituents independently selected from the group consisting of $(C_1-C_4)$alkyl, halo$(C_1-C_4)$ alkyl, halo, hydroxyl and (C₁-C₄)alkoxy; and R is cyano. In certain embodiments, the present invention relates to any of the aforementioned compounds, wherein R¹ is a 6-membered nitrogen-containing heterocyclyl substituted on said nitrogen with R and optionally substituted with one, two, three, four or five substituents independently selected from the group consisting of (C₁-C₄)alkyl, halo(C₁-C₄)alkyl, halo, hydroxyl and (C₁-C₄)alkoxy; and R is cyano. In certain embodiments, the present invention relates to any of the aforementioned compounds, wherein R¹ is a 7-membered nitrogen-containing heterocyclyl substituted on said nitrogen with R and optionally substituted with one, two, three, four or five substituents independently selected from the group consisting of (C₁-C₄)alkyl, halo(C₁-C₄)alkyl, halo, hydroxyl and (C₁-C₄)alkoxy and R is cyano. In certain embodiments, the present invention relates to any of the aforementioned compounds, wherein R¹ is a 8-membered nitrogen-containing heterocyclyl substituted on said nitrogen with R and optionally substituted with one, two, three, four or five substituents independently selected from the group consisting of (C₁-C₄)alkyl, (C₁-C₄)haloalkyl, halo, hydroxyl and (C₁-C₄)alkoxy; and R is cyano. In certain embodiments, the present invention relates to any of the aforementioned compounds, wherein R¹ is a 4-membered nitrogen-containing heterocyclyl substituted on said nitrogen with R and optionally further substituted with one, two, three, four or five substituents independently selected from the group consisting of (C₁-C₄)alkyl, (C₁-C₄)haloalkyl, halo, hydroxyl and (C₁-C₄)alkoxy; and R is cyano(C₁-C₃)alkyl. In certain embodiments, the present invention relates to any of the aforementioned compounds, wherein R¹ is a 5-membered nitrogen-containing heterocyclyl substituted on said nitrogen with R and optionally further substituted with one, two, three, four or five substituents independently selected from the group consisting of (C₁-C₄)alkyl, (C₁-C₄)haloalkyl, halo, hydroxyl and (C₁-C₄)alkoxy; and R is cyano(C₁-C₃)alkyl. In certain embodiments, the present invention relates to any of the aforementioned compounds, wherein R¹ is a 6-membered nitrogen-containing heterocyclyl substituted on said nitrogen with R and optionally further substituted with one, two, three, four or five substituents independently selected from the group consisting of (C₁-C₄)alkyl, (C₁-C₄)haloalkyl, halo, hydroxyl and (C₁-C₄)alkoxy; and R is cyano(C₁-C₃)alkyl. In certain embodiments, the present invention relates to any of the aforementioned compounds, wherein R¹ is a 7-membered nitrogen-containing heterocyclyl substituted on said nitrogen with R and optionally further substituted with one, two, three, four or five substituents independently selected from the group consisting of (C₁-C₄)alkyl, halo(C₁-C₄)alkyl, halo, hydroxyl and (C₁-C₄)alkoxy; and R is cyano(C₁-C₃)alkyl. In certain embodiments, the present invention relates to any of the aforementioned compounds, wherein R¹ is a 8-membered nitrogen-containing heterocyclyl substituted on said nitrogen with R and optionally further substituted with one, two, three, four or five substituents independently selected from the group consisting of (C₁-C₄)alkyl, (C₁-C₄)haloalkyl, halo, hydroxyl and (C₁-C₄)alkoxy; and R is cyano(C₁-C₃)alkyl. In certain embodiments, the present invention relates to any of the aforementioned compounds, wherein R¹

-continued optionally substituted with one, two, three, four or five substituents independently selected from the group consisting of (C₁-C₄)alkyl, halo(C₁-C₄)alkyl, halo, hydroxyl and (C₁-C₄)alkoxy. In certain embodiments, the present invention relates to any of the aforementioned compounds, wherein R¹ is

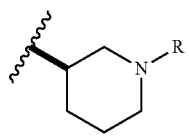

optionally substituted with one, two, three, four or five substituents independently selected from the group consisting of (C₁-C₄)alkyl, (C₁-C₄)haloalkyl, halo, hydroxyl and (C₁-C₄)alkoxy. In certain embodiments, the present invention relates to any of the aforementioned compounds, wherein R¹

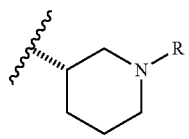

optionally substituted with one, two, three, four or five substituents independently selected from the group consisting of (C₁-C₄)alkyl, halo(C₁-C₄)alkyl, halo, hydroxyl and (C₁-C₄)alkoxy. In certain embodiments, the present invention relates to any of the aforementioned compounds, wherein R¹ is

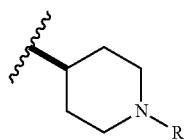

optionally substituted with one, two, three, four or five substituents independently selected from the group consisting of $(C_1-C_4)$alkyl, halo$(C_1-C_4)$alkyl, halo, hydroxyl and $(C_1-C_4)$alkoxy. In certain embodiments, the present invention relates to any of the aforementioned compounds, wherein $R^1$ is

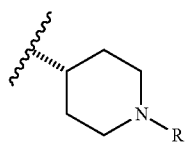

optionally substituted with one, two, three, four or five substituents independently selected from the group consisting of $(C_1-C_4)$alkyl, halo$(C_1-C_4)$alkyl, halo, hydroxyl and $(C_1-C_4)$alkoxy.

In certain embodiments, the present invention relates to any of the aforementioned compounds, wherein R is cyano or cyano$(C_1-C_3)$alkyl. In certain embodiments, the present invention relates to any of the aforementioned compounds, wherein R is cyano. In certain embodiments, the present invention relates to any of the aforementioned compounds, wherein R is cyano$(C_1-C_3)$alkyl; or wherein R is cyanomethyl.

In certain embodiments, the present invention relates to any of the aforementioned compounds, wherein $R^{2a}$ is hydrogen. In certain embodiments, the present invention relates to any of the aforementioned compounds, wherein $R^{2a}$ is $(C_1-C_3)$alkyl; or wherein $R^{2a}$ is methyl.

In certain embodiments, the present invention relates to any of the aforementioned compounds, wherein $R^{2b}$ is hydrogen. In certain embodiments, the present invention relates to any of the aforementioned compounds, wherein $R^{2b}$ is $(C_1-C_3)$alkyl; or wherein $R^{2b}$ is methyl.

In certain embodiments, the present invention relates to any of the aforementioned compounds, wherein $R^{3a}$ is hydrogen. In certain embodiments, the present invention relates to any of the aforementioned compounds, wherein $R^{3a}$ is $(C_1-C_3)$alkyl; or wherein $R^{3a}$ is methyl.

In certain embodiments, the present invention relates to any of the aforementioned compounds, wherein $R^{3b}$ is hydrogen. In certain embodiments, the present invention relates to any of the aforementioned compounds, wherein $R^{3b}$ is $(C_1-C_3)$alkyl; or wherein $R^{3b}$ is methyl.

In certain embodiments, the present invention relates to any of the aforementioned compounds, wherein $R^4$ is hydrogen. In certain embodiments, the present invention relates to any of the aforementioned compounds, wherein $R^4$ is $(C_1-C_3)$alkyl; or wherein $R^4$ is methyl.

In certain embodiments, the present invention relates to any of the aforementioned compounds, wherein $R^{5a}$ is hydrogen. In certain embodiments, the present invention relates to any of the aforementioned compounds, wherein $R^{5a}$ is $(C_1-C_3)$alkyl; or wherein $R^{5a}$ is methyl. In certain embodiments, the present invention relates to any of the aforementioned compounds, wherein $R^{5a}$ is halo.

In certain embodiments, the present invention relates to any of the aforementioned compounds, wherein $R^{5b}$ is hydrogen. In certain embodiments, the present invention relates to any of the aforementioned compounds, wherein $R^{5b}$ is $(C_1-C_3)$alkyl; or wherein $R^{5b}$ is methyl. In certain embodiments, the present invention relates to any of the aforementioned compounds, wherein $R^{5b}$ is halo.

In certain embodiments, the present invention relates to any of the aforementioned compounds, wherein R is

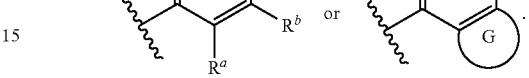

In certain embodiments, the present invention relates to any of the aforementioned compounds, wherein R is

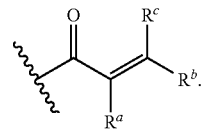

In certain embodiments the present invention relates to any of the aforementioned compounds, wherein R

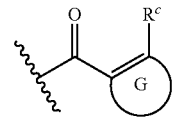

In certain embodiments, the present invention relates to any of the aforementioned compounds, wherein $R^a$ is hydrogen, halo or $(C_1-C_6)$alkoxy. In certain embodiments, the present invention relates to any of the aforementioned compounds, wherein $R^a$ is hydrogen. In certain embodiments, the present invention relates to any of the aforementioned compounds, wherein $R^a$ is halo. In certain embodiments, the present invention relates to any of the aforementioned compounds, wherein $R^a$ is $(C_1-C_6)$alkoxy. In certain embodiments, the present invention relates to any of the aforementioned compounds, wherein $R^a$ is methoxy.

In certain embodiments, the present invention relates to any of the aforementioned compounds, wherein $R^b$ is hydrogen, halo, cyano, $(C_1-C_6)$alkoxy, halo$(C_1-C_6)$alkoxy, or $(C_1-C_6)$alkyl optionally substituted with one, two or three $R^f$ independently selected from the group consisting of halo, hydroxyl, $N(R^e)_2$, $(C_1-C_6)$alkoxy, halo$(C_1-C_6)$alkoxy and aryl. In certain embodiments, the present invention relates to any of the aforementioned compounds, wherein $R^b$ is hydrogen. In certain embodiments, the present invention relates to any of the aforementioned compounds, wherein $R^b$ is halo. In certain embodiments, the present invention relates to any of the aforementioned compounds, wherein $R^b$ is cyano. In certain embodiments, the present invention relates to any of the aforementioned compounds, wherein $R^b$ is hydroxyl. In certain embodiments, the present invention relates to any of the aforementioned compounds, wherein $R^b$ is $(C_1-C_6)$alkoxy. In certain embodiments, the present invention relates to any of the aforementioned compounds, wherein $R^b$ is halo($C_1$-$C_6$)alkoxy. In certain embodiments, the present invention relates to any of the aforementioned compounds, wherein $R^b$ is ($C_1$-$C_6$)alkyl optionally substituted with one, two or three $R^f$ independently selected from the group consisting of halo, hydroxyl, $N(R^e)_2$, ($C_1$-$C_6$)alkoxy, halo ($C_1$-$C_6$)alkoxy and aryl. In certain embodiments, the present invention relates to any of the aforementioned compounds, wherein $R^b$ is $CH_3$, $CHF_2$, $CH_2F$, $CH_2OH$, $CH_2N(CH_3)_2$, $CH_2OCH_3$, $CH_2CH_2OH$, $CH(OH)(CH_3)$ or $C(OH)(CH_3)_2$. In certain embodiments, the present invention relates to any of the aforementioned compounds, wherein $R^b$ is $CHF_2$ or $CH_2F$. In certain embodiments, the present invention relates to any of the aforementioned compounds, wherein $R^b$ is $CH_2OCH_3$.

In certain embodiments, the present invention relates to any of the aforementioned compounds, wherein $R^c$ is hydrogen, halo, cyano, ($C_1$-$C_6$)alkoxy, halo($C_1$-$C_6$)alkoxy, or ($C_1$-$C_6$)alkyl optionally substituted with one, two or three $R^f$ independently selected from the group consisting of halo, hydroxyl, $N(R^e)_2$, ($C_1$-$C_6$)alkoxy, halo($C_1$-$C_6$)alkoxy and aryl. In certain embodiments, the present invention relates to any of the aforementioned compounds, wherein $R^c$ is hydrogen. In certain embodiments, the present invention relates to any of the aforementioned compounds, wherein $R^c$ is halo. In certain embodiments, the present invention relates to any of the aforementioned compounds, wherein $R^c$ is cyano. In certain embodiments, the present invention relates to any of the aforementioned compounds, wherein $R^c$ is hydroxyl. In certain embodiments, the present invention relates to any of the aforementioned compounds, wherein $R^c$ is ($C_1$-$C_6$) alkoxy. In certain embodiments, the present invention relates to any of the aforementioned compounds, wherein $R^c$ is halo($C_1$-$C_6$)alkoxy. In certain embodiments, the present invention relates to any of the aforementioned compounds, wherein $R^c$ is ($C_1$-$C_6$)alkyl optionally substituted with one, two or three $R^f$ independently selected from the group consisting of halo, hydroxyl, $N(R^e)_2$, ($C_1$-$C_6$)alkoxy, halo ($C_1$-$C_6$)alkoxy and aryl.

In certain embodiments, the present invention relates to any of the aforementioned compounds, wherein $R^b$ and $R^c$ taken together with the carbon to which they are bound form a 4-7 membered carbocycyl or heterocycy; optionally substituted with one, two or three $R^f$ independently selected from the group consisting of halo, hydroxyl, $N(R^e)_2$, ($C_1$-$C_6$)alkoxy, halo($C_1$-$C_6$)alkoxy and aryl. In certain embodiments, the present invention relates to any of the aforementioned compounds, wherein $R^b$ and $R^c$ taken together with the carbon to which they are bound form a 4-7 membered carbocycyl optionally substituted with one, two or three $R^f$ independently selected from the group consisting of halo, hydroxyl, $N(R^e)_2$, ($C_1$-$C_6$)alkoxy, halo($C_1$-$C_6$)alkoxy and aryl. In certain embodiments, the present invention relates to any of the aforementioned compounds, wherein $R^b$ and $R^c$ taken together with the carbon to which they are bound form a 4-7 membered heterocycyl optionally substituted with one, two or three $R^f$ independently selected from the group consisting of halo, hydroxyl, $N(R^e)_2$, ($C_1$-$C_6$)alkoxy, halo ($C_1$-$C_6$)alkoxy and aryl.

In certain embodiments, the present invention relates to any of the aforementioned compounds, wherein $R^d$ is ($C_1$-$C_6$)alkyl. In certain embodiments, the present invention relates to any of the aforementioned compounds, wherein $R^d$ is ($C_1$-$C_6$)alkoxy. In certain embodiments, the present invention relates to any of the aforementioned compounds, wherein $R^d$ is $N(R^e)_2$. In certain embodiments, the present invention relates to any of the aforementioned compounds, wherein $R^d$ is aryl.

In certain embodiments, the present invention relates to any of the aforementioned compounds, wherein $R^e$ is hydrogen. In certain embodiments, the present invention relates to any of the aforementioned compounds, wherein one $R^e$ is hydrogen and the other $R^e$ is ($C_1$-$C_4$) alkyl. In certain embodiments, the present invention relates to any of the aforementioned compounds, wherein $R^e$ is ($C_1$-$C_4$) alkyl. In certain embodiments, the present invention relates to any of the aforementioned compounds, wherein $R^e$ taken together with the nitrogen atom to which they are bound form a 4-7 membered heterocycyl.

In another embodiment are compounds of Formula (II)

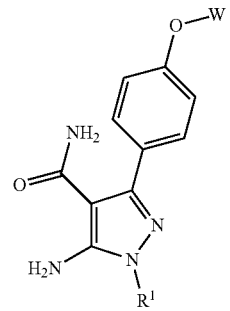

(II)

or pharmaceutically acceptable salts thereof, wherein
$R^1$ is

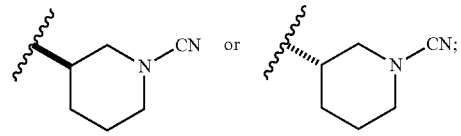 [SMILES: *[C@@H]1CCCN(C#N)C1 ; *[C@H]1CCCN(C#N)C1]

and
W is phenyl or pyridyl, optionally substituted with one, two, three, four or five substituents independently selected from the group consisting of ($C_1$-$C_4$)alkyl, ($C_1$-$C_3$)haloalkyl and halo.

In certain embodiments, the present invention relates to any of the aforementioned compounds, wherein $R^1$ is

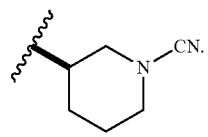 [SMILES: *[C@@H]1CCCN(C#N)C1]

In certain embodiments, the present invention relates to any of the aforementioned compounds, wherein $R^1$ is

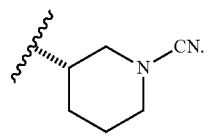 [SMILES: *[C@H]1CCCN(C#N)C1]

In certain embodiments, the present invention relates to any of the aforementioned compounds, wherein W is

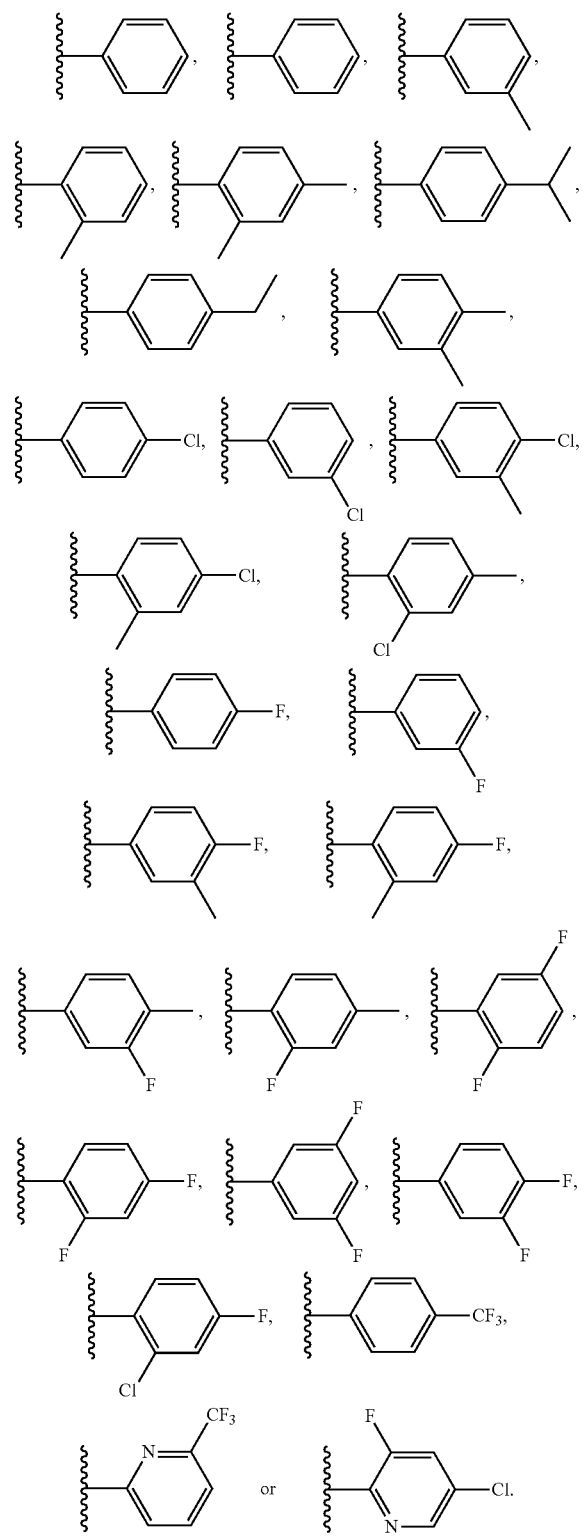

Another embodiment of the invention is a compound selected from the group consisting of the compounds of Examples 1-166 and pharmaceutically acceptable salts thereof.

Another embodiment of the Invention is a compound represented by

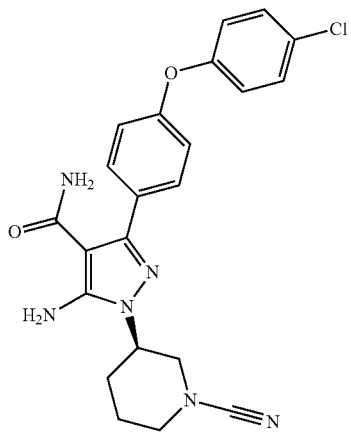 [SMILES: N#CN1CCC[C@@H](n2nc(-c3ccc(Oc4ccc(Cl)cc4)cc3)c(C(N)=O)c2N)C1]

and pharmaceutically acceptable salts thereof.

Another embodiment of the invention is a compound represented by

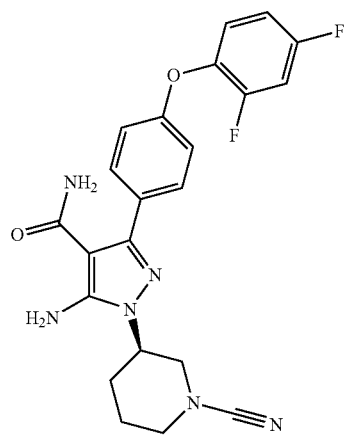 [SMILES: N#CN1CCC[C@@H](n2nc(-c3ccc(Oc4ccc(F)cc4F)cc3)c(C(N)=O)c2N)C1]

and pharmaceutically acceptable salts thereof.

Another embodiment of the invention is a compound represented by

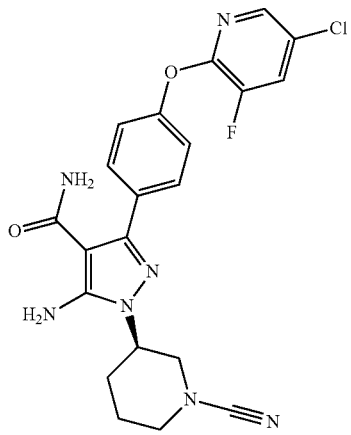 [SMILES: N#CN1CCC[C@@H](n2nc(-c3ccc(Oc4ncc(Cl)cc4F)cc3)c(C(N)=O)c2N)C1]

and pharmaceutically acceptable salts thereof.

Another embodiment of the Invention is a compound represented by

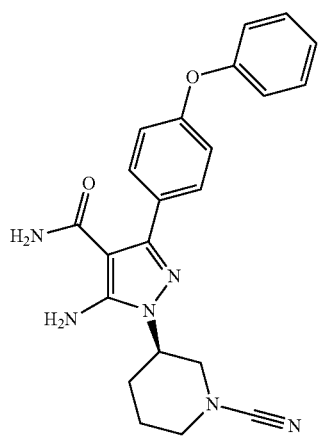 [SMILES: N#CN1CCC[C@@H](n2nc(-c3ccc(Oc4ccccc4)cc3)c(C(N)=O)c2N)C1]

and pharmaceutically acceptable salts thereof.

Another embodiment of the Invention is a compound represented by

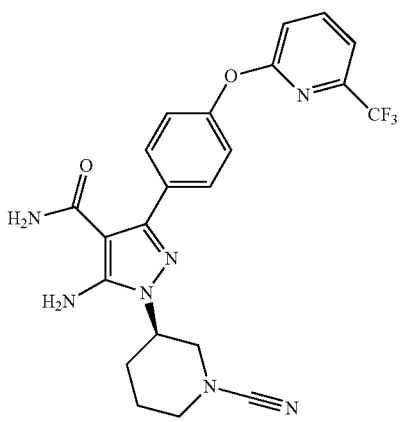 [SMILES: N#CN1CCC[C@@H](n2nc(-c3ccc(Oc4cccc(C(F)(F)F)n4)cc3)c(C(N)=O)c2N)C1]

and pharmaceutically acceptable salts thereof.

In another embodiment are compounds of Formula (II)

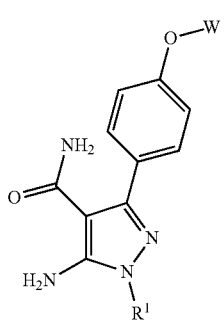

or pharmaceutically acceptable salts thereof, wherein $R^1$ is

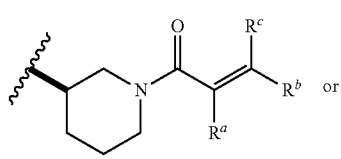

-continued

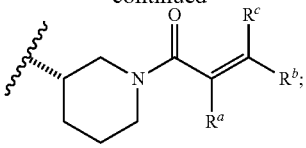

$R^a$ is hydrogen, halo, cyano, $(C_1-C_6)$alkoxy, halo$(C_1-C_6)$alkoxy, $(C_1-C_4)$alkylthio, $(C_1-C_4)$alkylsulfonyl, or $(C_1-C_6)$alkyl optionally substituted by halo, hydroxyl, $(C_1-C_6)$alkoxy or halo$(C_1-C_6)$alkoxy;

$R^b$ and $R^c$ are independently selected from the group consisting of hydrogen, halo, cyano, $(C_1-C_6)$alkoxy, halo$(C_1-C_6)$alkoxy, $(C_3-C_6)$cycloalkyl, $C(=O)R^d$ and $(C_1-C_6)$alkyl optionally substituted with one, two or three $R^f$ independently selected from the group consisting of halo, hydroxyl, $N(R^e)_2$, $(C_1-C_6)$alkoxy and halo$(C_1-C_6)$alkoxy or $R^b$ and $R^c$ taken together with the carbon to which they are bound form a 4-7 membered carbocycyl or heterocycly optionally substituted with one, two or three $R^f$ independently selected from the group consisting of halo, hydroxyl, $N(R^e)_2$, $(C_1-C_6)$alkoxy and halo$(C_1-C_6)$alkoxy;

$R^d$ is $(C_1-C_6)$alkyl, $(C_1-C_6)$alkoxy, $N(R^e)_2$ or aryl;

$R^e$ is independently selected for each occurrence from the group consisting of hydrogen and $(C_1-C_4)$ alkyl, or both $R^e$ taken together with the nitrogen atom to which they are bound form a 4-7 membered heterocycyl; and W is phenyl or pyridyl, optionally substituted with one, two, three, four or five substituents independently selected from the group consisting of $(C_1-C_4)$alkyl, $(C_1-C_3)$haloalkyl and halo.

In certain embodiments, the present invention relates to any of the aforementioned compounds, wherein $R^1$ is

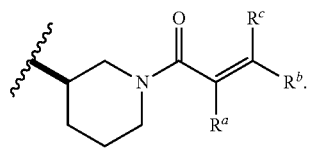

In certain embodiments, the present invention relates to any of the aforementioned compounds, wherein $R^1$ is.

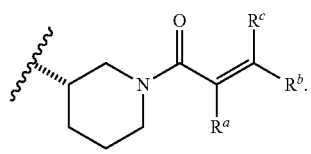

In certain embodiments, the present invention relates to any of the aforementioned compounds, wherein W is

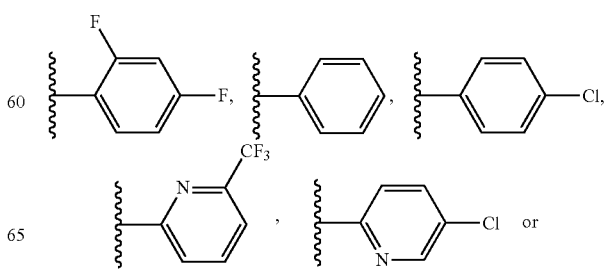

-continued

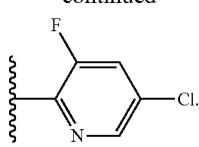

Another embodiment of the Invention is a compound selected from the group consisting of the compounds of Examples 126-166 and pharmaceutically acceptable salts thereof.

Another embodiment of the Invention is a compound represented by

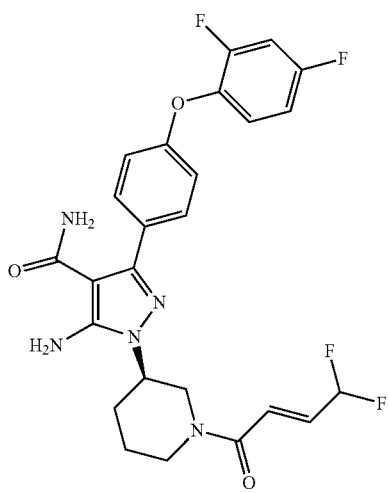 [SMILES: NC(=O)c1c(-c2ccc(Oc3ccc(F)cc3F)cc2)nn([C@@H]2CCCN(C(=O)/C=C/C(F)F)C2)c1N]

and pharmaceutically acceptable salts thereof.

Another embodiment of the Invention is a compound represented by

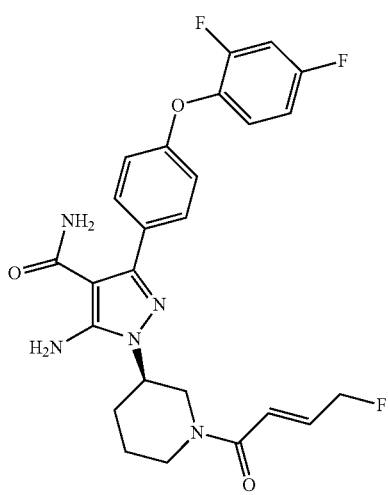 [SMILES: NC(=O)c1c(-c2ccc(Oc3ccc(F)cc3F)cc2)nn([C@@H]2CCCN(C(=O)/C=C/CF)C2)c1N]

and pharmaceutically acceptable salts thereof.

Another embodiment of the invention is a compound represented by

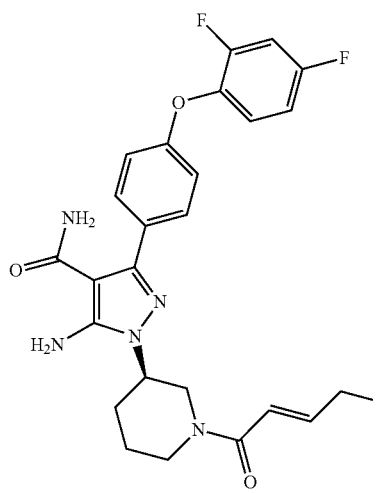

and pharmaceutically acceptable salts thereof.

Another embodiment of the invention is a compound represented by

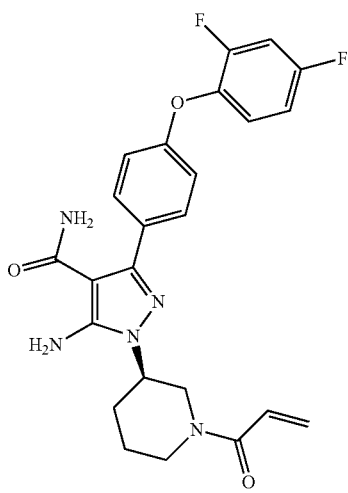 [SMILES: C=CC(=O)N1CCC[C@@H](n2nc(-c3ccc(Oc4ccc(F)cc4F)cc3)c(C(N)=O)c2N)C1]

and pharmaceutically acceptable salts thereof.

Methods

In one aspect, provided herein are methods for treating a patient by administering a compound provided herein. In some embodiments, provided herein is a method of inhibiting the activity of tyrosine kinase(s), such as BTK, or of treating a disease, disorder, or condition, which would benefit from inhibition of tyrosine kinase(s), such as BTK, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In another aspect, provided herein is the use of a compound disclosed herein for inhibiting Bruton's tyrosine kinase (BTK) activity or for the treatment of a disease, disorder, or condition, which would benefit from inhibition of Bruton's tyrosine kinase (BTK) activity.

In some embodiments, compounds provided herein are administered to a human.

In some embodiments, compounds provided herein are orally administered.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (BTK) activity.

In a further aspect, provided herein is a method for inhibiting Bruton's tyrosine kinase in a subject in need thereof by administering to the subject thereof a composition containing a therapeutically effective amount of at least one compound of the invention. In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjogren's syndrome, multiple sclerosis, Guillain-Barre syndrome, acute disseminated encephalomyelitis, Addison's disease, opsocionus-myocionus syndrome, ankylosing spondylitisis, antiphospholipid antibody syndrome, aplastic anemia, autoimmune hepatitis, coellac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of at least one compound of the invention. In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyrolditis, Graves' disease Sjogren's syndrome, multiple sclerosis, Guillain-Barre syndrome, acute disseminated encephalomyelitis, Addison's disease, opsocionus-myocionus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound of the invention. In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound of the Invention. In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound of the invention. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound of the invention. In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In a further or alternative embodiment, the compound forms a covalent bond with a cysteine residue on Bruton's tyrosine kinase.

In a further aspect, provided herein is a method for treating a heteroimmune condition or disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In a further or alternative embodiment, the compound forms a covalent bond with a cysteine residue on Bruton's tyrosine kinase.

In a further aspect, provided herein is a method for treating an inflammatory disease by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In a further or alternative embodiment, the compound forms a covalent bond with a cysteine residue on Bruton's tyrosine kinase. In yet another aspect, provided herein is a method for treating a cancer by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In a further or alternative embodiment, the compound forms a covalent bond with a cysteine residue on Bruton's tyrosine kinase. In another aspect, provided herein is a method for treating a thromboembolic disorder by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In a further or alternative embodiment, the compound forms a covalent bond with a cysteine residue on Bruton's tyrosine kinase.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the prevention or treatment of BTK-dependent or tyrosine kinase mediated diseases or conditions are further embodiments comprising identifying patients by screening for a tyrosine kinase gene haplotype. In further or alternative embodiments the tyrosine kinase gene haplotype is a tyrosine kinase pathway gene, while in still further or alternative embodiments, the tyrosine kinase gene haplotype is a BTK haplotype.

In a further or alternative embodiment, the compounds of the Invention are inhibitors of Bruton's tyrosine kinase (BTK), while in still further or alternative embodiments, such inhibitors are selective for BTK. In even further or alternative embodiments, such inhibitors have an $IC_{50}$ below 10 μM In enzyme assay. In one embodiment, such inhibitors have an $IC_{50}$ of less than 1 μM, and in another embodiment, less than 0.25 μM.

Pharmaceutical Compositions and Dosing Considerations

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in Isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

Pharmaceutical compositions of this invention suitable for parenteral administration comprise one or more compounds of the Invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the Injectable pharmaceutical form may be brought about by the Inclusion of agents which delay absorption such as aluminum monostearate and gelatin.

In some cases, in order to prolong the effect of a drug, it is desirable to slow the absorption of the drug from subcutaneous or Intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnold, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

Preferably, the compounds are administered at about 0.01 mg/kg to about 200 mg/kg, more preferably at about 0.1 mg/kg to about 100 mg/kg, even more preferably at about 0.5 mg/kg to about 50 mg/kg.

A number of animal models of are useful for establishing a range of therapeutically effective doses of BTK inhibitor compounds for treating any of the foregoing diseases.

For example, dosing of BTK inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), Am. J. Pathol 163:1827-1837.

In another example, dosing of BTK inhibitors for the treatment of B-cell proliferative disorders can be examined in, e.g., a human-to-mouse xenograft model in which human B-cell lymphoma cells (e.g. Ramos cells) are implanted into immunodeficient mice (e.g., "nude" mice) as described in, e.g., Pagel et al. (2005), Clin Cancer Res 11(13):4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo BTK activity achieved by administering a given dose of a BTK inhibitor. Cellular assays known in the art can be used to determine in vivo activity of BTK in the presence or absence of a BTK inhibitor. For example, since activated BTK is phosphorylated at tyrosine 223 (Y223) and tyrosine 551

(Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), Proc. Natl. Acad. Sci, USA 96:2221-2226. Thus, the amount of the BTK inhibitor inhibitor compound that is administered to a subject can be increased or decreased as needed so as to maintain a level of BTK inhibition optimal for treating the subject's disease state.

When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a compound of any one of Formula (I) and Formula (II) or a specific compound described herein, or pharmaceutically acceptable salts thereof, in a therapeutically effective amount for the treatment of an immune or Inflammatory disorder, such as one of the particular immune disorders or inflammatory disorders described herein.

In addition, articles of manufacture including packaging material, a compound or composition or pharmaceutically acceptable derivative thereof provided herein, which is effective for inhibiting the activity of tyrosine kinase(s), such as BTK, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of tyrosine kinase(s), such as BTK, are provided.

Combination Treatments

The BTK inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one BTK inhibitor compound described herein in combination with another therapeutic agent. By way of example only, if one of the side effects experienced by a patient upon receiving one of the BTK inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (i.e. compounds of the invention) may be administered in any order or even simultaneously. If simultaneously, the multiple therapeutic agents may be provided in a single, unified form, or In multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or In separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Where the subject is suffering from or at risk of suffering from an autoimmune disease, an inflammatory disease, or an allergy disease, a BTK inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-β, interferon-γ, Interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subjected can be treated with a BTK inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a BTK inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a BTK inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; tricirbine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelblne tartrate; vinrosidine sulfate; vinzolidine sulfate; vorozole; zeniplatin; zinostatin; zorubicin hydrochloride.

Other anti-cancer agents that can be employed in combination with a BTK inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; anglogenesis inhibitors; antagonist D; antagonist G; antarelix; anti-dorsalizing morphogenetic protein-1; antiandrogen, prostatic carcinoma; antiestrogen; antineoplaston; antisense ollgonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin b; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dadiximab; dedtabine; dehydrodidemnin B; deslorelin; dexamethasone; dexifosfamide; dexrazoxane; dexverapamil; diaziquone; didemnin B; didox; diethylnorspermine; dlhydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathlone inhibitors; hepsulfam; heregulln; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; Interferon agonists; Interferons; Interleukins; lobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhlbitors; menogaril; merbarone; meterelln; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porflmer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerle conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1;

sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a BTK inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a BTK inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a BTK inhibitor compound include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a BTK inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a BTK inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Dalichi), FR-182877 (Fujisawa, also known as WS-9885B), GS-164 (Takeda), GS-198 (Takeda), KAR-2 (Hungarian Academy of Sciences), BSF-223651 (BASF, also known as iLX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes institute, also known as DDE-261 and WHI-261), H10 (Kansas State University), H16 (Kansas State University), Oncocidin A1 (also known as BTO-956 and DIME), DDE-313 (Parker Hughes institute), Fijianolide B, Laulimalide, SPA-2 (Parker Hughes institute), SPA-1 (Parker Hughes institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a BTK inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexllate), factor Xa inhibitors (e.g., fondaparinux, draparinux, rivaroxaban, DX-9065a, otamixaban, LY517717, or YM150), ticiopidine, clopidogrel, CS-747 (prasugrel, LY640315), xlmelagatran, or BIBR 1048.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of BTK, or In which BTK is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

General Synthetic Procedures

The following schemes and experimental procedures are representative of the methods that can be used to prepare compounds of Formula (I) and are not intended to be limiting. Starting materials may be obtained by procedures described in the schemes, by procedures well known to one of ordinary skill in organic chemistry, and/or may be obtained commercially.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 2006. The need for, and the selection of, appropriate protecting groups can be readily determined by one skilled in the art.

The compounds of Formula (I) may be prepared as single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diastereomers by common methods (e.g. crystallization, chromatographic separation, or distillation) and chemical reversion to scalemic compound, Simulated Moving Bed technology, or high/medium-pressure liquid chromatography or supercritical fluid chromatography employing a chiral stationary phase. These techniques may be performed on the final compounds of Formula (I) or on any intermediates to compounds of Formula (I) which bear a stereogenic center. Also, to facilitate separation by any of the methods described above, the compounds of Formula (I) or any intermediates to the compounds of Formula (I) which bear a stereogenic center may be transiently reacted with an achiral reagent, separated, and then reverted to scalemic compound by standard synthetic techniques.

Compounds of formula (I) may be prepared as described in Scheme A. Compounds of the formula A1, prepared as described in Scheme C, are condensed with hydrazines of the formula A2, wherein the ring B is an optionally substituted 4-8 membered nitrogen-containing heterocycle and P is an appropriate amine protecting group (e.g. benzyloxycarbonyl, t-butoxycarbonyl, acetyl, or diphenylmethylene), to afford pyrazoles of the formula A3. Hydrazines of the formula A2 are commercially available or may be prepared as described in Schemes G-I. Compound A4 may be obtained by deprotection of the amine employing conditions such as catalytic hydrogenation in the case of benzyloxycarbonyl protection or trifluoroacetic acid in the case of t-butoxycarbonyl. Subsequent hydrolysis of the nitrile to afford carboxamides of the formula A5 may be accomplished by heating compounds A4 in the presence of strong base (e.g. sodium hydroxide) or strong acid (e.g. sulfuric acid). Alternatively, compounds of the formula A3 may be transformed to A5 directly under these conditions.

In certain embodiments, compound A5 is then reacted with cyanogen bromide in a polar solvent (e.g. N,N-dimethylformamide) in the presence of an inorganic base (e.g. potassium carbonate) to afford compounds of the formula A6.1. Similarly as described in Scheme B, amine A5 is reacted with bromoacetonitrile to provide compounds of the formula B1.

In certain embodiments, compound A5 is then reacted with an alkenoic acid or alkenoic acid chloride in the presence of an amine and an appropriate coupling agent as needed to afford compounds of the formula A6.2.

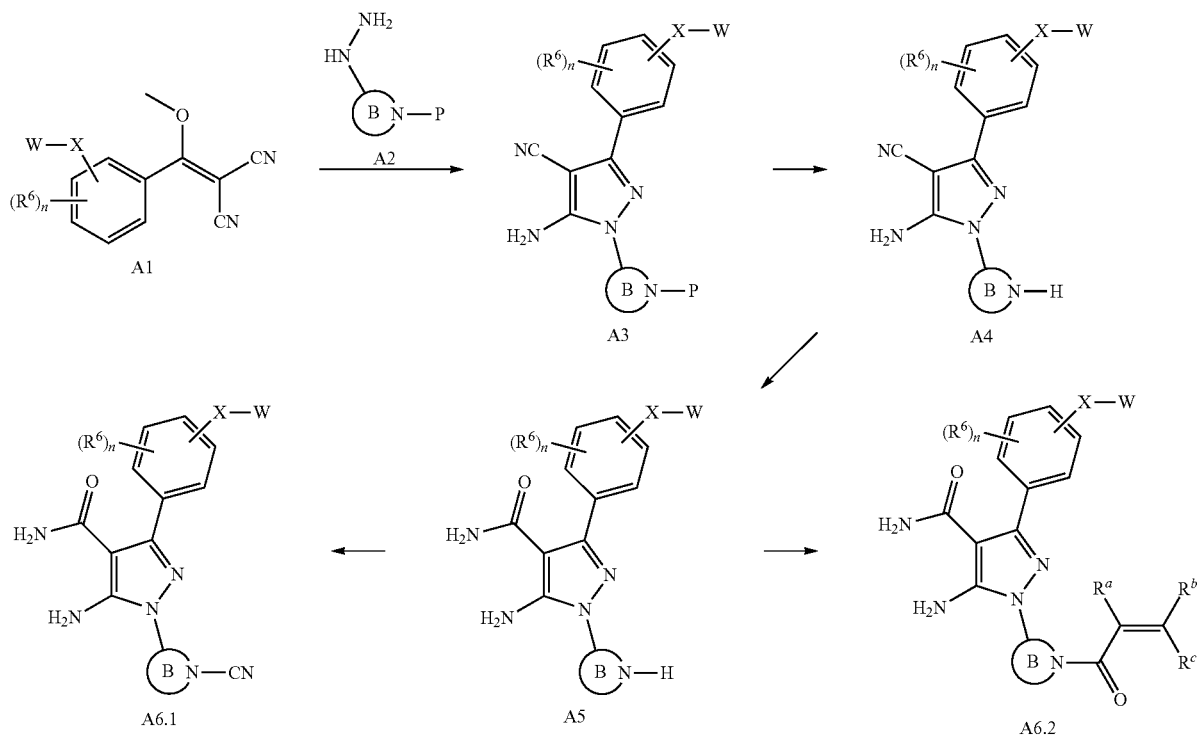

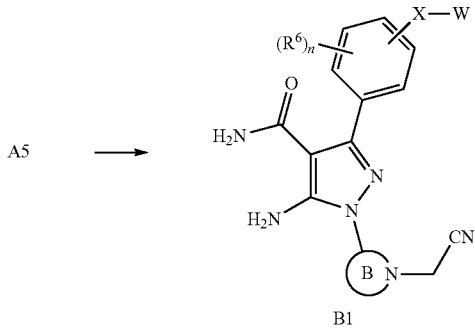

Compounds of the formula A1 employed in Scheme A may be prepared as described in Scheme C. Carboxylic acids of the formula C1, which are commercially available or prepared as described in Schemes D-F, are converted to the corresponding carboxylic acid chlorides C2 by the reaction with thionyl chloride or oxalyl chloride. Condensation of C2 with the sodium anion of malononitrile in anhydrous tetrahydrofuran affords compounds of the formula C3. Compounds of the formula A1 are then provided by the reaction of C3 with methyl sulfate in the presence of an inorganic base (e.g. sodium bicarbonate).

SCHEME C

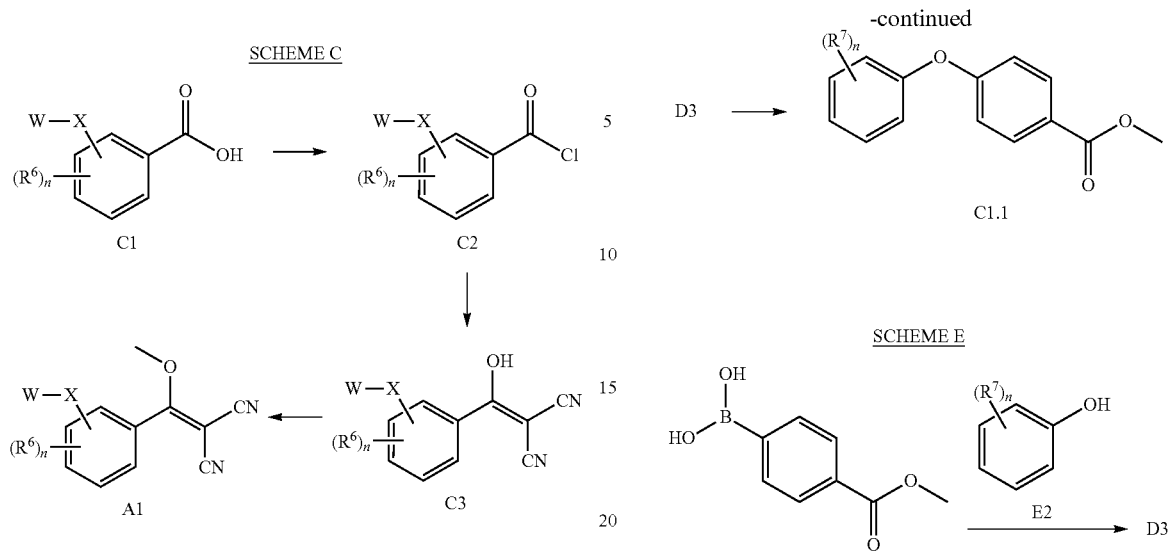

Carboxylic acids of the formula C1 employed in Scheme C may be prepared as described in Schemes D-F. In Scheme D, methyl 4-hydroxybenzoate may be coupled with substituted boronic acids of the formula D1 in the presence of 4-dimethylaminopyridine and copper (II) acetate to provide esters of the formula D3. Subsequent saponification of D3 employing an inorganic base such as sodium hydroxide provides carboxylic acids of the formula C1.1. Alternatively as described in Scheme E, (4-(methoxycarbonyl)phenyl) boronic acid may be coupled with substituted phenols of the formula E2 in the presence of 4-dimethylaminopyridine and copper (II) acetate to provide esters of the formula D3 which can be further transformed to acids C1.1 as described in Scheme D. Alternatively as described in Scheme F, 1-(4-fluorophenyl)ethanone can be heated in dimethylacetamide with substituted phenols of the formula E2 and an inorganic base such as potassium carbonate to afford ethers of the formula F2. Subsequent Baeyer Villiger oxidation of F2 with sodium hypochlorite solution provides carboxylic acids of the formula C1.1.

SCHEME D

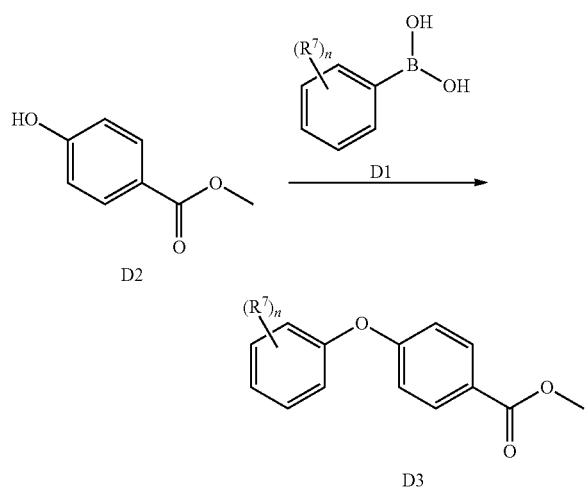

SCHEME E

SCHEME F

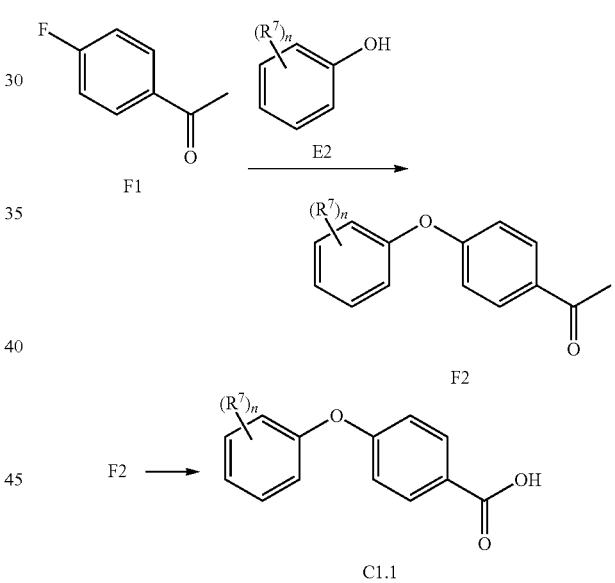

Compounds of the formula A2 employed in Scheme A may be prepared as described in Scheme G wherein ring B is an optionally substituted azetidine, pyrrolidine, piperidine, azepane and the like. The basic nitrogen atom present in hydroxy amines of the formula G1 is protected with an appropriate protecting group such as benzyloxycarbonyl, t-butoxycarbonyl, acetyl, or diphenylmethylene employing conditions well known by those skilled in the art to provide G2 wherein x=0-2, y=1-2, and R may include group such as $(C_1-C_4)$alkyl, $(C_1-C_4)$fluoroalkyl, halo, protected hydroxy and $(C_1-C_4)$alkoxy. Compound G2 is then oxidized to provide ketones of the formula G3 which is then condensed with t-butyl hydrazinecarboxylate to provide compounds of the G4. The resulting hydrazone is then reacted with an appropriate metal hydride reducing agent (e.g. sodium cyanoborohydride) to provide G5. Compound G5 is then treated with an acid (e.g. hydrochloric acid) to provide hydrazines of the formula A1.1.

SCHEME G

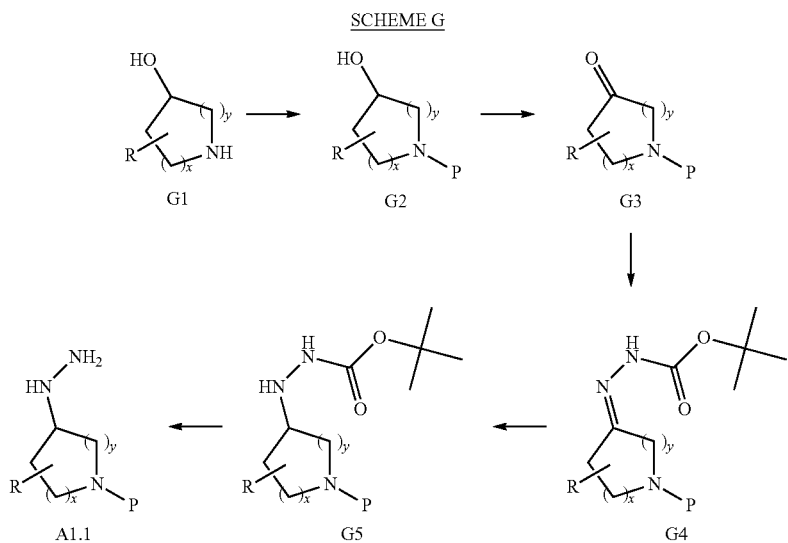

Additional examples of A2 employed in Scheme A may be prepared as described in Scheme H wherein ring B is an oxazepane. Condensation of 3-chloro-2-(chloromethyl)prop-1-ene and N-(t-butoxycarbonyl)-2-aminoethanol in the presence of sodium hydride base provides compound H3. Oxidative cleavage of the olefin with sodium periodate and osmium tetroxide provides ketone H4. Compound H4 is condensed with benzyl hydrazinecarboxylate followed by treatment with sodium cyanoborohydride to provide compound H5. Compound H5 is then treated with hydrogen gas in the presence of palladium on carbon to afford hydrazine A1.2.

SCHEME H

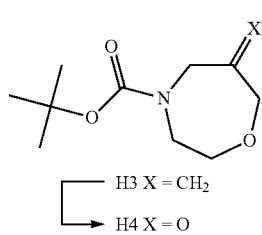

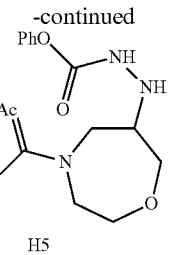

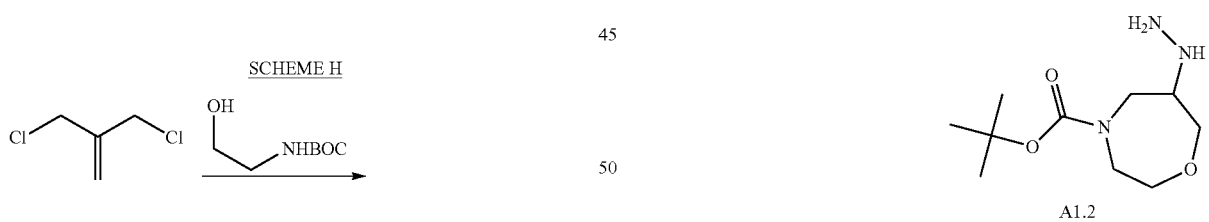

Additional examples of A2 employed in Scheme A may be prepared as described in Scheme I wherein ring B is an azabicyclo[2.2.1]heptane. Cyclopenta-1,3-diene is reacted with ammonium chloride, formaldehyde, and benzyl chloroformate to provide compound 12. Hydroboration of 12 employing borane methyl sulfide followed by oxidation with hydrogen peroxide provides alcohol 13 which is subsequently oxidized with Dess-Martin periodinane to provide ketone 15. The resulting ketone is then condensed with t-butyl hydrazinecarboxylate followed by treatment with sodium cyanoborohydride to provide compound 16. Compound 16 is then treated with an acid (e.g. hydrochloric acid) to provide hydrazines of the formula A1.3.

SCHEME I

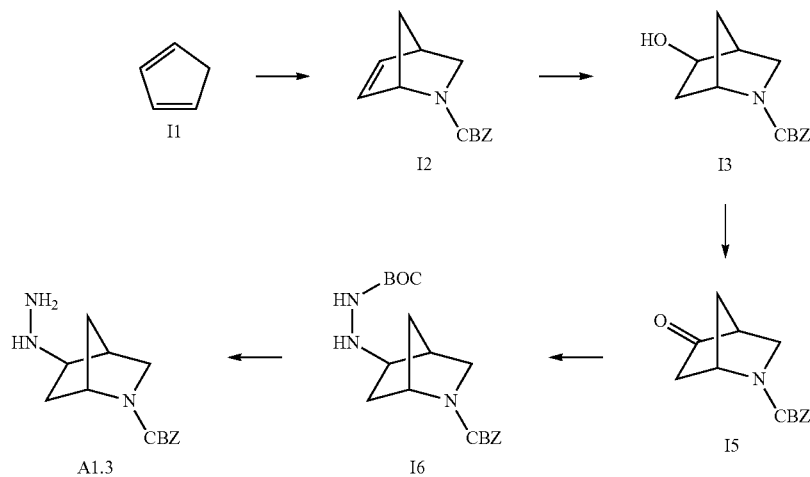

Alternatively, compounds of formula (I) may be prepared as described in Scheme J. Condensation of 4-iodobenzoyl chloride with the sodium anion of malonontrile in anhydrous tetrahydrofuran affords compound J2 which is then reacted with methyl sulfate in the presence of an Inorganic base (e.g. sodium bicarbonate) to provide compound J3. Compound J3 is condensed with hydrazines of the formula A2, wherein the ring B is an optionally substituted 4-8 membered nitrogen-containing heterocycle and P is an appropriate amine protecting group (e.g. benzyloxycarbonyl, t-butoxycarbonyl, acetyl, or diphenylmethylene), to afford pyrazoles of the formula J4. Hydrazines of the formula A2 are commercially available or may be prepared as described in Schemes G-I. Compound J4 is reacted with bis(pinacolato)diboron and potassium acetate catalyzed by PdCl$_2$(dppf)$_2$ to provide compounds of the formula J5. The resulting boronates depicted by J5 are then hydrolyzed in the presence of sodium periodate and ammonium acetate to afford boronic acids of the formula J6. Compound J6 may be coupled with optionally substituted phenols in the presence of copper (II) acetate and pyridine to afford aryl ethers of the formula A3.1 which may be subsequently converted to compounds of formula (I) according to procedures described in Scheme A. Similarly, starting from 3-iodobenzoyl chloride, compounds of formula (I) in which the aryl ether substituent is at the meta-position may be prepared.

SCHEME J

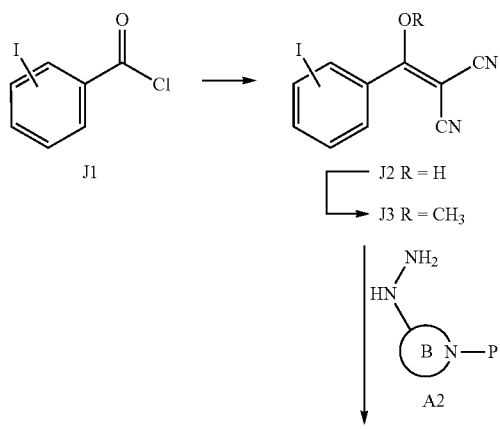

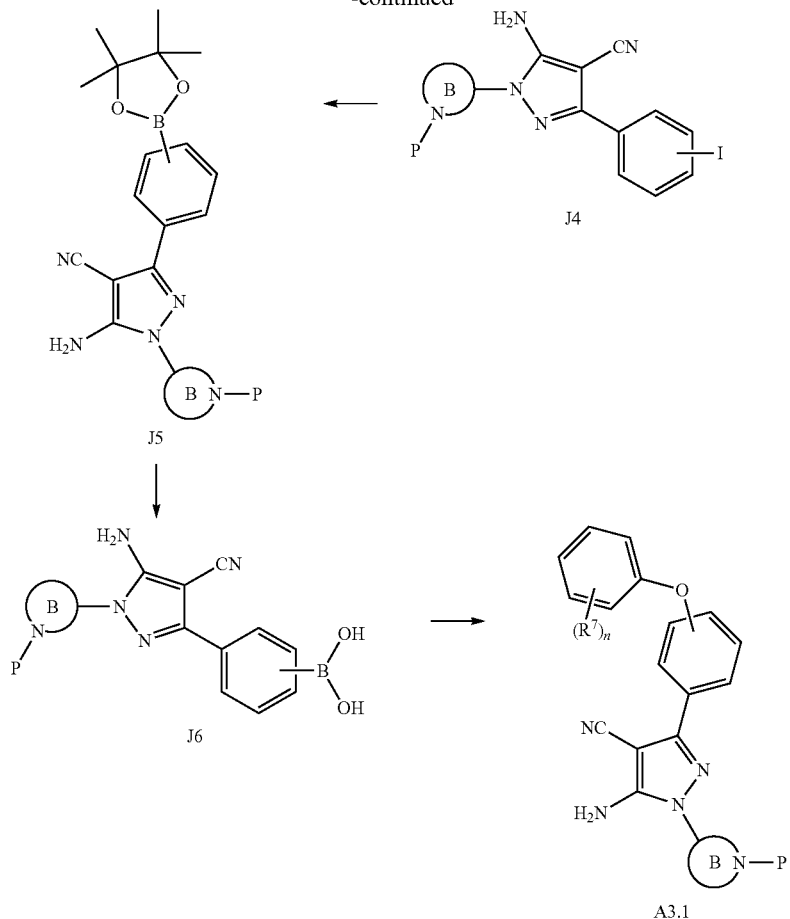

Compounds of formula (I) wherein X is CH₂ may be prepared as described in Scheme K. Compounds of the formula J4 described in Scheme J are reacted with optionally substituted benzyl zinc halides in the presence of S-PHOS and Pd₂(dba)₃ catalysts to afford compounds of the formula A3.2 which may be subsequently converted to compounds of formula (I) according to procedures described in Scheme A. Similarly, starting from 3-iodobenzoyl chloride, compounds of formula (I) in which the optionally substituted benzyl substituent is at the meta-position may be prepared.

SCHEME K

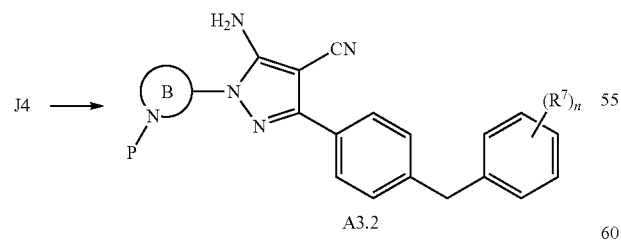

Alternatively as described in Scheme L, the amino substituent of J4 may be transiently protected as the corresponding N-acetyl to provide compounds of the formula L1. Compound L1 is reacted with optionally substituted benzyl zinc halides in the presence of S-PHOS and Pd₂(dba)₃ catalysts to afford compounds of the formula L2 wherein X=CH₂. In a similar fashion compound L1 is reacted with an optionally substituted phenol in the presence of cesium carbonate and copper (I) iodide to provide compounds of the formula L2 wherein X=O. In addition, compound L1 is reacted with an optionally substituted thiophenol in the presence of potassium carbonate and copper (I) iodide to provide compounds of the formula L2 wherein X=S. Compound L2 may then be treated with a strong base (e.g. sodium hydroxide) or a strong acid (e.g. concentrated sulfuric acid) to provide compounds of the formula A5 which may be subsequently converted to compounds of formula (I) according to procedures described in Scheme A.

SCHEME L

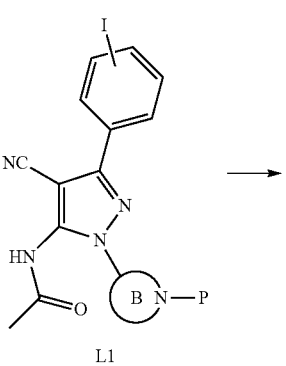

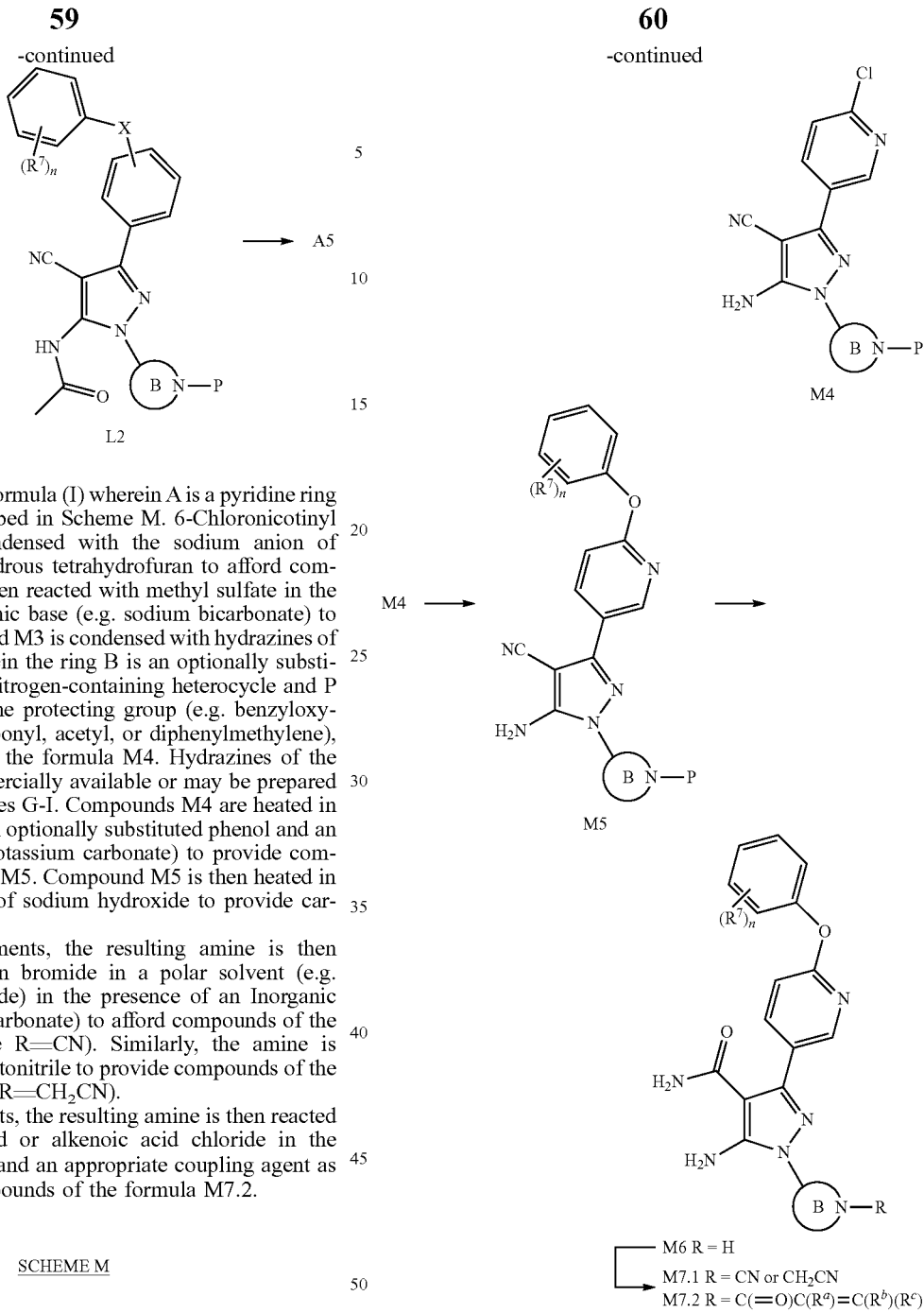

Compounds of the formula (I) wherein A is a pyridine ring are prepared as described in Scheme M. 6-Chloronicotinyl chloride (M1) is condensed with the sodium anion of malononitrile in anhydrous tetrahydrofuran to afford compound M2 which is then reacted with methyl sulfate in the presence of an inorganic base (e.g. sodium bicarbonate) to provide M3. Compound M3 is condensed with hydrazines of the formula A2, wherein the ring B is an optionally substituted 4-8 membered nitrogen-containing heterocycle and P is an appropriate amine protecting group (e.g. benzyloxycarbonyl, t-butoxycarbonyl, acetyl, or diphenylmethylene), to afford pyrazoles of the formula M4. Hydrazines of the formula A2 are commercially available or may be prepared as described in Schemes G-I. Compounds M4 are heated in a polar solvent with an optionally substituted phenol and an inorganic base (e.g. potassium carbonate) to provide compounds of the formula M5. Compound M5 is then heated in an ethanolic solution of sodium hydroxide to provide carboxamides M6.

In certain embodiments, the resulting amine is then reacted with cyanogen bromide in a polar solvent (e.g. N,N-dimethylformamide) in the presence of an Inorganic base (e.g. potassium carbonate) to afford compounds of the formula M7.1 (where R=CN). Similarly, the amine is reacted with bromoacetonitrile to provide compounds of the formula M7.1 (where R=CH$_2$CN).

In other embodiments, the resulting amine is then reacted with an alkenoic acid or alkenoic acid chloride in the presence of an amine and an appropriate coupling agent as needed to afford compounds of the formula M7.2.

SCHEME M

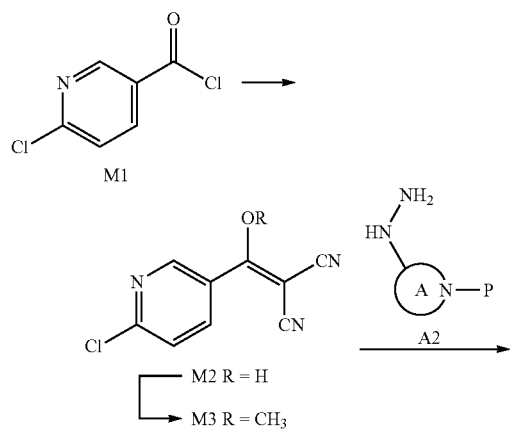

Compounds of the formula (I) wherein W is a pyridine ring may be prepared as described in Scheme N. 4-Hydroxybenzoic acid (N1) is reacted with t-butyl dimethylsilyl chloride in the presence of Imidazole to afford compound N2. Compound N2 is converted to the corresponding acid chloride by the reaction with isobutyl chloroformate which is then condensed with the sodium anion of malononitrile in anhydrous tetrahydrofuran and then treated with methyl sulfate in the presence of an inorganic base (e.g. sodium bicarbonate) to provide N3. Compound N3 is condensed with hydrazines of the formula A2, wherein the ring B is an optionally substituted 4-8 membered nitrogen-containing heterocycle and P is an appropriate amine protecting group (e.g. benzyloxycarbonyl, t-butoxycarbonyl, acetyl, or diphenylmethylene), to afford pyrazoles of the formula N4.

Hydrazines of the formula A2 are commercially available or may be prepared as described in Schemes G-I. Compound N4 is treated with acetyl chloride and triethylamine to afford compounds of the formula N5 which when treated with lithium hydroxide in a mixture of methanol and water provide compound N6. The resulting phenols are heated in a polar solvent (e.g. N,N-dimethylformamide) with an optionally substituted 2-halopyridine and an inorganic base (e.g. cesium carbonate) to provide compounds of the formula N7. Compound N7 is reacted with concentrated sulfuric acid to provide carboxamides of the formula N8.

In certain embodiments, the resulting amines are then reacted with cyanogen bromide in a polar solvent (e.g. N,N-dimethylformamide) in the presence of an inorganic base (e.g. potassium carbonate) to afford compounds of the formula N9.1 (where R=CN). Similarly, the amines are reacted with bromoacetonitrile to provide compounds of the formula N9.1 (where R=CH$_2$CN).

In other embodiments, the resulting amines are then reacted with an alkenoic acid or alkenoic acid chloride in the presence of an amine and an appropriate coupling agent as needed to afford compounds of the formula M9.2.

4-(ethoxycarbonyl)-1H-pyrazol-1-yl)piperidine-1-carboxylate (Compound 01) prepared as described in Scheme P is reacted with a boronic acid ester of the formula 02 which may be prepared as described in Scheme Q in the presence of Pd(dppf)$_2$Cl$_2$ and an Inorganic base (e.g. sodium carbonate) to provide compounds of the formula O3. The resulting esters are then treated with lithium hydroxide in a mixture of methanol and tetrahydrofuran to provide carboxylic acids of the formula O4 which are then coupled with ammonia after activation with 1-hydroxybenzotriazole and 3-(dimethylamino)propyl carbodiimide hydrochloride to provide amide O5. Compound O5 is then treated with and acid (e.g. trifluoroacetic acid) to provide amines of the formula O6.

In certain embodiments, the resulting amines are then reacted with cyanogen bromide in a polar solvent (e.g. N,N-dimethylformamide) in the presence of an inorganic base (e.g. potassium carbonate) to afford compounds of the formula O7 (R=CN). Similarly, the amines are reacted with bromoacetonitrile to provide compounds of the formula O8 (R=CH$_2$CN).

In other embodiments, the resulting amines are then reacted with an alkenoic acid or alkenoic acid chloride in the

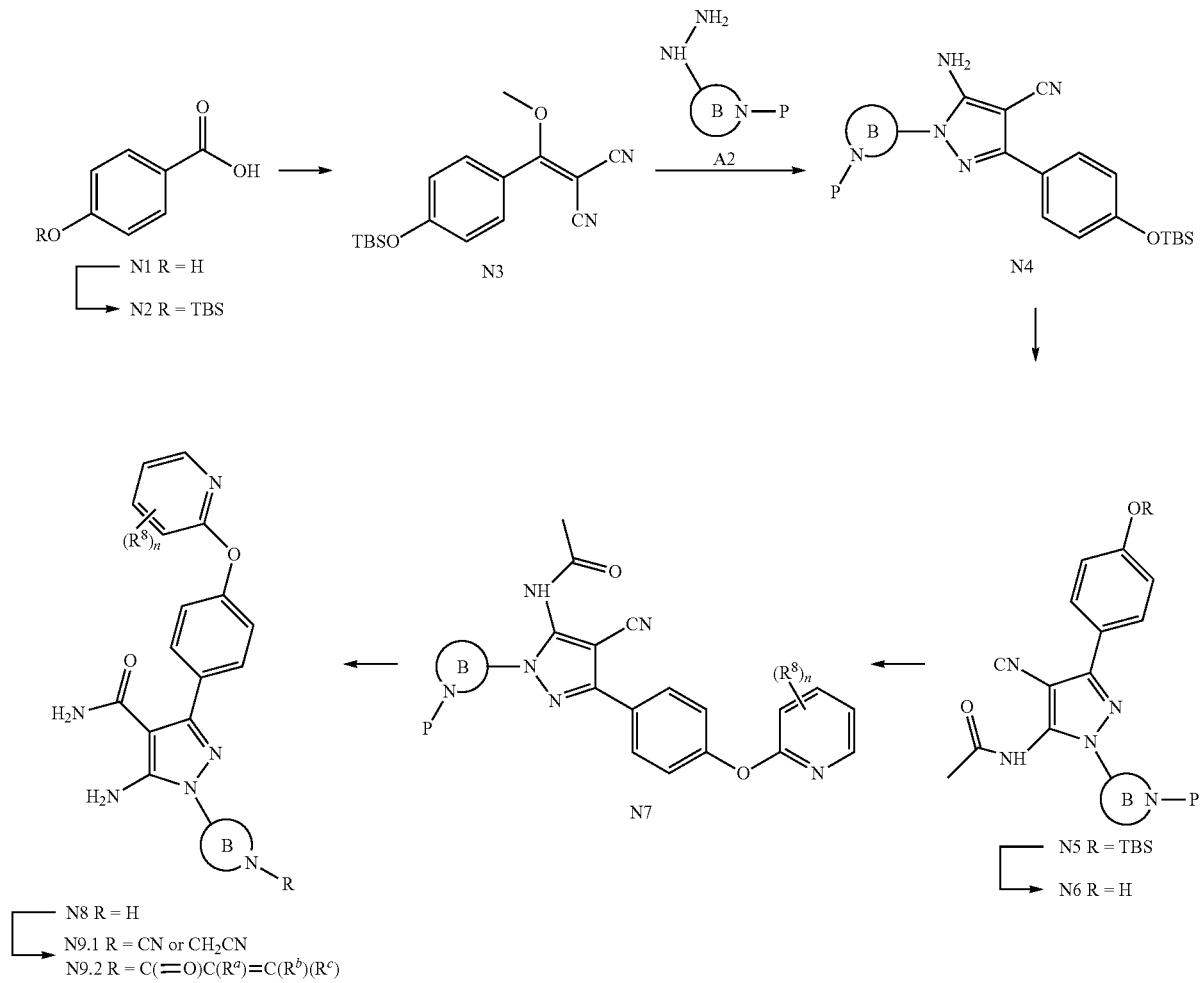

SCHEME N

Compounds of Formula (I) may also be prepared as described in Scheme 0. tert-Butyl 3-(5-acetamido-3-bromopresence of an amine and an appropriate coupling agent as needed to afford compounds of the formula O9.

SCHEME O

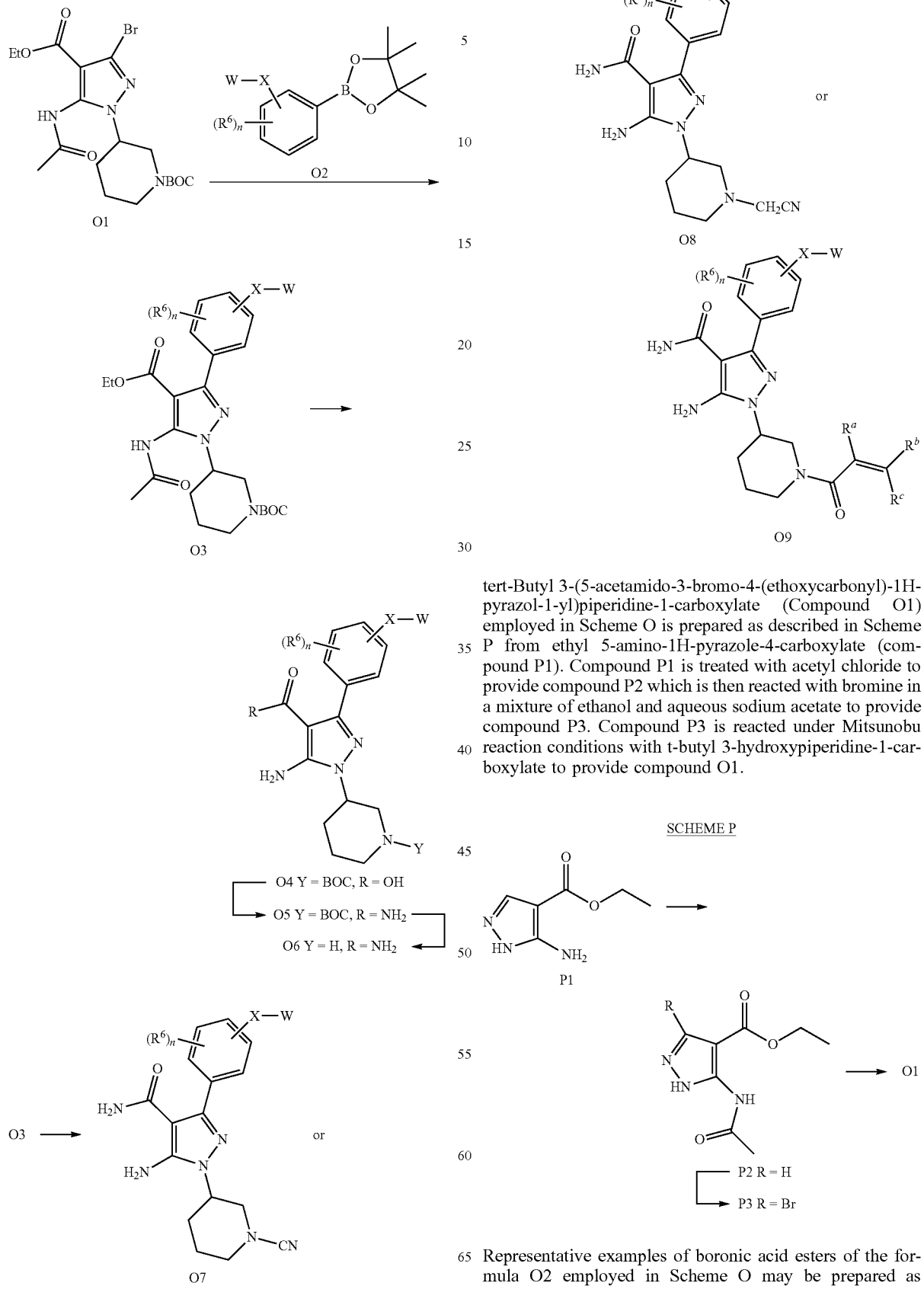

tert-Butyl 3-(5-acetamido-3-bromo-4-(ethoxycarbonyl)-1H-pyrazol-1-yl)piperidine-1-carboxylate (Compound O1) employed in Scheme O is prepared as described in Scheme P from ethyl 5-amino-1H-pyrazole-4-carboxylate (compound P1). Compound P1 is treated with acetyl chloride to provide compound P2 which is then reacted with bromine in a mixture of ethanol and aqueous sodium acetate to provide compound P3. Compound P3 is reacted under Mitsunobu reaction conditions with t-butyl 3-hydroxypiperidine-1-carboxylate to provide compound O1.

Representative examples of boronic acid esters of the formula O2 employed in Scheme O may be prepared as described in Scheme Q. Phenols of the formula Q1 are reacted with boronic acids of the formula D1 in the presence of copper (II) acetate and triethylamine to provide ethers of the formula Q2. Aryl bromides such as Q2 are then reacted with bis(pinacolato)diboron in the presence of an inorganic base (e.g. potassium acetate) and Pd(dppf)$_2$Cl$_2$ to provide compounds of the formula O2.

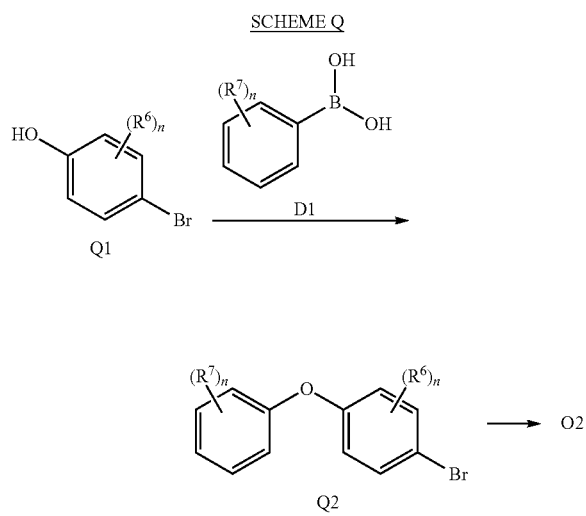

EXEMPLIFICATION

The invention now being generally described, will be more readily understood by reference to the following examples, which are included merely for purposes of illustration of certain aspects and embodiments of the present invention, and are not Intended to limit the Invention. The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Coupling constants (J values) are reported in Hertz.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: In general, solvents and the solvent ratios used for eluants/gradients were chosen to provide appropriate Rf's or retention times (RetT).

Example 1

5-amino-1-(1-cyanopiperidin-3-yl)-3-(4-phenoxy-phenyl)-1H-pyrazole carboxamide

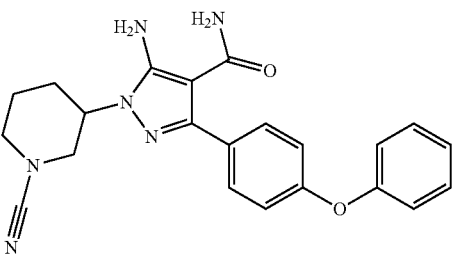 [SMILES: N#CN1CCCC(n2nc(-c3ccc(Oc4ccccc4)cc3)c(C(N)=O)c2N)C1]

Step 1: preparation of 4-phenoxy benzoyl chloride. A solution of 4-phenoxy benzoic acid (500 g, 2.33 mol) in thionyl chloride (1.2 L) was refluxed for 16 h, after which volatiles were removed in vacuo to afford the title compound as a brown gum, which was taken on to the next step without purification.

Step 2: preparation of 2-[hydroxy-(4-phenoxy-phenyl)-methylene]-malononitrile. A solution of malononitrile (154 mL, 2.55 mol) in anhydrous tetrahydrofuran (500 mL) was added drop wise under nitrogen to a suspension of sodium hydride (205 g, 5.12 mol) in tetrahydrofuran (2 L) over 1.5 h at 0° C. The reaction mixture was allowed to stir for an additional 30 min, after which addition of a solution of 4-phenoxy benzoyl chloride (540 g, 2.32 mol) in tetrahydrofuran (750 mL) was added. The reaction was then allowed to stir for 16 h at ambient temperature, cooled to 0° C. and quenched with 1N hydrochloric acid (1 L). Product was extracted into ethyl acetate and the combined organic layers were washed with water, then brine, dried over sodium sulfate, and concentrated in vacuo to afford the title compound as an off-white solid, which was carried on to the next step without purification. MS (M−H) m/z 261. $^1$H NMR (CDCl$_3$) δ 7.74 (d, J=8.8 Hz, 2H), 7.39 (t, J=7.6 Hz, 2H), 7.21 (t, J=7.2 Hz, 1H), 7.06 (d, J=8 Hz, 2H), 7.00 (d, J=8.8 Hz, 2H).

Step 3: preparation of 2-[(4-phenoxy-phenyl)-methoxy-methylene]-malononitrile. To a solution of 2-[hydroxy-(4-phenoxy-phenyl)-methylene]-malononitrile (600 g, 2.29 mol) in a mixture of dioxane/water (4/1, 5 L) at 0° C. was added sodium bicarbonate (1.34 kg, 16 mol) portion wise. Dimethyl sulfate (1.2 L, 13.74 mol) was added drop wise over 2 h, after which the reaction was warmed to 80° C. and allowed to stir for an additional 12 h. The reaction was cooled to ambient temperature, diluted with water and extracted into ethyl acetate. The combined organic layers were washed with water, then brine, dried over sodium sulfate, and concentrated in vacuo. The crude residue was purified by silica gel column chromatography to afford the title compound as an off white solid (300 g, 48%). MS (M+H) m/z 277. $^1$H NMR (CDCl$_3$) δ 7.47 (d, J=8.8 Hz, 2H), 7.42 (t, J=7.6 Hz, 2H), 7.23 (t, J=7.6 Hz, 1H), 7.07 (t, J=8.8 Hz, 4H), 3.97 (s, 3H).

Step 4: preparation of 3-Hydroxy-piperidine-1-carboxylic acid benzyl ester. To a suspension of piperidin-3-ol hydrochloride (134 g, 0.974 mol) and triethylamine (276 mL, 1.98 mol) in dichloromethane (2 L) at 0° C. was added a solution of benzyl chloroformate (140 mL, 0.981 mol) in dichloromethane (100 mL) drop wise over 2.5 h. The reaction was allowed to stir for an additional 30 min at 0° C., then allowed to warm to ambient temperature over 16 h, after which it was quenched with 1N hydrochloric acid (3 L) and allowed to stir for 30 min. The organic layer was separated, dried over sodium sulfate, and concentrated in vacuo to afford the title compound (218 g, 95%). $^1$H-NMR (CDCl$_3$) δ 7.29-7.41 (m, 5H), 5.14 (s, 2H), 3.59-3.85 (m, 3H), 3.13-3.27 (m, 2H), 2.18 (bs, 1H), 1.74-1.94 (m, 2H), 1.38-1.61 (m, 2H).

Step 5: preparation of 3-oxo-piperidine-1-carboxylic acid benzyl ester. To a suspension of pyridine sulfur trioxide complex (135.6 g, 0.85 mol) in dichloromethane (1.25 L) at 0° C. was added triethylamine (148 mL, 1.07 mol), followed by DMSO (151 mL, 2.13 mol). A solution of 3-hydroxy-piperidine-1-carboxylic acid benzyl ester (50.0 g, 0.21 mol) in dichloromethane (415 mL) was then added drop wise over 1 h, ensuring that the temperature did not exceed 0° C. The reaction was then allowed to warm to ambient temperature over 16 h, after which it was cooled to 15° C. and slowly quenched with saturated aqueous ammonium chloride (1 L) (exotherm!) The mixture was then allowed to stir for an additional 30 min, after which the organic layer was separated and the aqueous layer was extracted with dichloromethane. The combined organic layers were dried over sodium sulfate and concentrated in vacuo. The residue was dissolved in a 50% solution of heptane/ethyl acetate (300 mL), washed with 0.5N hydrochloric acid (600 mL), then brine. The organic layer was concentrated in vacuo and purified by silica gel column chromatography. $^1$H-NMR δ (CDCl$_3$): 7.32-7.41 (m, 5H), 5.17 (s, 2H), 4.10 (s, 2H), 3.69 (t, 2H), 2.50 (t, 2H), 1.97-2.08 (m, 2H).

Step 6: preparation of 3-(tert-butoxycarbonyl-hydrazono)-piperidine-1-carboxylic acid benzyl ester. To a solution of 3-oxo-piperidine-1-carboxylic acid benzyl ester (150 g, 0.64 mol) in tetrahydrofuran (1.5 L) was added tert-butyl hydrazinecarboxylate (85 g, 0.64 mol). The solution was heated to reflux for 2 h, after which it was cooled to ambient temperature and concentrated in vacuo to afford the title compound. MS (M+H) m/z 348. $^1$H-NMR (CDCl$_3$) δ 7.56 (s, 1H), 7.28-7.41 (m, 5H), 5.14-5.16 (d, 2H), 4.13-4.25 (d, 2H), 3.73-3.78 (m, 0.6H), 3.53-3.61 (m, 1.4H), 2.51-2.56 (t, 0.7H), 2.33-2.37 (t, 1.3H), 1.82-1.91 (m, 2H), 1.52 (s, 9H)

Step 7: preparation of benzyl 3-(2-(tert-butoxycarbonyl) hydrazinyl)piperidine-1-carboxylate. To a solution of 3-(tert-butoxycarbonyl-hydrazono)-piperidine-1-carboxylic acid benzyl ester (230 g, 0.66 mol) in tetrahydrofuran (1.5 L) was added sodium cyanoborohydride (41.6 g, 0.66 mol). A solution of para-toluenesulfonic acid mono-hydrate (126 g, 0.66 mol) in tetrahydrofuran (590 mL) was then added drop wise over 1.5 h, ensuring that the temperature did not exceed 21° C. The reaction was then allowed to stir over 16 h. Volatiles were removed in vacuo, and the resulting residue was dissolved in ethyl acetate (2.0 L), washed with saturated aqueous sodium bicarbonate (1 L), then added to 1N sodium hydroxide (1.5 L) and allowed to stir for 1 h. The organic layer was separated, washed with brine, dried over sodium sulfate, and concentrated in vacuo. The crude residue was purified by silica gel column chromatography (0-3% dichloromethane/methanol solvent gradient) affording the title compound as a colorless oil (169 g, 73%). $^1$H-NMR (CDCl$_3$): δ 7.29-7.36 (m, 5H), 6.33 (bs, 1H), 5.88 (bs, 1H), 5.12 (bs, 2H), 3.42-3.64 (m, 5H), 3.02-3.17 (m, 1H), 1.74-1.80 (m, 2H).

Step 8: preparation of 3-hydrazino-piperidine-1-carboxylic acid benzylester hydrochloride. To a solution of benzyl 3-(2-(tert-butoxycarbonyl)hydrazinyl)piperidine-1-carboxylate (50 g, 0.143 mol) in methanol (180 mL) was added a solution of 4N hydrochloric acid in dioxane (180 mL) drop wise, ensuring that the temperature did not exceed 10° C. The reaction was allowed to stir at ambient temperature over 16 h, after which a white precipitate had formed. The precipitate was filtered, then allowed to stir in ethyl acetate (700 mL) at ambient temperature for an additional 16 h, filtered, then dried under vacuum to afford the title compound as a white powder. MS (M+H) m/z 250.2. $^1$H-NMR (DMSO-d6) δ 7.28-7.41 (m, 5H), 5.08 (s, 2H), 4.10 (d, 1H), 3.72 (d, 1H), 2.95 (bs, 3H), 1.98 (m, 1H), 1.70 (m, 1H), 1.29-1.37 (m, 2H).

Step 9: preparation of benzyl 3-[5-amino-4-cyano-3-(4-phenoxy-phenyl)-pyrazol-1-yl]-piperidine-1-carboxylate.
To a solution of 2-[(4-phenoxy-phenyl)-methoxy-methylene]-malononitrile (step 3; 146 g, 0.53 mol) in ethanol (500 mL) was added benzyl 3-hydrazino-piperidine-1-carboxylate (step 8; 150.6 g, 0.53 mol) and triethylamine (107 g, 1.05 mol), causing the temperature of the solution to reach 55° C. The reaction was then allowed to cool to ambient temperature over 16 h, after which a precipitate had formed. The precipitate was filtered off and added to 2-methyl tetrahydrofuran (3.5 L), which dissolved the desired product, leaving behind triethyl amine-hydrochloric acid, which was then removed by vacuum filtration. The filtrate was then washed with brine (1 L) and concentrated in vacuo to afford the title compound as a white solid. MS (M+H) m/z 494.

Step 10: preparation of 5-amino-3-(4-phenoxy-phenyl)-1-piperidin-3-yl-1H-pyrazole-4-carbonitrile. A solution of benzyl 3-[5-amino-4-cyano-3-(4-phenoxy-phenyl)-pyrazol-1-yl]-piperidine-1-carboxylate (260 g, 527 mmol) in 2-methyl tetrahydrofuran (5 L) was passed through a Midi apparatus at 65° C., 7 mL/min, under full hydrogen, using a 10% Pd/C cartridge over a period of 16 h. Solvent was removed in vacuo to afford the title compound as a tan solid. MS (M+H) m/z 360.

Step 11: preparation of 5-amino-3-(4-phenoxyphenyl)-1-piperidin-3-yl-1H-pyrazole-4-carboxylic acid amide. To a 2 L SS Parr autoclave was added a solution of 5-amino-3-(4-phenoxy-phenyl)-1-piperidin-3-yl-1H-pyrazole-4-carbonitrile (189 g, 527 mmol) and ethanol (550 mL). A 2N sodium hydroxide solution (880 mL) was then added and the autoclave was sealed and heated at 150° C. for 30 min, after which the reaction was judged complete. The solution was cooled to ambient temperature and added to ethyl acetate (500 mL). The organic layer was separated, washed with brine, and concentrated in vacuo to afford a gummy solid, which was triturated with acetonitrile (500 mL), then purified further by silica gel column chromatography (15-40% methanol/dichloromethane solvent gradient) to afford the title compound as a white solid (135 g, 70%). MS (M+H) m/z 360.

Step 12: preparation of 5-amino-1-(1-cyanopiperidin-3-yl)-3-(4-phenoxyphenyl)-1H-pyrazole carboxamide. To a solution of 5-amino-3-(4-phenoxyphenyl)-1-piperidin-3-yl-1H-pyrazole-4-carboxylic acid amide (1.17 g, 3.10 mmol) in N,N-dimethylformamide was added potassium carbonate (643 mg, 4.65 mmol) followed by cyanogen bromide (398 mg, 3.72 mmol). The mixture was stirred at 50° C. over 16 h, after which volatiles were removed in vacuo. The resulting residue was dissolved in ethyl acetate, washed with brine, dried over magnesium sulfate and concentrated. The crude product was purified by reverse phase preparative HPLC to afford the title compound. MS (M+H) m/z 403.188. $^1$H NMR (DMSO-d6) δ 7.45 (d, J=8.79 Hz, 2H), 7.39 (t, J=7.87 Hz, 2H), 7.14 (t, J=7.32 Hz, 1H), 7.03 (t, J=8.79 Hz, 4H), 6.44 (bs, 2H), 4.31-4.38 (m, 1H), 3.48 (bs, 1H), 3.45 (d, J=3.66 Hz, 1H), 2.98-3.09 (m, 1H), 1.90 (bs, 2H), 1.76-1.88 (m, 2H), 1.68 (t, J=12.45 Hz, 1H).

Example 2

5-amino-1-[(3R)-1-cyanopiperidin-3-yl]-3-(4-phenoxyphenyl)-1H-pyrazole-4-carboxamide

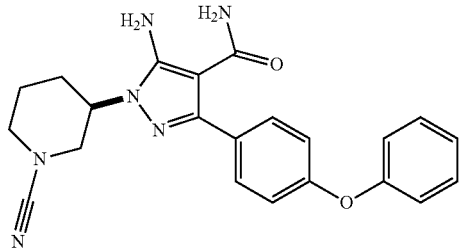

rac-5-amino-1-(1-cyanopiperidin-3-yl)-3-(4-phenoxyphenyl)-1H-pyrazole carboxamide (prepared as described in Example 1) was chirally separated by supercritical fluid chromatography (OJ-H 30×250 mm col, 50% MeOH, 70 mL/min). Isolation of the first eluting isomer afforded the title compound. MS (M+H) m/z 403. $^1$H NMR (DMSO-d6) δ 7.45 (d, J=8.79 Hz, 2H), 7.39 (t, J=7.87 Hz, 2H), 7.14 (t, J=7.32 Hz, 1H), 7.03 (t, J=8.79 Hz, 4H), 6.44 (bs, 2H), 4.31-4.38 (m, 1H), 3.48 (bs, 1H), 3.45 (d, J=3.66 Hz, 1H), 2.98-3.09 (m, 1H), 1.90 (bs, 2H), 1.76-1.88 (m, 2H), 1.68 (t, J=12.45 Hz, 1H).

Example 3

5-amino-1-[(3S)-1-cyanopiperidin-3-yl]-3-(4-phenoxyphenyl)-1H-pyrazole-4-carboxamide

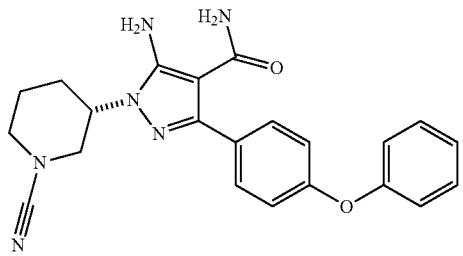

rac-5-amino-1-(1-cyanopiperidin-3-yl)-3-(4-phenoxyphenyl)-1H-pyrazole carboxamide (prepared as described in Example 1) was chirally separated by supercritical fluid chromatography (OJ-H 30×250 mm col, 50% MeOH, 70 mL/min). Isolation of the second eluting isomer afforded the title compound. MS (M+H) m/z 403. $^1$H NMR (DMSO-d6) δ 7.45 (d, J=8.79 Hz, 2H), 7.39 (t, J=7.87 Hz, 2H), 7.14 (t, J=7.32 Hz, 1H), 7.03 (t, J=8.79 Hz, 4H), 6.44 (bs, 2H), 4.31-4.38 (m, 1H), 3.48 (bs, 1H), 3.45 (d, J=3.66 Hz, 1H), 2.98-3.09 (m, 1H), 1.90 (bs, 2H), 1.76-1.88 (m, 2H), 1.68 (t, J=12.45 Hz, 1H).

Example 4

5-amino-1-[1-(cyanomethyl)piperidin-3-yl]-3-(4-phenoxyphenyl)-1H-pyrazole-4-carboxamide

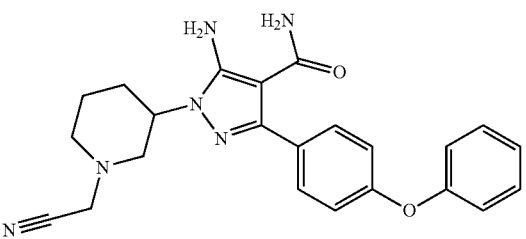 [SMILES: N#CCN1CCCC(n2nc(-c3ccc(Oc4ccccc4)cc3)c(C(N)=O)c2N)C1]

A mixture of 5-amino-3-(4-phenoxy-phenyl)-1-piperidin-3-yl-1H-pyrazole-4-carboxylic acid amide (100 mg, 0.27 mmol) (Example 1, Step 11), potassium carbonate (40 mg, 0.29 mmol), and bromoacetonitrile (38 mg, 0.32 mmol) in N,N-dimethylformamide was allowed to stir at 50° C. over 16 h. The suspension was cooled, diluted with water and extracted into ethyl acetate. The organic layers were combined and concentrated in vacuo. The crude product was purified by reverse phase preparative HPLC to afford the title compound. MS (M+H) m/z 417. $^1$H NMR (DMSO-d6) δ ppm 7.47 (d, J=8.79 Hz, 2H) 7.40 (t, J=8.1 Hz, 2H), 7.15 (t, J=7.3 Hz, 1H), 7.06 (t, J=8.8 Hz, 4H), 6.40 (bs, 2H), 4.23-4.33 (m, 1H), 3.77 (d, J=8.4 Hz, 2H), 2.86-2.95 (m, 1H), 2.78 (d, J=10.3 Hz, 1H), 2.55 (bs, 1H), 2.07-2.18 (m, 1H), 1.86 (bs, 1H), 1.79 (d, J=9.9 Hz, 1H), 1.59-1.71 (m, 2H).

Example 5

5-amino-1-(1-cyanopiperidin-4-yl)-3-(4-phenoxyphenyl)-1H-pyrazole-4-carboxamide

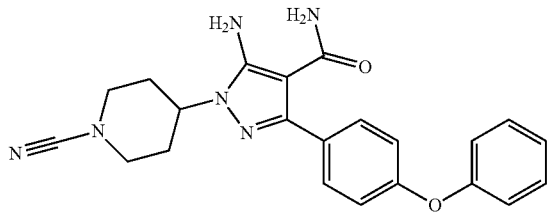 [SMILES: N#CN1CCC(n2nc(-c3ccc(Oc4ccccc4)cc3)c(C(N)=O)c2N)CC1]

Step 1: preparation of benzyl 4-oxopiperidine-1-carboxylate. To a solution of piperidin-4-one hydrochloride (150 g, 0.98 mol) in saturated aqueous sodium bicarbonate (3 L) was added a solution of benzyl chlorocarbonate (192 g, 1.13 mol) in dioxane (114 mL) drop wise. The reaction was allowed to stir 16 h at ambient temperature. The mixture was then extracted into ethyl acetate, and the combined organic layers were washed with brine, dried over sodium sulfate, and concentrated in vacuo to afford the title compound (236 g, >99%).

Step 2: preparation of benzyl 4-(2-(tert-butoxycarbonyl)hydrazono)piperidine-1-carboxylate. A solution of benzyl 4-oxopiperidine-1-carboxylate (236 g, 1.01 mol) and tert-butyl hydrazine carboxylate (133 g, 1.01 mol) in heptane (6.5 L) was heated to reflux for 1 h. The resulting precipitate was filtered affording the title compound (296 g, 0.84 mol).

Step 3: preparation of benzyl 4-(2-(tert-butoxycarbonyl)hydrazinyl)piperidine-1-carboxylate. A solution of benzyl 4-(2-(tert-butoxycarbonyl)hydrazono)piperidine-1-carboxylate (250 g, 0.72 mol) in tetrahydrofuran (1.7 L) was allowed to stir at ambient temperature for 30 min, then cooled to 4° C. Sodium cyanoborohydride (50 g, 0.79 mol) was then added portion wise, ensuring that the reaction temperature did not exceed 10° C. The reaction was stirred for an additional 10 min, after which a solution of para-toluene sulfonic acid (150 g, 0.79 mol) in tetrahydrofuran (700 mL) was added drop wise. The reaction was allowed to stir for an additional 3 h. Solvent was removed in vacuo, and the crude residue was extracted into ethyl acetate, washed with saturated aqueous sodium bicarbonate, 1N sodium hydroxide, brine, then dried over sodium sulfate and concentrated in vacuo to afford the title compound which was taken on to the next step without purification (224 g, 90%).

Step 4: preparation of benzyl 4-hydrazinylpiperidine-1-carboxylate hydrochloride. A solution of benzyl 4-(2-(tert-butoxycarbonyl)hydrazinyl)piperidine-1-carboxylate (174 g, 0.5 mol) in a 50% solution of methanol/4N hydrochloric acid in dioxane (2 L) was allowed to stir at ambient temperature for 48 h, after which it was concentrated in vacuo. The resulting crude white solid was triturated with warm dichloromethane, to afford the title compound (131 g, 96%).

Step 5: preparation of 5-amino-3-(4-phenoxyphenyl)-1-piperidin-4-yl-1H-pyrazole-4-carboxamide. Prepared according to the procedures described for 5-amino-3-(4-phenoxyphenyl)-1-piperidin-3-yl-1H-pyrazole-4-carboxylic acid amide (Example 1, steps 9-11), beginning from 2-[(4-phenoxy-phenyl)-methoxy-methylene]-malononitrile (Example 1, Step 3) and benzyl 4-hydrazinylpiperidine-1-carboxylate hydrochloride to afford the title compound.

Step 6: preparation of 5-amino-1-(1-cyanopiperidin-4-yl)-3-(4-phenoxyphenyl)-1H-pyrazole-4-carboxamide. Prepared according to the procedure for 5-amino-1-(1-cyanopiperidin-3-yl)-3-(4-phenoxyphenyl)-1H-pyrazole carboxamide (Example 1, Step 12) employing 5-amino-3-(4-phenoxyphenyl)-1-piperidin-4-yl-1H-pyrazole-4-carboxamide to afford the title compound (9 mg, 8%). MS (M+H) m/z 403. $^1$H NMR (DMSO-d6) δ 7.49 (d, J=8.8 Hz, 2H), 7.37-7.44 (m, 2H) 7.12-7.19 (m, 1H), 7.05 (d, J=8.79 Hz, 2H), 7.07 (d, J=7.7 Hz, 2H), 6.35 (s, 2H), 4.21-4.30 (m, 1H), 3.51 (d, J=12.8 Hz, 2H), 3.09-3.18 (m, 2H), 1.94-2.05 (m, 2H), 1.85 (d, J=10.6 Hz, 2H).

Example 6

5-amino-1-[1-(cyanomethyl)piperidin-3-yl]-3-(4-phenoxyphenyl)-1H-pyrazole-4-carboxamide

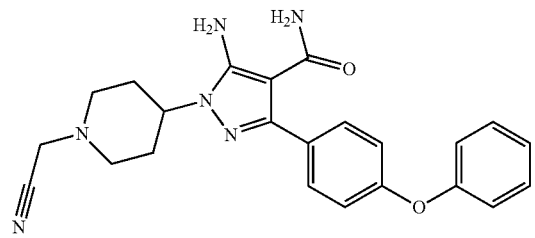 [SMILES: N#CCN1CCC(n2nc(-c3ccc(Oc4ccccc4)cc3)c(C(N)=O)c2N)CC1]

Prepared according to the procedure described for 5-amino-1-[1-(cyanomethyl)piperidin-3-yl]-3-(4-phenoxyphenyl)-1H-pyrazole-4-carboxamide (Example 4) from 5-amino-3-(4-phenoxyphenyl)-1-piperidin-4-yl-1H-pyrazole-4-carboxamide (Example 5, Step 5) to afford the title compound (13 mg, 12%). MS (M+H) m/z 417. $^1$H NMR (DMSO-d6) δ 7.47 (d, J=8.4 Hz, 2H), 7.40 (t, J=7.9 Hz, 2H), 7.16 (t, J=7.3 Hz, 1H), 7.07 (d, J=8.1 Hz, 2H), 7.04 (d, J=8.79 Hz, 2H) 6.36 (s, 2H), 4.08-4.18 (m, 1H), 3.76 (s, 2H), 2.88 (d, J=11.0 Hz, 2H), 2.29-2.39 (m, 2H), 1.98 (qd, J=12.0, 3.7 Hz, 2H), 1.83 (d, J=10.3 Hz, 2H).

Example 7

5-amino-1-(1-cyanopyrrolidin-3-yl)-3-(4-phenoxyphenyl)-1H-pyrazole-4-carboxamide

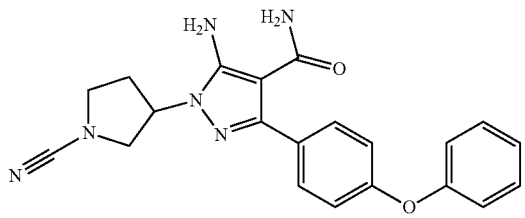 [SMILES: N#CN1CCC(n2nc(-c3ccc(Oc4ccccc4)cc3)c(C(N)=O)c2N)C1]

Step 1: preparation of benzyl (3S)-3-hydroxypyrrolidine-1-carboxylate. A solution of (3S)-pyrrolidin-3-ol (10.0 g, 0.12 mol) in dichloromethane (130 mL) was cooled to 5° C. Triethylamine (16.9 mL, 0.12 mol) was added, followed by drop wise addition of benzyl chloroformate (13.9 mL, 0.10 mol), ensuring that the temperature did not exceed 5° C. The reaction mixture was then allowed to stir at ambient temperature for 48 h, after which it was poured into aqueous saturated sodium bicarbonate and extracted into dichloromethane. The combined organic layers were washed with aqueous saturated sodium bicarbonate, dried over magnesium sulfate, and concentrated in vacuo. The resulting crude oil was purified by silica gel column chromatography (50% ether/hexanes followed by ether) to afford the title compound as a clear oil (14 g, 92%).

Step 2: preparation of benzyl 3-oxopyrrolidine-1-carboxylate. To a solution of benzyl (3S)-3-hydroxypyrrolidine-1-carboxylate (7.5 g, 33.9 mmol) in dichloromethane (1.2 L) was added 4-methylmorpholine N-oxide (5.96 g, 50.0 mmol), tetrapropylammonium perruthenate (0.60 g, 1.7 mmol), and 4 Å molecular sieves (7.0 g). The reaction mixture was allowed to stir under nitrogen for 2 h, after which it was filtered through a silica gel plug and eluted with diethyl ether. The filtrate can concentrated to afford the title compound as clear oil (6.5 g, 88%).

Step 3: preparation of benzyl 3-[2-(tert-butoxycarbonyl)hydrazino]pyrrolidine-1-carboxylate. To a solution of benzyl 3-oxopyrrolidine-1-carboxylate (3.0 g, 13.7 mmol) in tetrahydrofuran (30 mL) was added tert-butyl hydrazinecarboxylate (1.81 g, 13.7 mmol). The mixture was heated to reflux for 24 h, then cooled to 15° C., after which sodium cyanoborohydride (0.86 g, 13.7 mmol) was added, followed by drop wise addition of para-toluene sulfonic acid (2.6 g, 15.1 mmol) in tetrahydrofuran (15 mL). The reaction mixture was allowed to stir at ambient temperature for an additional 16 h, then concentrated in vacuo. The resulting residue was partitioned between saturated aqueous sodium bicarbonate and ethyl acetate. The organic layer was separated, then added to 30 mL of 1N aqueous sodium hydroxide and allowed to stir for 30 min. The aqueous layer was removed and the organic washed with water, dried over magnesium sulfate and concentrated in vacuo to afford the title compound as a clear oil (4.4 g, 97%).

Step 4: preparation of benzyl 3-hydrazinopyrrolidine-1-carboxylate. To a solution of benzyl 3-[2-(tert-butoxycarbonyl)hydrazino]pyrrolidine-1-carboxylate (2.0 g, 6.4 mmol) in tetrahydrofuran (25 mL) was added 4M hydrochloric acid in dioxane (6.0 mL). The solution was allowed to stir at 60° C. for 3 h. The solvent was removed in vacuo, and the resulting residue was partitioned between water and ethyl acetate. The organic layer was discarded and the aqueous layer then concentrated in vacuo to afford the title compound as a white foam (1.7 g, >99%).

Step 5: preparation of 5-amino-3-(4-phenoxyphenyl)-1-pyrrolidin-3-yl-1H-pyrazole-4-carboxamide. Prepared according to the procedures described for 5-amino-3-(4-phenoxyphenyl)-1-piperidin-3-yl-1H-pyrazole-4-carboxylic acid amide (Example 1, steps 9-11), beginning from 2-[(4-phenoxy-phenyl)-methoxy-methylene]-malononitrile (Example 1, Step 3) and benzyl 3-hydrazinopyrrolidine-1-carboxylate to afford the title compound.

Step 6: preparation of 5-amino-1-(1-cyanopyrrolidin-3-yl)-3-(4-phenoxyphenyl)-1H-pyrazole-4-carboxamide. Prepared according to the procedure for 5-amino-1-(1-cyanopiperidin-3-yl)-3-(4-phenoxyphenyl)-1H-pyrazole carboxamide (Example 1, Step 12) employing 5-amino-3-(4-phenoxyphenyl)-1-pyrrolidin-3-yl-1H-pyrazole-4-carboxamide to afford the title compound (9 mg, 8%). MS (M+H) m/z 389. $^1$H NMR (DMSO-d6) δ 7.51 (d, J=8.8 Hz, 2H), 7.41 (t, J=7.9 Hz, 2H), 7.16 (t, J=7.5 Hz, 1H), 7.06 (dd, J=10.8, 8.24 Hz, 4H), 6.42 (s, 2H), 4.88-4.98 (m, 1H), 3.74 (dd, J=10.3, 6.6 Hz, 1H), 3.43-3.67 (m, 3H), 2.14-2.33 (m, 2H).

Example 8

5-amino-1-[1-(cyanomethyl)pyrrolidin-3-yl]-3-(4-phenoxyphenyl)-1H-pyrazole-4-carboxamide

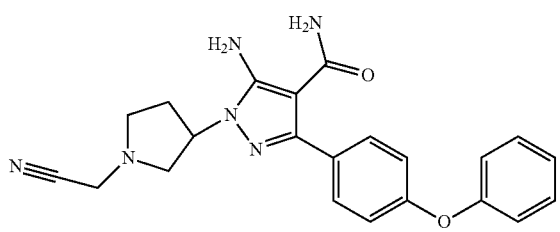 [SMILES: N#CCN1CCC(n2nc(-c3ccc(Oc4ccccc4)cc3)c(C(N)=O)c2N)C1]

Prepared according to the procedure described for 5-amino-1-[1-(cyanomethyl)piperidin-3-yl]-3-(4-phenoxyphenyl)-1H-pyrazole-4-carboxamide (Example 4) from 5-amino-3-(4-phenoxyphenyl)-1-piperidin-4-yl-1H-pyrazole-4-carboxamide (Example 7, Step 5) and bromoacetonitrile to afford the title compound. MS (M+H) m/z 402.7. $^1$H NMR (DMSO-d6) m/z 7.48 (d, J=8.4 Hz, 2H), 7.35-7.45 (m, 2H), 7.12-7.21 (m, 1H), 7.00-7.12 (m, 4H), 6.41 (s, 2H), 4.81-4.96 (m, 1H), 3.81-3.90 (m, 2H), 3.01 (t, J=8.4 Hz, 1H), 2.75-2.88 (m, 2H), 2.64-2.75 (m, 1H), 2.10-2.36 (m, 2H).

Example 9

5-amino-1-(1-cyanoazetidin-3-yl)-3-(4-phenoxyphenyl)-1H-pyrazole-4-carboxamide

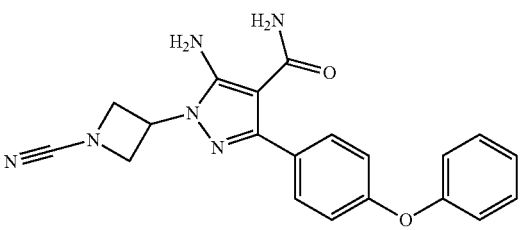 [SMILES: N#CN1CC(n2nc(-c3ccc(Oc4ccccc4)cc3)c(C(N)=O)c2N)C1]

Step 1: preparation of 1-(diphenylmethyl)azetidin-3-one. To a stirred solution of sulfur trioxide-pyridine complex (69 g, 432.95 mmol) in dimethylsulfoxide (172.6 mL) was added a solution of 1-(diphenylmethyl)azetidin-3-ol hydrochloric acid (20 g, 72.52 mmol) and triethylamine (50.5 mL, 362.6 mmol) in tetrahydrofuran (69 mL) drop wise over 10 minutes. The solution was allowed to stir for 2 h. The reaction mixture was then poured into water and extracted into 50% ethyl acetate/hexanes. The organic layers were combined and washed with brine, dried over sodium sulfate, and concentrated in vacuo to afford the title compound (11.4 g, 66%).

Step 2: preparation of tert-butyl 2-[1-(diphenylmethyl)azetidin-3-ylidene]hydrazinecarboxylate. A solution of 1-(diphenylmethyl)azetidin-3-one (11.4 g, 48.0 mmol) in methanol (110 mL) was cooled to 0° C. tert-Butyl hydrazinecarboxylate (6.3 g, 48.0 mmol) was added, followed by drop wise addition of acetic acid (5.56 mL). The reaction was allowed to stir over 16 h. The solvents were removed in vacuo, and the resulting residue was dissolved in dichloromethane and washed with 1N sodium hydroxide, then with brine. The organic layer was dried over sodium sulfate and concentrated in vacuo. The crude solid was purified by trituration with diethyl ether to afford the title compound as a white solid (15.8 g, 94%).

Step 3: preparation of tert-butyl 2-[1-(diphenylmethyl)azetidin-3-yl]hydrazinecarboxylate. A solution of tert-butyl 2-[1-(diphenylmethyl)azetidin-3-ylidene]hydrazinecarboxylate (15.8 g, 45.0 mmol) in acetic acid (120 mL) was cooled to 0° C. Sodium cyanoborohydride (2.82 g, 45.0 mmol) was then added portion wise, and the reaction was allowed to warm to ambient temperature for 4 h. The majority of solvent was removed in vacuo, and the resulting slurry was then neutralized to pH=7 with 1N sodium hydroxide. The desired compound was extracted into dichloromethane. The organic layer was washed with water and brine, dried over sodium sulfate, and concentrated in vacuo. The resulting residue was purified by trituration with diethyl ether to afford the title compound (15 g, 95%).

Step 4: preparation of 1-benzhydryl-3-hydrazinylazetidine. To a solution of tert-butyl 2-[1-(diphenylmethyl)azetidin-3-yl]hydrazinecarboxylate (19.3 g, 54.6 mmol) in dioxane (633 mL) at 0° C. was slowly added 4M hydrochloric acid in dioxane (290 mL). The reaction was allowed to stir at ambient temperature for 4 h. The solvent was removed in vacuo, and the resulting residue was purified via trituration with diethyl ether, affording the hydrochloride salt of the title compound as a white solid (16.5 g, >99%).

Step 5: preparation of 5-amino-1-(1-benzhydrylazetidin-3-yl)-3-(4-phenoxyphenyl)-1H-pyrazole-4-carbonitrile. Prepared according to the procedures described for benzyl 3-[5-amino-4-cyano-3-(4-phenoxy-phenyl)-pyrazol-1-yl]-piperidine-1-carboxylate (Example 1, step 9) employing 2-[(4-phenoxy-phenyl)-methoxy-methylene]-malononitrile (Example 1, Step 3) (1.0 g, 3.25 mmol) and 1-benzhydryl-3-hydrazinylazetidine (0.69 g, 6.82 mmol) at ambient temperature to afford the title compound as the hydrochloric acid salt (1.04 g, 64%). MS (M+H) m/z 498. $^1$H NMR (DMSO-d6) δ 7.88-7.78 (m, 2H), 7.50-7.38 (m, 5H), 7.34-7.24 (m, 4H), 7.24-7.15 (m, 4H), 7.15-7.03 (m, 4H), 6.82 (s, 2H), 4.97 (t, J=7.03 Hz, 1H), 4.57 (s, 1H), 3.63-3.52 (m. 2H), 3.39 (t, J=7.5 Hz, 2H).

Step 6: preparation of 5-amino-1-(azetidin-3-yl)-3-(4-phenoxyphenyl)-1H-pyrazole-4-carbonitrile. A solution of 5-amino-1-(1-benzhydrylazetidin-3-yl)-3-(4-phenoxyphenyl)-1H-pyrazole-4-carbonitrile (0.29 g, 0.58 mmol) and concentrated hydrochloric acid (0.5 mL) in methanol (30 mL) was run through a 20% palladium hydroxide cartridge in an H-cube apparatus at 50° C. twice. The solution was then concentrated in vacuo to afford the title compound (0.19 g, 98%).

Step 7: preparation of 5-amino-1-(azetidin-3-yl)-3-(4-phenoxyphenyl)-1H-pyrazole-4-carboxamide. Prepared from 5-amino-1-(azetidin-3-yl)-3-(4-phenoxyphenyl)-1H-pyrazole-4-carbonitrile (414 mg, 0.580 mmol) according to the procedure described for 5-amino-3-(4-phenoxyphenyl)-1-piperidin-3-yl-1H-pyrazole-4-carboxylic acid amide (Example 1, Step 11) to afford the title compound (120 mg, 20%). MS (M+H) m/z 350. $^1$H NMR (DMSO-d$_6$) δ 9.03-8.87 (m, 2H), 7.61-7.50 (m, 2H), 7.49-7.39 (m, 2H), 7.23-7.16 (m, 1H), 7.14-7.05 (m, 4H), 6.49 (s, 2H), 5.41-5.31 (m, 1H), 4.44-4.26 (m, 4H), 3.43-3.27 (m, 1H).

Step 8: preparation of 5-amino-1-(1-cyanoazetidin-3-yl)-3-(4-phenoxyphenyl)-1H-pyrazole-4-carboxamide. Prepared according to the procedure described for 5-amino-1-(1-cyanopiperidin-3-yl)-3-(4-phenoxyphenyl)-1H-pyrazole carboxamide (Example 1, Step 12) from 5-amino-1-(azetidin-3-yl)-3-(4-phenoxyphenyl)-1H-pyrazole-4-carboxamide to afford the title compound (32 mg, 67%). MS (M+H) m/z 375. $^1$H NMR (DMSO-d6) m/z 7.55 (d, J=8.79 Hz, 2H), 7.41 (t, J=7.9 Hz, 2H), 7.17 (t, J=7.5 Hz, 1H), 7.08 (dd, J=8.6, 2.0 Hz, 4H), 6.41 (s, 2H), 5.28 (quin, J=7.0 Hz, 1H), 4.50 (d, J=7.0 Hz, 5H).

Example 10

5-amino-1-(4-cyano-1,4-oxazepan-6-yl)-3-(4-phenoxyphenyl)-1H-pyrazole-4-carboxamide

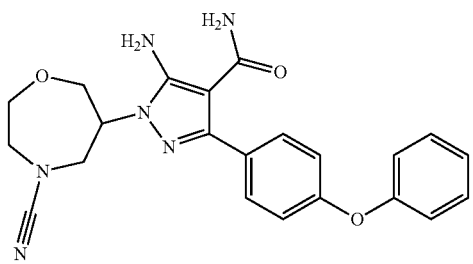 [SMILES: N#CN1CCOCC(n2nc(-c3ccc(Oc4ccccc4)cc3)c(C(N)=O)c2N)C1]

Step 1: preparation of tert-butyl 6-methylene-1,4-oxazepane-4-carboxylate. To a solution of 3-chloro-2-(chloromethyl)prop-1-ene (10.0 g, 80.0 mmol) in N,N-dimethylformamide (130 mL) at 0° C. was added sodium hydride (5.8 g, 174.0 mmol) in a single portion. The reaction was allowed to stir at 0° C. for 10 min, after which a solution of N-(tert-butoxycarbonyl)-2-aminoethanol (12.9 g, 80.0 mmol) in tetrahydrofuran (100 mL) was added slowly via cannula. The reaction was then allowed to warm to ambient temperature for an additional 2 h, after which solvent was removed in vacuo. The resulting residue was partitioned between water and a 2:1 ethyl acetate:hexanes mixture. After extraction the combined organic layers were washed with water, dried over magnesium sulfate and concentrated in vacuo. The resulting crude oil was purified by distillation (2 mm Hg, 85° C.) to afford the title compound as a clear oil (7.9 g, 46%).

Step 2: preparation of tert-butyl 6-oxo-1,4-oxazepane-4-carboxylate. To a solution of tert-butyl 6-methylene-1,4-oxazepane-4-carboxylate (4.0 g, 18.76 mmol) in dioxane (80 mL) was added a solution of sodium periodate (8.0 g, 37.4 mmol) in water (80 mL), followed by 1.2 mL of a 2.5% wt solution of osmium tetroxide in tert-butanol. The reaction was allowed to stir at ambient temperature for 48 h, after which water and brine were added, and the desired product was extracted into ethyl acetate. The combined organic layers were dried over magnesium sulfate and concentrated in vacuo. The resulting brown oil was passed through a silica gel plug to afford the title compound as a clear oil.

Step 3: preparation of tert-butyl 6-{2-[(benzyloxy)carbonyl]hydrazino}-1,4-oxazepane-4-carboxylate. To a solution of tert-butyl 6-oxo-1,4-oxazepane-4-carboxylate (2.0 g, 9.29 mmol) in tetrahydrofuran (30 mL) was added benzyl hydrazinecarboxylate (1.54 g, 9.29 mmol). The reaction was allowed to stir at ambient temperature over 24 h, then cooled to 0° C., after which sodium cyanoborohydride (584 mg, 9.29 mmol) was added, followed by drop wise addition of a solution of para-toluene sulfonic acid (1.77 g, 9.29 mmol) in tetrahydrofuran (30 mL). The reaction was then allowed to warm to ambient temperature for an additional 24 h, then concentrated in vacuo. The resulting residue was dissolved in ethyl acetate and washed with saturated aqueous sodium bicarbonate. To the organic layer was then added 1N sodium hydroxide (15 mL), and the mixture was allowed to stir for 3 h, after which the organic layer was washed with brine, dried over magnesium sulfate and concentrated in vacuo. The resulting residue was dissolved in diethyl ether and passed through a silica gel plug to afford the title compound as an oil (2.9 g, 89%).

Step 4: preparation of tert-butyl 6-hydrazino-1,4-oxazepane-4-carboxylate. To a solution of tert-butyl 6-{2-[(benzyloxy)carbonyl]hydrazino}-1,4-oxazepane-4-carboxylate (2.9 g, 8.3 mmol) in ethanol (30 mL) was added 10% Pd/C (500 mg, 50% wet). The mixture was placed under hydrogen (50 psi, Parr shaker) for 24 h, after which it was filtered through Celite and wash several times with ethanol. The filtrate was concentrated in vacuo to afford the title compound as an oil (1.8 g, 94%).

Step 5: preparation of tert-butyl 6-[5-amino-4-cyano-3-(4-phenoxyphenyl)-1H-pyrazol-1-yl]-1,4-oxazepane-4-carboxylate. Prepared according to the procedure described for benzyl 3-[5-amino-4-cyano-3-(4-phenoxy-phenyl)-pyrazol-1-yl]-piperidine-1-carboxylate (Example 1, Step 9) from 2-[(4-phenoxy-phenyl)-methoxy-methylene]-malononitrile (Example 1, Step 3) and tert-butyl 6-hydrazino-1,4-oxazepane-4-carboxylate to afford the title compound. MS (M+H) m/z 475.9.

Step 6: preparation of 5-amino-1-(1,4-oxazepan-6-yl)-3-(4-phenoxyphenyl)-1H-pyrazole-4-carbonitrile. A solution of tert-butyl 6-[5-amino-4-cyano-3-(4-phenoxyphenyl)-1H-pyrazol-1-yl]-1,4-oxazepane-4-carboxylate in equal parts dichloromethane, trifluoroacetic acid, and triethyl silane (30 mL) was allowed to stir at ambient temperature for 1 h. The mixture was partitioned between ethyl acetate and water, and the organic layer was separated, dried over magnesium sulfate, and concentrated in vacuo, to afford the title compound. MS (M+H) m/z 376.9.

Step 7: preparation of 5-amino-1-(1,4-oxazepan-6-yl)-3-(4-phenoxyphenyl)-1H-pyrazole-4-carboxamide. The title compound was prepared from 5-amino-1-(1,4-oxazepan-6-yl)-3-(4-phenoxyphenyl)-1H-pyrazole-4-carbonitrile according to the procedure described for 5-amino-3-(4-phenoxyphenyl)-1-piperidin-3-yl-1H-pyrazole-4-carboxylic acid amide (Example 1, Step 11).

Step 8: preparation of 5-amino-1-(4-cyano-1,4-oxazepan-6-yl)-3-(4-phenoxyphenyl)-1H-pyrazole-4-carboxamide. The title compound was prepared from 5-amino-1-(1,4-oxazepan-6-yl)-3-(4-phenoxyphenyl)-1H-pyrazole-4-carboxamide according to the procedures described for 5-amino-1-(1-cyanopiperidin-3-yl)-3-(4-phenoxyphenyl)-1H-pyrazole carboxamide (Example 1, Step 12). MS (M+H) m/z 419. $^1$H NMR (DMSO-d6) δ 7.47 (d, J=8.8 Hz, 2H), 7.40 (t, J=8.1 Hz, 2H), 7.15 (t, J=7.3 Hz, 1H), 7.06 (t, J=8.8 Hz, 4H), 6.40 (bs, 2H), 4.23-4.33 (m, 1H), 3.77 (d, J=8.4 Hz, 2H), 3.77 (d, J=8.4 Hz, 2H), 2.86-2.95 (m, 1H), 2.78 (d, J=10.3 Hz, 1H), 2.55 (bs, 1H), 2.07-2.18 (m, 1H), 1.86 (bs, 1H), 1.79 (d, J=9.9 Hz, 1H), 1.59-1.71 (m, 2H).

Example 11

5-amino-1-(2-cyano-2-azabicyclo[2.2.1]hept-5-yl)-3-(4-phenoxyphenyl)-1H-pyrazole-4-carboxamide

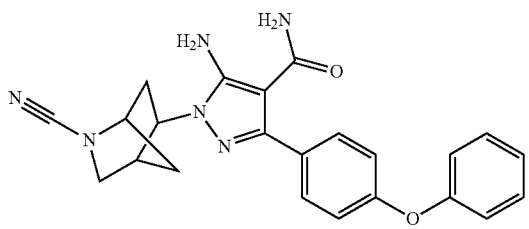 [SMILES: N#CN1CC2CC1CC2n1nc(-c2ccc(Oc3ccccc3)cc2)c(C(N)=O)c1N]

Step 1: preparation of benzyl 2-azabicyclo[2.2.1]hept-5-ene-2-carboxylate. A mixture of cyclopenta-1,3-diene (220 g, 3.33 mol), ammonium chloride (535 g, 10 mol) in water (2.5 L) and formaldehyde solution (405 mL, 5 mol, 37%) was stirred at room temperature for 36 h. The mixture was neutralized with solid $Na_2CO_3$ and cooled to 0° C. The mixture was added benzyl chloroformate (568 g, 3.33 mol) and saturated aqueous $Na_2CO_3$ (1 L) with mechanical stirring for 2 h at 0° C. Then the mixture was diluted with water (1 L) and extracted with dichloromethane (1 L×4). The combined organic layers were dried over $Na_2SO_4$, filtered and concentrated. The crude product was purified by column chromatography on silica gel (petroleum ether/EtOAc, 50:1 to 5:1) to afford the title compound (252 g, 33.0%) as a yellow oil.

Step 2: preparation of benzyl 5-hydroxy-2-azabicyclo[2.2.]heptane-2-carboxylate. To a solution of benzyl 2-azabicyclo[2.2.1]hept-5-ene-2-carboxylate (100 g, 0.44 mol) in anhydrous tetrahydrofuran (550 mL) was added a solution of borane methylsulfide (86.3 g, 108 mL, 1.135 mol) in tetrahydrofuran (1140 mL) dropwise at −70° C. After 15 min, the mixture was allowed to warm to room temperature and stirred for 3 h. The reaction mixture was quenched by sequential addition of water (250 mL), aqueous NaOH (250 mL, 6M, 1.54 mol) and then hydrogen peroxide (250 mL, 250 g, 30%, 2.2 mol) between 0-10° C. The mixture was stirred at room temperature for another 1 h and then concentrated. The residue was partitioned between ether (2 L) and water (1 L). The organic layer was dried over $Na_2SO_4$, filtered and concentrated. The crude product was purified by column chromatography on silica gel (petroleum ether/EtOAc, 4:1; 1/1) to afford the title compound (58 g, 26.6%) as a colorless oil. $^1$H NMR (400 MHz, CDCl$_3$) δ 7.30-7.39 (m, 5H), 5.12-5.22 (m, 2H), 4.05-4.35 (m, 2H), 3.29-3.32 (m, 1H), 2.93-3.02 (m, 1H), 2.51 (m, 1H), 1.86-1.99 (m, 2H), 1.48-1.63 (m, 2H).

Step 3: preparation of benzyl 5-oxo-2-azabicyclo[2.2.1]heptane-2-carboxylate. To a solution of benzyl 5-hydroxy-2-azabicyclo[2.2.1]heptane-2-carboxylate (29 g, 0.117 mol) in anhydrous dichloromethane (600 mL) was added Dess-Martin periodinane (75 g, 0.175 mol) in portions at 10° C. The mixture was stirred at room temperature for 3 h. Aqueous $Na_2CO_3$ (1M, 1100 mL) and aqueous $Na_2S_2O_3$ (1 M, 1100 mL) were added and the mixture was stirred at room temperature for 0.5 h. The mixture was separated and the water layer was extracted with dichloromethane (1000 mL). The combined organic layers were washed with brine (500 mL), dried over $Na_2SO_4$, filtered and concentrated to afford the title compound (48 g, 82%) as a yellow oil.

Step 4: preparation of benzyl 5-(2-(tert-butoxycarbonyl)hydrazinyl)-2-azabicyclo[2.2.1]heptane-2-carboxylate. To a solution of benzyl 5-oxo-2-azabicyclo[2.2.1]heptane-2-carboxylate (24 g, 0.098 mol) in tetrahydrofuran (380 mL×2) was added Boc hydrazine (13 g, 0.098 mol) at room temperature. The mixture was heated to reflux and stirred overnight. The reaction mixture was cooled to 15° C. and NaCNBH$_3$ (6.2 g, 0.098 mol) was added. A solution of p-toluenesulfonic acid (18.6 g, 0.098 mol) in tetrahydrofuran (180 mL) was added drop wise keeping the temperature bellow 20° C. The mixture was stirred at room temperature overnight. and then concentrated in vacuo. The residue was dissolved in EtOAc (800 mL) and the solution was washed with saturated aqueous sodium bicarbonate (800 mL). The organic layer was stirred with aqueous NaOH (1N, 300 mL) for 1 h. After that, the organic layer was separated and dried over sodium sulfate, filtered and concentrated. The crude product was purified by column chromatography on silica gel (petroleum ether/EtOAc, 1:1) to afford the title compound (38 g, 53.7%) as a white solid.

Step 5: preparation of benzyl 5-hydrazinyl-2-azabicyclo[2.2.1]heptane-2-carboxylate. To a solution of benzyl 5-(2-(tert-butoxycarbonyl)hydrazinyl)-2-azabicyclo[2.2.1]heptane-2-carboxylate (19 g, 0.053 mol) in methanol (200 mL) was added a solution of hydrochloric add in 1,4-dioxane (200 mL, 4 M, 0.8 mol) at −5° C. The mixture was stirred at room temperature for 4 hours and then concentrated. The residue was purified by reverse phase preparative HPLC to afford the title compound (12 g, 29%). $^1$H NMR (400 MHz, D$_2$O) δ 7.40-7.45 (m, 5H), 5.10-5.14 (m, 2H), 4.25-4.36 (m, 1H), 3.68-3.71 (m, 1H), 3.43-3.52 (m, 2H), 2.89 (m, 1H), 2.12-2.16 (m, 2H), 1.69-1.87 (m, 2H).

Step 6: preparation of benzyl 5-(5-amino-4-cyano-3-(4-phenoxyphenyl)-1H-pyrazol-1-yl)-2-azabicyclo[2.2.1]heptane-2-carboxylate. To a solution of benzyl 5-hydrazinyl-2-azabicyclo[2.2.1]heptane-2-carboxylate (6.5 g, 0.017 mol) and 2-[(4-phenoxy-phenyl)-methoxy-methylene]-malononitrile (Example 1, Step 3) (4.78 g, 0.017 mol) in ethanol (200 mL) was added triethylamine (5 mL, 0.035 mol) at −10° C. The mixture was stirred at room temperature for 2 h and then filtered to afford the title compound (7.0 g, 80.1%) as a white solid.

Step 7: preparation of 5-amino-1-(2-azabicyclo[2.2.1]heptan-5-yl)-3-(4-phenoxyphenyl)-1H-pyrazole-4-carboxamide. A mixture of benzyl 5-(5-amino-4-cyano-3-(4-phenoxyphenyl)-1H-pyrazol-1-yl)-2-azabicyclo[2.2.1]heptane-2-carboxylate (0.9 g, 1.78 mmol) and aqueous NaOH (2.5 N, 5 mL, 12.5 mmol) in ethanol (10 mL) was treated with microwave irradiation at 145° C. for 20 min. The mixture was poured into water (10 mL) and extracted with EtOAc (20 mL×3). The combined organic layers were dried over sodium sulfate, filtered and concentrated in vacuo to afford the title compound (0.69 g).

Step 8: preparation of 5-amino-1-(2-cyano-2-azabicyclo[2.2.]hept-5-yl)-3-(4-phenoxyphenyl)-1H-pyrazole-4-carboxamide. To a mixture of 5-amino-1-(2-azabicyclo[2.2.1]heptan-5-yl)-3-(4-phenoxyphenyl)-1H-pyrazole-4-carboxamide (1.2 g, 3.08 mmol) and cyanogen bromide (3.08 mmol) in N,N-dimethylformamide (20 mL) was added $Cs_2CO_3$ (2 g, 6.16 mmol) at room temperature and the mixture was stirred at room temperature overnight. The mixture was poured into water (20 mL) and then extracted with EtOAc (20 mL×3). The combined organic layers were dried over sodium sulfate, filtered and concentrated. The crude product was purified by preparative reverse phase HPLC to afford the title compound (252 mg) as a solid. MS (M+H) m/z 415. $^1$H NMR (400 MHz, DMSO-d6) δ 7.59-7.61 (m, 2H), 7.39-7.43 (m, 2H), 7.03-7.19 (m, 5H), 6.37 (s, 2H), 4.72-4.75 (m, 1H), 4.02 (m, 1H), 3.17-3.23 (m, 2H), 2.91 (m, 1H), 2.66-2.69 (m, 1H), 2.07-2.12 (m, 1H), 1.77-1.83 (m, 2H).

Example 12

5-amino-1-[2-(cyanomethyl)-2-azabicyclo[2.2.1]hept-5-yl]-3-(4-phenoxyphenyl)-1H-pyrazole-4-carboxamide

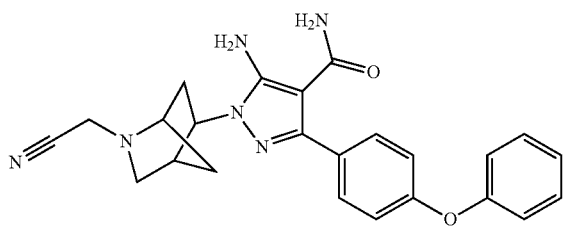 [SMILES: N#CCN1CC2CC1CC2n1nc(-c2ccc(Oc3ccccc3)cc2)c(C(N)=O)c1N]

The title compound was prepared according to the procedure described for 5-amino-1-[1-(cyanomethyl)piperidin-3-yl]-3-(4-phenoxyphenyl)-1H-pyrazole-4-carboxamide (Example 4) from 5-amino-1-(2-azabicyclo[2.2.1]heptan-5-yl)-3-(4-phenoxyphenyl)-1H-pyrazole-4-carboxamide (Example 11, Step 7) and bromoacetonitrile. MS (M+H) m/z 429. $^1$H NMR (400 MHz, DMSO-d6) δ 7.35-7.52 (m, 4H), 7.05-7.19 (m, 5H), 6.36 (s, 2H), 4.57-4.60 (m, 1H), 3.75-3.88 (m, 2H), 3.33 (m, 1H), 2.53-2.63 (m, 2H), 1.84-1.86 (m, 2H), 1.57-1.60 (m, 1H).

Example 13

5-amino-3-[4-(4-chlorophenoxy)phenyl]-1-(1-cyanopiperidin-3-yl)-1H-pyrazole-4-carboxamide

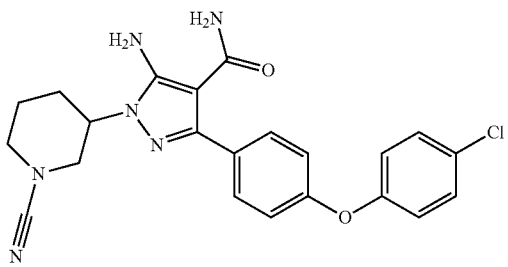

Step 1: preparation of methyl 4-(4-chlorophenoxy)benzoate. (4-Chlorophenyl)boronic acid (25.4 g, 162.82 mmol), 4 Å molecular sieves powder (16 g), 4-dimethylaminopyridine (39.5 g, 325.65 mmol) and anhydrous copper (II) acetate (39.0 g, 217.11 mmol) were added to a solution of methyl 4-hydroxybenzoate (16.5 g, 108.55 mmol) in dry dichloromethane (1000 mL) at room temperature, and the resulting mixture was stirred for 48 h. The reaction mixture was then filtered through a Celite pad. The filtrate was concentrated and the residue was purified by column chromatography on silica (8% EtOAc in petroleum ether) to afford the title compound (14 g, 48% yield) as off white solid. MS (M+H) m/z 263. $^1$H NMR (CDCl$_3$, 400 MHz) δ 8.02 (d, 2H), 7.35 (d, 2H), 7.02 (d, 2H), 6.97 (d, 2H), 3.88 (s, 3H).

Step 2: preparation of 4-(4-chlorophenoxy)benzoic acid. To a suspension of methyl 4-(4-chlorophenoxy)benzoate (14.0 g, 53.43 mmol) in methanol-water (5:1, 360 mL), NaOH (10.68 g, 267.11 mmol) was added at 0° C., the cooling batch was then removed and the reaction mixture was stirred at 60° C. for 3 h. Methanol was distilled off, water (500 mL) was added to the residue and washed with diethyl ether (3×100 mL). The aqueous layer was acidified with 2N HCl and then extracted with ethyl acetate (3×100 mL). The combined organic layer was dried over sodium sulfate, filtered and concentrated to afford the title compound (10.5 g, 79% yield) as off white solid. MS (M+H) m/z 247. $^1$H NMR (DMSO-do, 300 MHz) δ 12.83 (bs, 1H), 7.95 (d, 2H), 7.51 (d, 2H), 7.17 (d, 2H), 7.07 (d, 2H).

Step 3: preparation of 4-(4-chlorophenoxy)benzoyl chloride. 4-(4-chlorophenoxy)-benzoic acid (10.5 g, 42.33 mmol) in thionyl chloride (110 mL) was refluxed for 4 h. The volatiles were evaporated and the crude title compound was taken to the next step.

Step 4: preparation of 2-((4-(4-chlorophenoxy)phenyl)(methoxy)methylene)-malononitrile. A solution of malononitrile (3.54 g, 53.66 mmol) in tetrahydrofuran (25 mL) was added drop wise to a stirred suspension of sodium hydride (3.96 g, 60% in mineral oil, 158.4 mmol) in tetrahydrofuran (50 mL) at 0° C. under nitrogen atmosphere. After stirring for 30 min, 4-(4-chlorophenoxy)benzoyl chloride (11.0 g, 41.35 mmol) In tetrahydrofuran (35 mL) was added drop wise. Cooling bath was removed and the reaction mixture was stirred at room temperature for 3 h. The reaction mixture was heated to reflux and dimethyl sulfate (28 mL, 288.89 mmol) was added drop wise, and the resulting mixture was refluxed for 18 h. After cooling to room temperature, water (100 mL) was added and extracted with ethyl acetate (3×100 mL). The combined organic layer was dried over sodium acetate, concentrated and purified by flash chromatography on silica (5-8% EtOAc in petroleum ether) to afford the title compound (6.0 g, 47% yield) as pale yellow oil. $^1$H NMR (DMSO-d$_6$, 400 MHz) δ 7.73 (d, 2H), 7.52 (d, 2H), 7.2 (d, 2H), 7.18 (d, 2H), 3.92 (s, 3H).

Step 5: preparation of benzyl 3-(5-amino-3-(4-(4-chlorophenoxy)phenyl)-4-cyano-1H-pyrazol-1-yl)piperidine-1-carboxylate. Triethylamine (8.6 mL 19.35 mmol) was added to a stirred mixture of 2-((4-(4-chlorophenoxy)phenyl)(methoxy)methylene)malononitrile (6.0 g, 19.35 mmol) and 3-hydrazino-piperidine-1-carboxylic acid benzylester hydrochloride (Example 1, Step 8) (5.5 g, 57.89 mmol) in ethanol (6 0 mL) at room temperature. After stirring for 3 h the precipitated solid was filtered off. The solid was washed with ethanol and dried under vacuum to afford the title compound (7.2 g, 70% yield). MS (M+H) m/z 526. $^1$H NMR (DMSO-de, 400 MHz) δ 8.0 (d, 2H), 7.45 (d, 2H), 7.37 (m, 5H), 7.12 (d, 2H), 7.08 (d, 2H), 6.77 (s, 2H), 5.06 (bs, 2H), 4.23 (m, 1H), 4.0 (m, 2H), 2.97 (m, 2H), 1.87 (m, 3H), 1.50 (m, 1H).

Step 6: preparation of 5-amino-3-(4-(4-chlorophenoxy)phenyl)-1-(piperidin-3-yl)-1H-pyrazole-4-carboxamide. A cold 2.5M aq. NaOH solution (70 mL) was added to a solution of benzyl 3-(5-amino-3-(4-(4-chlorophenoxy)phenyl)-4-cyano-1H-pyrazol-1-yl)piperidine-1-carboxylate (7.2 g, 13.66 mmol) in ethanol (70 mL) in a 250 mL sealed tube and the resulting mixture was heated with stirring at 140° C. for 48 h. After cooling to room temperature water was added to the reaction mixture and extracted with ethyl acetate (3×100 mL). The combined organic layer was dried over sodium sulfate, filtered, concentrated to afford the title compound (2.6 g). $^1$H NMR (DMSO-de, 400 MHz) δ 8.21 (s, 1H), 7.49 (m, 4H), 7.45 (d, 2H), 7.10 (m, 4H), 6.36 (s, 2H), 4.20 (m, 1H), 3.11 (m, 1H), 2.97 (m, 2H), 2.50 (m, 1H), 1.93 (m, 2H), 1.76 (m, 1H), 1.60 (m, 1H).

Step 7: preparation of 5-amino-3-[4-(4-chlorophenoxy)phenyl]-1-(1-cyanopiperidin-3-yl)-1H-pyrazole-4-carboxamide. Potassium carbonate (1.33 g, 9.52 mmol) was added to a solution of 5-amino-3-(4-(4-chlorophenoxy)phenyl)-1-(piperidin-3-yl)-1H-pyrazole-4-carboxamide (2.6 g, 6.35 mmol) in N,N-dimethylformamide (20 mL), after stirring for 5 minutes cyanogen bromide (670 mg, 6.99 mmol) was added and the resulting mixture was stirred at 60° C. for 3 h. The reaction mixture was cooled to room temperature, water was added and extracted with ethyl acetate (3×100 mL). The combined organic layer was dried over sodium sulfate, filtered, concentrated. The crude compound was purified by flash column chromatography on silica gel (100-200 mesh) using 30-50% EtOAc in hexane to afford the title compound (6.2 g, 77%). MS (M+H) m/z 437. $^1$H NMR (DMSO-d$_6$, 400 MHz) δ 7.5 (d, 2H), 7.45 (d, 2H), 7.12 (d, 2H), 7.08 (d, 2H), 6.45 (s, 2H), 5.6 (br, 1H), 4.37 (m, 1H), 3.48 (dd, 1H), 3.35 (m, 2H), 3.07 (dt, 1H), 1.87 (m, 3H), 1.70 (m, 1H).

Example 14

5-amino-3-[4-(4-chlorophenoxy)phenyl]-1-[(3S)-1-cyanopiperidin-3-yl]-1H-pyrazole-4-carboxamide

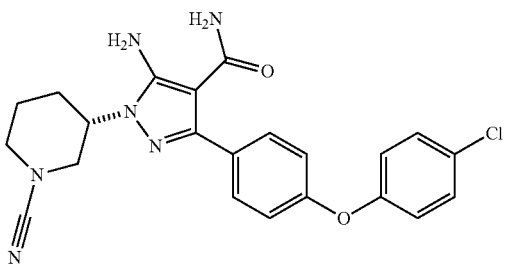 [SMILES: N#CN1CCCC(n2nc(-c3ccc(Oc4ccc(Cl)cc4)cc3)c(C(N)=O)c2N)C1]

rac-5-amino-3-(4-(4-chlorophenoxy)phenyl)-1-(1-cyanopiperidin-3-yl)-1H-pyrazole-4-carboxamide (prepared as described in Example 13) was chirally separated by preparative HPLC (ChiralPak IA, 4.6×250 mm, 5 μm column, hexane/ethanol, 50/50, 0.8 mL/min flow rate). Isolation of the first eluting isomer afforded the title compound. MS (M+H) m/z 436.8. $^1$H NMR (DMSO-d6, 300 MHz) δ 7.5 (d, 2H), 7.45 (d, 2H), 7.12 (d, 2H), 7.08 (d, 2H), 6.45 (s, 2H), 5.6 (br, 1H), 4.37 (m, 1H), 3.48 (dd, 1H), 3.35 (m, 2H), 3.07 (dt, 1H), 1.87 (m, 3H), 1.70 (m, 1H). SOR+57.6 (c, 0.5% in MeOH)

Example 15

5-amino-3-[4-(4-chlorophenoxy)phenyl]-1-[(3R)-1-cyanopiperidin-3-yl]-1H-pyrazole-4-carboxamide

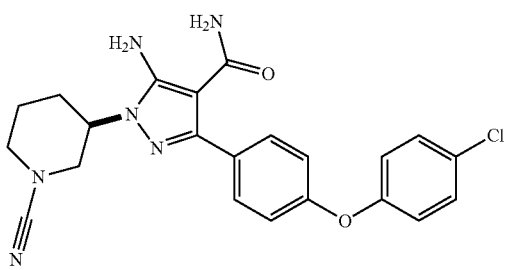

rac-5-amino-3-(4-(4-chlorophenoxy)phenyl)-1-(1-cyanopiperidin-3-yl)-1H-pyrazole-4-carboxamide (prepared as described in Example 13) was chirally separated by preparative HPLC (ChiralPak IA, 4.6×250 mm, 5 μm column, hexane/ethanol, 50/50, 0.8 mL/min flow rate). Isolation of the second eluting isomer afforded the title compound. MS (M+H) m/z 436.8. $^1$H NMR (DMSO-d6, 300 MHz) δ 7.5 (d, 2H), 7.45 (d, 2H), 7.12 (d, 2H), 7.08 (d, 2H), 6.45 (s, 2H), 5.6 (br, 1H), 4.37 (m, 1H), 3.48 (dd, 1H), 3.35 (m, 2H), 3.07 (dt, 1H), 1.87 (m, 3H), 1.70 (m, 1H). SOR −56.8 (c, 0.5% in MeOH).

Example 16

5-amino-1-(1-cyanopiperidin-3-yl)-3-[4-(3,4-dimethylphenoxy)phenyl]-1H-pyrazole-4-carboxamide

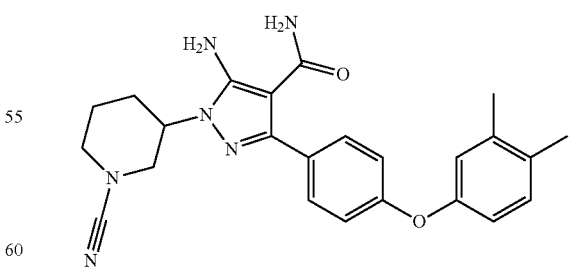

Prepared analogous to 5-amino-3-[4-(4-chlorophenoxy)phenyl]-1-(1-cyanopiperidin-3-yl)-1H-pyrazole-4-carboxamide (Example 15) employing (3,4-dimethylphenyl)boronic acid to afford the title compound. MS (M+H) m/z 431. $^1$H NMR (DMSO-d6, 300 MHz) δ 7.45 (d, 2H), 7.17 (d, 1H), 6.98 (d, 2H), 6.90 (s, 1H), 6.80 (d, 1H), 6.42 (s, 2H), 4.37 (m, 1H), 3.44 (m, 1H), 3.35 (m, 2H), 3.07 (t, 1H), 2.20 (s, 6H), 1.7-1.97 (m, 4H).

Example 17

(R)-5-amino-1-(1-cyanopiperidin-3-yl)-3-[4-(3,4-dimethylphenoxy)phenyl]-1H-pyrazole-4-carboxamide

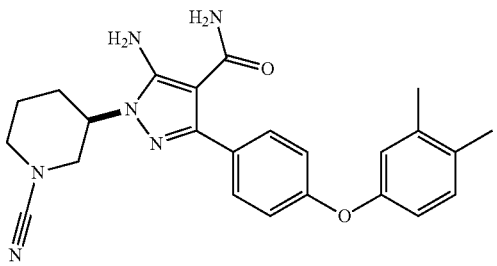

rac-5-amino-1-(1-cyanopiperidin-3-yl)-3-[4-(3,4-dimethylphenoxy)phenyl]-1H-pyrazole-4-carboxamide (prepared as described in Example 16) was chirally separated by preparative HPLC (ChiralPak IA, 4.6×250 mm, 5 μm column, hexane/ethanol, 70/30, 1.0 mL/min flow rate). Isolation of the first eluting isomer afforded the title compound. MS (M+H) m/z 431. $^1$H NMR (DMSO-d6, 400 MHz) δ 7.45 (d, 2H), 7.17 (d, 1H), 6.98 (d, 2H), 6.90 (s, 1H), 6.80 (d, 1H), 6.42 (s, 2H), 4.37 (m, 1H), 3.44 (m, 1H), 3.35 (m, 2H), 3.07 (t, 1H), 2.20 (s, 6H), 1.7-1.97 (m, 4H).

Example 18

(S)-5-amino-1-(1-cyanopiperidin-3-yl)-3-[4-(3,4-dimethylphenoxy)phenyl]-1H-pyrazole-4-carboxamide

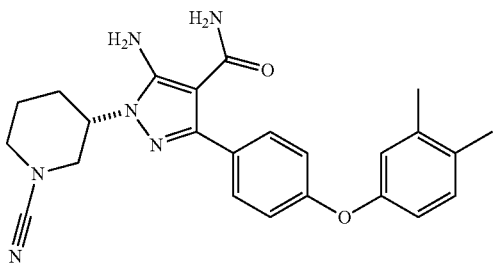 [SMILES: Cc1ccc(Oc2ccc(-c3nn(C4CCCN(C#N)C4)c(N)c3C(N)=O)cc2)cc1C]

rac-5-amino-1-(1-cyanopiperidin-3-yl)-3-[4-(3,4-dimethylphenoxy)phenyl]-1H-pyrazole-4-carboxamide (prepared as described in Example 16) was chirally separated by preparative HPLC (ChiralPak IA, 4.6×250 mm, 5 μm column, hexane/ethanol, 70/30, 1.0 mL/min flow rate). Isolation of the second eluting isomer afforded the title compound. MS (M+H) m/z 431. $^1$H NMR (DMSO-d6, 400 MHz) δ 7.45 (d, 2H), 7.17 (d, 1H), 6.98 (d, 2H), 6.90 (s, 1H), 6.80 (d, 1H), 6.42 (s, 2H), 4.37 (m, 1H), 3.44 (m, 1H), 3.35 (m, 2H), 3.07 (t, 1H), 2.20 (s, 6H), 1.7-1.97 (m, 4H).

Example 19

5-amino-1-(1-cyanopiperidin-3-yl)-3-[4-(4-ethylphenoxy)phenyl]-1H-pyrazole-4-carboxamide

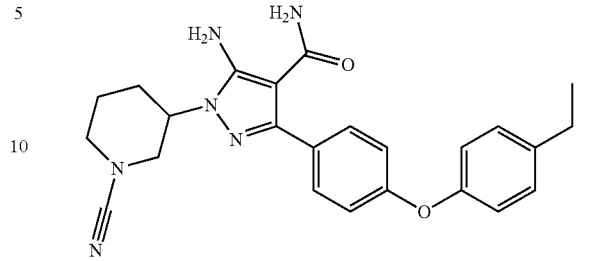

Prepared analogous to 5-amino-3-[4-(4-chlorophenoxy)phenyl]-1-(1-cyanopiperidin-3-yl)-1H-pyrazole-4-carboxamide (Example 15) employing (4-ethylphenyl)boronic acid to afford the title compound. MS (M+H) m/z 431. $^1$H NMR (DMSO-d6, 300 MHz) δ 7.46 (d, 2H), 7.21 (d, 2H), 7.0 (m, 4H), 6.35 (s, 2H), 5.06 (bs, 2H), 4.16 (m, 1H), 3.12 (m, 1H), 2.90 (m, 2H), 2.30 (s, 3H), 1.87 (m, 2H), 1.73 (m, 1H), 1.45 (m, 1H.)

Example 20

5-amino-3-[4-(4-chloro-2-methylphenoxy)phenyl]-1-(1-cyanopiperidin-3-yl)-1H-pyrazole-4-carboxamide

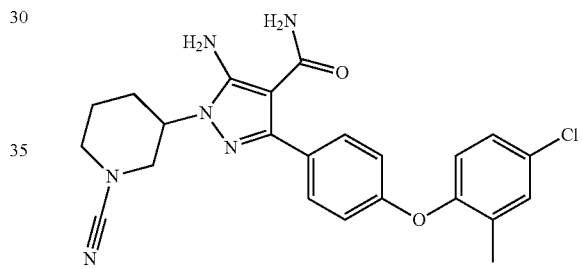

Prepared analogous to 5-amino-3-[4-(4-chlorophenoxy)phenyl]-1-(1-cyanopiperidin-3-yl)-1H-pyrazole-4-carboxamide (Example 15) employing (4-methylphenyl)boronic acid to afford the title compound. MS (M+H) m/z 451. $^1$H NMR (DMSO-d6, 300 MHz) δ 7.43 (m, 3H), 7.27 (dd, 1H), 6.90 (m, 3H), 6.43 (s, 2H), 4.35 (m, 1H), 3.50 (dd, 1H), 3.35 (m, 2H), 3.05 (dt, 1H), 2.18 (s, 3H), 1.65-1.95 (m, 4H).

Example 21

(S)-5-amino-3-[4-(4-chloro-2-methylphenoxy)phenyl]-1-(1-cyanopiperidin-3-yl)-1H-pyrazole-4-carboxamide

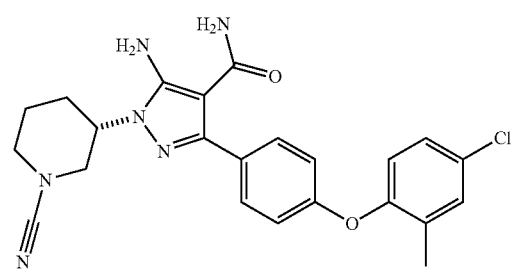

rac-5-amino-3-[4-(4-chloro-2-methylphenoxy)phenyl]-1-(1-cyanopiperidin-3-yl)-1H-pyrazole-4-carboxamide (prepared as described in Example 20) was chirally separated by preparative HPLC (ChiralPak IA, 4.6×250 mm, 5 μm column, hexane/ethanol, 30/70, 0.8 mL/min flow rate). Isolation of the first eluting isomer afforded the title compound. MS (M+H) m/z 451. $^1$H NMR (DMSO-d6, 300 MHz) δ 7.45 (m, 3H), 7.27 (dd, 1H), 7.0 (m, 3H), 6.43 (s, 2H), 5.5-6.3 (br, 2H), 4.35 (m, 1H), 3.50 (dd, 1H), 3.35 (m, 2H), 3.05 (dt, 1H), 2.18 (s, 3H), 1.65-1.95 (m, 4H). SOR+61.2 (c, 0.5% in chloroform)

Example 22

(R)-5-amino-3-[4-(4-chloro-2-methylphenoxy)phenyl]-1-(1-cyanopiperidin-3-yl)-1H-pyrazole-4-carboxamide

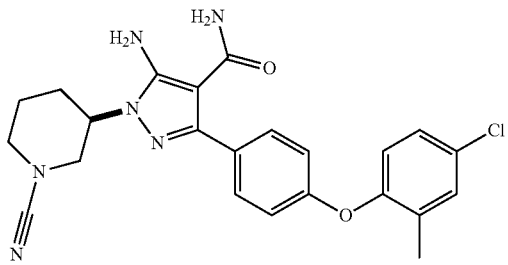

rac-5-amino-3-[4-(4-chloro-2-methylphenoxy)phenyl]-1-(1-cyanopiperidin-3-yl)-1H-pyrazole-4-carboxamide (prepared as described in Example 20) was chirally separated by preparative HPLC (ChiralPak IA, 4.6×250 mm, 5 μm column, hexane/ethanol, 30/70, 0.8 mL/min flow rate). Isolation of the second eluting isomer afforded the title compound. MS (M+H) m/z 451. $^1$H NMR (DMSO-d6, 300 MHz) δ 7.45 (m, 3H), 7.27 (dd, 1H), 7.0 (m, 3H), 6.45 (s, 2H), 5.5-6.3 (br, 2H), 4.35 (m, 1H), 3.50 (dd, 1H), 3.35 (m, 2H), 3.05 (dt, 1H), 2.18 (s, 3H), 1.65-1.95 (m, 4H). SOR −59.2 (c, 0.5% in chloroform)

Example 23

5-amino-1-(1-cyanopiperidin-3-yl)-3-[4-(2,4-dimethylphenoxy)phenyl]-1H-pyrazole-4-carboxamide

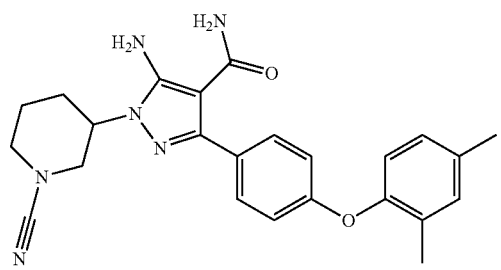 [SMILES: Cc1ccc(Oc2ccc(-c3nn(C4CCCN(C#N)C4)c(N)c3C(N)=O)cc2)c(C)c1]

Prepared analogous to 5-amino-3-[4-(4-chlorophenoxy)phenyl]-1-(1-cyanopiperidin-3-yl)-1H-pyrazole-4-carboxamide (Example 15) employing (2,4-dimethylphenyl)boronic acid to afford the title compound. MS (M+H) m/z 431. $^1$H NMR (400 MHz, methanol-d4) δ 7.44 (d, J=8.4 Hz, 2H), 7.12 (s, 1H), 7.04 (d, J=8.0 Hz, 1H), 6.93 (d, J=8.4 Hz, 2H), 6.85 (d, J=8.0 Hz, 1H), 4.36 (m, 1H), 3.55 (m, 1H), 3.44 (m, 2H), 3.11 (m, 1H), 2.32 (s, 3H), 2.14 (s, 3H), 2.03 (m, 2H), 1.90 (m, 2H).

Example 24

5-amino-1-(1-cyanopiperidin-3-yl)-3-[4-(4-isopropylphenoxy)phenyl]-1H-pyrazole-4-carboxamide

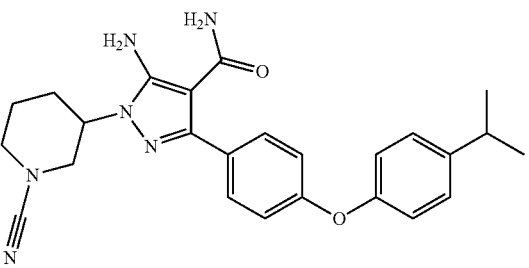 [SMILES: CC(C)c1ccc(Oc2ccc(-c3nn(C4CCCN(C#N)C4)c(N)c3C(N)=O)cc2)cc1]

Prepared analogous to 5-amino-3-[4-(4-chlorophenoxy)phenyl]-1-(1-cyanopiperidin-3-yl)-1H-pyrazole-4-carboxamide (Example 15) employing (4-isopropylphenyl)boronic acid to afford the title compound. MS (M+H) m/z 445. $^1$H NMR (400 MHz, methanol-d4) δ 7.46 (d, J=8.4 Hz, 2H), 7.27 (d, J=8.4 Hz, 2H), 7.05 (d, J=8.4 Hz, 2H), 6.98 (d, J=8.4 Hz, 2H), 4.37 (m, 1H), 3.56 (m, 1H), 3.45 (m, 2H), 3.11 (m, 1H), 2.92 (m, 1H), 2.06 (m, 2H), 1.91 (m, 2H), 1.27 (d, 6H).

Example 25

5-amino-1-(1-cyanopiperidin-3-yl)-3-[4-(2,4-difluorophenoxy)phenyl]-1H-pyrazole-4-carboxamide

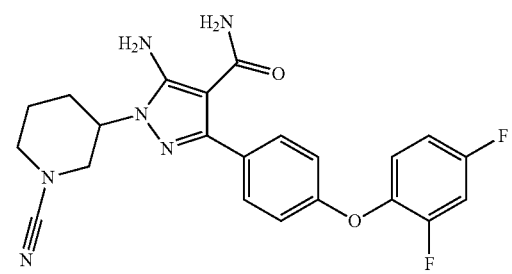 [SMILES: N#CN1CCCC(n2nc(-c3ccc(Oc4ccc(F)cc4F)cc3)c(C(N)=O)c2N)C1]

Step 1: preparation of methyl 4-(2,4-difluorophenoxy)benzoate. 4 Å molecular sieves powder (17 g), (4-(methoxycarbonyl)phenyl)boronic acid (17.34 g, 133.33 mmol), DMAP (27.13 g, 222.22 mmol) and anhydrous copper (II) acetate (30.3 g, 166.7 mmol) were added to a solution of 2,4-difluorophenol (20.0 g, 111.11 mmol) in dry dichloromethane (800 mL) at room temperature, and the resulting mixture was stirred for 48 h. The reaction mixture was then filtered through celite pad, the filtrate was concentrated and purified by column chromatography on silica (100-200 mesh), eluting with 8% EtOAc in petroleum ether to give compd-2×10 (15 g, 51.2%) as solid. MS (M+H) m/z 265. $^1$H NMR (DMSO-d6, 300 MHz) δ 7.97 (d, 2H), 7.56 (m, 1H), 7.45 (m, 1H), 7.20 (t, 1H), 7.05 (d, 2H), 3.83 (s, 3H).

Step 2: preparation of 4-(2,4-difluorophenoxy)benzoic acid. To a suspension of methyl 4-(2,4-difluorophenoxy)benzoate (15.0 g, 56.82 mmol) in methanol (525 mL) were added water (63 mL) and NaOH pellets (12.22 g, 284.11 mmol) at 0° C., the cooling batch was then removed and the reaction mixture was stirred at 50° C. for 3 h. Methanol was distilled off and water was added. The residue was acidified with 1N HCl and then extracted with EtOAc. The combined organic layer was dried over sodium sulfate, filtered and concentrated to afford the title compound (12.0 g, 91.5%) as white solid. MS (M+H) m/z 249. $^1$H NMR (DMSO-d6, 300 MHz) δ 12.85 (bs, 1H), 7.92 (d, 2H), 7.52 (m, 1H), 7.40 (m, 1H), 7.20 (t, 1H), 7.00 (d, 2H).

Step 3: preparation of 4-(2,4-difluorophenoxy)benzoyl chloride. 4-(2,4-difluorophenoxy)benzoic acid (3.0 g, 30 mmol) in thionyl chloride (80 mL) was refluxed overnight. The volatiles were evaporated to afford the title compound.

Step 4: preparation of 2-((4-(2,4-difluorophenoxy)phenyl)methoxy)methylene)-malononitrile. A solution of malononitrile (1.0 g, 15.52 mmol) in tetrahydrofuran (10 mL) was added drop wise to a stirred suspension of NaH (574 mg, 23.9 mmol) in tetrahydrofuran (50 mL) at 0° C. In $N_2$ atmosphere. After stirring for 30 min, 4-(2,4-difluorophenoxy)benzoyl chloride (3.2 g, 11.94 mmol) in tetrahydrofuran (15 mL) was added dropwise. The reaction mixture was brought to room temperature and stirred (~3 h). The reaction mixture was then heated to reflux and dimethyl sulfate (7.7 mL, 83.6 mmol) was added drop wise. The mixture was refluxed for 18 h. After cooling to room temperature, the mixture was quenched with ice water (100 mL) and extracted with EtOAc (2×). The combined organic layers were dried over sodium sulfate, concentrated and purified by flash chromatography on silica gel (100-200 mesh) eluting with 12% EtOAc in petroleum ether to afford the title compound (1.8 g) as liquid. MS (M+H) m/z 297. $^1$H NMR (DMSO-d6, 400 MHz) δ 7.71 (d, 2H), 7.52 (m, 1H), 7.43 (m, 1H), 7.20 (t, 1H), 7.16 (d, 2H), 3.93 (s, 3H).

Step 5: preparation of benzyl 3-(5-amino-4-cyano-3-(4-(2,4-difluorophenoxy)phenyl)-1H-pyrazol-1-yl)piperidine-1-carboxylate. Triethylamine (2.2 mL 14.4 mmol) was added to a stirred mixture of 2-((4-(2,4-difluorophenoxy)phenyl)(methoxy)methylene)malononitrile (1.5 g, 4.8 mmol) and 3-hydrazino-piperidine-1-carboxylic acid benzylester hydrochloride (Example 1, Step 8) (1.4 g, 4.8 mmol) in ethanol (30 mL) at room temperature. After stirring for 3 h the precipitate was filtered. The resulting solid was washed with ethanol and dried under vacuum to afford the title compound (1.8 g, 40%). MS (M+H) m/z 530. $^1$H NMR (DMSO-d6, 300 MHz) δ 7.78 (d, 2H), 7.50 (m, 1H), 7.33 (m, 6H), 7.18 (m, 1H), 7.05 (d, 2H), 6.78 (s, 2H), 5.06 (bs, 2H), 4.26 (m, 1H), 3.99 (m, 2H), 3.30 (m, 1H), 2.97 (t, 1H), 2.21 (s, 3H), 1.90 (m, 3H), 1.48 (m, 1H).

Step 6: preparation of 5-amino-3-(4-(2,4-difluorophenoxy)phenyl)-1-(piperidin-3-yl)-1H-pyrazole-4-carboxamide. A cold 2.5M aq. NaOH solution (20 mL) was added to a mixture of benzyl 3-(5-amino-4-cyano-3-(4-(2,4-difluorophenoxy)phenyl)-1H-pyrazol-1-yl)piperidine-1-carboxylate (1.8 g, 3.39 mmol) in ethanol (20 mL) charged to a 100 mL sealed tube. The mixture was heated with stirring at 140° C. for 24 h. After cooling to room temperature, the reaction mixture was diluted with water and extracted with EtOAc (2×). The combined organic layers were dried over $Na_2SO_4$, filtered, and concentrated to afford the title compound (1.4 g). MS (M+H) m/z 414. $^1$H NMR (DMSO-d6, 300 MHz) δ 7.45 (d, 2H), 7.32 (m, 1H), 7.23 (m, 1H), 7.18 (m, 1H), 7.01 (d, 2H), 6.30 (s, 2H), 5.17 (t, 1H), 4.07 (m, 1H), 3.0 (d, 1H), 2.7-2.90 (m, 3H), 1.90 (m, 2H), 1.70 (m, 1H), 1.48 (m, 1H).

Step 7: preparation of 5-amino-1-(1-cyanopiperidin-3-yl)-3-[4-(2,4-difluorophenoxy)phenyl]-1H-pyrazole-4-carboxamide. Potassium carbonate (450 mg, 3.3 mmol) was added to a solution of 5-amino-3-(4-(2,4-difluorophenoxy)phenyl)-1-(piperidin-3-yl)-1H-pyrazole-4-carboxamide (0.9 g, 2.2 mmol) in N,N-dimethylformamide (10 mL). After stirring for 5 min, cyanogen bromide (260 mg, 2.42 mmol) was added and the resulting mixture was stirred at 60° C. for 2 h. The reaction mixture was cooled to room temperature and water was added. The resulting precipitate was filtered. The crude product was purified by flash column chromatography on silica gel (100-200 mesh) with 50% EtOAc/hexane as eluent to afford the title compound (1.3 g). MS (M+H) m/z 439. $^1$H NMR (DMSO-d6, 400 MHz) 7.52 (m, 1H), 7.48 (d, 2H), 7.35 (m, 1H), 7.18 (t, 1H), 7.01 (d, 2H), 6.43 (s, 2H), 4.35 (m, 1H), 3.50 (d, 1H), 3.35 (m, 2H), 3.03 (t, 1H), 1.92 (m, 1H), 1.80 (m, 2H), 1.48 (m, 1H).

Example 26

5-amino-1-[(3S)-1-cyanopiperidin-3-yl]-3-[4-(2,4-difluorophenoxy)phenyl]-1H-pyrazole-4-carboxamide

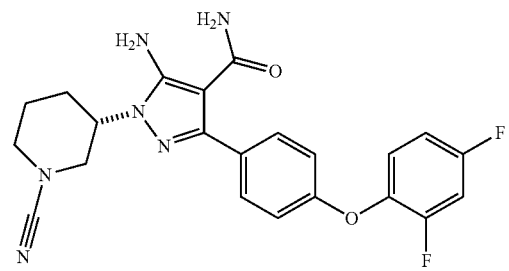

rac-5-amino-1-(1-cyanopiperidin-3-yl)-3-[4-(2,4-difluorophenoxy)phenyl]-1H-pyrazole-4-carboxamide (prepared as described in Example 25) was chirally separated by preparative HPLC (ChiralPak IA, 4.6×250 mm, 5 μm column, hexane/ethanol, 30/70, 0.8 mL/min flow rate). Isolation of the first eluting isomer afforded the title compound. $^1$H NMR (DMSO-d6, 300 MHz) δ 7.52 (m, 1H), 7.48 (d, 2H), 7.35 (m, 1H), 7.18 (t, 1H), 7.01 (d, 2H), 6.43 (s, 2H), 5.2-6.2 (br, 2H), 4.35 (m, 1H), 3.50 (d, 1H), 3.35 (m, 2H), 3.03 (t, 1H), 1.92 (m, 1H), 1.80 (m, 2H), 1.48 (m, 1H). MS (M+H) m/z 439. SOP: +56.8° (C=0.5% in MeOH).

Example 27

5-amino-1-[(3R)-1-cyanopiperidin-3-yl]-3-[4-(2,4-difluorophenoxy)phenyl]-1H-pyrazole-4-carboxamide

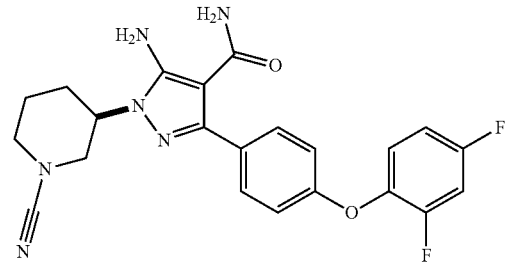

rac-5-amino-1-(1-cyanopiperidin-3-yl)-3-[4-(2,4-difluorophenoxy)phenyl]-1H-pyrazole-4-carboxamide (prepared as described in Example 25) was chirally separated by preparative HPLC (ChiralPak IA, 4.6×250 mm, 5 μm column, hexane/ethanol, 30/70, 0.8 mL/min flow rate). Isolation of the second eluting isomer afforded the title compound. MS (M+H) m/z 439. $^1$H NMR (DMSO-d6, 300 MHz) δ 7.52 (m, 1H), 7.48 (d, 2H), 7.35 (m, 1H), 7.18 (t, 1H), 7.01 (d, 2H), 6.43 (s, 2H), 4.35 (m, 1H), 3.50 (d, 1H), 3.35 (m, 2H), 3.03 (t, 1H), 1.92 (m, 1H), 1.80 (m, 2H), 1.48 (m, 1H). SOP: −52.4° (C=0.5% In MeOH).

Example 28

5-amino-1-(1-cyanopiperidin-3-yl)-3-[4-(3-fluoro-4-methylphenoxy)phenyl]-1H-pyrazole-4-carboxamide

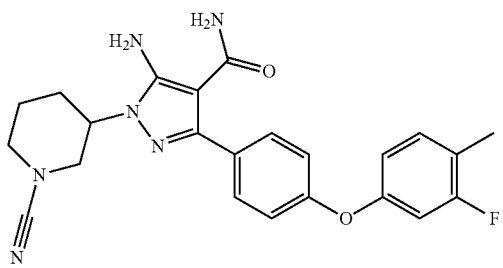 [SMILES: Cc1ccc(Oc2ccc(-c3nn(C4CCCN(C#N)C4)c(N)c3C(N)=O)cc2)cc1F]

Prepared analogous to 5-amino-1-(1-cyanopiperidin-3-yl)-3-[4-(2,4-difluorophenoxy)phenyl]-1H-pyrazole-4-carboxamide (Example 25) employing 3-fluoro-4-methylphenol to afford the title compound. MS (M+H) m/z 435. $^1$H NMR (DMSO-d6, 400 MHz) δ 7.50 (d, 2H), 7.28 (t, 1H), 7.17 (d, 2H), 6.90 (dd, 1H), 6.82 (dd, 1H), 6.43 (s, 2H), 4.35 (m, 1H), 3.50 (dd, 1H), 3.35 (m, 2H), 3.05 (dt, 1H), 2.22 (s, 3H), 1.65-1.95 (m, 4H).

Example 29

(S)-5-amino-1-(1-cyanopiperidin-3-yl)-3-[4-(3-fluoro-1-methylphenoxy)phenyl]-1H-pyrazole-4-carboxamide

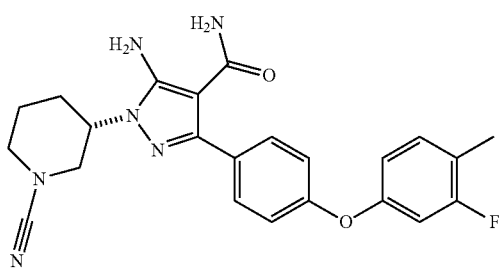

rac-5-amino-1-(1-cyanopiperidin-3-yl)-3-[4-(3-fluoro-4-methylphenoxy)phenyl]-1H-pyrazole-4-carboxamide (prepared as described in Example 28) was chirally separated by preparative HPLC (ChiralPak IB, 4.6×250 mm, 5 μm column, hexane/ethanol, 50/50, 1.0 mL/min flow rate). Isolation of the first eluting isomer afforded the title compound. $^1$H NMR (DMSO-d6, 400 MHz) δ 7.50 (d, 2H), 7.28 (t, 1H), 7.08 (d, 2H), 6.90 (dd, 1H), 6.82 (dd, 1H), 6.43 (s, 2H), 4.35 (m, 1H), 3.50 (dd, 1H), 3.35 (m, 2H), 3.05 (dt, 1H), 2.22 (s, 3H), 1.65-1.95 (m, 4H). SOP: +59.6° (C=0.5% in MeOH).

Example 30

(R)-5-amino-1-(1-cyanopiperidin-3-yl)-3-[4-(3-fluoro-4-methylphenoxy)phenyl]-1H-pyrazole-4-carboxamide

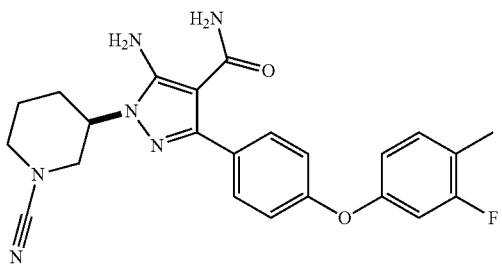

rac-5-amino-1-(1-cyanopiperidin-3-yl)-3-[4-(3-fluoro-4-methylphenoxy)phenyl]-1H-pyrazole-4-carboxamide (prepared as described in Example 28) was chirally separated by preparative HPLC (ChiralPak IB, 4.6×250 mm, 5 μm column, hexane/ethanol, 50/50, 1.0 mL/min flow rate). Isolation of the second eluting isomer afforded the title compound. MS (M+H) m/z 435. $^1$H NMR (DMSO-d6, 300 MHz) δ 7.50 (d, 2H), 7.28 (t, 1H), 7.08 (d, 2H), 6.90 (dd, 1H), 6.82 (dd, 1H), 6.43 (s, 2H), 4.35 (m, 1H), 3.50 (dd, 1H), 3.35 (m, 2H), 3.05 (dt, 1H), 2.22 (s, 3H), 1.65-1.95 (m, 4H). SOP: −64° (C=0.5% In MeOH).

Example 31

5-amino-1-(1-cyanopiperidin-3-yl)-3-[4-(4-fluoro-3-methylphenoxy)phenyl]-1H-pyrazole-4-carboxamide

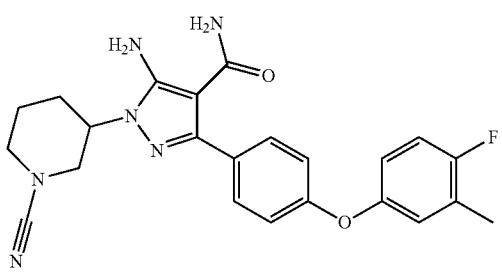 [SMILES: Cc1cc(Oc2ccc(-c3nn(C4CCCN(C#N)C4)c(N)c3C(N)=O)cc2)ccc1F]

Prepared analogous to 5-amino-1-(1-cyanopiperidin-3-yl)-3-[4-(2,4-difluorophenoxy)phenyl]-1H-pyrazole-4-carboxamide (Example 25) employing 4-fluoro-3-methylphenol to afford the title compound. MS (M+H) m/z 435. $^1$H NMR (DMSO-d6, 300 MHz) δ 7.48 (d, 2H), 7.18 (t, 1H), 7.03 (m, 3H), 6.92 (m, 1H), 6.43 (s, 2H), 4.36 (m, 1H), 3.50 (d, 1H), 3.35 (m, 2H), 3.04 (t, 1H), 2.21 (s, 3H), 1.65-1.95 (m, 4H).

Example 32

5-amino-1-(1-cyanopiperidin-3-yl)-3-[4-(4-fluoro-2-methylphenoxy)phenyl]-1H-pyrazole-4-carboxamide

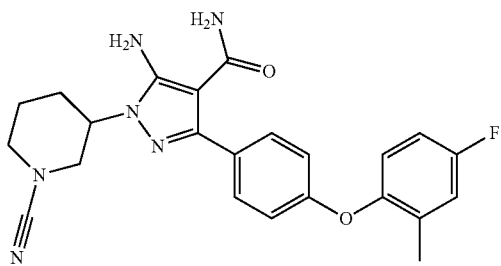 [SMILES: Cc1cc(F)ccc1Oc1ccc(-c2nn(C3CCCN(C#N)C3)c(N)c2C(N)=O)cc1]

Prepared analogous to 5-amino-1-(1-cyanopiperidin-3-yl)-3-[4-(2,4-difluorophenoxy)phenyl]-1H-pyrazole-4-carboxamide (Example 25) employing 4-fluoro-2-methylphenol to afford the title compound. MS (M+H) m/z 435. $^1$H NMR (DMSO-d6, 400 MHz) δ 7.42 (d, 2H), 7.23 (d, 1H), 7.04 (m, 2H), 6.91 (d, 2H), 6.42 (s, 2H), 4.36 (m, 1H), 3.47 (m, 1H), 3.32 (m, 2H), 3.06 (t, 1H), 2.18 (s, 3H), 1.62-1.92 (m, 4H).

Example 33

(S)-5-amino-1-(1-cyanopiperidin-3-yl)-3-[4-(4-fluoro-2-methylphenoxy)phenyl]-1H-pyrazole-4-carboxamide

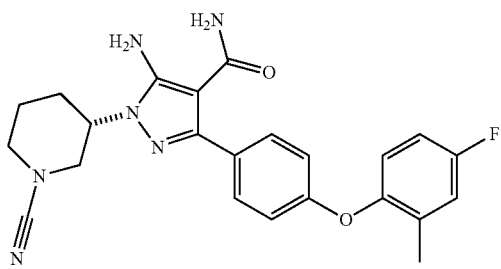

rac-5-amino-1-(1-cyanopiperidin-3-yl)-3-[4-(4-fluoro-2-methylphenoxy)phenyl]-1H-pyrazole-4-carboxamide (prepared as described in Example 32) was chirally separated by preparative HPLC (ChiralPak IB, 4.6×250 mm, 5 µm column, hexane/ethanol, 50/50, 1.0 mL/min flow rate). Isolation of the first eluting isomer afforded the title compound. MS (M+H) m/z 435. $^1$H NMR (DMSO-d6, 400 MHz) δ 7.42 (d, 2H), 7.23 (d, 1H), 7.04 (m, 2H), 6.91 (d, 2H), 6.42 (s, 2H), 5.2-6.0 (br, 2H), 4.36 (m, 1H), 3.47 (m, 1H), 3.32 (m, 2H), 3.06 (t, 1H), 2.18 (s, 3H), 1.62-1.92 (m, 4H). SOR: +53.2° (C=0.5% in MeOH).

Example 34

(R)-5-amino-1 (1-cyanopiperidin-3-yl)-3-[4-(4-fluoro-2-methylphenoxy)phenyl]-1H-pyrazole-4-carboxamide

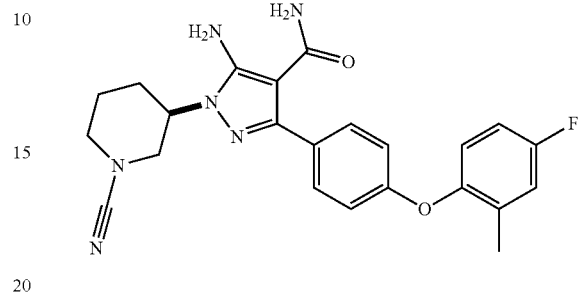

rac-5-amino-1-(1-cyanopiperidin-3-yl)-3-[4-(4-fluoro-2-methylphenoxy)phenyl]-1H-pyrazole-4-carboxamide (prepared as described in Example 32) was chirally separated by preparative HPLC (ChiralPak IB, 4.6×250 mm, 5 µm column, hexane/ethanol, 50/50, 1.0 mL/min flow rate). Isolation of the second eluting isomer afforded the title compound. MS (M+H) m/z 435. $^1$H NMR (DMSO-d6, 400 MHz) δ 7.42 (d, 2H), 7.23 (d, 1H), 7.04 (m, 2H), 6.91 (d, 2H), 6.42 (s, 2H), 5.2-6.0 (br, 2H), 4.36 (m, 1H), 3.47 (m, 1H), 3.32 (m, 2H), 3.06 (t, 1H), 2.18 (s, 3H), 1.62-1.92 (m, 4H). SOR: −64.8° (C=0.5% in MeOH).

Example 35

5-amino-3-[4-(2-chloro-4-fluorophenoxy)phenyl]-1-(1-cyanopiperidin-3-yl)-1H-pyrazole-4-carboxamide

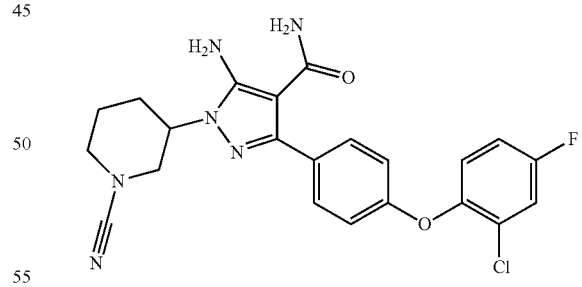

Prepared analogous to 5-amino-1-(1-cyanopiperidin-3-yl)-3-[4-(2,4-difluorophenoxy)phenyl]-1H-pyrazole-4-carboxamide (Example 25) employing 2-chloro-4-fluorophenol to afford the title compound. MS (M+H) m/z 454.9. $^1$H NMR (DMSO-d6, 300 MHz) δ 7.63 (d, 1H), 7.48 (d, 2H), 7.30 (d, 2H), 6.98 (d, 2H), 6.43 (s, 2H), 4.37 (m, 1H), 3.5 (m, 1H), 3.35 (m, 2H), 3.06 (t, 1H), 1.65-1.95 (m, 4H).

Example 36

(S)-5-amino-3-[4-(2-chloro-4-fluorophenoxy)phenyl]-1-(1-cyanopiperidin-3-yl)-1H-pyrazole-4-carboxamide

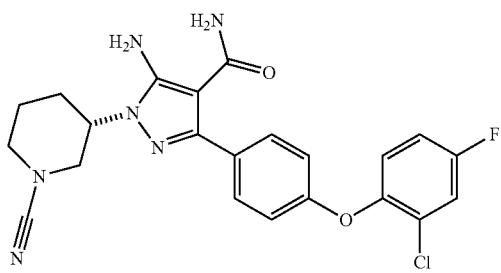

rac-5-amino-3-[4-(2-chloro-4-fluorophenoxy)phenyl]-1-(1-cyanopiperidin-3-yl)-1H-pyrazole-4-carboxamide (prepared as described in Example 35) was chirally separated by preparative HPLC (ChiralPak IB, 4.6×250 mm, 5 μm column, hexane/ethanol, 50/50, 1.0 mL/min flow rate). Isolation of the first eluting isomer afforded the title compound. MS (M+H) m/z 454.9. $^1$H NMR (DMSO-d6, 400 MHz) δ 7.63 (d, 1H), 7.48 (d, 2H), 7.30 (d, 2H), 6.98 (d, 2H), 6.43 (s, 2H), 5.2-6.2 (br, 2H), 4.37 (m, 1H), 3.5 (m, 1H), 3.35 (m, 2H), 3.06 (t, 1H), 1.65-1.95 (m, 4H). SOR: +49.2 (C=0.5% in MeOH).

Example 37

(R)-5-amino-3-[4-(2-chloro-4-fluorophenoxy)phenyl]-1-(1-cyanopiperidin-3-yl)-1H-pyrazole-4-carboxamide

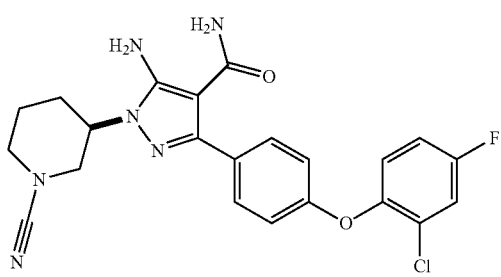

rac-5-amino-3-[4-(2-chloro-4-fluorophenoxy)phenyl]-1-(1-cyanopiperidin-3-yl)-1H-pyrazole-4-carboxamide (prepared as described in Example 35) was chirally separated by preparative HPLC (ChiralPak IB, 4.6×250 mm, 5 μm column, hexane/ethanol, 50/50, 1.0 mL/min flow rate). Isolation of the second eluting isomer afforded the title compound. MS (M+H) m/z 454.9. $^1$H NMR (DMSO-d6, 300 MHz) δ 7.63 (d, 1H), 7.48 (d, 2H), 7.30 (d, 2H), 6.98 (d, 2H), 6.43 (s, 2H), 5.2-6.2 (br, 2H), 4.37 (m, 1H), 3.5 (m, 1H), 3.35 (m, 2H), 3.06 (t, 1H), 1.65-1.95 (m, 4H).

Example 38

5-amino-3-[4-(2-chloro-4-methylphenoxy)phenyl]-1-(1-cyanopiperidin-3-yl)-1H-pyrazole-4-carboxamide

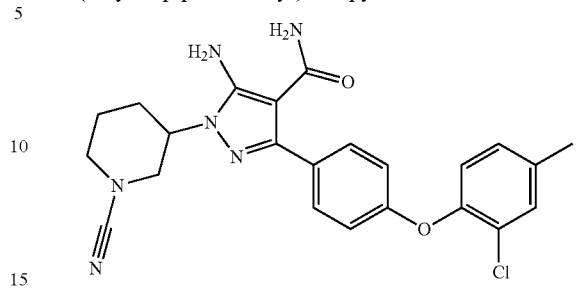

Prepared analogous to 5-amino-1-(1-cyanopiperidin-3-yl)-3-[4-(2,4-difluorophenoxy)phenyl]-1H-pyrazole-4-carboxamide (Example 25) employing 2-chloro-4-methylphenol to afford the title compound. MS (M+H) m/z 451. $^1$H NMR (400 MHz, methanol-d4) δ 7.47 (d, J=8.8 Hz, 2H), 7.36 (s, 1H), 7.17 (d, J=8.4 Hz, 1H), 7.05 (d, J=8.0 Hz, 1H), 6.98 (d, J=8.8 Hz, 2H), 4.37 (m, 1H), 3.57 (m, 1H), 3.44 (m, 2H), 3.11 (m, 1H), 2.36 (s, 3H), 2.06 (m, 2H), 1.92 (m, 2H).

Example 39

5-amino-1-(1-cyanopiperidin-3-yl)-3-[4-(2-fluoro-4-methylphenoxy)phenyl]-1H-pyrazole-4-carboxamide

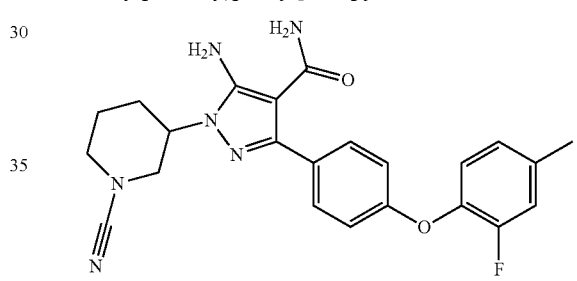

Prepared analogous to 5-amino-1-(1-cyanopiperidin-3-yl)-3-[4-(2,4-difluorophenoxy)phenyl]-1H-pyrazole-4-carboxamide (Example 25) employing 2-fluoro-4-methylphenol to afford the title compound. MS (M+H) m/z 435. $^1$H NMR (400 MHz, methanol-d4) δ 7.47 (d, J=8.8 Hz, 2H), 7.10 (m, 2H), 7.03 (m, 3H), 4.37 (m, 1H), 3.55 (m, 1H), 3.44 (m, 2H), 3.11 (m, 1H), 2.37 (s, 3H), 2.04 (m, 2H), 1.90 (m, 2H).

Example 40

5-amino-3-[4-(4-chloro-3-methylphenoxy)phenyl]-1-(1-cyanopiperidin-3-yl)-1H-pyrazole-4-carboxamide

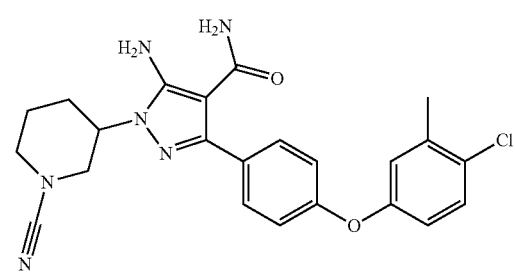 [SMILES: Cc1cc(Oc2ccc(-c3nn(C4CCCN(C#N)C4)c(N)c3C(N)=O)cc2)ccc1Cl]

Step 1: preparation of 1-[4-(4-chloro-3-methylphenoxy)phenyl]ethanone. To a solution of 4-fluoroacetophenone (1.0 g, 7.2 mmol) in dimethylacetamide (4 mL) was added 4-chloro-3-methylphenol (1.24 g, 8.69 mmol), followed by potassium carbonate (1.38 g, 9.99 mmol). The reaction mixture was heated at 100° C. for 3 h and then allowed to cool, quenched with water and extracted into ethyl acetate. The combined organic layers were concentrated in vacuo to afford the title compound. MS (M+H) m/z 260.9. $^1$H NMR (DMSO-d6) δ 7.99 (m, 2H) 7.48 (d, J=8.5 Hz, 1H), 7.16 (d, J=3.1 Hz, 1H), 7.07 (m, 2H), 6.98 (dd, J=8.5, 3.07 Hz, 1H) 2.55 (s, 3H), 2.33 (s, 3H).

Step 2: preparation of 4-(4-chloro-3-methylphenoxy)benzoic acid. To a solution of 1-[4-(4-chloro-3-methylphenoxy)phenyl]ethanone (1.8 g, 6.9 mmol) in ethanol (10 mL) was added 20 mL of a 10-15% sodium hypochlorite solution and the mixture was stirred at ambient temperature. A solution of aqueous sodium bisulfite (50 mL) was added and the mixture was then acidified with 12N hydrochloric acid. The resulting precipitate was filtered to afford the title compound.

Step 3: preparation of 4-(4-chloro-3-methylphenoxy)benzoyl chloride. Anhydrous oxalyl chloride (1.23 g, 9.71 mmol) was added drop-wise followed by 4 drops of N,N-dimethylformamide to a solution of 4-(4-chloro-3-methylphenoxy)benzoic acid (1.701 g, 6.475 mmol) in tetrahydrofuran (30 mL) at 0° C. The mixture was allowed to warm to ambient temperature over 16 h and then concentrated to afford the title compound as a yellow solid.

Step 4: preparation of 2-((4-(4-chloro-3-methylphenoxy)phenyl)(methoxy)methylene)-malononitrile. A solution of malononitrile (252 mg, 3.81 mmol) in anhydrous tetrahydrofuran (3 mL) was added to a suspension of sodium hydride (183 mg, 3.807 mmol) in tetrahydrofuran (15 mL) at 0° C. A solution of 4-(4-chloro-3-methylphenoxy)benzoyl chloride (1.0 g, 3.81 mmol) in tetrahydrofuran (5 mL) was then added drop wise over 10 min. The mixture was then treated with dimethyl sulfate and heated to reflux for 3 h, after which it was quenched with saturated aqueous ammonium chloride and extracted into ethyl acetate. The combined organic layers were washed with brine and concentrated in vacuo to afford the title compound as an oil.

Step 5: preparation of 1-(3-hydroxypiperidin-1-yl)ethanone. A suspension of 3-hydroxy-piperidine (100 g, 0.73 mol) and triethylamine (121 mL, 0.87 mol) in dichloromethane (1 L) was cooled to 0° C. Acetic anhydride (79 mL, 0.84 mol) was then added drop wise over 1.5 h, ensuring that the temperature did not surpass 0° C. The mixture was allowed to stir at ambient temperature for an additional 16 h and then was washed with water, saturated aqueous sodium bicarbonate, and finally brine. The combined aqueous layers were then re-extracted with a solution of 10% methanol/dichloromethane. The combined organic layers were concentrated in vacuo and the resulting residue was then added to ethyl acetate (500 mL) and allowed to stir for 15 min, after which a white precipitate had formed. The precipitate was filtered off and washed with ethyl acetate. The filtrate was concentrated in vacuo. The residue was purified via removal of residual anhydride by vacuum distillation (140° C., 4 mbar) to afford the title compound as a brown oil (192 g, 61%). $^1$H-NMR (CDCl$_3$) δ 3.59-3.92 (m, 3H), 3.21-3.49 (m, 3H), 2.12 (s, 3H), 1.73-2.07 (m, 2H), 1.44-1.68 (m, 2H).

Step 6: preparation of 1-acetylpiperidin-3-one. To a cold suspension of pyridine.SO$_3$ (372.0 g, 2.338 mol) in dichloromethane (2.0 L) was added in sequence triethylamine (408.5 mL, 2.923 mol) and dimethylsulfoxide (414 mL, 5.846 mol) keeping the temperature at 0° C. A solution of 1-(3-hydroxypiperidin-1-yl)ethanone (76.0 g, 0.531 mol) in dichloromethane (500 mL) was drop wise added over 1 h keeping the temperature below 0° C. The reaction mixture was allowed to stir at room temperature for 16 h. The reaction mixture was quenched with saturated ammonium chloride (1 L) at 0-5° C. and stirred for another 1 h. The organic layer was separated and the aqueous layer was extracted with 10% methanol in dichloromethane (4×250 mL). The combined organic layers were concentrated in vacuum. The residue was dissolved in ethyl acetate (1 L) and filtered through glass sintered and concentrated in vacuum. Residual dimethylsulfoxide and triethylamine were removed by high vacuum distillation. The crude product was purified by silica gel column chromatography to afford the title compound (16 g) as a brown semi solid. $^1$H NMR (400 MHz, CDCl$_3$) δ 4.15 (s, 1H), 3.98 (s, 1H), 3.72 (t, J=12 Hz, 2H), 3.61 (t, J=12 Hz, 2H), 2.12 (s, 1.5H), 2.06 (s, 1.5H), 1.94-2.03 (m, 4H).

Step 7: preparation of tert-butyl 2-(1-acetylpiperidin-3-yl)hydrazinecarboxylate. To a solution of 1-acetyl-piperidin-3-one (123 g, 0.87 mol) in tetrahydrofuran (1.5 L) was added tert-butyl hydrazinecarboxylate (115 g, 0.87 mol). The solution was heated to reflux for 16 h, after which it was cooled to 15° C. and sodium cyanoborohydride (54.8 g, 0.87 mol) was added in a single portion. A solution of p-toluenesulfonic acid mono-hydrate (166 g, 0.87 mol) in tetrahydrofuran (700 mL) was then added drop wise over 2 h, ensuring that the temperature did not exceed 20° C. The mixture was allowed to stir at ambient temperature for 16 h, after which volatiles were removed in vacuo. The resulting oil was dissolved in ethyl acetate (1.5 L) and washed with saturated aqueous sodium bicarbonate (1 L). The organic layer was then added to 1N sodium hydroxide (1 L) and allowed to stir for 1 h. The organic layer was separated, washed with brine, dried over sodium sulfate and concentrated in vacuo. The crude product was purified by silica gel column chromatography (1-7% dichloromethane/2-propanol), then re-purified using a 10-50% ethyl acetate/2-propanol solvent gradient to afford the title compound as an oil (74.5 g, 33%). $^1$H NMR (CDCl$_3$) δ 6.42 (bs, 1H), 6.03 (bs, 1H), 3.34-4.14 (m, 4H), 2.85-3.04 (m, 2H), 2.08 (ds, 3H), 1.49-1.91 (m, 3H), 1.44 (bs, 9H).

Step 8: preparation of 1-(3-hydrazinylpiperidin-1-yl)ethanone hydrochloride. To a solution of tert-butyl 2-(1-acetylpiperidin-3-yl)hydrazinecarboxylate (45.1 g, 0.18 mol) in methanol (220 mL) at 0° C. was added 4N hydrochloric acid in dioxane (221 mL) ensuring that the temperature did not exceed 10° C. The mixture was allowed to stir at ambient temperature for 16 h, after which volatiles were removed in vacuo. The residue was dissolved in water (75 mL), extracted into 10% dichloromethane/methanol. The combined organic layers were concentrated to afford the title compound. MS (M+H) m/z 158. $^1$H NMR (DMSO-d6) δ 4.15 (q, 0.5H), 4.00 (d, 0.5H), 3.85-3.92 (m, 0.5H), 3.53-3.59 (m, 0.5H), 2.71-3.16 (m, 3H), 2.01 (ds, 3H), 1.91-2.01 (m, 1H), 1.61-1.80 (m, 1H), 1.25-1.52 (m, 2H).

Step 9: preparation of 1-(1-acetylpiperidin-3-yl)-5-amino-3-[4-(4-chloro-3-methylphenoxy)phenyl]-1H-pyrazole-4-carbonitrile. Triethylamine (156 mg, 1.54 mmol) was added to a slurry of 1-(3-hydrazinylpiperidin-1-yl)ethanone hydrochloride (133 mg, 0.68 mmol) and 2-((4-(4-chloro-3-methylphenoxy)phenyl)(methoxy)methylene)-malononitrile (200 mg, 0.62 mmol) and the mixture was stirred at room temperature for 18 h. The reaction mixture was partitioned between water and ethyl acetate. The organic layer was dried (MgSO$_4$), filtered and concentrated to afford the title compound. MS (M+H) m/z 450.

Step 10: preparation of 5-amino-3-[4-(4-chloro-3-methylphenoxy)phenyl]-1-piperidin-3-yl-1H-pyrazole-4-carboxamide. The title compound was prepared analogous to 5-amino-3-(4-(2,4-difluorophenoxy)phenyl)-1-(piperidin-3-yl)-1H-pyrazole-4-carboxamide (Example 25, Step 6) employing 1-(1-acetylpiperidin-3-yl)-5-amino-3-[4-(4-chloro-3-methylphenoxy)phenyl]-1H-pyrazole-4-carbonitrile. ¹H NMR (400 MHz, DMSO-d6) δ ppm 7.50 (m, J=–8.53 Hz, 2H), 7.43 (d, J=8.54 Hz, 1H), 7.08 (m, 2H), 7.11 (d, J=3.41 Hz, 1H), 6.90-6.97 (m, 1H), 6.34 (s, 2H), 4.13 (d, J=4.78 Hz, 1H), 3.01-3.10 (m, 1H), 2.80-2.96 (m, 2H), 2.32 (s, 4H), 1.90-1.96 (m, 1H), 1.82-1.90 (m, 1H), 1.68-1.78 (m, 1H), 1.47-1.59 (m, 2H), Step 11: preparation of 5-amino-3-[4-(4-chloro-3-methylphenoxy)phenyl]-1-(1-cyanopiperidin-3-yl)-1H-pyrazole-4-carboxamide. The title compound was prepared analogous to 5-amino-1-(1-cyanopiperidin-3-yl)-3-[4-(2,4-difluorophenoxy)phenyl]-1H-pyrazole-4-carboxamide (Example 25, Step 7) employing 5-amino-3-[4-(4-chloro-3-methylphenoxy)phenyl]-1-piperidin-3-yl-1H-pyrazole-4-carboxamide. MS (M+H) m/z 451. ¹H NMR (DMSO-d6) δ 7.09 (d, 2H), 7.06 (d, J=8.30 Hz, 2H) 6.91 (dd, J=8.79, 2.93 Hz, 1H), 6.43 (s, 2H), 4.33-4.39 (m, 1H), 3.49 (dd, J=12.21, 3.91 Hz, 1H), 3.30-3.36 (m, 2H), 3.02-3.09 (m, 1H), 2.31 (s, 3H), 1.94 (td, J=13.18, 3.42 Hz, 1H), 1.82-1.89 (m, 1H), 1.80 (bs, 1H), 1.65-1.74 (m, 1H).

Example 41

5-amino-1-(1-cyanopiperidin-3-yl)-3-[4-(4-fluorophenoxy)phenyl]-1H-pyrazole-4-carboxamide

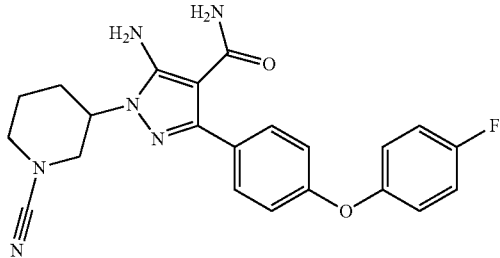 [SMILES: N#CN1CCCC(n2nc(-c3ccc(Oc4ccc(F)cc4)cc3)c(C(N)=O)c2N)C1]

The title compound was prepared analogous to 5-amino-3-[4-(4-chloro-3-methylphenoxy)phenyl]-1-(1-cyanopiperidin-3-yl)-1H-pyrazole-4-carboxamide (Example 40) employing 4-fluorophenol. MS (M+H) m/z 421. ¹H NMR (DMSO-d6) δ 7.45 (d, J=8.8 Hz, 2H), 7.39 (t, J=7.9 Hz, 2H), 7.14 (t, J=7.3 Hz, 1H), 7.03 (t, J=8.8 Hz, 4H), 6.44 (bs, 2H), 4.31-4.38 (m, 1H), 3.48 (bs, 1H), 3.45 (d, J=3.7 Hz, 1H), 2.98-3.09 (m, 1H), 1.90 (bs, 2H), 1.76-1.88 (m, 2H), 1.68 (t, J=12.5 Hz, 1H).

Example 42

5-amino-1-(1-cyanopiperidin-3-yl)-3-[4-(4-methylphenoxy)phenyl]-1H-pyrazole-4-carboxamide

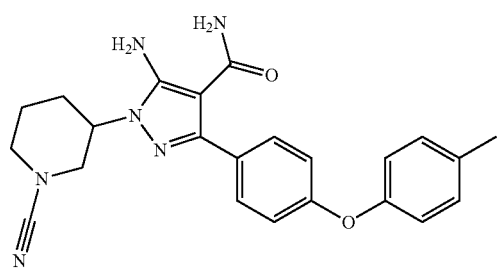 [SMILES: Cc1ccc(Oc2ccc(-c3nn(C4CCCN(C#N)C4)c(N)c3C(N)=O)cc2)cc1]

The title compound was prepared analogous to 5-amino-3-[4-(4-chloro-3-methylphenoxy)phenyl]-1-(1-cyanopiperidin-3-yl)-1H-pyrazole-4-carboxamide (Example 40) employing 4-methylphenol. MS (M+H) m/z 417. ¹H NMR (DMSO-d6) δ 7.45 (d, J=8.4 Hz, 2H), 7.21 (d, J=8.4 Hz, 2H), 6.97 (d, J=8.8 Hz, 2H), 7.00 (d, J=8.8 Hz, 2H), 6.73 (bs, 1H), 6.53-6.67 (m, 1H), 6.40 (d, J=8.8 Hz, 2H), 4.95-5.08 (m, 1H), 4.32-4.53 (m, 1H), 4.12 (bs, 4H), 3.40-3.50 (m, 1H), 3.01 (bs, 1H), 2.29 (s, 3H), 1.77-2.02 (m, 3H), 1.45 (bs, 1H).

Example 43

5-amino-1-(1-cyanopiperidin-3-yl)-3-[4-(2, 5-difluorophenoxy)phenyl]-1H-pyrazole-4-carboxamide

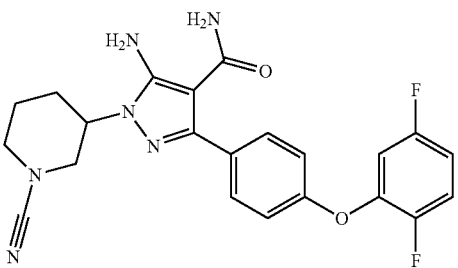 [SMILES: N#CN1CCCC(n2nc(-c3ccc(Oc4cc(F)ccc4F)cc3)c(C(N)=O)c2N)C1]

Step 1: preparation of 4-iodo benzoyl chloride. To a suspension of 4-iodo benzoic acid (60 g, 0.24 mol) in oxalylchloride (417 mL, 4.83 mol) at 0° C. was added N,N-dimethylformamide (1 mL) drop wise. The mixture was then heated to reflux for 16 h, after which it was cooled to ambient temperature and concentrated in vacuo. The resulting oil was dissolved in toluene and purified by vacuum distillation to afford the title compound.

Step 2: preparation of 2-(hydroxy(4-iodophenyl)methylene)malononitrile. To a stirred suspension of sodium hydride (60%, 64.36 g, 1.61 mol) in tetrahydrofuran (600 mL) at 0° C. was added a solution of malononitrile (53.09 g, 804.5 mmol) in tetrahydrofuran (600 mL) and the resulting reaction mixture was stirred for 30 min at same temperature. 4-iodo benzoyl chloride (214 g, 804.5 mmol) in tetrahydrofuran (600 mL) was added to the suspension at 0° C. and then stirred at room temperature for 16 h. The reaction mixture was cooled to 0° C. and quenched with saturated ammonium chloride solution (1000 ml). The resulting aqueous solution was extracted with ethyl acetate (2×1.5 L). The combined organic layers were washed with brine (1 L), dried over sodium sulfate and concentrated to afford the title compound (250 g) as brown solid. MS (M–H) m/z 295. ¹H NMR (400 MHz, DMSO-d6) δ 7.73 (d, J=8.0 Hz, 2H), 7.35 (d, J=8.0 Hz, 2H).

Step 3: preparation of 2-((4-iodophenyl)(methoxy)methylene)malononitrile. To a stirred suspension of sodium hydride (60%, 37.16 g, 929 mmol) in tetrahydrofuran (500 mL) at 0° C. was added a solution of 2-(hydroxy(4-iodophenyl)methylene)malononitrile (250 g, 844.6 mmol) in tetrahydrofuran (500 mL) and the resulting reaction mixture was stirred for 30 min at same temperature. Dimethyl sulfate (241 mL, 253.8 mmol) in tetrahydrofuran (500 mL) was added to the above stirred suspension at 0° C. and the resulting reaction mixture was stirred at 80° C. for 16 h. The reaction mixture was cooled to 0° C. and quenched with saturated ammonium chloride solution (1000 mL). The resulting aqueous solution was extracted with ethyl acetate (2×1.5 L). The combined organic layers were washed with brine solution (1 L), dried over sodium sulfate and concentrated to afford the title compound (200 g). LCMS (M–H) m/z 308.

Step 4: preparation of benzyl 3-[5-amino-4-cyano-3-(4-iodophenyl)-1H-pyrazol-1-yl]piperidine-1-carboxylate. To the stirred suspension of 2-((4-iodophenyl)(methoxy)-methylene)malononitrile (100 g, 322.6 mmol) in ethanol (1 L) was added freshly distilled triethylamine (49.1 mL, 354.8 mmol) followed by addition of 2-(methoxy(3-iodo)methylene)-malononitrile and benzyl 3-hydrazino-piperidine-1-carboxylate (Example 1, Step 8) (91.93 g, 322.6 mmol) at room temperature and the resulting mixture was stirred at 80° C. for 16 hours. The reaction mixture was cooled to room temperature and concentrated to a volume of 500 mL. The resulting solids were filtered, washed with water (2×500 ml) and dried under vacuum to afford the title compound (98 gm, 58%) as off white solid. MS (M+H) m/z 527.8. $^1$H NMR (400 MHz, DMSO-d6) δ 7.82 (d, J=8.0 Hz, 2H), 7.57 (d, J=8.0 Hz, 2H), 7.34 (br, 5H), 6.82 (s, 2H), 5.06 (br, 2H), 4.27 (br, 1H), 4.01-3.91 (m, 2H), 3.32-3.27 (m, 1H), 2.99-2.93 (m, 1H), 1.98-1.85 (m, 3H), 1.54-1.48 (m, 1H).

Step 5: preparation of benzyl 3-{5-amino-4-cyano-3-[4-(4,4,5,5-tetramethyl-1,3,2-dioxaborolan-2-yl)phenyl]-1H-pyrazol-1-yl}piperidine-1-carboxylate. To a stirred suspension of benzyl 3-[5-amino-4-cyano-3-(4-iodophenyl)-1H-pyrazol-1-yl]piperidine-1-carboxylate (86.7 g, 341.6 mmol), bis(pinacolato)diborane (95.4 g, 375.8 mmol), and potassium acetate (34 g, 347.2 mmol) in dimethylsulfoxide (300 mL) which had been degassed under nitrogen for 20 min, was added PdCl$_2$(dppf) (7.4 g, 9.1 mmol). The reaction mixture was then heated to 80° C. for 2 h, allowed to cool to ambient temperature, and filtered through Celite. The filtrate was diluted with ethyl acetate, washed with water and brine, dried over sodium sulfate and concentrated in vacuo. The crude residue was purified by silica gel column chromatography to afford the title compound as pale yellow oil (45 g, 75%). MS (M+H) m/z 528. $^1$H NMR: (400 MHz, DMSO-d6) δ ppm: 7.83 (d, J=8 Hz, 2H), 7.57 (d, J=8 Hz, 2H), 7.36 (s, 5H), 6.83 (br s, 2H), 5.0 (bs, 2H), 4.30 (d, J=28 Hz, 2H), 3.98 (d, J=40 Hz, 2H), 3.22-3.20 (m, 1H), 2.95 (t, J=24 Hz, 1H), 1.97-1.84 (dd, J=52 Hz, 3H), 1.56-1.46 (bs, 1H), 1.30 (s, 12H).

Step 6: preparation of preparation of [4-(5-amino-1-{1-[(benzyloxy)carbonyl]piperidin-3-yl}-4-cyano-1H-pyrazol-3-yl)phenyl]boronic acid. To a solution of benzyl-3-{5-amino-4-cyano-3-[4-(4,4,5,5-tetramethyl-1,3,2-dioxaborolan-2-yl)phenyl]-1H-pyrazol-1-yl}piperidine-1-carboxylate (2.97 g, 5.63 mmol) in 33% aqueous acetone (67.5 mL) was added sodium periodate (3.61 g, 16.88 mmol) and ammonium acetate (1.30 g, 16.88 mmol). The reaction mixture was stirred at 30° C. over 16 h, after which the desired product was extracted into ethyl acetate. The combined organic layers were dried over magnesium sulfate and concentrated in vacuo to afford the title compound. MS (M+H) m/z 445.9.

Step 7: preparation of benzyl 3-{5-amino-4-cyano-3-[4-(2,5-difluorophenoxy)phenyl]-1H-pyrazol-1-yl}piperidine-1-carboxylate. To a solution of 2,4-difluorophenol (16 mg, 0.125 mmol) and [4-(5-amino-1-{1-[(benzyloxy)carbonyl]piperidin-3-yl}-4-cyano-1H-pyrazol-3-yl)phenyl]boronic acid (56 mg, 0.125 mmol) in dichloromethane (1 mL) in an 8 mL vial was added copper (II) acetate (18 mg, 0.100 mmol), 4 Å molecular sieves (10 mg), and pyridine (20 μL, 0.200 mmol). The vial was capped and allowed to shake at 30° C. for 16 h. The reaction mixture was then filtered and the filtrate was concentrated using a Speedvac. The resulting residue was then purified by preparative TLC to afford the title compound.

Step 8: preparation of 5-amino-3-[4-(2,5-difluorophenoxy)phenyl]-1-piperidin-3-yl-1H-pyrazole-4-carboxamide. To a solution of benzyl 3-{5-amino-4-cyano-3-[4-(2,5-difluorophenoxy)phenyl]-1H-pyrazol-1-yl}piperidine-1-carboxylate (66 mg, 0.125 mmol) in isopropanol (1 mL) in an 8 mL vial was added 5M aqueous sodium hydroxide (0.5 mL, 2.50 mmol). The vial was capped and allowed to shake at 155° C. for 48 h. Water was added to the vial (1 mL) and the desired product was extracted into ethyl acetate (3×1 mL). The combined organic layers were dried over magnesium sulfate, and concentrated using a Speedvac to afford the title compound.

Step 9: preparation of 5-amino-1-(1-cyanopiperidin-3-yl)-3-[4-(2, 5-difluorophenoxy)phenyl]-1H-pyrazole-4-carboxamide. To an 8 mL vial containing 5-amino-3-[4-(2, 5-difluorophenoxy)phenyl]-1-piperidin-3-yl-1H-pyrazole-4-carboxamide (52 mg, 0.125 mmol) was added a 0.5M solution of cyanogen bromide 0.250 mmol) in N,N-dimethylformamide (0.5 mL), followed by potassium carbonate (52 mg, 0.375 mmol). The vial was capped and allowed to shake at 30° C. for 16 h. Solvent was removed using a Speedvac, and the resulting residue was purified via preparative HPLC to afford the title compound. LCMS (M+H) m/z 439.

Examples 44-66

The compounds in the table below were prepared analogous to 5-amino-1-(1-cyanopiperidin-3-yl)-3-[4-(2, 5-difluorophenoxy)phenyl]-1H-pyrazole-4-carboxamide (Example 43).

| EX | Structure | Name | MS (M + 1) |
|---|---|---|---|
| 44 | 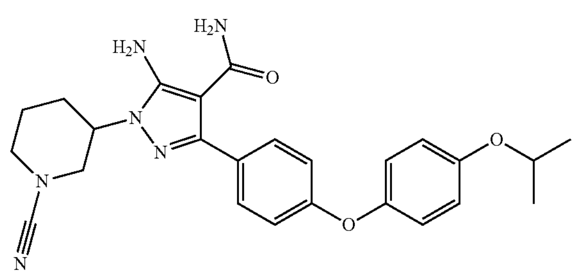 [SMILES: CC(C)Oc1ccc(Oc2ccc(-c3nn(C4CCCN(C#N)C4)c(N)c3C(N)=O)cc2)cc1] | 5-amino-1-(1-cyanopiperidin-3-yl)-3-[4-(4-isopropoxyphenoxy)phenyl]-1H-pyrazole-4-carboxamide | 461 |

-continued

| EX | Structure | Name | MS (M + 1) |
|---|---|---|---|
| 45 | 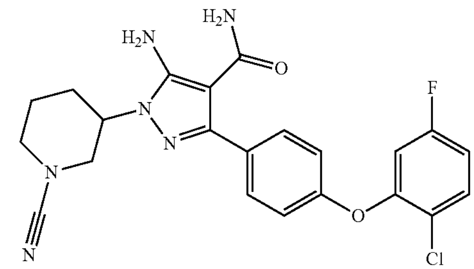 [SMILES: N#CN1CCCC(n2nc(-c3ccc(Oc4cc(F)ccc4Cl)cc3)c(C(N)=O)c2N)C1] | 5-amino-3-[4-(2-chloro-5-fluoro-phenoxy)phenyl]-1-(1-cyanopiperidin-3-yl)-1H-pyrazole-4-carboxamide | 455 |
| 46 | 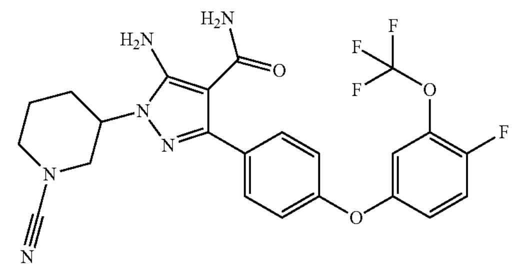 [SMILES: N#CN1CCCC(n2nc(-c3ccc(Oc4ccc(F)c(OC(F)(F)F)c4)cc3)c(C(N)=O)c2N)C1] | 5-amino-1-(1-cyanopiperidin-3-yl)-3-{4-[4-fluoro-3-(trifluoromethoxy)-phenoxy]phenyl}-1H-pyrazole-4-carboxamide | 505 |
| 47 | 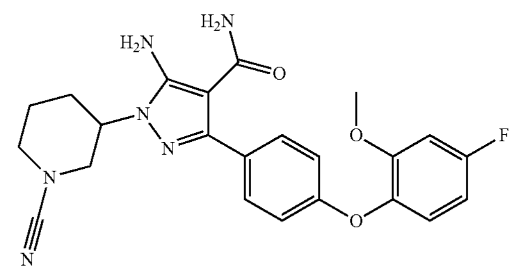 [SMILES: COc1cc(F)ccc1Oc1ccc(-c2nn(C3CCCN(C#N)C3)c(N)c2C(N)=O)cc1] | 5-amino-1-(1-cyanopiperidin-3-yl)-3-{4-[4-fluoro-2-methoxyphenoxy]phenyl}-1H-pyrazole-4-carboxamide | 451 |
| 48 | 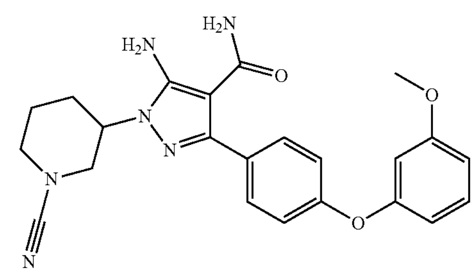 [SMILES: COc1cccc(Oc2ccc(-c3nn(C4CCCN(C#N)C4)c(N)c3C(N)=O)cc2)c1] | 5-amino-1-(1-cyanopiperidin-3-yl)-3-[4-(3-methoxyphenoxy)phenyl]-1H-pyrazole-4-carboxamide | 433 |
| 49 | 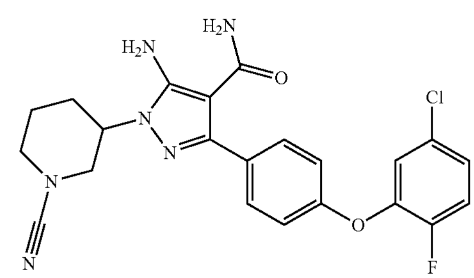 [SMILES: N#CN1CCCC(n2nc(-c3ccc(Oc4cc(Cl)ccc4F)cc3)c(C(N)=O)c2N)C1] | 5-amino-3-[4-(5-chloro-2-fluorophenoxy)phenyl]-1-(1-cyanopiperidin-3-yl)-1H-pyrazole-4-carboxamide | 455 |

| EX | Structure | Name | MS (M + 1) |
|---|---|---|---|
| 50 | 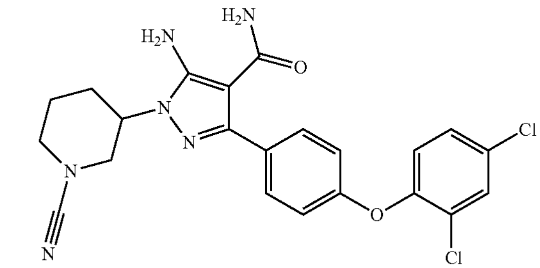 [SMILES: N#CN1CCCC(n2nc(-c3ccc(Oc4ccc(Cl)cc4Cl)cc3)c(C(N)=O)c2N)C1] | 5-amino-1-(1-cyanopiperidin-3-yl)-3-[4-(2,4-dichlorophenoxy)phenyl]-1H-pyrazole-4-carboxamide | 471 |
| 51 | 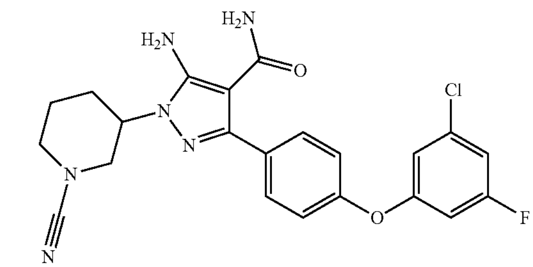 [SMILES: N#CN1CCCC(n2nc(-c3ccc(Oc4cc(F)cc(Cl)c4)cc3)c(C(N)=O)c2N)C1] | 5-amino-3-[4-(3-chloro-5-fluorophenoxy)phenyl]-1-(1-cyanopiperidin-3-yl)-1H-pyrazole-4-carboxamide | 455 |
| 52 | 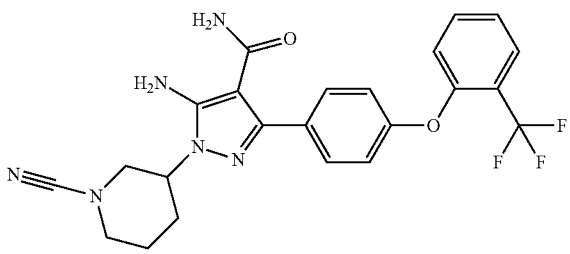 [SMILES: N#CN1CCCC(n2nc(-c3ccc(Oc4ccccc4C(F)(F)F)cc3)c(C(N)=O)c2N)C1] | 5-amino-1-(1-cyanopiperidin-3-yl)-3-{4-[2-(trifluoromethyl)phenoxy]phenyl}-1H-pyrazole-4-carboxamide | 471 |
| 53 | 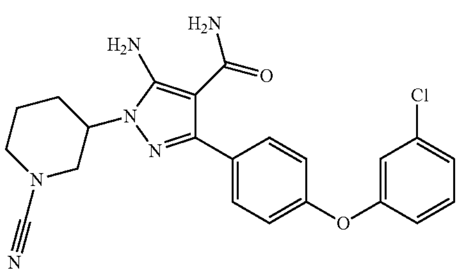 [SMILES: N#CN1CCCC(n2nc(-c3ccc(Oc4cccc(Cl)c4)cc3)c(C(N)=O)c2N)C1] | 5-amino-3-[4-(3-chlorophenoxy)phenyl]-1-(1-cyanopiperidin-3-yl)-1H-pyrazole-4-carboxamide | 437 |
| 54 | 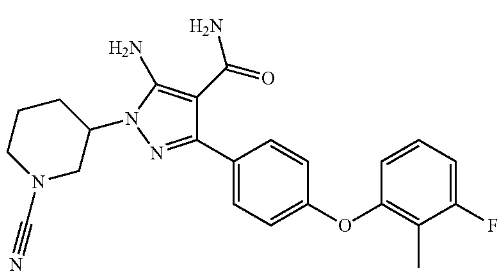 [SMILES: Cc1c(F)cccc1Oc1ccc(-c2nn(C3CCCN(C#N)C3)c(N)c2C(N)=O)cc1] | 5-amino-1-(1-cyanopiperidin-3-yl)-3-[4-(3-fluoro-2-methylphenoxy)phenyl]-1H-pyrazole-4-carboxamide | 435 |

-continued

| EX | Structure | Name | MS (M + 1) |
|---|---|---|---|
| 55 | 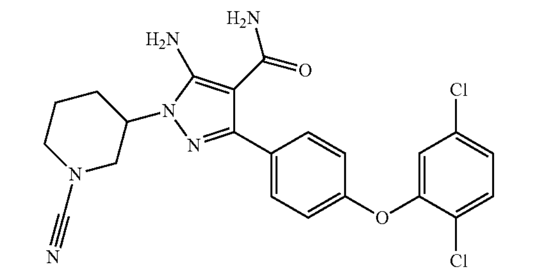 [SMILES: N#CN1CCCC(n2nc(-c3ccc(Oc4cc(Cl)ccc4Cl)cc3)c(C(N)=O)c2N)C1] | 5-amino-1-(1-cyanopiperidin-3-yl)-3-[4-(2,5-dichlorophenoxy)phenyl]-1H-pyrazole-4-carboxamide | 471 |
| 56 | 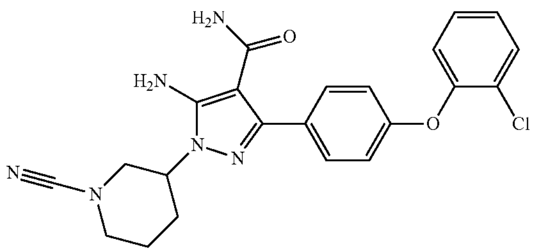 [SMILES: N#CN1CCCC(n2nc(-c3ccc(Oc4ccccc4Cl)cc3)c(C(N)=O)c2N)C1] | 5-amino-3-[4-(2-chlorophenoxy)phenyl]-1-(1-cyanopiperidin-3-yl)-1H-pyrazole-4-carboxamide | 437 |
| 57 | 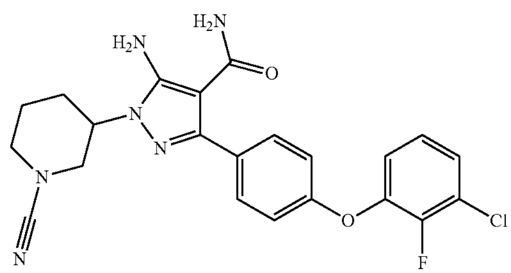 [SMILES: N#CN1CCCC(n2nc(-c3ccc(Oc4cccc(Cl)c4F)cc3)c(C(N)=O)c2N)C1] | 5-amino-3-[4-(3-chloro-2-fluorophenoxy)phenyl]-1-(1-cyanopiperidin-3-yl)-1H-pyrazole-4-carboxamide | 455 |
| 58 | 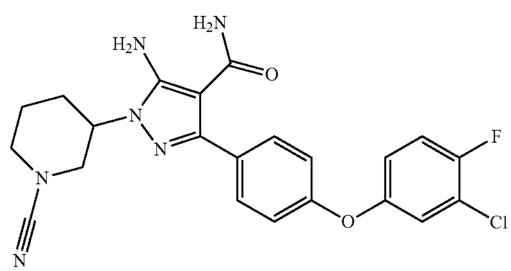 [SMILES: N#CN1CCCC(n2nc(-c3ccc(Oc4ccc(F)c(Cl)c4)cc3)c(C(N)=O)c2N)C1] | 5-amino-3-[4-(3-chloro-4-fluorophenoxy)phenyl]-1-(1-cyanopiperidin-3-yl)-1H-pyrazole-4-carboxamide | 455 |
| 59 | 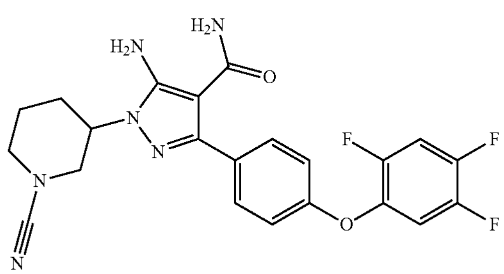 [SMILES: N#CN1CCCC(n2nc(-c3ccc(Oc4cc(F)c(F)cc4F)cc3)c(C(N)=O)c2N)C1] | 5-amino-1-(1-cyanopiperidin-3-yl)-3-[4-(2,4,5-trifluorophenoxy)phenyl]-1H-pyrazole-4-carboxamide | 457 |

| EX | Name | MS (M + 1) |
|---|---|---|
| 60 | 5-amino-1-(1-cyanopiperidin-3-yl)-3-[4-(3,5-dichlorophenoxy)phenyl]-1H-pyrazole-4-carboxamide | 471 |
| 61 | 5-amino-1-(1-cyanopiperidin-3-yl)-3-[4-(2,3,4-trifluorophenoxy)phenyl]-1H-pyrazole-4-carboxamide | 457 |
| 62 | 5-amino-1-(1-cyanopiperidin-3-yl)-3-{4-[2-(trifluoromethoxy)phenoxy]phenyl}-1H-pyrazole-4-carboxamide | 487 |
| 63 | 5-amino-3-[4-(2-chloro-6-fluorophenoxy)phenyl]-1-(1-cyanopiperidin-3-yl)-1H-pyrazole-4-carboxamide | 455 |
| 64 | 5-amino-1-(1-cyanopiperidin-3-yl)-3-{4-[4-fluoro-3-(trifluoromethyl)phenoxy]phenyl}-1H-pyrazole-4-carboxamide | 489 |

| EX | Structure | Name | MS (M + 1) |
|---|---|---|---|
| 65 | 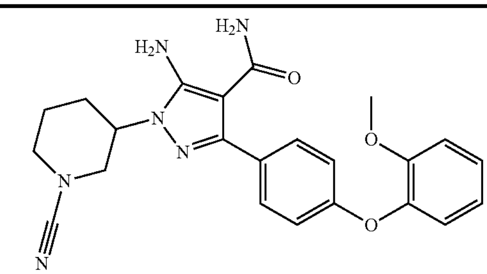 | 5-amino-1-(1-cyanopiperidin-3-yl)-3-[4-(2-methoxyphenoxy)phenyl]-1H-pyrazole-4-carboxamide | 433 |
| 66 | 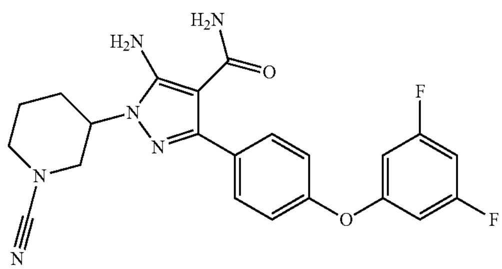 [SMILES: N#CN1CCCC(n2nc(-c3ccc(Oc4cc(F)cc(F)c4)cc3)c(C(N)=O)c2N)C1] | 5-amino-1-(1-cyanopiperidin-3-yl)-3-[4-(3,5-difluorophenoxy)phenyl]-1H-pyrazole-4-carboxamide | 439 |

Example 67

5-amino-3-(4-benzylphenyl)-1-(1 cyanopiperidin-3-1H-pyrazole-4-carboxamide

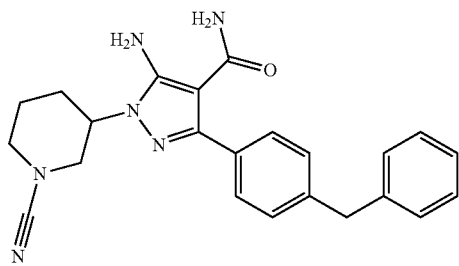 [SMILES: N#CN1CCCC(n2nc(-c3ccc(Cc4ccccc4)cc3)c(C(N)=O)c2N)C1]

Step 1: preparation of benzyl 3-(5-amino-3-(4-benzylphenyl)-4-cyano-1H-pyrazol-1-yl)piperidine-1-carboxylate. To a mixture of benzyl 3-[5-amino-4-cyano-3-(4-Iodophenyl)-1H-pyrazol-1-yl]piperidine-1-carboxylate (Example 43, Step 4) (1 eq), 2-dicyclohexylphosphino-2',6'-dimethoxybiphenyl (0.073 eq), $Pd_2(dba)_3$ (0.065 eq) in N,N-dimethylformamide (50 mL) was added dropwise a solution of benzyl zinc bromide (3 eq, 0.5 M in tetrahydrofuran) at room temperature under $N_2$. The mixture was stirred at room temperature overnight. The reaction mixture was quenched by saturated aqueous ammonium chloride and ethyl acetate (100 mL) was added. The mixture was filtered and the filtrate was extracted with ethyl acetate twice. The combine organic layers were washed with brine, dried over sodium sulfate, filtered and concentrated. The crude product was purified by column chromatography on silica gel ($CH_2Cl_2$/$CH_3OH$, 4/1-1/1) to afford the title compound as a yellow oil.

Step 2: preparation of 5-amino-3-(4-benzylphenyl)-1-(piperidin-3-yl)-1H-pyrazole-4-carboxamide. A mixture of benzyl 3-(5-amino-3-(4-benzylphenyl)-4-cyano-1H-pyrazol-1-yl)piperidine-1-carboxylate (1 eq), NaOH solution (7-10 eq, 2.5M), EtOH (8 mL) was irradiated in the microware at 145° C. for 1 h. The reaction mixture was extracted with EtOAc (50 mL×3). The combine organic layers were washed with brine, dried over sodium sulfate, and concentrated in vacuum to afford the title compound as a yellow oil.

Step 3: preparation of 5-amino-3-(4-benzylphenyl)-1-(1-cyanopiperidin-3-yl)-1H-pyrazole-4-carboxamide. A mixture of 5-amino-3-(4-benzylphenyl)-1-(piperidin-3-yl)-1H-pyrazole-4-carboxamide (1 eq.), $Cs_2CO_3$ (2 eq.), cyanogen bromide (1.1 eq.) in N,N-dimethylformamide (10 mL) was stirred at room temperature overnight. The reaction mixture was extracted with EtOAc (50 mL×2). The combine organic layers were washed with brine, dried over sodium sulfate, and concentrated. The crude product was purified by reverse phase preparative HPLC to afford the title compound as a white solid. LCMS (M+H): 401. $^1$H NMR (DMSO-d6) δ 7.05-7.51 (m, 9H), 6.45 (s, 2H), 4.24-4.43 (m, 1H), 3.97 (s, 2H), 3.47 (dd, J=12.1, 4.0 Hz, 1H), 3.03 (td, J=12.5, 2.2 Hz, 1H), 1.75-2.01 (m, 3H), 1.58-1.73 (m, 1H).

Example 68

5-amino-1-(1-cyanopiperidin-3-yl)-3-[4-(3-methylbenzyl)phenyl]-1H-pyrazole-4-carboxamide

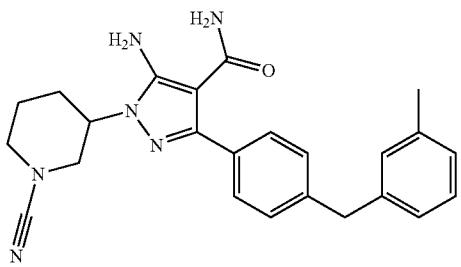 [SMILES: Cc1cccc(Cc2ccc(-c3nn(C4CCCN(C#N)C4)c(N)c3C(N)=O)cc2)c1]

The title compound was prepared analogous to 5-amino-3-(4-benzylphenyl)-1-(1-cyanopiperidin-3-yl)-1H-pyrazole-4-carboxamide (Example 67) employing (3-methylbenzyl)zinc chloride. MS (M+H) m/z 415. ¹H NMR (CDCl₃, 400 MHz) δ 1.77-1.84 (m, 2H), 2.07-2.11 (m, 2H), 2.25 (s, 3H), 2.93-2.99 (m, 1H), 3.35-3.53 (m, 3H), 3.90 (s, 2H), 4.0-4.02 (m, 1H), 5.13 (d, 2H), 5.47 (s, 2H), 6.92-6.97 (m, 3H), 7.10-7.74 (m, 1H), 7.22 (d, 2H), 7.36 (d, 2H).

Example 69

(R)-5-amino-1-(1-cyanopiperidin-3-yl)-3-(4-(3-methylbenzyl)phenyl)-1H-pyrazole-4-carboxamide

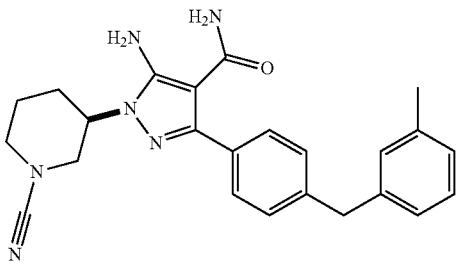

rac-5-amino-1-(1-cyanopiperidin-3-yl)-3-[4-(3-methylbenzyl)phenyl]-1H-pyrazole-4-carboxamide (prepared as described in Example 68) was chirally separated by supercritical fluid chromatography (ChiralPak AD 5µ, 21×250 mm col, 27% MeOH, 70 mL/min). Isolation of the first eluting isomer afforded the title compound. MS (M+H) m/z 415. ¹H NMR (400 MHz, DMSO-d₆) δ ppm 7.39 (d, J=8.6 Hz, 2H), 7.29 (d, J=8.1 Hz, 2H), 7.15-7.21 (m, 1H), 6.98-7.09 (m, 3H), 6.46 (s, 2H), 4.31-4.41 (m, 1H), 3.94 (s, 2H), 3.49 (dd, J=12.1, 4.3 Hz, 1H), 3.32 (m, 2H), 3.00-3.10 (m, 1H), 2.26 (s, 3H), 1.76-2.00 (m, 3H), 1.58-1.76 (m, 1H)

Example 70

(S)-5-amino-1-(1-cyanopiperidin-3-yl)-3-(4-(3-methylbenzyl)phenyl)-1H-pyrazole-4-carboxamide

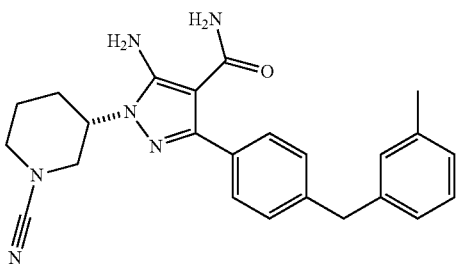 [SMILES: Cc1cccc(Cc2ccc(-c3nn([C@H]4CCCN(C#N)C4)c(N)c3C(N)=O)cc2)c1]

rac-5-amino-1-(1-cyanopiperidin-3-yl)-3-[4-(3-methylbenzyl)phenyl]-1H-pyrazole-4-carboxamide (prepared as described in Example 68) was chirally separated by supercritical fluid chromatography (ChiralPak AD 5µ, 21×250 mm col, 27% MeOH, 70 mL/min). Isolation of the second eluting isomer afforded the title compound. MS (M+H) m/z 415. ¹H NMR (400 MHz, DMSO-d₆) δ ppm 7.39 (d, J=8.6 Hz, 2H), 7.29 (d, J=8.1 Hz, 2H), 7.15-7.21 (m, 1H), 6.98-7.09 (m, 3H), 6.46 (s, 2H), 4.31-4.41 (m, 1H), 3.94 (s, 2H), 3.49 (dd, J=12.1, 4.3 Hz, 1H), 3.32 (m, 2H), 3.00-3.10 (m, 1H), 2.26 (s, 3H), 1.76-2.00 (m, 3H), 1.58-1.76 (m, 1H)

Example 71

5-amino-3-(4-(2-chlorobenzyl)phenyl)-1-(1-cyanopiperidin-3-yl)-1H-pyrazole-4-carboxamide

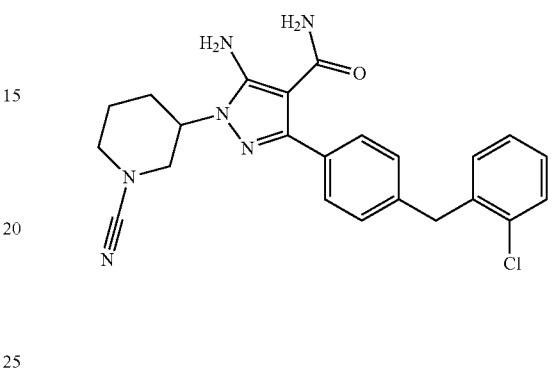

The title compound was prepared analogous to 5-amino-3-(4-benzylphenyl)-1-(1-cyanopiperidin-3-yl)-1H-pyrazole-4-carboxamide (Example 67) employing (2-chlorobenzyl)zinc chloride. MS (M+H) m/z 435. ¹H NMR (CDCl₃, 400 MHz) δ 1.78-1.87 (m, 2H), 2.05-2.11 (m, 2H), 2.93-3.00 (m, 1H), 3.35-3.53 (m, 3H), 4.00-4.05 (m, 1H), 4.074 (s, 2H), 5.15 (d, 2H), 5.48 (s, 2H), 7.10-7.13 (m, 2H), 7.22 (d, 2H), 7.31-7.33 (m, 1H), 7.37 (d, 2H).

Example 72

(R)-5-amino-3-(4-(2-chlorobenzyl)phenyl)-1-(1-cyanopiperidin-3-yl)-1H-pyrazole-4-carboxamide

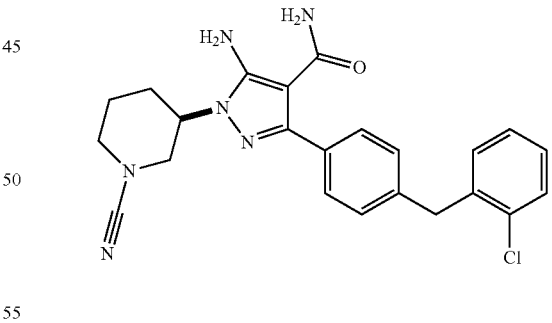

rac-5-amino-3-(4-(2-chlorobenzyl)phenyl)-1-(1-cyanopiperidin-3-yl)-1H-pyrazole-4-carboxamide (prepared as described in Example 71) was chirally separated by supercritical fluid chromatography (ChiralPak AD 5µ, 21×250 mm col, 30% MeOH, 70 mL/min). Isolation of the first eluting isomer afforded the title compound. MS (M+H) m/z 435. ¹H NMR (400 MHz, DMSO-d₆) δ ppm 7.24-7.48 (m, 8H), 6.46 (s, 2H), 4.31-4.41 (m, 1H), 4.12 (s, 2H), 3.49 (dd, J=12.1, 4.3 Hz, 1H), 3.30-3.38 (m, 2H), 3.04 (td, J=12.4, 2.9 Hz, 1H), 1.77-2.00 (m, 3H), 1.64-1.76 (m, 1H).

Example 73

(S)-5-amino-3-(4-(2-chlorobenzyl)phenyl)-1-(1-cyanopiperidin-3-yl)-1H-pyrazole-4-carboxamide

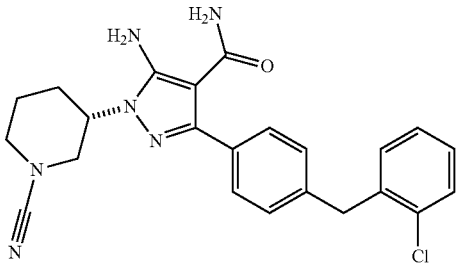

rac-5-amino-3-(4-(2-chlorobenzyl)phenyl)-1-(1-cyanopiperidin-3-yl)-1H-pyrazole-4-carboxamide (prepared as described in Example 71) was chirally separated by supercritical fluid chromatography (ChiralPak AD 5μ, 21×250 mm col, 30% MeOH, 70 mL/min). Isolation of the second eluting isomer afforded the title compound. MS (M+H) m/z 435. $^1$H NMR (400 MHz, DMSO-d$_6$) δ ppm 7.24-7.48 (m, 8H), 6.46 (s, 2H), 4.31-4.41 (m, 1H), 4.12 (s, 2H), 3.49 (dd, J=12.1, 4.3 Hz, 1H), 3.30-3.38 (m, 2H), 3.04 (td, J=12.4, 2.9 Hz, 1H), 1.77-2.00 (m, 3H), 1.64-1.76 (m, 1H).

Example 74

5-amino-1-(1-cyanopiperidn-3-yl)-3-[4-(2-fluorobenzyl)phenyl]-1H-pyrazole-4-carboxamide

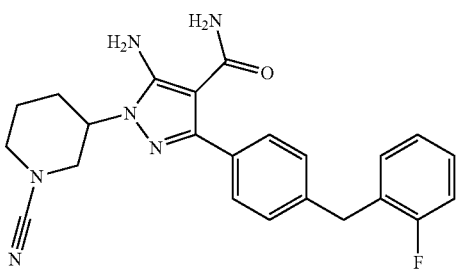

The title compound was prepared analogous to 5-amino-3-(4-benzylphenyl)-1-(1-cyanopiperidin-3-yl)-1H-pyrazole-4-carboxamide (Example 67) employing (2-chlorobenzyl) zinc chloride. MS (M+H) m/z 419. $^1$H NMR (300 MHz, DMSO-d) δ ppm 7.40 (d, 2H), 7.25-7.37 (m, 4H), 7.12-7.21 (m, 2H), 6.46 (s, 2H), 4.30-4.40 (m, 1H), 4.02 (s, 2H), 3.48 (dd, 1H), 3.33-3.38 (m, 2H), 3.04 (td, 1H), 1.60-1.99 (m, 4H).

Example 75

(R)-5-amino-1-(1-cyanopiperidin-3-yl)-3-(4-(2-fluorobenzyl)phenyl)-1H-pyrazole-4-carboxamide

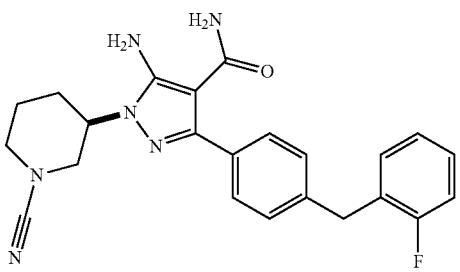 [SMILES: N#CN1CCC[C@@H](n2nc(-c3ccc(Cc4ccccc4F)cc3)c(C(N)=O)c2N)C1]

rac-5-amino-1-(1-cyanopiperidin-3-yl)-3-[4-(2-fluorobenzyl)phenyl]-1H-pyrazole-4-carboxamide (prepared as described in Example 74) was chirally separated by supercritical fluid chromatography (ChiralPak AD 5μ, 21×250 mm col, 27% MeOH, 70 mL/min). Isolation of the first eluting isomer afforded the title compound. MS (M+H) m/z 419. $^1$H NMR (400 MHz, DMSO-d) δ ppm 7.40 (d, J=8.3 Hz, 2H), 7.25-7.37 (m, 4H), 7.12-7.21 (m, 2H), 6.46 (s, 2H), 4.30-4.40 (m, 1H), 4.02 (s, 2H), 3.48 (dd, J=12.3, 4.2 Hz, 1H), 3.33-3.38 (m, 2H), 3.04 (td, J=12.4, 2.9 Hz, 1H), 1.76-1.99 (m, 3H), 1.70 (tt, J=12.5, 4.1 Hz, 1H).

Example 76

(S)-5-amino-1-(1-cyanopiperidin-3-yl)-3-(4-(2-fluorobenzyl)phenyl)-1H-pyrazole-4-carboxamide

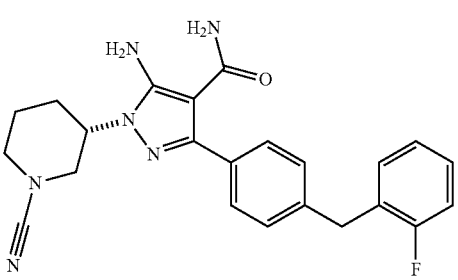

rac-5-amino-1-(1 cyanopiperidin-3-yl)-3-[4-(2-fluorobenzyl)phenyl]-1H-pyrazole-4-carboxamide (prepared as described in Example 74) was chirally separated by supercritical fluid chromatography (ChiralPak AD 5μ, 21×250 mm col, 27% MeOH, 70 mL/min). Isolation of the second eluting isomer afforded the title compound. MS (M+H) m/z 419. $^1$H NMR (400 MHz, DMSO-d$_6$) δ ppm 7.40 (d, J=8.3 Hz, 2H), 7.25-7.37 (m, 4H), 7.12-7.21 (m, 2H), 6.46 (s, 2H), 4.30-4.40 (m, 1H), 4.02 (s, 2H), 3.48 (dd, J=12.3, 4.2 Hz, 1H), 3.33-3.38 (m, 2H), 3.04 (td, J=12.4, 2.9 Hz, 1H), 1.76-1.99 (m, 3H), 1.70 (tt, J=12.5, 4.1 Hz, 1H).

Example 77

5-amino-1-(1-cyanopiperidin-3-yl)-3-[4-(3-fluorobenzyl)phenyl]-1H-pyrazole-4-carboxamide

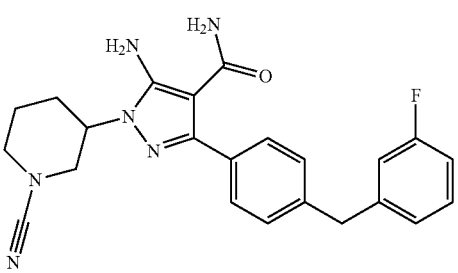 [SMILES: N#CN1CCCC(n2nc(-c3ccc(Cc4cccc(F)c4)cc3)c(C(N)=O)c2N)C1]

The title compound was prepared analogous to 5-amino-3-(4-benzylphenyl)-1-(1-cyanopiperidin-3-yl)-1H-pyrazole-4-carboxamide (Example 67) employing (3-fluorobenzyl) zinc chloride. MS (M+H) m/z 419. $^1$H NMR (CDCl$_3$, 400 MHz) δ 1.78-1.88 (m, 2H), 2.05-2.11 (m, 2H), 2.93-3.00 (m, 1H), 3.35-3.53 (m, 3H), 3.94 (s, 2H), 3.98-4.06 (m, 1H), 5.09-5.19 (s, 2H), 5.49 (s, 2H), 6.80-6.92 (m, 3H), 7.21 (d, 2H), 7.38 (d, 2H).

Example 78

(R)-5-amino-1-(1-cyanopiperidin-3-yl)-3-(4-(3-fluorobenzyl)phenyl)-1H-pyrazole-4-carboxamide

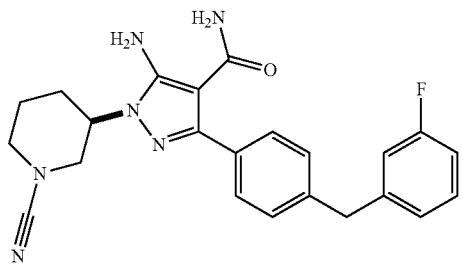

rac-5-amino-1-(1-cyanopiperidin-3-yl)-3-[4-(2-fluorobenzyl)phenyl]-1H-pyrazole-4-carboxamide (prepared as described in Example 77) was chirally separated by supercritical fluid chromatography (ChiralPak AD 5μ, 21×250 mm col, 27% MeOH, 70 mL/min). Isolation of the first eluting isomer afforded the title compound. MS (M+H) m/z 419. $^1$H NMR (400 MHz, DMSO-d) δ ppm 7.38-7.44 (m, 2H), 7.29-7.38 (m, 3H), 7.07-7.13 (m, 3H), 6.99-7.06 (m, 1H), 6.46 (s, 2H), 4.31-4.41 (m, 1H), 4.01 (s, 2H), 3.49 (dd, J=12.1, 4.5 Hz, 1H), 3.36 (br. s., 1H), 3.05 (td, J=12.4, 2.5 Hz, 1H), 1.76-1.98 (m, 3H), 1.60-1.75 (m, 1H).

Example 79

(S)-5-amino-1-(1-cyanopiperidin-3-yl)-3-(4-(3-fluorobenzyl)phenyl)-1H-pyrazole-4-carboxamide

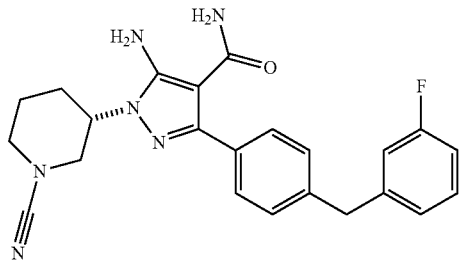

rac-5-amino-1-(1-cyanopiperidin-3-yl)-3-[4-(2-fluorobenzyl)phenyl]-1H-pyrazole-4-carboxamide (prepared as described in Example 77) was chirally separated by supercritical fluid chromatography (ChiralPak AD 5μ, 21×250 mm col, 27% MeOH, 70 mL/min). Isolation of the second eluting isomer afforded the title compound. MS (M+H) m/z 419. $^1$H NMR (400 MHz, DMSO-d) δ ppm 7.38-7.44 (m, 2H), 7.29-7.38 (m, 3H), 7.07-7.13 (m, 3H), 6.99-7.06 (m, 1H), 6.46 (s, 2H), 4.31-4.41 (m, 1H), 4.01 (s, 2H), 3.49 (dd, J=12.1, 4.5 Hz, 1H), 3.36 (br. s., 1H), 3.05 (td, J=12.4, 2.5 Hz, 1H), 1.76-1.98 (m, 3H), 1.60-1.75 (m, 1H)

Example 80

5-amino-1-(1-cyanopiperidin-3-yl)-3-[4-(2,4-difluorobenzyl)phenyl]-1H-pyrazole-4-carboxamide

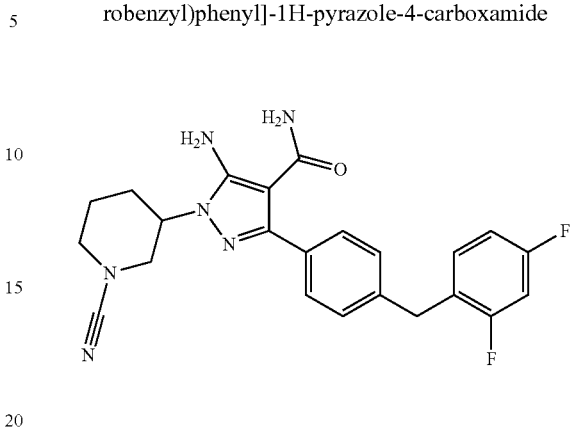

The title compound was prepared analogous to 5-amino-3-(4-benzylphenyl)-1-(1-cyanopiperidin-3-yl)-1H-pyrazole-4-carboxamide (Example 67) employing (3-fluorobenzyl) zinc chloride. MS (M+H) m/z 437. $^1$H NMR (CDCl$_3$, 400 MHz) δ 1.80-1.84 (m, 2H), 2.04-2.08 (m, 2H), 2.93-3.00 (m, 1H), 3.35-3.53 (m, 3H), 3.918 (s, 2H), 3.98-4.05 (m, 1H), 5.14 (s, 2H), 5.49 (s, 2H), 6.72-6.76 (m, 2H), 7.03-7.09 (m, 1H), 7.22 (d, 2H), 7.37 (d, 2H).

Example 81

(R)-5-amino-1-(1-cyanopiperidin-3-yl)-3-(4-(2,4-difluorobenzyl)phenyl)-1H-pyrazole-4-carboxamide

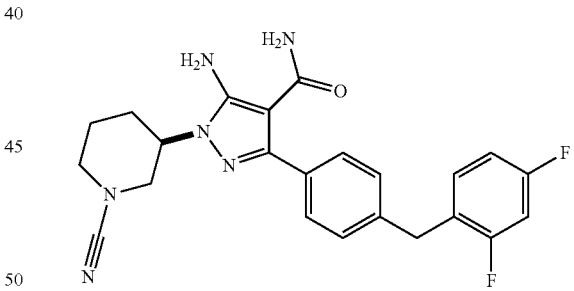

rac-5-amino-1-(1-cyanopiperidin-3-yl)-3-[4-(2,4-difluorobenzyl)phenyl]-1H-pyrazole-4-carboxamide (prepared as described in Example 80) was chirally separated by supercritical fluid chromatography (ChiralPak AD 5μ, 21×250 mm col, 27% MeOH, 70 mL/min). Isolation of the first eluting isomer afforded the title compound. MS (M+H) m/z 437. $^1$H NMR (400 MHz, DMSO-d$_6$) δ ppm 7.35-7.44 (m, 3H), 7.27 (d, J=7.8 Hz, 2H), 7.18-7.25 (m, 1H), 7.05 (tt, J=8.5, 1.4 Hz, 1H), 6.46 (s, 2H), 4.30-4.40 (m, 1H), 3.99 (s, 2H), 3.49 (dd, J=12.4, 4.3 Hz, 1H), 3.26-3.38 (m, 4H), 3.04 (td, J=12.4, 2.8 Hz, 1H), 1.77-1.99 (m, 3H), 1.70 (tt, J=12.8, 4.0 Hz, 1H).

Example 82

(S)-5-amino-1-(1-cyanopiperidin-3-yl)-3-(4-(2,4-difluorobenzyl)phenyl)-1H-pyrazole-4-carboxamide

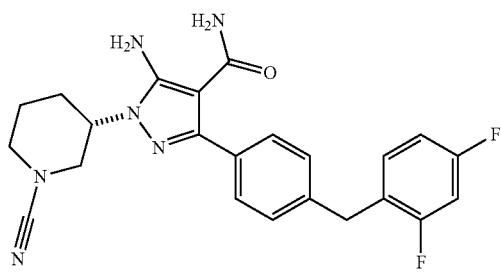

rac-5-amino-1-(1-cyanopiperidin-3-yl)-3-[4-(2,4-difluorobenzyl)phenyl]-1H-pyrazole-4-carboxamide (prepared as described in Example 80) was chirally separated by supercritical fluid chromatography (ChiralPak AD 5μ, 21×250 mm col, 27% MeOH, 70 mL/min). Isolation of the second eluting isomer afforded the title compound. MS (M+H) m/z 437. $^1$H NMR (400 MHz, DMSO-d) δ ppm 7.35-7.44 (m, 3H), 7.27 (d, J=7.8 Hz, 2H), 7.18-7.25 (m, 1H), 7.05 (tt, J=8.5, 1.4 Hz, 1H), 6.46 (s, 2H), 4.30-4.40 (m, 1H), 3.99 (s, 2H), 3.49 (dd, J=12.4, 4.3 Hz, 1H), 3.26-3.38 (m, 4H), 3.04 (td, J=12.4, 2.8 Hz, 1H), 1.77-1.99 (m, 3H), 1.70 (tt, J=12.8, 4.0 Hz, 1H).

Example 83

5-amino-1-(1-cyanopiperidin-3-yl)-3-[4-(3,4-difluorobenzyl)phenyl]-1H-pyrazole-4-carboxamide

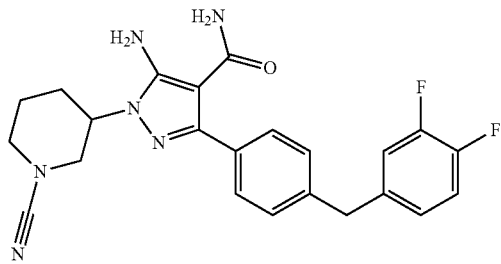 [SMILES: N#CN1CCCC(n2nc(-c3ccc(Cc4ccc(F)c(F)c4)cc3)c(C(N)=O)c2N)C1]

The title compound was prepared analogous to 5-amino-3-(4-benzylphenyl)-1-(1-cyanopiperidin-3-yl)-1H-pyrazole-4-carboxamide (Example 67) employing (3,4-difluorobenzyl)zinc chloride. MS (M+H) m/z 437. $^1$H NMR (CDCl$_3$, 400 MHz) δ 7.39 (d, 2H), 7.18 (d, 2H), 6.84-7.04 (m, 2H), 5.67 (s, 2H), 5.26 (s, 2H), 4.10-4.11 (m, 1H), 3.89 (s, 2H), 3.34-3.54 (m, 3H), 2.93-3.00 (m, 1H), 2.07-2.08 (m, 2H), 1.71-1.83 (m, 2H).

Example 84

(R)-5-amino-1-(1-cyanopiperidin-3-yl)-3-(4-(3,4-difluorobenzyl)phenyl)-1H-pyrazole-4-carboxamide

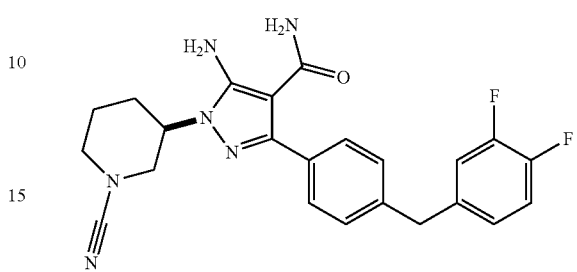

rac-5-amino-1-(1-cyanopiperidin-3-yl)-3-(4-(3,4-difluorobenzyl)phenyl)-1H-pyrazole-4-carboxamide (prepared as described in Example 83) was chirally separated by supercritical fluid chromatography (ChiralPak AD 5μ, 21×250 mm col, 27% MeOH, 70 mL/min). Isolation of the first eluting isomer afforded the title compound. MS (M+H) m/z 437. $^1$H NMR (400 MHz, DMSO-d$_6$) δ ppm 7.29-7.44 (m, 6H), 7.11 (ddd, J=6.3, 4.2, 2.4 Hz, 1H), 6.46 (s, 2H), 4.31-4.41 (m, 1H), 3.98 (s, 2H), 3.49 (dd, J=12.1, 4.3 Hz, 1H), 3.30-3.38 (s, 4H), 3.05 (td, J=12.4, 2.7 Hz, 1H), 1.76-1.98 (m, 3H), 1.64-1.76 (m, 1H).

Example 85

(S)-5-amino-1-(1-cyanopiperidin-3-yl)-3-(4-(3,4-difluorobenzyl)phenyl)-1H-pyrazole-4-carboxamide

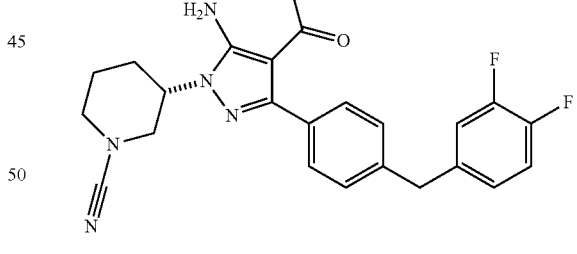

rac-5-amino-1-(1-cyanopiperidin-3-yl)-3-(4-(3,4-difluorobenzyl)phenyl)-1H-pyrazole-4-carboxamide (prepared as described in Example 83) was chirally separated by supercritical fluid chromatography (ChiralPak AD 5μ, 21×250 mm col, 27% MeOH, 70 mL/min). Isolation of the second eluting isomer afforded the title compound. MS (M+H) m/z 437. $^1$H NMR (400 MHz, DMSO-d$_6$) δ ppm 7.29-7.44 (m, 6H), 7.11 (ddd, J=6.3, 4.2, 2.4 Hz, 1H), 6.46 (s, 2H), 4.31-4.41 (m, 1H), 3.98 (s, 2H), 3.49 (dd, J=12.1, 4.3 Hz, 1H), 3.30-3.38 (s, 4H), 3.05 (td, J=12.4, 2.7 Hz, 1H), 1.76-1.98 (m, 3H), 1.64-1.76 (m, 1H).

Example 86

5-amino-3-[4-(4-chlorobenzyl)phenyl]-(1-cyanopiperidin-3-yl)-1H-pyrazole-4-carboxamide

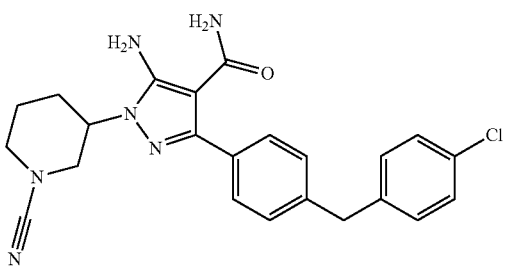

Step 1: preparation of 3-[5-acetylamino-4-cyano-3-(4-iodophenyl)-pyrazol-1-yl]-piperidine-1-carboxylic acid benzyl ester. To the stirred suspension of benzyl 3-[5-amino-4-cyano-3-(4-iodophenyl)-1H-pyrazol-1-yl]piperidine-1-carboxylate (100 g, 189.8 mmol) (Example 43, Step 4) in dichloromethane (1.6 L) was added acetyl chloride (145 mL, 1.897 mol) drop wise at 0° C. under nitrogen atmosphere. After 30 min, freshly distilled triethylamine (49.1 mL, 354.8 mmol) was added drop wise at 0° C. and the resulting mixture was stirred at room temperature for 16 hours. The reaction mixture was quenched with saturated sodium-bicarbonate solution and the aqueous part was separated. The aqueous layer was back extracted with dichloromethane (500 mL) and the combined organic layers were washed with water followed by brine and dried over sodium sulfate and concentrated to afford the title compound (70 gm, 65%) as light yellow solid. MS (M+H) m/z 570. $^1$H NMR (400 MHz, DMSO-d6) δ 10.56 (s, 1H), 7.89 (d, J=8.0 Hz, 2H), 7.63 (d, J=8.0 Hz, 2H), 7.33 (br, 5H), 5.05 (s, 2H), 4.29 (br, 1H), 4.08 (m, 1H), 3.88 (m, 1H), 3.0 (m, 1H), 2.13 (s, 3H), 1.99 (m, 3H), 1.54-1.51 (m, 1H).

Step 2: preparation of benzyl 3-{5-acetamido-3-[4-(4-chlorobenzyl)phenyl]-4-cyano-1H-pyrazol-1-yl}piperidine-1-carboxylate. To a solution of benzyl 3-[5-acetamido-4-cyano-3-(4-iodophenyl)-1H-pyrazol-1-yl]piperidine-1-carboxylate (0.41 g, 0.73 mmol), palladium acetate (12 mg, 0.053 mmol), 2-dicyclohexylphosphino-2',6'-dimethoxybiphenyl (18 mg, 0.043 mmol) and lithium chloride (80 mg, 1.89 mmol) in tetrahydrofuran (6 mL) at 0° C. was added a solution of 4-chlorobenzyl zinc chloride in tetrahydrofuran (3.4 mL, 1.7 mmol). The reaction was allowed to stir at 0° C. for 20 min, then allowed to stir at ambient temperature for 16 h. A second aliquot of 4-chlorobenzyl zinc chloride solution (3 mL) was added and the reaction was then allowed to stir for an additional 27 h, after which it was quenched with saturated aqueous ammonium chloride, and extracted into ethyl acetate. The combined organic layers were washed with brine, dried over magnesium sulfate and concentrated in vacuo. The crude residue was then purified by silica gel column chromatography (60% ethyl acetate/heptanes) to afford the title compound as a brown oil. MS (M+H) m/z 568.

Step 3: preparation of 5-amino-3-[4-(4-chlorobenzyl)phenyl]-1-piperidin-3-yl-H-pyrazole-4-carboxamide. Prepared according to the procedure described for 5-amino-3-(4-phenoxyphenyl)-1-piperidin-3-yl-1H-pyrazole-4-carboxylic acid amide (Example 1, Step 11) from benzyl 3-{5-acetamido-3-[4-(4-chlorobenzyl)phenyl]-4-cyano-1H-pyrazol-1-yl}piperidine-1-carboxylate to afford the title compound, which was taken on to the next step without purification. MS (M+H) m/z 410.

Step 4: preparation of 5-amino-3-[4-(4-chlorobenzyl)phenyl]-1-(1-cyanopiperidin-3-yl)-1H-pyrazole-4-carboxamide. Prepared according to the procedure described for 5-amino-1-(1-cyanopiperidin-3-yl)-3-(4-phenoxyphenyl)-1H-pyrazole carboxamide (Example 1, Step 12) from 5-amino-3-[4-(4-chlorobenzyl)phenyl]-1-piperidin-3-yl-1H-pyrazole-4-carboxamide to afford the title compound. MS (M+H) m/z 435. $^1$H NMR (DMSO-d6) δ 7.39 (d, J=8.3 Hz, 2H), 7.34 (d, J=8.3 Hz, 2H), 7.30-7.25 (m, 4H), 6.43 (s, 2H), 4.38-4.31 (m, 1H), 3.97 (s, 2H), 3.52-3.45 (m, 1H), 3.37-3.29 (m, 2H), 3.07-3.00 (m, 1H), 1.99-1.91 (m, 1H), 1.87-1.79 (m, 2H), 1.73-1.64 (m, 1H).

Example 87

5-Amino-3-(4-benzoyl-phenyl)-1-(1-cyano)-piperidin-3-yl-1H-pyrazole-4-carboxylic acid amide

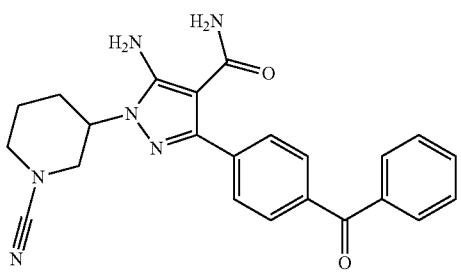 [SMILES: N#CN1CCCC(n2nc(-c3ccc(C(=O)c4ccccc4)cc3)c(C(N)=O)c2N)C1]

Step 1: preparation of 4-benzoylbenzoyl chloride. Oxalyl chloride (1.3 mL, 15 mmol) was added dropwise to a solution of 4-benzoylbenzoic acid (2.2 gm, 10 mmol) in tetrahydrofuran, with few drops of N,N-dimethylformamide, over 15 min. The mixture was stirred at room temperature for 1 h and then concentrated under reduce pressure to afford the title compound (2.4 gm).

Step 2: preparation of 2-((4-benzoylphenyl)(methoxy)methylene)malononitrile. To a suspension of sodium hydride (640 mg, 16 mmol) in dry tetrahydrofuran (10 mL) at 0° C. was added a solution of malononitrile (528 mg, 8 mmol) in tetrahydrofuran (5 mL) dropwise over 15 min, under nitrogen atmosphere. 4-Benzoylbenzoyl chloride (2.45 g, mmol) in tetrahydrofuran was then added dropwise followed by dimethyl sulfate (528 mg, 8 mmol). The mixture was then heated to reflux for 18 h. The reaction mixture was cooled to room temperature and quenched with aqueous ammonium chloride and extracted with ethyl acetate (3×). The combined organic layers were washed with brine, dried over sodium sulfate, and concentrated. The residue was purified by silica gel column chromatography (heptane/ethyl acetate) to afford the title compound (700 mg, 30%) as an off-white solid. MS (M+H) m/z 289.2.

Step 3: preparation of benzyl 3-(5-amino-3-(4-benzoylphenyl)-4-cyano-1H-pyrazol-1-yl)piperidine-1-carboxylate. Benzyl 3-hydrazino-piperidine-1-carboxylate (Example 1, Step 8) (694 mg, 2.43 mmol) and triethylamine (1.2 mL, 8.5 mmol) were added to a solution of 2-((4-benzoylphenyl)(methoxy)methylene)malononitrile (700 mg, 2.43 mmol) in ethanol (20 mL). The mixture was heated to 70° C. and stirred overnight. After cooling to room temperature, the solution was partitioned between ethyl acetate and water.

The aqueous layer was extracted with ethyl acetate (3×). The combined organic layers washed with brine, dried over sodium sulfate, and concentrated to afford the title compound (1.1 g, 90%). MS (M+H) m/z 506.4.

Step 4: preparation of 5-amino-3-(4-benzoyl-phenyl)-1-(1-cyano)-piperidin-3-yl-1H-pyrazole-4-carboxylic acid amide. To a into a 25 mL SS Parr autoclave was added benzyl 3-(5-amino-3-(4-benzoylphenyl)-4-cyano-1H-pyrazol-1-yl)piperidine-1-carboxylate (2 g, 4 mmol) and ethanol (3 mL). A solution of sodium hydroxide (2.5 N, 10 mmol, 4 mL). The autoclave was sealed and heated until internal temperature reached 150° C. for 15 min. After cooling to room temperature and the mixture was partitioned between water and ethyl acetate. The aqueous layer was extracted with ethyl acetate (3×). The combined organic layers were washed with brine, dried over sodium sulfate, and concentrated to afford the title compound (1.15 g, 76%). MS (M+H) m/z 390.3.

Step 5: preparation of 5-amino-3-(4-benzoyl-phenyl)-1-(1-cyano)-piperidin-3-yl-1H-pyrazole-4-carboxylic acid amide. Cyanogen bromide (38 mg, 0.36 mmol) and potassium carbonate (62 mg, 0.45 mmol) were added to a solution of 5-amino-3-(4-benzoyl-phenyl)-1-(1-cyano)-piperidin-3-yl-1H-pyrazole-4-carboxylic acid amide (117 mg, 0.3 mmol) in N,N-dimethylformamide (4 mL). The mixture was heated to 50° C. and stirred for 2 hr. After cooling to room temperature, the mixture was partitioned between ethyl acetate and water. The aqueous layer was extracted with ethyl acetate (3×). The combined organic layers were washed with brine, dried over sodium sulfate, and concentrated. The crude product was purified by reverse phase preparative HPLC to afford the title compound. MS (M+H) m/z 515.3. $^1$H NMR (DMSO-d6) δ 5 7.76-7.86 (m, 4H), 7.67-7.76 (m, 3H), 7.54-7.65 (m, 2H), 6.44 (s, 2H), 4.33-4.49 (m, 1H), 3.55 (dd, J=12.1, 3.9 Hz, 1H), 3.02-3.17 (m, 1H), 1.81-2.07 (m, 3H), 1.67-1.81 (m, 1H).

Example 88

5-amino-1-(1-cyanopiperidin-3-yl)-3-{4-[hydroxy(phenyl)methyl]phenyl}-1H-pyrazole-4-carboxamide

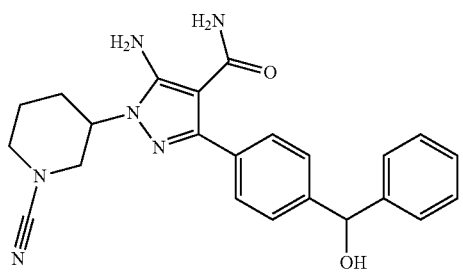 [SMILES: N#CN1CCCC(n2nc(-c3ccc(C(O)c4ccccc4)cc3)c(C(N)=O)c2N)C1]

Step 1: preparation of 5-amino-3-{4-[hydroxy(phenyl)methyl]phenyl}-1-piperidin-3-yl-1H-pyrazole-4-carbonitrile. Methanol (20 mL) was added to benzyl 3-(5-amino-3-(4-benzoylphenyl)-4-cyano-1H-pyrazol-1-yl)piperidine-1-carboxylate (Example 87, Step 3) and 10% palladium on carbon in a Fisher-Porter bottle. A few drops of acetic acid were added and the bottle was charged with hydrogen gas (43 psi). The mixture was stirred 18 h at room temperature and then filtered through Celite. The filtrate was concentrated to afford the title compound.

Step 2: preparation of 5-amino-3-(4-(hydroxy(phenyl)methyl)phenyl)-1-(piperidin-3-yl)-1H-pyrazole-4-carboxamide. The title compound was prepared analogous to 5-amino-3-(4-benzoyl-phenyl)-1-(1-cyano)-piperidin-3-yl-1H-pyrazole-4-carboxylic acid amide (Example 87, Step 4) employing 5-amino-3-{4-[hydroxy(phenyl)methyl]phenyl}-1-piperidin-3-yl-1H-pyrazole-4-carbonitrile. MS (M+H) m/z 392.3.

Step 3: preparation of 5-amino-1-(1-cyanopiperidin-3-yl)-3-{4-[hydroxy(phenyl)methyl]phenyl}-1H-pyrazole-4-carboxamide. The title compound was prepared analogous to 5-amino-3-(4-benzoyl-phenyl)-1-(1-cyano)-piperidin-3-yl-1H-pyrazole-4-carboxylic acid amide (Example 87, Step 5) employing 5-amino-3-(4-(hydroxy(phenyl)methyl)phenyl)-1-(piperidin-3-yl)-1H-pyrazole-4-carboxamide. MS (M+H) m/z 417.3. $^1$H NMR (DMSO-d6) δ 7.36-7.45 (m, 6H), 7.34-7.49 (m, 6H), 7.29 (t, J=7.5 Hz, 2H), 7.25-7.34 (m, 2H), 7.17-7.23 (m, 1H), 7.14-7.24 (m, 1H), 6.45 (s, 2H), 6.36-6.52 (m, 2H), 5.94 (d, J=4.1 Hz, 1H), 5.84-6.02 (m, 1H), 5.72 (d, J=4.0 Hz, 1H), 5.64-5.79 (m, 1H), 4.29-4.39 (m, 1H), 4.23-4.43 (m, 1H), 3.47 (dd, J=12.1, 4.0 Hz, 1H), 3.40-3.54 (m, 1H), 3.25-3.31 (m, 1H), 2.99-3.06 (m, 1H), 2.99 (bs, 1H), 1.88 (d, J=3.7 Hz, 1H), 1.76-1.86 (m, 2H), 1.74-1.98 (m, 3H), 1.62-1.73 (m, 1H), 1.59-1.74 (m, 1H).

Example 89

5-amino-1-(1-cyanopiperidin-3-yl)-3-(3-phenoxyphenyl)-1H-pyrazole-4-carboxamide

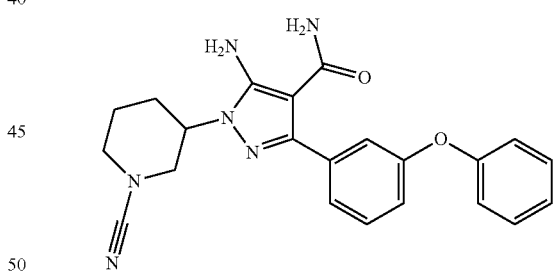

2-(Methoxy(3-phenoxyphenyl)methylene)malononitrile was prepared analogous to 4-(4-chloro-3-methylphenoxy)phenyl](methoxy)methylene}malononitrile (Example 40, step 4) from commercially available 3-phenoxy benzoic acid. The title compound was then prepared analogous to 5-amino-1-(1-cyanopiperidin-3-yl)-3-(4-phenoxyphenyl)-1H-pyrazole carboxamide (Example 1) to afford the title compound (23 mg, 28%). MS (M+H) m/z 403. $^1$H-NMR (DMSO-d6) δ 7.36-7.46 (M, 3H), 7.26 (d, J=7.69 Hz, 1H), 7.11-7.17 (m, 1H), 7.01-7.08 (m, 4H), 6.42 (s, 2H), 4.30-4.38 (m, 1H), 3.47 (dd, J=11.90, 3.84 Hz, 1H), 3.27-3.32 (m, 1H), 3.05 (td, J=12.5, 2.2 Hz, 1H), 1.74-2.00 (m, 4H), 1.62-1.73 (m, 1H).

Example 90

5-amino-1-[(3R)-1-cyanopiperidin-3-yl]-3-(3-phenoxyphenyl)-1H-pyrazole-4-carboxamide

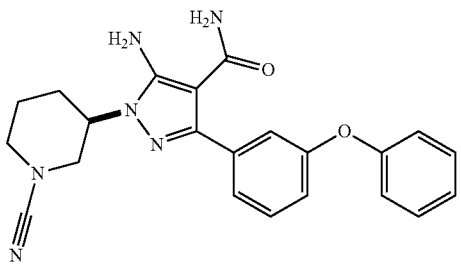

rac-5-amino-1-(1-cyanopiperidin-3-yl)-3-(3-phenoxyphenyl)-1H-pyrazole-4-carboxamide (prepared as described in Example 89) was chirally separated by supercritical fluid chromatography (ChiralPak 5 u, 21×250 mm, modifier 30% MeOH, flow rate 70 mL/min). Isolation of the first eluting isomer afforded the title compound as a white solid. MS (M+H): 403. $^1$H NMR (400 MHz, CDCl$_3$) δ ppm 7.32-7.46 (m, 3H) 7.21-7.27 (m, 1H), 7.12-7.17 (m, 2H), 7.00-7.08 (m, 3H), 5.72 (s, 2H), 5.31 (bs., 2H), 4.08-4.21 (m, 1H), 3.39-3.62 (m, 3H), 2.98-3.11 (m, 1H), 2.07-2.18 (m, 2H), 1.82-1.94 (m, 2H).

Example 91

5-amino-1-[(3S)-1-cyanopiperidin-3-yl]-3-(3-phenoxyphenyl)-1H-pyrazole-4-carboxamide

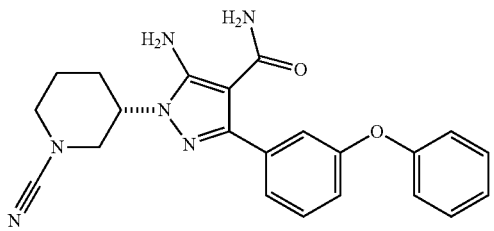

rac-5-amino-1-(1-cyanopiperidin-3-yl)-3-(3-phenoxyphenyl)-1H-pyrazole-4-carboxamide (prepared as described in Example 89) was chirally separated by supercritical fluid chromatography (ChiralPak 5 u, 21×250 mm, modifier 30% MeOH, flow rate 70 mL/min). Isolation of the second eluting isomer afforded the title compound as a white solid. MS (M+H) m/z 403. $^1$H NMR (400 MHz, CDCl$_3$) δ ppm 7.31-7.46 (m, 3H), 7.21-7.28 (m, 1H), 7.12-7.18 (m, 2H), 7.00-7.09 (m, 3H), 5.72 (s, 2H), 5.31 (bs., 2H), 4.09-4.21 (m, 1H), 3.38-3.62 (m, 3H), 2.97-3.11 (m, 1H), 2.08-2.18 (m, 2H), 1.82-1.95 (m, 2H).

Example 92

5-amino-3-[3-(4-chlorobenzyl)phenyl]-1-(1-cyanopiperidin-3-yl)-1H-pyrazole-4-carboxamide

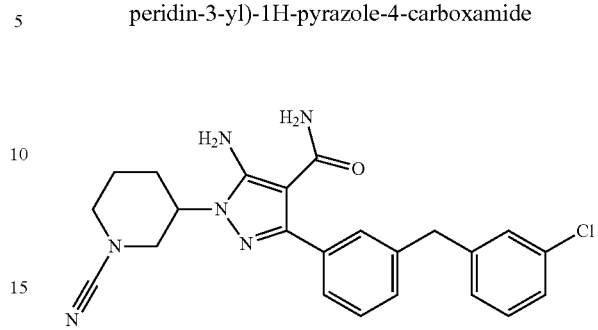

Step 1: preparation of 2-((3-iodophenyl)(methoxy)methylene)malononitrile. Prepared analogous to 2-[(4-phenoxyphenyl)-methoxy-methylene]malononitrile (Example 1, step 3) from 3-iodo benzoic acid to afford the title compound. $^1$H NMR δ (300 MHz, DMSO-d6): 8.05 (t, J=18.3 Hz, 2H), 7.70 (d, J=8.7 Hz, 1H), 7.42 (t, J=17.4 Hz, 1H), 3.42 (s, 3H).

Step 2: preparation of benzyl 3-[5-amino-4-cyano-3-(3-iodophenyl)-1H-pyrazol-1-yl]piperidine-1-carboxylate. Prepared analogous to benzyl 3-[5-amino-4-cyano-3-(4-phenoxy-phenyl)-pyrazol-1-yl]-piperidine-1-carboxylate (Example 1, Step 9) from 2-((3-iodophenyl)(methoxy)methylene)malononitrile and benzyl 3-hydrazino-piperidine-1-carboxylate (Example 1, Step 8) to afford the title compound (80 g, 62%). MS (M+H) m/z 528. $^1$H NMR (300 MHz, DMSO-d6) δ 8.12 (t, J=3.6 Hz, 1H), 7.75-7.81 (m, J=18 Hz, 2H), 7.24-7.29 (m, J=15 Hz, 5H), 6.85 (s, 1H), 5.07 (bs, 2H), 4.27 (t, J=27 Hz, 1H), 3.98 (dd, J=41.7 Hz, 2H), 2.99 (t, J=21 Hz, 1H), 1.83-1.98 (m, J=45 Hz, 3H), 1.51 (d, J=12 Hz, 1H).

Step 3: preparation of benzyl 3-(5-acetamido-4-cyano-3-(3-iodophenyl)-1H-pyrazol-1-yl)piperidine-1-carboxylate. Prepared analogous to 3-[5-acetylamino-4-cyano-3-(4-iodophenyl)-pyrazol-1-yl]-piperidine-1-carboxylic acid benzyl ester (Example 86, Step 1) employing benzyl 3-[5-amino-4-cyano-3-(3-iodophenyl)-1H-pyrazol-1-yl]piperidine-1-carboxylate to afford the title compound. MS (M+H) m/z 570. $^1$H NMR (400 MHz, DMSO-d6) δ 8.24 (s, 1H), 7.89 (d, J=8 Hz, 1H), 7.74 (d, J=8 Hz, 1H), 7.74 (s, 5H), 7.17 (t, J=16 Hz, 1H), 5.13 (s, 2H), 4.07-4.27 (dd, J=84 Hz, 3H), 3.33 (bs, 1H), 2.96 (d, J=12 Hz, 1H), 1.91 (d, 1H, J=12 Hz), 1.73 (s, 2H), 1.60 (d, J=16 Hz, 1H).

Step 4: preparation of benzyl 3-{5-acetamido-3-[3-(4-chlorobenzyl)phenyl]-4-cyano-1H-pyrazol-1-yl}piperidine-1-carboxylate. To a solution of benzyl 3-(5-acetamido-4-cyano-3-(3-iodophenyl)-1H-pyrazol-1-yl)piperidine-1-carboxylate (498 mg, 0.875 mmol), 2'-dicyclohexylphosphino-2,6-dimethyoxybiphenyl (29.6 mg, 0.07 mmol), and tris(dibenzylideneacetone)dipalladium (55.8 mg, 0.061 mmol) in tetrahydrofuran (5 mL), was added a 0.5M solution of 4-chlorobenzylzinc chloride in tetrahydrofuran (8.0 mL) under nitrogen. The reaction was allowed to stir at ambient temperature over 16 h, after which water (10 mL) was added and the desired product was extracted into dichloromethane (2×15 mL). The combined organic layers were concentrated in vacuo, then purified by silica gel column chromatography to afford the title compound as a light yellow solid (430 mg, 86%). MS (M+H) m/z 568.

Step 5: preparation of 5-amino-3-[3-(4-chlorobenzyl)phenyl]-1-piperidin-3-yl-H-pyrazole-4-carboxamide. A solution of benzyl 3-{5-acetamido-3-[3-(4-chlorobenzyl)phenyl]-4-cyano-1H-pyrazol-1-yl}piperidine-1-carboxylate (430 mg, 0.74 mmol) and sodium hydroxide (888 mg, 22.2 mmol) in 33% aqueous ethanol (6 mL) was heated to 165° C. After 50 min. solvents were removed in vacuo to afford the title compound as a white solid. MS (M+H) m/z 410.

Step 6: preparation of 5-amino-3-[2-chloro-4-(4-fluorophenoxy)phenyl]-1-(1-cyanopiperidin-3-yl)-1H-pyrazole-4-carboxamide. A solution of 5-amino-3-[3-(4-chlorobenzyl)phenyl]-1-piperidin-3-yl-H-pyrazole-4-carboxamide (100 mg, 0.24 mmol), cyanogen bromide (40 mg, 0.37 mmol), and sodium carbonate (78 mg, 0.73 mmol) in N,N-dimethylformamide (5 mL) was allowed to stir at ambient temperature over 16 h. The reaction mixture was then diluted with ethyl acetate and treated with saturated aqueous ammonium chloride. The layers were separated and the organic layer was washed with water, saturated aqueous sodium chloride, then dried over sodium sulfate, and concentrated in vacuo. The crude oil was purified by silica gel column chromatography (ethyl acetate/hexane) to afford the title compound as a light yellow solid (31 mg, 29%). MS (M+H) m/z 435. $^1$H NMR (400 MHz, CDCl$_3$) δ ppm: 7.60-7.75 (m, 2H), 7.56-7.55 (m, 1H), 7.43-7.50 (m, 1H), 7.18-7.29 (m, 2H), 7.12 (d, J=8.28 Hz, 2H), 5.62-5.74 (s, 2H), 5.20 (br. s., 2H), 4.08-4.20 (m, 1H), 3.98 (s, 2H), 3.96-4.02 (m, 1H), 3.36-3.62 (m, 4H), 3.04 (td, J=12.23, 3.89 Hz, 1H), 2.14 (dq, J=8.91, 4.56 Hz, 1H), 1.83-1.94 (m, 1H).

Example 93

5-amino-1-(1-cyanopiperidin-3-yl)-3-[3-(4-fluorobenzyl)phenyl]-1H-pyrazole-4-carboxamide

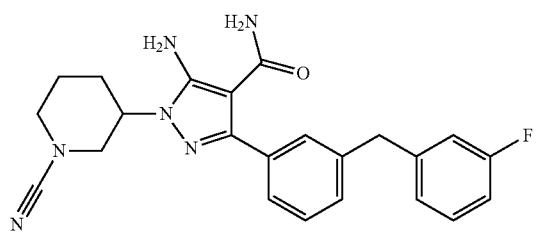 [SMILES: N#CN1CCCC(n2nc(-c3cccc(Cc4cccc(F)c4)c3)c(C(N)=O)c2N)C1]

Prepared according to the procedures described for 5-amino-3-[2-chloro-4-(4-fluorophenoxy)phenyl]-1-(1-cyanopiperidin-3-yl)-1H-pyrazole-4-carboxamide (Example 92) employing 4-fluorobenzylzinc chloride to afford the title compound. MS (M+H) m/z 418. $^1$H NMR (400 MHz, DMSO-d6) δ ppm 7.11-7.39 (m, 4H), 7.11 (t, J=8.35 Hz, 2H), 6.49 (s, 1H), 4.37 (t, J=10.40 Hz, 1H), 3.98 (s, 2H), 3.49 (d, J=8.8 Hz, 1H), 3.06 (t, J=12.1 Hz, 1H), 1.69-1.96 (m, 5H).

Example 94

5-Amino-1-(1-cyanopiperidin-3-yl)-3-(3-(4-fluorophenoxy)phenyl)-1H-pyrazole-4-carboxamide

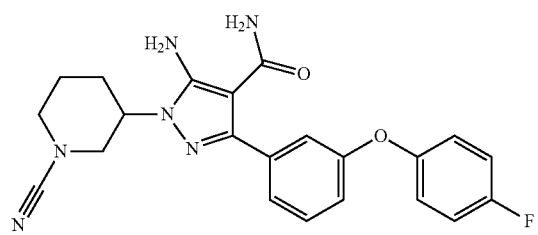 [SMILES: N#CN1CCCC(n2nc(-c3cccc(Oc4ccc(F)cc4)c3)c(C(N)=O)c2N)C1]

Step 1: preparation of benzyl 3-(5-acetamido-4-cyano-3-(3-(4-fluorophenoxy)phenyl)-1H-pyrazol-1-yl)piperidine-1-carboxylate. Cesium carbonate (81 mg, 250 μmol) and CuI (2.4 mg, 12.5 μmol) were added to a mixture of 4-fluorophenol (125 μmol) and benzyl 3-(5-acetamido-4-cyano-(3-iodophenyl)-1H-pyrazol-1-yl)piperidine-1-carboxylate (Example 92, step 3) (75 mg, 125 μmol) in N,N-dimethylacetamide (1 mL). A solution of 2,2,6,6-tetramethylheptane-3,5-dione (1.25 M, 100 μL) in anhydrous N,N-dimethylacetamide was added. The vial was shaken at 120° C. for 16 h. The mixture was filtered and the filtrate concentrated. The crude product was purified by preparative TLC to afford the title compound.

Step 2: preparation of 5-amino-3-(3-(4-fluorophenoxy)phenyl)-1-(piperidin-3-yl)-1H-pyrazole-4-carboxamide. A 5 N aqueous solution of NaOH (2.5 mL) was added to a solution of benzyl 3-(5-acetamido-4-cyano-3-(3-(4-fluorophenoxy)phenyl)-1H-pyrazol-1-yl)piperidine-1-carboxylate (125 μmol) in isopropanol (1 mL). The mixture was shaken at 155° C. for 48 h. Water (1 mL) was added and the mixture was extracted with EtOAc (3×1 mL). The combined organic layers were dried over magnesium sulfate, filtered, and concentrated to afford the title compound.

Step 3: preparation of 5-amino-1-(1-cyanopiperidin-3-yl)-3-(3-(4-fluorophenoxy)phenyl)-1H-pyrazole-4-carboxamide. 5-Amino-3-(3-(4-fluorophenoxy)phenyl)-1-(piperidin-3-yl)-1H-pyrazole-4-carboxamide (125 μmol) and K$_2$CO$_3$ (52 mg, 375 μmol) were added to a 0.5 M solution of cyanogen bromide (0.5 mL). The mixture was shaken at 30° C. for 16 h and then concentrated. The crude product was purified by reverse phase preparative HPLC to afford the title compound. MS (M+H) m/z 421.

Examples 95-106

The compounds in the table below were prepared analogous to 5-amino-1-(1-cyanopiperidin-3-yl)-3-(3-(4-fluorophenoxy)phenyl)-1H-pyrazole-4-carboxamide (Example 94).

| EX | Structure | Name | MS (M + 1) |
|---|---|---|---|
| 95 | 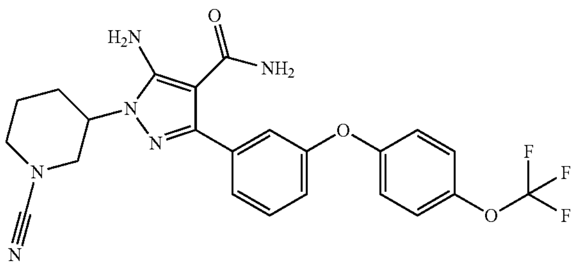 [SMILES: N#CN1CCCC(n2nc(-c3cccc(Oc4ccc(OC(F)(F)F)cc4)c3)c(C(N)=O)c2N)C1] | 5-Amino-1-(1-cyanopiperidin-3-yl)-3-{3-[4-(trifluoromethoxy)phenoxy]phenyl}-1H-pyrazole-4-carboxamide | 487 |
| 96 | 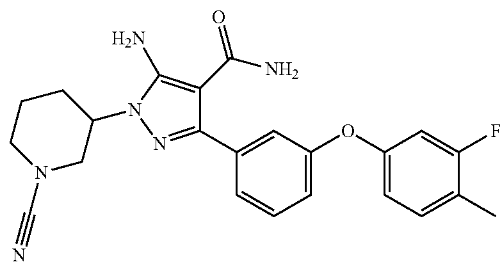 [SMILES: Cc1ccc(Oc2cccc(-c3nn(C4CCCN(C#N)C4)c(N)c3C(N)=O)c2)cc1F] | 5-amino-1-(1-cyanopiperidin-3-yl)-3-[3-(3-fluoro-4-methylphenoxy)phenyl]-1H-pyrazole-4-carboxamide | 435 |
| 97 | 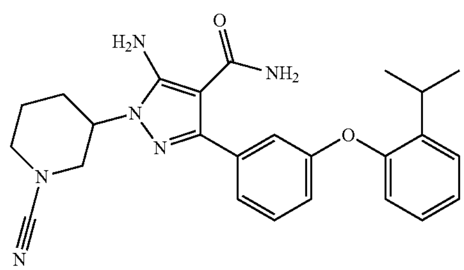 [SMILES: CC(C)c1ccccc1Oc1cccc(-c2nn(C3CCCN(C#N)C3)c(N)c2C(N)=O)c1] | 5-amino-1-(1-cyanopiperidin-3-yl)-3-[3-(2-isopropylphenoxy)phenyl]-1H-pyrazole-4-carboxamide | 445 |
| 98 | 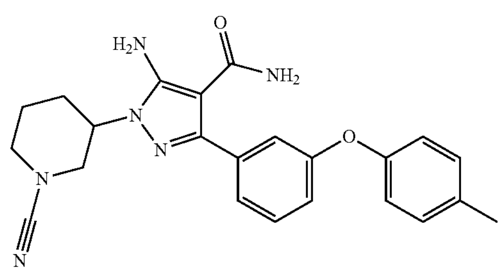 [SMILES: Cc1ccc(Oc2cccc(-c3nn(C4CCCN(C#N)C4)c(N)c3C(N)=O)c2)cc1] | 5-amino-1-(1-cyanopiperidin-3-yl)-3-[3-(4-methylphenoxy)phenyl]-1H-pyrazole-4-carboxamide | 417 |
| 99 | 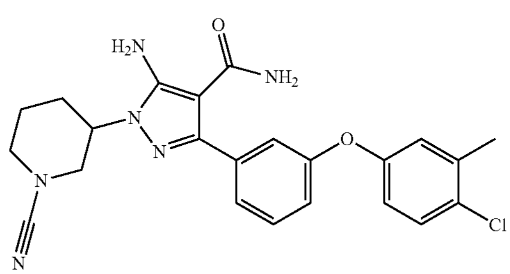 [SMILES: Cc1cc(Oc2cccc(-c3nn(C4CCCN(C#N)C4)c(N)c3C(N)=O)c2)ccc1Cl] | 5-amino-3-[3-(4-chloro-3-methylphenoxy)-phenyl]-1-(1-cyanopiperidin-3-yl)-1H-pyrazole-4-carboxamide | 451 |
| 100 | 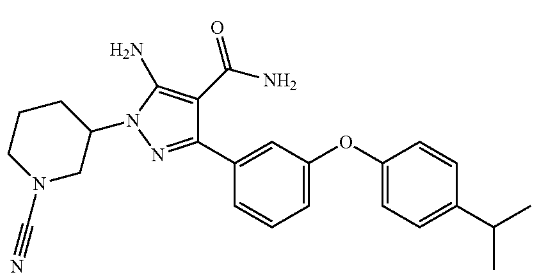 [SMILES: CC(C)c1ccc(Oc2cccc(-c3nn(C4CCCN(C#N)C4)c(N)c3C(N)=O)c2)cc1] | 5-amino-1-(1-cyanopiperidin-3-yl)-3-[3-(4-isopropylphenoxy)phenyl]-1H-pyrazole-4-carboxamide | 445 |

| EX | Structure | Name | MS (M + 1) |
|---|---|---|---|
| 101 | 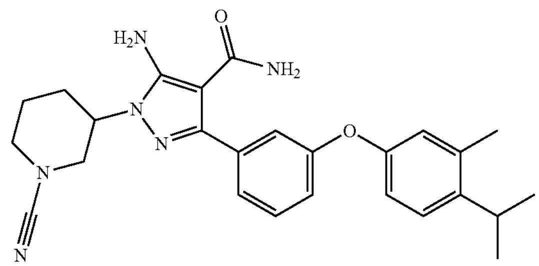 [SMILES: Cc1cc(Oc2cccc(-c3nn(C4CCCN(C#N)C4)c(N)c3C(N)=O)c2)ccc1C(C)C] | 5-amino-1-(1-cyanopiperidin-3-yl)-3-[3-(4-isopropyl-3-methylphenoxy)phenyl]-1H-pyrazole-4-carboxamide | 459 |
| 102 | 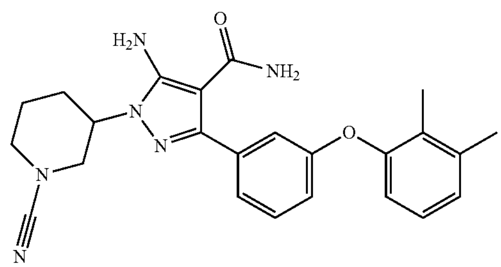 [SMILES: Cc1cccc(Oc2cccc(-c3nn(C4CCCN(C#N)C4)c(N)c3C(N)=O)c2)c1C] | 5-amino-1-(1-cyanopiperidin-3-yl)-3-[3-(3,4-dimethylphenoxy)phenyl]-1H-pyrazole-4-carboxamide | 431 |
| 103 | 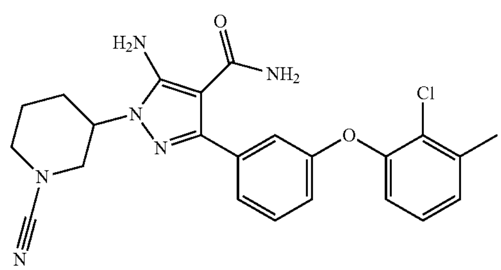 [SMILES: Cc1cccc(Oc2cccc(-c3nn(C4CCCN(C#N)C4)c(N)c3C(N)=O)c2)c1Cl] | 5-amino-3-[3-(3-chloro-4-methylphenoxy)-phenyl]-1-(1-cyanopiperidin-3-yl)-1H-pyrazole-4-carboxamide | 447 |
| 104 | 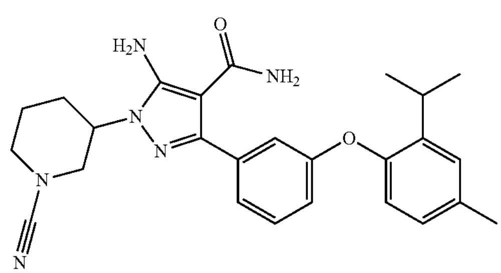 [SMILES: Cc1ccc(Oc2cccc(-c3nn(C4CCCN(C#N)C4)c(N)c3C(N)=O)c2)c(C(C)C)c1] | 5-amino-1-(1-cyanopiperidin-3-yl)-3-[3-(3-isopropyl-5-methylphenoxy)phenyl]-1H-pyrazole-4-carboxamide | 459 |
| 105 | 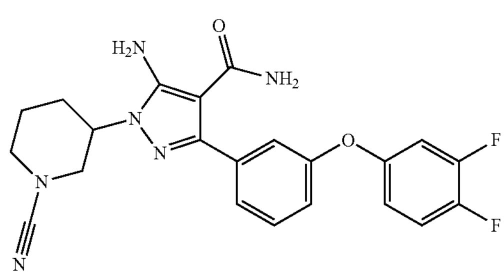 [SMILES: N#CN1CCCC(n2nc(-c3cccc(Oc4ccc(F)c(F)c4)c3)c(C(N)=O)c2N)C1] | 5-amino-1-(1-cyanopiperidin-3-yl)-3-[3-(3,4-difluorophenoxy)phenyl]-1H-pyrazole-4-carboxamide | 439 |

| EX | Structure | Name | MS (M + 1) |
|---|---|---|---|
| 106 | 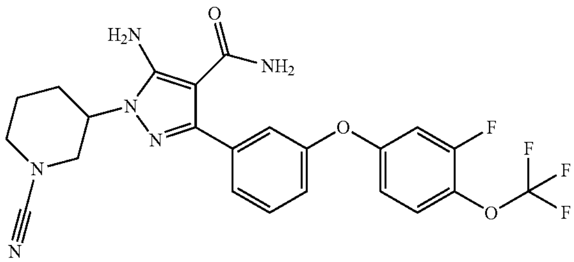 [SMILES: N#CN1CCCC(n2nc(-c3cccc(Oc4ccc(OC(F)(F)F)c(F)c4)c3)c(C(N)=O)c2N)C1] | 5-amino-1-(1-cyanopiperidin-3-yl)-3-{3-[3-fluoro-4-(trifluoromethoxy)phenoxy]phenyl}-1H-pyrazole-4-carboxamide | 505 |

Example 107

5-amino-1-(1-cyanopiperidin-3-yl)-3-(6-phenoxypyridin-3-yl)-1H-pyrazole-4-carboxamide

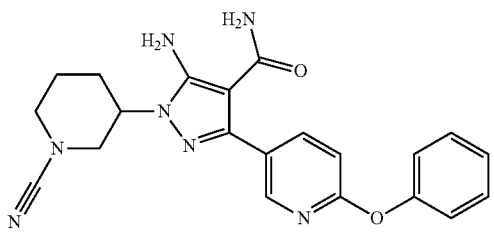 [SMILES: N#CN1CCCC(n2nc(-c3ccc(Oc4ccccc4)nc3)c(C(N)=O)c2N)C1]

Step 1: preparation of 2-((6-chloropyridin-3-yl)(methoxy)methylenemalononitrile. To a suspension of sodium hydride (454 mg, 11.4 mmol) in tetrahydrofuran (5 mL) at 0° C. was added malononitrile (474 mg, 7.10 mmol) followed by a solution of 6-chloronicotinyl chloride (1.0 g, 5.7 mmol) in tetrahydrofuran (5 mL) added drop wise over five minutes, and finally, dimethyl sulfate (0.55 mL, 5.68 mmol). The reaction was allowed to stir at reflux for 3 h, then at ambient temperature for 18 h, after which it was quenched with saturated aqueous ammonium chloride and extracted into ethyl acetate. The combined organic layers were washed with brine, dried over magnesium sulfate, and concentrated in vacuo to afford the title compound as an orange oil which was taken on to the next step without purification.

Step 2: preparation of benzyl 3-(5-amino-3-(6-chloropyridin-3-yl)-4-cyano-1H-pyrazol-1-yl)piperidine-1-carboxylate. Prepared analogous to benzyl 3-[5-amino-4-cyano-3-(4-phenoxy-phenyl)-pyrazol-1-yl]-piperidine-1-carboxylate (Example 1, Step 9) by the reaction of 2-((6-chloropyridin-3-ylmethoxy)methylenemalononitrile and 3-hydrazino-piperidine-1-carboxylic acid benzyl ester (Example 1, Step 8) and 2-((6-chloropyridin-3-yl)(methoxy)methylenemalononitrile at ambient temperature over 16 h with the exception of aqueous workup and purification via normal phase $SiO_2$ column chromatography to afford the title compound as a yellow solid (590 mg, 10%).

Step 3: preparation of benzyl 3-(5-amino-4-cyano-3-(6-phenoxypyridin-3-yl)-1H-pyrazol-1-yl)piperidine-1-carboxylate. To a solution benzyl 3-(5-amino-3-(6-chloropyridin-3-yl)-4-cyano-1H-pyrazol-1-yl)piperidine-1-carboxylate (590 mg, 1.35 mmol) in dimethylsulfoxide (3 mL) was added phenol (134 mg, 1.42 mmol) and potassium carbonate (280 mg, 2.02 mmol). The reaction was allowed to stir at 105° C. over 72 h, after which it was cooled to ambient temperature and partitioned between dichloromethane and water, filtered through a phase separator tube and concentrated in vacuo. The residue was purified by silica gel column chromatography (ethyl acetate/heptane) to afford the title compound (260 mg, 39%).

Step 4: preparation of 5-amino-3-(6-phenoxypyridin-3-yl)-1-(piperidin-3-yl)-1H-pyrazole-4-carboxamide. Prepared according to the procedure described for 5-amino-3-(4-phenoxyphenyl)-1-piperidin-3-yl-1H-pyrazole-4-carboxylic acid amide (Example 1, Step 11) from benzyl 3-(5-amino-4-cyano-3-(6-phenoxypyridin-3-yl)-1H-pyrazol-1-yl)piperidine-1-carboxylate to afford the title compound (150 mg, 78%).

Step 5: preparation of 5-amino-1-(1-cyanopiperidin-3-yl)-3-(6-phenoxypyridin-3-yl)-1H-pyrazole-4-carboxamide. Prepared analogous to the procedures described for 5-amino-1-(1-cyanopiperidin-3-yl)-3-(4-phenoxyphenyl)-1H-pyrazole carboxamide (Example 1, Step 12) from 5-amino-3-(6-phenoxypyridin-3-yl)-1-(piperidin-3-yl)-1H-pyrazole-4-carboxamide (67 mg, 0.18 mmol) to afford the title compound (3 mg, 4%). MS (M+H) m/z 404. $^1$H NMR (DMSO-d6) δ 8.23 (s, 1H), 7.91 (dd, J=8.55, 2.2 Hz, 1H), 7.42 (t, J=8.06 Hz, 2H), 7.21 (t, J=7.57 Hz, 1H), 7.15 (d, J=7.81 Hz, 2H), 7.04 (d, J=8.79 Hz, 1H), 6.37 (s, 2H), 4.34-4.40 (m, 1H), 3.49 (dd, J=12.21, 3.42 Hz, 1H), 3.30-3.38 (m, 2H), 3.03-3.10 (m, 1H), 1.91-1.97 (m, 1H), 1.83-1.90 (m, 1H), 1.81 (bs, 1H), 1.65-1.74 (m, 1H).

Example 108

5-amino-3-(4-((5-chloropyridin-2-yl)oxy)phenyl)-1-(1-cyanopiperidin-3-yl)-1H-pyrazole-4-carboxamide

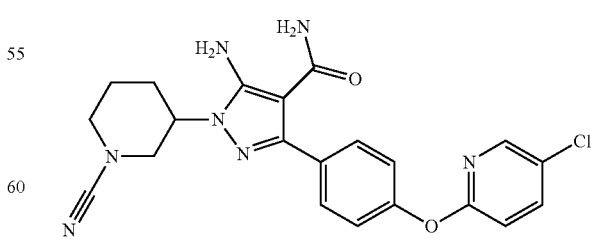

Step 1: preparation of 4-((tert-butyldimethylsilyl)oxy)benzoic acid. To a stirred solution of 4-hydroxybenzoic acid (200 g, 1.45 mol) in N,N-dimethylformamide (3.25 L), was added imidazole (595 g, 8.67 mol) followed by addition of tert-butyl dimethylsilyl chloride (327 g, 2.17 mol) at 0° C. The resulting reaction mixture was stirred at room temperature for 16 h. The reaction mixture was poured onto crushed ice and extracted with ethyl acetate (2×2 L). The combined organic layers were washed with water (2×1 L) followed by brine, dried over sodium sulfate and concentrated under reduced pressure. The crude product was purified by column chromatography in hexanes to afford the title compound (170 g, 47%) as white solid. $^1$H NMR (400 MHz, CDCl$_3$): 7.96-7.98 (d, J=8.68 Hz, 2H), 6.86-6.88 (d, J=8.68 Hz, 2H), 0.98 (s, 9H), 0.23 (s, 6H).

Step 2: preparation of 2-((4-((tert-butyldimethylsilyl)oxy)phenyl)(methoxy)-methylene)malononitrile. To a stirred suspension of sodium hydride (60%, 22.8 g, 0.95 mol) in 600 mL tetrahydrofuran, was added malononitrile (31.4 g, 0.47 mol, dissolved in 600 mL of tetrahydrofuran) at 0° C. The resulting suspension was stirred at 0° C. for 1 h. To another 3 necked round bottom flask was charged 4-((tert-butyldimethylsilyl)oxy)benzoic acid (120 g, 0.47 mol dissolved in 1200 mL of tetrahydrofuran) followed by N-methylmorpholine (52.9 mL, 0.47 mol) and isobutylchloroformate (61.94 mL, 0.47 mol, dissolved in 600 mL tetrahydrofuran) at −30° C. The resulting white suspension was stirred at −30° C. for 1 h. This acid chloride suspension was slowly added (through cannula) at 0° C. to the stirred suspension of NaH. The resulting suspension was stirred at room temperature for 3 h. Dimethyl sulfate (135.9 mL, 1.4 mol) was added to the suspension at room temperature and the resulting reaction mixture was heated at reflux for 16 h. The reaction mixture was poured onto crushed ice and extracted with ethyl acetate (2×2 L). The combined organic layers were washed with water (2×1 L) followed by brine, dried over sodium sulfate and concentrated under reduced pressure. The crude product was purified by silica gel column chromatography to afford the title compound (76 g, 61%) as light yellow solid. MS (M+H) m/z 315.6. $^1$H NMR (400 MHz, CDCl$_3$): 7.43 (d, J=8.68 Hz, 2H), 6.95 (d, J=11.4 Hz, 2H), 3.95 (s, 3H), 0.98 (s, 9H), 0.24 (s, 6H).

Step 3: preparation of benzyl 3-(5-amino-3-(4-((tert-butyldimethylsilyl)oxy)phenyl)-4-cyano-1H-pyrazol-1-yl)piperidine-1-carboxylate. To a stirred solution of 2-((4-((tert-butyldimethylsilyl)oxy)phenyl)methoxy)methylene)malononitrile (76 g, 0.24 mol) in ethanol (760 mL) was added benzyl 3-hydrazinylpiperidine-1-carboxylate (Example 1, Step 8) (68.9 g, 0.24 mol) followed by addition of triethylamine (37 mL, 0.26 mol) at room temperature. The resulting reaction mixture was heated to reflux for 16 h and then concentrated under reduced pressure. The residue was diluted with water (500 mL) and extracted with ethyl acetate (2×500 mL). The combined organic layers were washed with water (500 mL) followed by brine, dried over sodium sulfate and concentrated under reduced pressure to afford the title compound (102 g, 89%) as off white solid. MS (M+H) m/z 532. $^1$H NMR (400 MHz, CDCl$_3$): 7.76 (d, J=8.48 Hz, 2H), 7.31-7.38 (m, 5H), 6.86 (d, J=8.48 Hz, 2H), 5.10-5.18 (m, 2H), 4.44 (m, 1H), 4.28 (m, 1H), 4.16 (m, 1H), 3.82 (m, 1H), 3.2 (m, 1H), 2.83-2.90 (t, J=12 Hz, 1H), 2.25 (m, 1H), 2.09-2.12 (m, 1H), 1.88 (m, 1H), 0.97 (s, 9H), 0.20 (s, 6H).

Step 4: preparation of benzyl 3-(5-acetamido-3-(4-((tert-butyldimethylsilyl)oxy)phenyl)-4-cyano-1H-pyrazol-1-yl)piperidine-1-carboxylate. To a stirred solution of benzyl 3-(5-amino-3-(4-((tert-butyldimethylsilyl)oxy)phenyl)-4-cyano-1H-pyrazol-1-yl)piperidine-1-carboxylate (120 g, 0.19 mol) in dichloromethane (1.2 L) was added triethylamine (133 mL, 0.96 mol) followed by drop-wise addition of acetyl chloride (78.5 mL, 1.9 mol) at 0° C. The resulting reaction mixture was stirred at 0° C. for 30 minutes and then at room temperature for 16 h. The reaction mixture was diluted with cold water (500 mL). The resulting aqueous layer was extracted with dichloromethane (2×500 mL). The combined organic layers were washed with water (500 mL) followed by brine, dried over sodium sulfate and concentrated under reduced pressure. The crude product was purified by silica gel column chromatography (30% ethyl acetate/hexanes) to afford the title compound (100 g). MS (M+H) m/z 574. $^1$H NMR (400 MHz, CDCl$_3$) δ 7.79 (d, J=8.48 Hz, 2H), 7.33 (m, 5H), 6.88 (d, J=8.48 Hz, 2H), 5.11 (s, 2H), 4.03-4.24 (m, 3H), 3.31-3.32 (m, 2H), 2.90 (t, J=12 Hz, 1H), 2.21 (m, 5H), 1.88 (m, 1H), 0.97 (s, 9H), 0.20 (s, 6H).

Step 5: preparation of benzyl 3-(5-acetamido-4-cyano-3-(4-hydroxyphenyl)-1H-pyrazol-1-yl)piperidine-1-carboxylate. To a stirred solution of benzyl 3-(5-acetamido-3-(4-((tert-butyldimethylsilyl)oxy)phenyl)-4-cyano-1H-pyrazol-1-yl)piperidine-1-carboxylate (165 g, 0.35 mol) in methanol:water (4:1, 2.8 L) was added LiOH.H$_2$O (43.8 g, 1.04 mol) at 0° C. The resulting reaction mixture was stirred at 0° C. for 2 h. The reaction mixture was concentrated under reduced pressure and the residue was dissolved in water (1 L) and neutralized with 1N HCl (1.8 L) to pH 6.5. The precipitated solid was filtered, washed with water (500 mL×2) followed by hexanes and dried under vacuum. The solid was dissolved in ethyl acetate (1 L) and washed with water (2×500 mL). The organic layer was dried over sodium sulfate and concentrated under reduced pressure to afford the title compound (104 g) as off white solid. MS (M+H) m/z 460. $^1$H NMR (400 MHz, CDCl$_3$): 10.48 (s, 1H), 9.83 (s, 1H), 7.67 (d, J=8.48 Hz, 2H), 7.33 (m, 5H), 6.87 (d, J=8.48 Hz, 2H), 5.06 (s, 2H), 4.23 (bs, 1H), 4.05 (m, 1H), 3.90 (m, 1H), 3.00 (t, J=11.0 Hz, 1H), 2.17 (s, 3H), 2.0 (m, 1H), 1.87 (m, 1H), 1.51 (m, 1H).

Step 6: preparation of benzyl 3-(5-acetamido-3-{4-[(5-chloropyridin-2-yl)oxy]phenyl}-4-cyano-1H-pyrazol-1-yl)piperidine-1-carboxylate. To a solution of benzyl 3-(5-acetamido-4-cyano-3-(4-hydroxyphenyl)-1H-pyrazol-1-yl)piperidine-1-carboxylate (500 mg, 1.20 mmol) in N,N-dimethylformamide (1 mL) was added 5-chloro-2-fluoropyridine (237 mg, 1.80 mmol) and cesium carbonate (1.95 g, 5.99 mmol). The reaction mixture was then heated to 100° C. for 30 minutes under microwave conditions, after which it was diluted with water and extracted into ethyl acetate (3×5 mL). The combined organic layers were dried over sodium sulfate, concentrated in vacuo, and purified by silica gel column chromatography to afford the title compound (300 mg, 44%). $^1$H NMR (400 MHz, CDCl$_3$) δ ppm 8.10-8.18 (m, 1H), 7.93 (d, J=8.78 Hz, 2H), 7.66 (dd, J=8.66, 2.64 Hz, 1H), 7.33 (s, 5H), 7.11-7.20 (m, 2H), 6.90 (d, J=8.78 Hz, 1H), 5.12 (s, 2H), 4.27 (d, J=11.04 Hz, 1H), 4.08-4.20 (m, 2H), 3.18-3.43 (m, 1H), 2.91 (t, J=11.92 Hz, 1H), 2.21 (s, 2H), 1.83-1.95 (m, 1H), 1.48-1.68 (m, 1H).

Step 7: preparation of 5-amino-3-(4-((5-chloropyridin-2-yl)oxy)phenyl)-1-(piperidin-3-yl)-1H-pyrazole-4-carboxamide. To a stirred solution of concentrated sulfuric acid (6 mL) at 0° C., was added benzyl 3-(5-acetamido-3-{4-[(5-chloropyridin-2-yl)oxy]phenyl}-4-cyano-1H-pyrazol-1-yl)piperidine-1-carboxylate (300 mg, 0.53 mmol), portion wise over 10 min. The reaction mixture was then allowed to stir at 30° C. over 16 h, after which it was cooled back down to 0° C. Concentrated ammonium hydroxide was carefully added to neutralize the acid to pH=7, ensuring that the temperature did not exceed 5° C. The mixture was then extracted with ethyl acetate (3×5 mL), and the combined organic layers were dried over sodium sulfate, and concentrated in vacuo to afford the title compound. $^1$H NMR (400

MHz, DMSO-d$_6$) ppm: 8.19-8.27 (m, 1H), 7.91-8.02 (m, 1H), 7.48-7.56 (m, 2H), 7.19-7.22 (m, 2H), 7.16 (s, 1H), 6.32 (s, 2H), 4.03-4.16 (m, 1H), 3.31 (br. s., 1H), 3.01 (dd, J=11.8, 3.5 Hz, 1H), 2.87 (d, J=12.3 Hz, 1H), 2.79 (dd, J=11.5, 10.3 Hz, 1H), 2.38-2.48 (m, 1H), 1.81-1.96 (m, 2H), 1.71 (d, J=13.1 Hz, 1H), 1.42-1.57 (m, 1H).

Step 8: preparation of 5-amino-3-(4-((5-chloropyridin-2-yl)oxy)phenyl)-1-(1-cyanopiperidin-3-yl)-1H-pyrazole-4-carboxamide. To a solution of 5-amino-3-(4-((5-chloropyridin-2-yl)oxy)phenyl)-1-(piperidin-3-yl)-1H-pyrazole-4-carboxamide (217 mg, 0.53 mmol) in N,N-dimethylformamide was added cesium carbonate (516 mg, 1.59 mmol) and cyanogen bromide (281 mg, 2.65 mmol). The reaction was allowed to stir at ambient temperature for 6 h, after which water was added, and extracted into ethyl acetate. The combined organic layers were dried over sodium sulfate, concentrated in vacuo and purified by silica gel column chromatography (ethyl acetate/hexanes) to afford the title compound. $^1$H NMR (500 MHz, DMSO-d$_6$) δ ppm: 8.21 (d, J=2.29 Hz, 1H), 7.96 (dd, J=8.71, 2.75 Hz, 1H), 7.52 (d, J=8.71 Hz, 2H), 7.21 (d, J=8.71 Hz, 2H), 7.13 (d, J=8.71 Hz, 1H), 6.44 (br. s., 2H), 4.26-4.42 (m, 1H), 3.43-3.52 (m, 1H), 3.25-3.39 (m, 2H), 2.96-3.11 (m, 1H), 1.78-2.00 (m, 3H), 1.62-1.77 (m, 1H).

Example 109

(S)-5-amino-3-(4-((5-chloropyridin-2-yl)oxy)phenyl)-1-(1-cyanopiperidin-3-yl)-1H-pyrazole-4-carboxamide

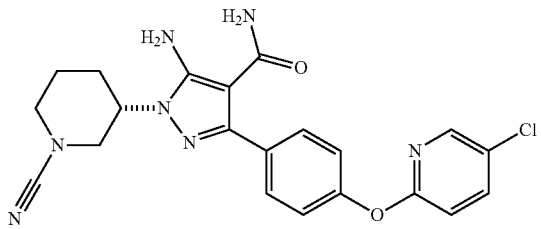

rac-5-amino-3-{4-[(5-chloropyridin-2-yl)oxy]phenyl}-1-(1-cyanopiperidin-3-yl)-1H-pyrazole-4-carboxamide (prepared as described in Example 108) was chirally separated by supercritical fluid chromatography (ChiralPak OD-H 30×250 mm column, 55% methanol, 1% isopropylamine, 80 mL/min). Isolation of the first eluting isomer afforded the title compound. $^1$H NMR (500 MHz, DMSO-d$_6$) δ ppm: 8.21 (d, J=2.29 Hz, 1H), 7.96 (dd, J=8.71, 2.75 Hz, 1H), 7.52 (d, J=8.71 Hz, 2H), 7.21 (d, J=8.71 Hz, 2H), 7.13 (d, J=8.71 Hz, 1H), 6.44 (br. s., 2H), 4.26-4.42 (m, 1H), 3.43-3.52 (m, 1H), 3.25-3.39 (m, 2H), 2.96-3.11 (m, 1H), 1.78-2.00 (m, 3H), 1.62-1.77 (m, 1H).

Example 110

(R)-5-amino-3-(4-((5-chloropyridin-2-yl)oxy)phenyl)-1-(1-cyanopiperidin-3-yl)-1H-pyrazole-4-carboxamide

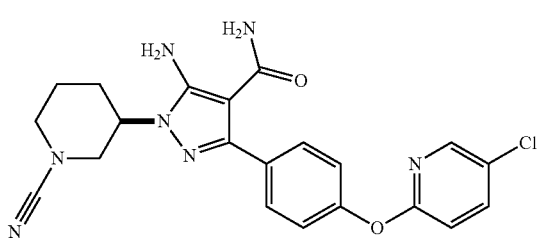

rac-5-amino-3-{4-[(5-chloropyridin-2-yl)oxy]phenyl}-1-(1-cyanopiperidin-3-yl)-1H-pyrazole-4-carboxamide (prepared as described in Example 108) was chirally separated by supercritical fluid chromatography (ChiralPak OD-H 30×250 mm column, 55% methanol, 1% isopropylamine, 80 mL/min). Isolation of the second eluting isomer afforded the title compound. $^1$H NMR (500 MHz, DMSO-d$_6$) δ ppm: 8.21 (d, J=2.29 Hz, 1H), 7.96 (dd, J=8.71, 2.75 Hz, 1H), 7.52 (d, J=8.71 Hz, 2H), 7.21 (d, J=8.71 Hz, 2H), 7.13 (d, J=8.71 Hz, 1H), 6.44 (br. s., 2H), 4.26-4.42 (m, 1H), 3.43-3.52 (m, 1H), 3.25-3.39 (m, 2H), 2.96-3.11 (m, 1H), 1.78-2.00 (m, 3H), 1.62-1.77 (m, 1H).

Example 111

5-amino-1-(1-cyanopiperidin-3-yl)-3-{4-[(5-fluoropyridin-2-yl)oxy]phenyl}-1H-pyrazole-4-carboxamide

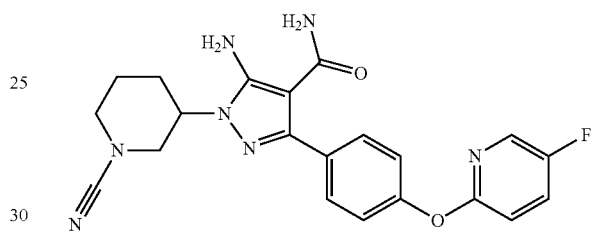

Prepared analogous to 5-amino-3-{4-[(5-chloropyridin-2-yl)oxy]phenyl}-1-(1-cyanopiperidin-3-yl)-1H-pyrazole-4-carboxamide (Example 108) employing 2,5-difluoropyridine. $^1$H NMR (500 MHz, DMSO-d$_6$) δ ppm: 8.16 (d, J=3.21 Hz, 1H), 7.82 (td, J=8.48, 3.21 Hz, 1H), 7.51 (d, J=8.71 Hz, 2H), 7.10-7.21 (m, 3H), 6.44 (s, 1H), 4.28-4.44 (m, 1H), 3.49 (dd, J=11.91, 4.12 Hz, 1H), 3.28-3.41 (m, 2H), 3.05 (td, J=12.49, 2.52 Hz, 1H), 1.80-2.03 (m, 3H), 1.61-1.77 (m, 1H).

Example 112

5-amino-1-(1-cyanopiperidin-3-yl)-3-(4-((5-methylpyridin-2-yl)oxy)phenyl)-1H-pyrazole-4-carboxamide

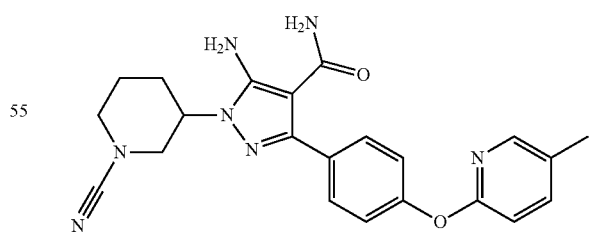

Prepared analogous to 5-amino-3-{4-[(5-chloropyridin-2-yl)oxy]phenyl}-1-(1-cyanopiperidin-3-yl)-1H-pyrazole-4-carboxamide (Example 108) employing 4-methyl-2-fluoropyridine. $^1$H NMR (500 MHz, DMSO-d$_6$) δ ppm 8.00 (s, 1H), 7.65-7.77 (m, 1H), 7.49 (d, J=8.25 Hz, 2H), 7.14 (d, J=8.71 Hz, 2H), 6.98 (d, J=8.25 Hz, 1H), 6.45 (s, 2H), 4.30-4.42 (m, 1H), 3.48 (d, J=4.12 Hz, 1H), 3.29-3.39 (m, 2H), 3.06 (td, J=12.49, 2.52 Hz, 1H), 2.25 (s, 3H), 1.78-2.01 (m, 3H), 1.64-1.77 (m, 1H).

Example 113

(S)-5-amino-1-(1-cyanopiperidin-3-yl)-3-(4-((5-methyl pyridin-2-yl)oxy)phenyl)-1H-pyrazole-4-carboxamide

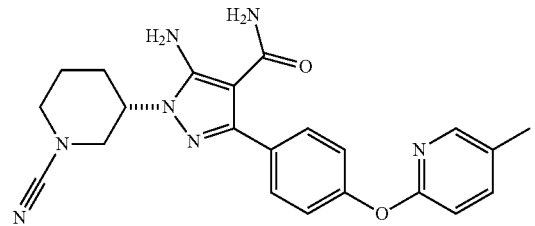

rac-5-amino-1-(1 cyanopiperidin-3-yl)-3-{4-[(5-methyl-pyridin-2-yl)oxy]phenyl}-1H-pyrazole-4-carboxamide (prepared as described in Example 112) was chirally separated by supercritical fluid chromatography (ChiralPak OD-H 46×250 mm column, 45% methanol, 1% isopropylamine, 4 mL/min). Isolation of the first eluting isomer afforded the title compound. $^1$H NMR (500 MHz, DMSO-d) δ ppm 8.00 (s, 1H), 7.65-7.77 (m, 1H), 7.49 (d, J=8.25 Hz, 2H), 7.14 (d, J=8.71 Hz, 2H), 6.98 (d, J=8.25 Hz, 1H), 6.45 (s, 2H), 4.30-4.42 (m, 1H), 3.48 (d, J=4.12 Hz, 1H), 3.29-3.39 (m, 2H), 3.06 (td, J=12.49, 2.52 Hz, 1H), 2.25 (s, 3H), 1.78-2.01 (m, 3H), 1.64-1.77 (m, 1H).

Example 114

(R)-5-amino-1-(1-cyanopiperidin-3-yl)-3-(4-((5-methylpyridin-2-yl)oxy)phenyl)-1H-pyrazole-4-carboxamide

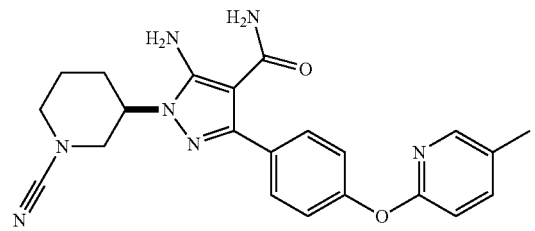

rac-5-amino-1-(1-cyanopiperidin-3-yl)-3-{4-[(5-methyl-pyridin-2-yl)oxy]phenyl}-1H-pyrazole-4-carboxamide (prepared as described in Example 112) was chirally separated by supercritical fluid chromatography (ChiralPak OD-H 46×250 mm column, 45% methanol, 1% isopropylamine, 4 mL/min). Isolation of the second eluting isomer afforded the title compound. $^1$H NMR (500 MHz, DMSO-d$_6$) δ ppm 8.00 (s, 1H), 7.65-7.77 (m, 1H), 7.49 (d, J=8.25 Hz, 2H), 7.14 (d, J=8.71 Hz, 2H), 6.98 (d, J=8.25 Hz, 1H), 6.45 (s, 2H), 4.30-4.42 (m, 1H), 3.48 (d, J=4.12 Hz, 1H), 3.29-3.39 (m, 2H), 3.06 (td, J=12.49, 2.52 Hz, 1H), 2.25 (s, 3H), 1.78-2.01 (m, 3H), 1.64-1.77 (m, 1H).

Example 115

5-amino-1-(1-cyanopiperidin-3-yl)-3-{4-[(3, 5-difluoropyridin-2-yl)oxy]phenyl}-1H-pyrazole-4-carboxamide

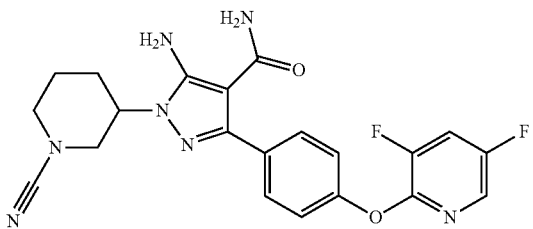 [SMILES: N#CN1CCCC(n2nc(-c3ccc(Oc4ncc(F)cc4F)cc3)c(C(N)=O)c2N)C1]

Prepared analogous to 5-amino-3-{4-[(5-chloropyridin-2-yl)oxy]phenyl}-1-(1-cyanopiperidin-3-yl)-1H-pyrazole-4-carboxamide (Example 108) employing 2,3,5-trifluoropyridine. $^1$H NMR (500 MHz, DMSO-d$_6$) δ ppm 8.15 (ddd, J=10.3, 8.0, 2.7 Hz, 1H), 8.09 (d, J=2.7 Hz, 1H), 7.54 (d, J=8.7 Hz, 2H), 7.24 (d, J=8.7 Hz, 2H), 6.45 (s, 2H), 4.34-4.42 (m, 1H), 3.51 (dd, J=12.4, 4.1 Hz, 1H), 3.31-3.39 (m, 2H), 3.07 (td, J=12.5, 2.5 Hz, 1H), 1.81-2.00 (m, 3H), 1.67-1.76 (m, 1H).

Example 116

(R)-5-amino-1-(1-cyanopiperidin-3-yl)-3-(4-((6-(trifluoromethyl)pyridin-2-yl)oxy)phenyl)-1H-pyrazole-4-carboxamide

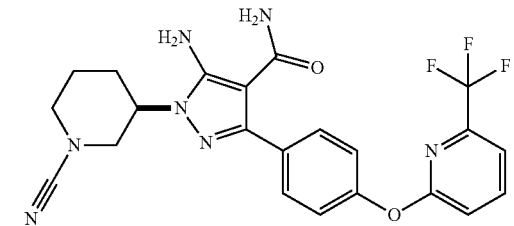

Step 1: preparation of (R)-benzyl 3-(5-acetamido-4-cyano-3-(4-hydroxyphenyl)-1H-pyrazol-1-yl)piperidine-1-carboxylate. (rac)-benzyl 3-(5-acetamido-4-cyano-3-(4-hydroxyphenyl)-1H-pyrazol-1-yl)piperidine-1-carboxylate (prepared as described in Example 108) was chirally separated by supercritical fluid chromatography (ChiralPak AS-H 50×250 mm column, 25% methanol, 250 mL/min). Isolation of the first eluting isomer afforded the title compound. MS (M+H) m/z 460. $^1$H NMR (400 MHz, CDCl$_3$): 10.48 (s, 1H), 9.83 (s, 1H), 7.67 (d, J=8.48 Hz, 2H), 7.33 (m, 5H), 6.87 (d, J=8.48 Hz, 2H), 5.06 (s, 2H), 4.23 (bs, 1H), 4.05 (m, 1H), 3.90 (m, 1H), 3.00 (t, J=11.0 Hz, 1H), 2.17 (s, 3H), 2.0 (m, 1H), 1.87 (m, 1H), 1.51 (m, 1H).

Step 2: preparation of (R)-5-amino-1-(1-cyanopiperidin-3-yl)-3-(4-((6-(trifluoromethyl)pyridin-2-yl)oxy)phenyl)-1H-pyrazole-4-carboxamide. Prepared analogous to 5-amino-3-{4-[(5-chloropyridin-2-yl)oxy]phenyl}-1-(1-cyanopiperidin-3-yl)-1H-pyrazole-4-carboxamide (Example 108) employing (R)-benzyl 3-(5-acetamido-4-cyano-3-(4-hydroxyphenyl)-1H-pyrazol-1-yl)piperidine-1-carboxylate and 2-chloro-6-(trifluoromethyl)pyridine. MS (M+H) m/z 472. ¹H NMR (500 MHz, DMSO-d₆) δ ppm 8.09 (t, J=7.90 Hz, 1H), 7.61 (d, J=7.33 Hz, 1H), 7.52 (d, J=8.48 Hz, 2H), 7.32 (d, J=8.25 Hz, 1H), 7.23 (d, J=8.48 Hz, 2H), 6.41 (s, 2H), 4.30-4.39 (m, 1H), 3.46 (dd, J=12.03, 3.78 Hz, 1H), 3.28-3.37 (m, 2H), 3.03 (td, J=12.50, 2.50 Hz, 1H), 1.60-1.98 (m, 4H).

Example 117

(S)-5-amino-1-(1-cyanopiperidin-3-yl)-3-(4-((6-(trifluoromethyl)pyridin-2-yl)oxy)phenyl)-1H-pyrazole-4-carboxamide

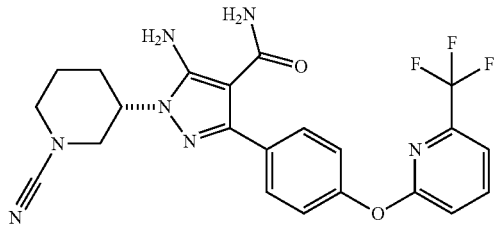

Step 1: preparation of (S)-benzyl 3-(5-acetamido-4-cyano-3-(4-hydroxyphenyl)-1H-pyrazol-1-yl)piperidine-1-carboxylate. (rac)-benzyl 3-(5-acetamido-4-cyano-3-(4-hydroxyphenyl)-1H-pyrazol-1-yl)piperidine-1-carboxylate (prepared as described in Example 108) was chirally separated by supercritical fluid chromatography (ChiralPak AS-H 50×250 mm column, 25% methanol, 250 mL/min). Isolation of the second eluting isomer afforded the title compound. MS (M+H) m/z 460. ¹H NMR (400 MHz, CDCl₃): 10.48 (s, 1H), 9.83 (s, 1H), 7.67 (d, J=8.48 Hz, 2H), 7.33 (m, 5H), 6.87 (d, J=8.48 Hz, 2H), 5.06 (s, 2H), 4.23 (bs, 1H), 4.05 (m, 1H), 3.90 (m, 1H), 3.00 (t, J=11.0 Hz, 1H), 2.17 (s, 3H), 2.0 (m, 1H), 1.87 (m, 1H), 1.51 (m, 1H).

Step 2: preparation of (S)-5-amino-1-(1-cyanopiperidin-3-yl)-3-(4-((6-(trifluoromethyl)pyridin-2-yl)oxy)phenyl)-1H-pyrazole-4-carboxamide. Prepared analogous to 5-amino-3-{4-[(5-chloropyridin-2-yl)oxy]phenyl}-1-(1-cyanopiperidin-3-yl)-1H-pyrazole-4-carboxamide (Example 108) employing (S)-benzyl 3-(5-acetamido-4-cyano-3-(4-hydroxyphenyl)-1H-pyrazol-1-yl)piperidine-1-carboxylate and 2-chloro-6-(trifluoromethyl)pyridine. MS (M+H) m/z 472. ¹H NMR (500 MHz, DMSO-d₆) δ ppm 8.09 (t, J=7.90 Hz, 1H), 7.61 (d, J=7.33 Hz, 1H), 7.52 (d, J=8.48 Hz, 2H), 7.32 (d, J=8.25 Hz, 1H), 7.23 (d, J=8.48 Hz, 2H), 6.41 (s, 2H), 4.30-4.39 (m, 1H), 3.46 (dd, J=12.03, 3.78 Hz, 1H), 3.28-3.37 (m, 2H), 3.03 (td, J=12.50, 2.50 Hz, 1H), 1.60-1.98 (m, 4H).

Example 118

(R)-5-amino-3-(4-((5-chloro-3-fluoropyridin-2-yl)oxy)phenyl)-1-(1-cyanopiperidin-3-yl)-1H-pyrazole-4-carboxamide

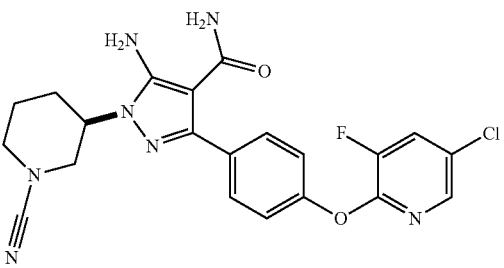 [SMILES: N#CN1CCC[C@@H](n2nc(-c3ccc(Oc4ncc(Cl)cc4F)cc3)c(C(N)=O)c2N)C1]

Prepared analogous to (R)-5-amino-1-(1-cyanopiperidin-3-yl)-3-(4-((6-(trifluoromethyl)pyridin-2-yl)oxy)phenyl)-1H-pyrazole-4-carboxamide (Example 116) employing 5-chloro-2,3-difluoropyridine. MS (M+H) m/z 456. ¹H NMR (400 MHz, DMSO-de) δ ppm 8.24 (dd, J=9.76, 1.76 Hz, 1H), 8.08 (d, J=1.76 Hz, 1H), 7.54 (d, J=8.39 Hz, 2H), 7.27 (d, J=8.39 Hz, 2H), 6.44 (s, 2H), 4.32-4.44 (m, 1H), 3.50 (dd, J=11.81, 3.41 Hz, 1H), 3.34-3.39 (m, 2H), 3.07 (t, J=11.51 Hz, 1H), 1.67-2.02 (m, 4H).

Example 119

(S)-5-amino-3-(4-((5-chloro-3-fluoropyridin-2-yl)oxy)phenyl)-1-(1-cyanopiperidin-3-yl)-1H-pyrazole-4-carboxamide

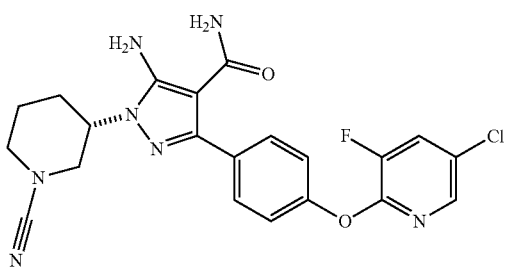 [SMILES: N#CN1CCC[C@H](n2nc(-c3ccc(Oc4ncc(Cl)cc4F)cc3)c(C(N)=O)c2N)C1]

Prepared analogous to (S)-5-amino-1-(1-cyanopiperidin-3-yl)-3-(4-((6-(trifluoromethyl)pyridin-2-yl)oxy)phenyl)-1H-pyrazole-4-carboxamide (Example 117) employing 5-chloro-2,3-difluoropyridine. MS (M+H) m/z 456. ¹H NMR (400 MHz, DMSO-de) δ ppm 8.24 (dd, J=9.76, 1.76 Hz, 1H), 8.08 (d, J=1.76 Hz, 1H), 7.54 (d, J=8.39 Hz, 2H), 7.27 (d, J=8.39 Hz, 2H), 6.44 (s, 2H), 4.32-4.44 (m, 1H), 3.50 (dd, J=−11.81, 3.41 Hz, 1H), 3.34-3.39 (m, 2H), 3.07 (t, J=11.51 Hz, 1H), 1.67-2.02 (m, 4H).

Example 120

5-amino-3-[2-chloro-4-(4-fluorophenoxy)phenyl]-1-(1-cyanopiperidin-3-yl)-1H-pyrazole-4-carboxamide

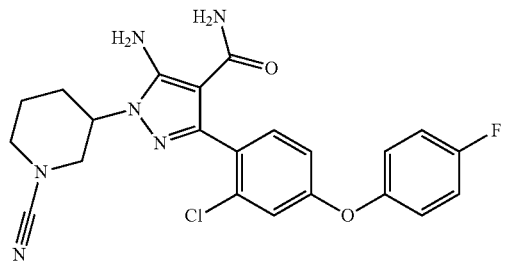 [SMILES: N#CN1CCCC(n2nc(-c3ccc(Oc4ccc(F)cc4)cc3Cl)c(C(N)=O)c2N)C1]

Step 1: preparation of 1-bromo-2-chloro-4-(4-fluorophenoxy)benzene. To a mixture of 4-bromo-3-chlorophenol (1.2 g, 5.8 mmol), copper (II) acetate (1.79 g, 9.83 mmol), triethylamine (4.82 mL, 34.7 mmol), and 1.5 g activated 4 Å molecular sieves in anhydrous dichloromethane (80 mL) at 0° C. was added (4-fluorophenyl)boronic acid (2.43 g, 17.4 mmol, 3.0 equiv) portion-wise over 30 min. The reaction mixture was allowed to warm to ambient temperature over 16 h, after which it was filtered. The filtrate concentrated in vacuo and purified by silica gel column chromatography to afford the title compound as a light yellow oil (0.60 g, 35%). MS (M+H) m/z 302.

Step 2: preparation of 2-[2-chloro-4-(4-fluorophenoxy) phenyl]-4,4,5,5-tetramethyl-1,3,2-dioxaborolane. A mixture of 1-bromo-2-chloro-4-(4-fluorophenoxy)benzene (600 mg, 1.99 mmol), bis(pinacolato)diboron (664 mg, 2.59 mmol), potassium acetate (684 mg, 6.96), and 1,1'-bis-(diphenyl-phosino)-ferrocene)palladium dichloride (107 mg, 0.139 mmol) in anhydrous 1,4 dioxane (30 mL) was allowed to stir at 80° C. under nitrogen over 16 h, after which it was cooled to ambient temperature and filtered. The filtrate was then concentrated in vacuo and purified by silica gel column chromatography to afford the title compound as a light yellow solid (0.18 g, 26%). MS (M+H) m/z 349. $^1$H NMR (400 MHz, CDCl$_3$) δ ppm: 7.67 (d, J=8.34 Hz, 1H) 6.96-7.10 (m, 4H) 6.92 (d, J=2.53 Hz, 1H) 6.81 (dd, J=8.34, 2.27 Hz, 1H) 1.36 (s, 12H).

Step 3: preparation of ethyl 5-acetamido-1H-pyrazole-4-carboxylate. A mixture of ethyl 5-amino-H-pyrazole-4-carboxylate (100 g, 0.65 mol) and acetyl chloride (441.2 g, 5.62 mol) at 0° C. was heated to reflux for 4 h. The reaction was concentrated in vacuo to remove excess acetyl chloride. Water (1.0 L) was added and the mixture was stirred for 16 h, after which it was filtered to afford the title compound as an off white solid (120 g, 94%). MS (M+H) m/z 198. $^1$H NMR (400 MHz, CDCl$_3$) δ ppm: 9.57 (1H, s), 7.75 (1H, s), 4.33-4.28 (2H, q, J=7.08), 2.27 (3H, s), 1.37-1.34 (3H, s).

Step 4: preparation of ethyl 5-acetamido-3-bromo-1H-pyrazole-4-carboxylate. To a solution of ethyl 5-acetamido-1H-pyrazole-4-carboxylate (120 g, 0.61 mol) in ethanol (2.5 L) was added 4.0 L of aqueous sodium acetate (484 g, 5.91 mol), followed by drop wise addition of bromine (565 g, 3.53 mol). The reaction was allowed to stir at ambient temperature for 3 h, after which it was judged complete by TLC. The reaction was poured in water (6.8 L), and desired product was extracted into ethyl acetate (3×5.0 L).

The combined organic layers were washed with saturated aqueous sodium thiosulfate (2×1.5 L), dried over sodium sulfate and concentrated in vacuo. The resulting crude solid was washed with hexanes (500 mL) to afford the title compound as an off-white solid (105 g, 62.5%). MS (M+H) m/z 278. $^1$H NMR (400 MHz, CDCl$_3$) δ ppm: 11.8 (s, 1H), 9.75 (s, 1H), 4.38-4.32 (q, J=7.04, 2H), 2.27 (s, 3H), 1.42-1.38 (t, J=7.04, 3H).

Step 5: preparation of tert-butyl 3-[5-acetamido-3-bromo-4-(ethoxycarbonyl)-1H-pyrazol-1-yl]piperidine-1-carboxylate. To a solution of ethyl 5-acetamido-3-bromo-1H-pyrazole-4-carboxylate (500 mg, 1.81 mmol), triphenyl phosphine (582 mg, 2.17 mmol), and tert-butyl 3-hydroxypiperidine-1-carboxylate (547 mg, 2.72 mmol, 1.5 equiv) in diethyl ether (5 mL) was added diisopropyl diazene-1,2-dicarboxylate (476 mg, 2.17 mmol). The reaction was then heated to 80° C. for 4 h, after which it was allowed to cool to ambient temperature and treated with saturated aqueous ammonium chloride solution. The organic layer was separated, washed with water, brine, then dried over sodium sulfate, and concentrated in vacuo. The resulting crude oil was purified by reversed phase HPLC, to afford the title compound as a light yellow solid (0.12 g, 15%). MS (M+H) m/z 459.

Step 6: preparation of tert-butyl 3-{5-acetamido-3-[2-chloro-4-(4-fluorophenoxy)phenyl]-4-(ethoxycarbonyl)-1H-pyrazol-1-yl}piperidine-1-carboxylate. A solution of tert-butyl 3-[5-acetamido-3-bromo-4-(ethoxycarbonyl)-1H-pyrazol-1-yl]piperidine-1-carboxylate (130 mg, 2.48 mmol), 2-[2-chloro-4-(4-fluorophenoxy)phenyl]-4,4,5,5-tetramethyl-1,3,2-dioxaborolane (98.7 mg, 0.283 mmol), sodium carbonate (60 mg, 0.566 mmol), and (1,1'-bis-(diphenylphosphino)-ferrocene)palladium dichloride (15.4 mg, 0.02 mmol) in a N,N-dimethylformamide (8 mL)/water (2 mL)/dioxane (16 mL) was heated to 80° C. for 1 h under microwave conditions, after which it was poured into ethyl acetate and treated with saturated aqueous ammonium chloride. The organic layer was separated and washed with water and brine, dried over sodium sulfate, and concentrated in vacuo. The resulting crude oil was purified by silica gel column chromatography to afford the title compound as a light yellow solid (0.16 g, 53%). MS (M+H) m/z 601.

Step 7: preparation of 5-acetamido-1-(1-(tert-butoxycarbonyl)piperidin-3-yl)-3-(2-chloro-4-(4-fluorophenoxy)phenyl)-1H-pyrazole-4-carboxylic acid. A solution of tert-butyl 3-{5-acetamido-3-[2-chloro-4-(4-fluorophenoxy)phenyl]-4-(ethoxycarbonyl)-1H-pyrazol-1-yl}piperidine-1-carboxylate (110 mg, 0.18 mmol) and lithium hydroxide (268 mg, 11.0 mmol) in 50% methanolic tetrahydrofuran (8 mL) was allowed to stir at 95° C. over 16 h, after which it was concentrated in vacuo to a volume of 0.1 mL. Water (3 mL) was added, and the mixture was cooled 0° C. and acidified to pH=3 with 1N hydrochloric acid. The resulting white precipitate was collected by vacuum filtration to afford the title compound (97 mg, >99%). MS (M+H) m/z 531.

Step 8: preparation of tert-butyl 3-{5-amino-4-carbamoyl-3-[2-chloro-4-(4-fluorophenoxy)phenyl]-1H-pyrazol-1-yl}piperidine-1-carboxylate. To a solution of 5-acetamido-1-(1-(tert-butoxycarbonyl)piperidin-3-yl)-3-(2-chloro-4-(4-fluoro-phenoxy)phenyl)-1H-pyrazole-4-carboxylic acid (100 mg, 0.18 mmol), 1-hydroxylbenzotriazole (38.5 mg, 0.282 mmol), 3-(dimethylamino)propyl carbodiimide hydrochloride (54.6 mg, 0.282 mmol), N,N-dimethylformamide (5 mL), was added a 0.5N solution of ammonia in 1,4-dioxane (3.76 mL, 1.88 mmol). The reaction was allowed to stir at ambient temperature over 16 h, after which it was concentrated in vacuo. Water (10 mL) was added, and the resulting white precipitate was collected by vacuum filtration to afford the title compound (100 mg, >99%). MS (M+H) m/z 530.

Step 9: preparation of 5-amino-3-[2-chloro-4-(4-fluorophenoxy)phenyl]-1-(1-cyanopiperidin-3-yl)-1H-pyrazole-4-carboxamide. To a solution of tert-butyl 3-{5-amino-4-carbamoyl-3-[2-chloro-4-(4-fluorophenoxy)phenyl]-1H-pyrazol-1-yl}piperidine-1-carboxylate (100 mg, 0.18 mmol) in dichloromethane (3 mL) was added trifluoroacetic acid (1 mL). The reaction was allowed to stir at ambient temperature for 2 h after which it was concentrated in vacuo to afford the title compound (78 mg, >99%). MS (M+H) m/z 430.

Step 10: preparation of 5-amino-3-[2-chloro-4-(4-fluorophenoxy)phenyl]-1-(1-cyanopiperidin-3-yl)-1H-pyrazole-4-carboxamide. Prepared analogous to the procedure described for 5-amino-1-(1-cyanopiperidin-3-yl)-3-(4-phenoxyphenyl)-1H-pyrazole carboxamide (Example 1, Step 12) at ambient temperature and purified by reversed phase HPLC to afford the title compound as a light yellow solid (64 mg, 57%). MS (M+H) m/z 455. $^1$H NMR (400 MHz, CDCl$_3$) δ ppm 7.36 (d, J=8.59 Hz, 1H), 6.99-7.14 (m, 5H), 6.94 (dd, J=8.46, 2.40 Hz, 1H), 5.56 (s, 2H), 5.02 (s, 2H), 4.11-4.12 (m, 1H), 3.58 (d, J=4.55 Hz, 1H), 3.39-3.54 (m, 2H), 3.04-3.05 (m, 1H), 2.06-2.21 (m, 2H), 1.92-1.93 (m, 2H).

Example 121

5-amino-1-[(3R*,6S*)-1-cyano-6-methylpiperidin-3-yl]-3-[4-(2,4-difluorophenoxy)phenyl]-1H-pyrazole-4-carboxamide

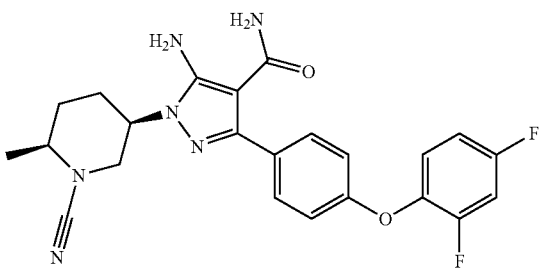 [SMILES: C[C@H]1CC[C@@H](n2nc(-c3ccc(Oc4ccc(F)cc4F)cc3)c(C(N)=O)c2N)CN1C#N]

Step 1: preparation of 6-methylpiperidin-3-ol. To a solution of 6-methylpyridin-3-ol (8.54 g, 77 mmol) in acetic acid (100 mL) was added platinum oxide (1.68 g, 7.4 mmol). The mixture was placed in a Parr apparatus under hydrogen pressure (50 psi) and shaken for 16 h. The solvent was removed in vacuo to afford the title compound.

Step 2: preparation of benzyl 5-hydroxy-2-methylpiperidine-1-carboxylate. To a solution of 6-methylpiperidin-3-ol (9.0 g, 78.1 mmol) in dichloromethane (100 mL) was added drop wise triethylamine (101 mL, 703 mmol), followed by benzyl chloroformate (14 mL, 93.8 mmol). The reaction was allowed to stir over 16 h, after which it was concentrated in vacuo, and the resulting residue purified by silica gel column chromatography to afford the title compound as colorless oil (8.1 g 42%).

Step 3: preparation of benzyl 2-methyl-5-oxopiperidine-1-carboxylate. To a solution of benzyl 5-hydroxy-2-methylpiperidine-1-carboxylate (0.986 g, 3.96 mmol) in dichloromethane (10 mL) at 0° C. was added Dess Martin reagent (3.96 mmol). The reaction mixture was allowed to stir at 0° C. for 30 min, then warmed to ambient temperature and allowed to stir for an additional 3 h. The reaction mixture was then carefully quenched with saturated aqueous sodium thiosulfate, and diluted with both water and dichloromethane. The organic layer was separated and washed with brine, water, then dried over sodium sulfate and concentrated in vacuo to afford the title compound which was taken on to the next step without purification.

Step 4: preparation of benzyl 5-[(tert-butoxycarbonyl)hydrazono]-2-methylpiperidine-1-carboxylate. To a solution benzyl 2-methyl-5-oxopiperidine-1-carboxylate (2.00 g, 8.09 mmol) in tetrahydrofuran (10 mL) was added tert-butyl hydrazinecarboxylate (1.25 g, 9.71 mmol). The reaction mixture was heated to reflux for 2.5 h, after which it was cooled to ambient temperature and concentrated in vacuo to afford the title compound as a white solid. MS (M+H) m/z 418.

Step 5: preparation of benzyl 5-[2-(tert-butoxycarbonyl)hydrazino]-2-methylpiperidine-1-carboxylate. To a solution benzyl 5-[(tert-butoxycarbonyl)hydrazono]-2-methylpiperidine-1-carboxylate (1.53 g, 4.23 mmol) in tetrahydrofuran (10 mL) was added sodium cyanoborohydride (0.27 g, 4.23 mmol) was added drop wise a solution of para-toluenesulfonic acid monohydrate (0.80 g, 4.23 mmol) in tetrahydrofuran (2 mL). The reaction was allowed to stir at ambient temperature over 16 h, after which it was concentrated in vacuo. The resulting residue was dissolved in ethyl acetate and washed with saturated aqueous sodium bicarbonate, 1N sodium hydroxide, brine and water, then dried over sodium sulfate and concentrated in vacuo to afford the title compound.

Step 6: preparation of benzyl 5-hydrazino-2-methylpiperidine-1-carboxylate. To a solution of benzyl 5-[2-(tert-butoxycarbonyl)hydrazino]-2-methylpiperidine-1-carboxylate (1.78 g, 4.9 mmol) in dichloromethane (10 mL) was added drop wise trifluoroacetic acid (5 mL). The reaction was allowed to stir at ambient temperature for 5 h, after which it was concentrated in vacuo to afford the title compound as a pale yellow solid.

Step 7: preparation of (2S*,5R*)-benzyl 5-(5-amino-4-cyano-3-(4-(2,4-difluorophenoxy)phenyl)-1H-pyrazol-1-yl)-2-methylpiperidine-1-carboxylate. To a solution of benzyl 5-hydrazino-2-methylpiperidine-1-carboxylate (1.71 g, 6.5 mmol) in anhydrous ethanol (30 mL) was added 2-((4-(2,4-difluorophenoxy)phenylmethoxy)-methylene)malononitrile (Example 25, Step 4) (2.03 g, 6.5 mmol) and triethyl amine (4.66 mL, 32.4 mmol). The solution was stirred at ambient temperature over 16 h. Solvent was removed in vacuo and the crude product was purified by preparative HPLC to afford the title compound (2.12 g, 60%) as a white product. MS (M+H) m/z 544. $^1$H NMR (400 MHz, CDCl$_3$) δ ppm 7.83-7.89 (m, 2H), 7.30-7.41 (m, 5H), 7.09 (td, J=9.0, 5.4 Hz, 1H), 6.93-7.01 (m, 3H), 6.83-6.91 (m, 1H), 5.11-5.20 (m, 2H), 4.50-4.61 (m, 1H), 4.39 (br. s., 2H), 4.13-4.25 (m, 1H), 3.82 (br. s., 1H), 3.35 (t, J=11.7 Hz, 1H), 2.36-2.49 (m, 1H), 1.70-1.95 (m, 4H), 1.29 (d, J=7.1 Hz, 3H)

Step 8: preparation of 5-amino-3-(4-(2,4-difluorophenoxy)phenyl)-1-((3S*,6R*)-6-methylpiperidin-3-yl)-1H-pyrazole-4-carboxamide. To a stirred solution of concentrated sulfuric acid (3 mL) at 0° C., was added (2S*,5R*)-benzyl 5-(5-amino-4-cyano-3-(4-(2,4-difluorophenoxy)phenyl)-1H-pyrazol-1-yl)-2-methylpiperidine-1-carboxylate (450 mg, 0.77 mmol), portion wise over 10 min. The reaction mixture was then allowed to stir at 30° C. over 16 h, after which it was cooled to 0° C. Concentrated ammonium hydroxide was carefully added to pH=7, ensuring that the temperature did not exceed 5° C. The mixture was then extracted with ethyl acetate (3×10 mL), and the combined organic layers were dried over sodium sulfate, and concentrated in vacuo to afford the title compound.

Step 9: preparation of 5-amino-1-[(3R*,6S*)-1-cyano-6-methylpiperidin-3-yl]-3-[4-(2,4-difluorophenoxy)phenyl]-1H-pyrazole-4-carboxamide. To a solution of 5-amino-3-(4-(2,4-difluorophenoxy)phenyl)-1-((3S*,6R)-6-methylpiperidin-3-yl)-1H-pyrazole-4-carboxamide (398 mg, 0.93 mmol) in N,N-dimethylformamide (8 mL) was added cesium carbonate (911 mg, 2.77 mmol) and cyanogen bromide (586 mg, 5.54 mmol). The reaction was allowed to stir at ambient temperature for 6 h, after which water was added, and the desired product was extracted into ethyl acetate. The combined organic layers were dried over sodium sulfate, concentrated in vacuo and purified via normal phase SiO$_2$ column chromatography (ethyl acetate/hexanes) to afford the title compound as a white solid. MS (M+H) m/z 453. $^1$H NMR (500 MHz, DMSO-d$_6$) δ ppm: 1.25 (d, J=6.9 Hz, 8H), 1.77-1.87 (m, 7H), 2.04-2.14 (m, 2H), 2.51 (s, 1H), 3.36 (d, J=4.6 Hz, 2H), 3.39 (d, J=4.6 Hz, 2H), 3.47-3.57 (m, 5H), 4.35 (ddd, J=8.4, 4.4, 4.2 Hz, 2H), 6.43 (s, 5H), 7.03 (d, J=8.71 Hz, 5H), 7.11-7.21 (m, 2H), 7.36 (td, J=9.2, 5.5 Hz, 2H), 7.46-7.56 (m, 3H), 7.52 (d, J=8.7 Hz, 5H).

Example 122

5-amino-1-[(3R,6S)-1-cyano-6-methylpiperidin-3-yl]-3-[4-(2,4-difluorophenoxy)phenyl]-1H-pyrazole-4-carboxamide

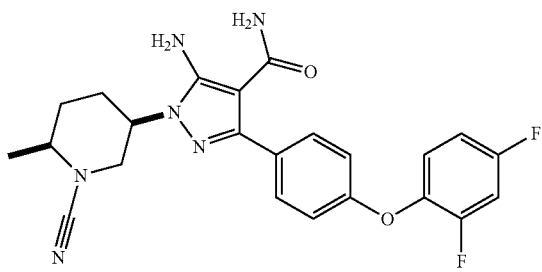 [SMILES: C[C@H]1CC[C@@H](n2nc(-c3ccc(Oc4ccc(F)cc4F)cc3)c(C(N)=O)c2N)CN1C#N]

rac-5-amino-1-[(3R*,6S*)-1-cyano-6-methylpiperidin-3-yl]-3-[4-(2,4-difluorophenoxy)phenyl]-1H-pyrazole-4-carboxamide (prepared as described in Example 121) was chirally separated by supercritical fluid chromatography (RegisPack 30×250 mm col, 23% EtOH, 80 mL/min). Isolation of the first eluting isomer afforded the title compound. MS (M+H) m/z 453. $^1$H NMR (500 MHz, DMSO-$d_6$) δ ppm: 1.25 (d, J=6.9 Hz, 8H), 1.77-1.87 (m, 7H), 2.04-2.14 (m, 2H), 2.51 (s, 1H), 3.36 (d, J=4.6 Hz, 2H), 3.39 (d, J=4.6 Hz, 2H), 3.47-3.57 (m, 5H), 4.35 (ddd, J=8.4, 4.4, 4.2 Hz, 2H), 6.43 (s, 5H), 7.03 (d, J=8.7 Hz, 5H), 7.11-7.21 (m, 2H), 7.36 (td, J=9.2, 5.5 Hz, 2H), 7.46-7.56 (m, 3H), 7.52 (d, J=8.7 Hz, 5H).

Example 123

5-amino-1-[(3S,6R)-1-cyano-6-methylpiperidin-3-yl]-3-[4-(2,4-difluorophenoxy)phenyl]-1H-pyrazole-4-carboxamide

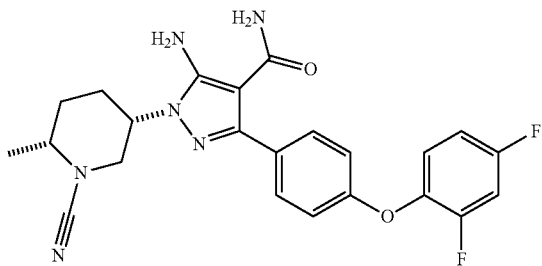 [SMILES: C[C@@H]1CC[C@H](n2nc(-c3ccc(Oc4ccc(F)cc4F)cc3)c(C(N)=O)c2N)CN1C#N]

rac-5-amino-1-[(3R*,6S*)-1-cyano-6-methylpiperidin-3-yl]-3-[4-(2,4-difluorophenoxy)phenyl]-1H-pyrazole-4-carboxamide (prepared as described in Example 121) was chirally separated by supercritical fluid chromatography (RegisPack 30×250 mm col, 23% EtOH, 80 mL/min). Isolation of the second eluting isomer afforded the title compound. MS (M+H) m/z 453. $^1$H NMR (500 MHz, DMSO-$d_6$) δ ppm: 1.25 (d, J=6.9 Hz, 8H), 1.77-1.87 (m, 7H), 2.04-2.14 (m, 2H), 2.51 (s, 1H), 3.36 (d, J=4.6 Hz, 2H), 3.39 (d, J=4.6 Hz, 2H), 3.47-3.57 (m, 5H), 4.35 (ddd, J=8.4, 4.4, 4.2 Hz, 2H), 6.43 (s, 5H), 7.03 (d, J=8.7 Hz, 5H), 7.11-7.21 (m, 2H), 7.36 (td, J=9.2, 5.5 Hz, 2H), 7.46-7.56 (m, 3H), 7.52 (d, J=8.7 Hz, 5H).

Example 124

5-amino-3-{4-[(4-chlorophenyl)thio]phenyl}-1-(1-cyanopiperidin-3-yl)-1H-pyrazole-4-carboxamide

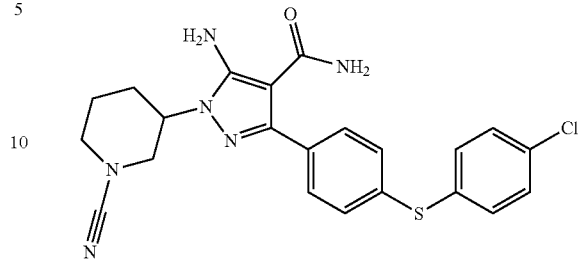

Step 1: preparation of benzyl 3-(5-acetamido-3-(4-((4-chlorophenyl)thio)phenyl)-4-cyano-1H-pyrazol-1-yl)piperidine-1-carboxylate. A glass tube was charged with potassium carbonate (267 mg, 1.93 mmol, 1.1 eq) followed by the addition of 3-[5-acetylamino-4-cyano-3-(4-iodophenyl)-pyrazol-1-yl]-piperidine-1-carboxylic acid benzyl ester (100 mg, 1.76 mmol, 1.0 eq) (Example 86, Step 1), 4-chlorothiophenol (330 mg, 2.28 mmol, 1.3 eq), copper iodide (191 mg, 1 mmol, 0.57 eq) and N-methylpyrrolidine (0.4 ml). The glass tube was closed and placed under stirring in a preheated 100° C. oil bath for 6-8 hr. The reaction mixture was diluted with water and was then extracted with ethyl acetate (5 mL×3). The combined organic layers were dried over anhydrous sodium sulfate, and then filtered. The filtrate was concentrated in vacuo and purified by silica gel chromatography (heptane/ethyl acetate) to afford the title compound.

Step 2: preparation of 5-amino-3-(4-((4-chlorophenyl)thio)phenyl)-1-(piperidin-3-yl)-1H-pyrazole-4-carbonitrile. Benzyl 3-(5-acetamido-3-(4-((4-chlorophenyl)thio)phenyl)-4-cyano-1H-pyrazol-1-yl)piperidine-1-carboxylate (96 mg) was added portion-wise over 10 min to a stirred solution of concentrated sulfuric acid while maintaining the temperature at 0° C. and then stirred at 30° C. for 18 hr. The reaction mixture was cooled to 0° C. and neutralized by the addition of ammonium hydroxide solution maintaining the temperature below 20° C. The mixture was extracted with ethyl acetate. The organic layer was washed with brine, dried over sodium sulfate and concentrated in vacuo to afford the title compound.

Step 3: preparation of 5-amino-3-{4-[(4-chlorophenyl)thio]phenyl}-1-(1-cyanopiperidin-3-yl)-1H-pyrazole-4-carboxamide. The title compound was prepared analogous to 5-amino-1-(1-cyanopiperidin-3-yl)-3-(4-phenoxyphenyl)-1H-pyrazole carboxamide (Example 1, Step 12) employing 5-amino-3-(4-((4-chlorophenyl)thio)-phenyl)-1-(piperidin-3-yl)-1H-pyrazole-4-carbonitrile. MS (M+H) m/z 453.

Example 125

5-amino-1-(1-cyanopiperidin-3-yl)-3-[4-(phenylthio)phenyl]-1H-pyrazole-4-carboxamide

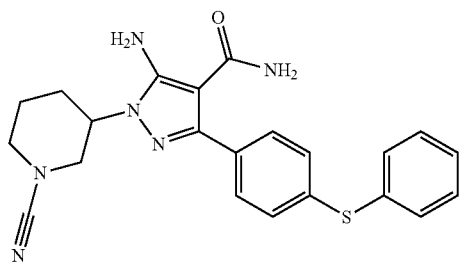 [SMILES: N#CN1CCCC(n2nc(-c3ccc(Sc4ccccc4)cc3)c(C(N)=O)c2N)C1]

The title compound was prepared analogous to 5-amino-3-{4-[(4-chlorophenyl)thio]phenyl}-1-(1-cyanopiperidin-3-yl)-1H-pyrazole-4-carboxamide (Example 124) employing thiophenol. MS (M+H) m/z 419.

Example 126

1-[(3S)-1-acryloyl piperidin-3-yl]-5-amino-3-(4-phenoxyphenyl)-1H-pyrazole-4-carboxamide

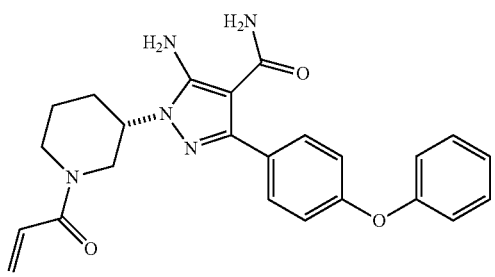 [SMILES: C=CC(=O)N1CCC[C@H](n2nc(-c3ccc(Oc4ccccc4)cc3)c(C(N)=O)c2N)C1]

Step 1: preparation of 4-phenoxy benzoyl chloride. A solution of 4-phenoxy benzoic acid (500 g, 2.33 mol) in thionyl chloride (1.2 L) was refluxed for 16 h, after which volatiles were removed in vacuo to afford the title compound as a brown gum, which was taken on to the next step without purification.

Step 2: preparation of 2-[hydroxy-(4-phenoxy-phenyl)-methylene]-malononitrile. A solution of malononitrile (154 mL, 2.55 mol) in anhydrous tetrahydrofuran (500 mL) was added drop wise under nitrogen to a suspension of sodium hydride (205 g, 5.12 mol) in tetrahydrofuran (2 L) over 1.5 h at 0° C. The reaction mixture was allowed to stir for an additional 30 min, after which addition of a solution of 4-phenoxy benzoyl chloride (540 g, 2.32 mol) in tetrahydrofuran (750 mL) was added. The reaction was then allowed to stir for 16 h at ambient temperature, cooled to 0° C. and quenched with 1N hydrochloric acid (1 L). Product was extracted into ethyl acetate and the combined organic layers were washed with water, then brine, dried over sodium sulfate, and concentrated in vacuo to afford the title compound as an off-white solid, which was carried on to the next step without purification. MS (M−H) m/z 261. $^1$H NMR (CDCl$_3$) δ 7.74 (d, J=8.8 Hz, 2H), 7.39 (t, J=7.6 Hz, 2H), 7.21 (t, J=7.2 Hz, 1H), 7.06 (d, J=8 Hz, 2H), 7.00 (d, J=8.8 Hz, 2H).

Step 3: preparation of 2-[(4-phenoxy-phenyl)-methoxy-methylene]-malononitrile

To a solution of 2-[hydroxy-(4-phenoxy-phenyl)-methylene]-malononitrile (600 g, 2.29 mol) in a mixture of dioxane/water (4/1, 5 L) at 0° C. was added sodium bicarbonate (1.34 kg, 16 mol) portion wise. Dimethyl sulfate (1.2 L, 13.74 mol) was added drop wise over 2 h, after which the reaction was warmed to 80° C. and allowed to stir for an additional 12 h. The reaction was cooled to ambient temperature, diluted with water and extracted into ethyl acetate. The combined organic layers were washed with water, then brine, dried over sodium sulfate, and concentrated in vacuo. The crude residue was purified by silica gel column chromatography to afford the title compound as an off white solid (300 g, 48%). MS (M+H) m/z 277. $^1$H NMR (CDCl$_3$) δ 7.47 (d, J=8.8 Hz, 2H), 7.42 (t, J=7.6 Hz, 2H), 7.23 (t, J=7.6 Hz, 1H), 7.07 (t, J=8.8 Hz, 4H), 3.97 (s, 3H).

Step 4: preparation of 3-Hydroxy-piperidine-1-carboxylic acid benzyl ester. To a suspension of piperidin-3-ol hydrochloride (134 g, 0.974 mol) and triethylamine (276 mL, 1.98 mol) in dichloromethane (2 L) at 0° C. was added a solution of benzyl chloroformate (140 mL, 0.981 mol) in dichloromethane (100 mL) drop wise over 2.5 h. The reaction was allowed to stir for an additional 30 min at 0° C., then allowed to warm to ambient temperature over 16 h, after which it was quenched with 1N hydrochloric add (3 L) and allowed to stir for 30 min. The organic layer was separated, dried over sodium sulfate, and concentrated in vacuo to afford the title compound (218 g, 95%). $^1$H-NMR (CDCl$_3$) δ 7.29-7.41 (m, 5H), 5.14 (s, 2H), 3.59-3.85 (m, 3H), 3.13-3.27 (m, 2H), 2.18 (bs, 1H), 1.74-1.94 (m, 2H), 1.38-1.61 (m, 2H).

Step 5: preparation of 3-oxo-piperidine-1-carboxylic acid benzyl ester. To a suspension of pyridine sulfur trioxide complex (135.6 g, 0.85 mol) in dichloromethane (1.25 L) at 0° C. was added triethylamine (148 mL, 1.07 mol), followed by DMSO (151 mL, 2.13 mol). A solution of 3-hydroxy-piperidine-1-carboxylic acid benzyl ester (50.0 g, 0.21 mol) in dichloromethane (415 mL) was then added drop wise over 1 h, ensuring that the temperature did not exceed 0° C. The reaction was then allowed to warm to ambient temperature over 16 h, after which it was cooled to 15° C. and slowly quenched with saturated aqueous ammonium chloride (1 L) (exotherm!) The mixture was then allowed to stir for an additional 30 min, after which the organic layer was separated and the aqueous layer was extracted with dichloromethane. The combined organic layers were dried over sodium sulfate and concentrated in vacuo. The residue was dissolved in a 50% solution of heptane/ethyl acetate (300 mL), washed with 0.5N hydrochloric acid (600 mL), then brine. The organic layer was concentrated in vacuo and purified by silica gel column chromatography. $^1$H-NMR δ (CDCl$_3$): 7.32-7.41 (m, 5H), 5.17 (s, 2H), 4.10 (s, 2H), 3.69 (t, 2H), 2.50 (t, 2H), 1.97-2.08 (m, 2H).

Step 6: preparation of 3-(tert-butoxycarbonyl-hydrazono)-piperidine-1-carboxylic acid benzyl ester. To a solution of 3-oxo-piperidine-1-carboxylic acid benzyl ester (150 g, 0.64 mol) in tetrahydrofuran (1.5 L) was added tert-butyl hydrazinecarboxylate (85 g, 0.64 mol). The solution was heated to reflux for 2 h, after which it was concentrated in vacuo to afford the title compound. MS (M+H) m/z 348. $^1$H-NMR (CDCl$_3$) δ 7.56 (s, 1H), 7.28-7.41 (m, 5H), 5.14-5.16 (d, 2H), 4.13-4.25 (d, 2H), 3.73-3.78 (m, 0.6H), 3.53-3.61 (m, 1.4H), 2.51-2.56 (t, 0.7H), 2.33-2.37 (t, 1.3H), 1.82-1.91 (m, 2H), 1.52 (s, 9H)

Step 7: preparation of benzyl 3-(2-(tert-butoxycarbonyl)hydrazinyl)piperidine-1-carboxylate. To a solution of 3-(tert-butoxycarbonyl-hydrazono)-piperidine-1-carboxylic acid benzyl ester (230 g, 0.66 mol) in tetrahydrofuran (1.5 L) was added sodium cyanoborohydride (41.6 g, 0.66 mol). A solution of para-toluenesulfonic acid mono-hydrate (126 g, 0.66 mol) in tetrahydrofuran (590 mL) was then added drop wise over 1.5 h, ensuring that the temperature did not exceed 21° C. The reaction was then allowed to stir over 16 h. Volatiles were removed in vacuo, and the resulting residue was dissolved in ethyl acetate (2.0 L), washed with saturated aqueous sodium bicarbonate (1 L), then added to 1N sodium hydroxide (1.5 L) and allowed to stir for 1 h. The organic layer was separated, washed with brine, dried over sodium sulfate, and concentrated in vacuo. The crude residue was purified by silica gel column chromatography (0-3% dichloromethane/methanol solvent gradient) affording the title compound as a colorless oil (169 g, 73%). $^1$H-NMR (CDCl₃): δ 7.29-7.36 (m, 5H), 6.33 (bs, 1H), 5.88 (bs, 1H), 5.12 (bs, 2H), 3.42-3.64 (m, 5H), 3.02-3.17 (m, 1H), 1.74-1.80 (m, 2H).

Step 8: preparation of 3-hydrazino-piperidine-1-carboxylic acid benzylester hydrochloride. To a solution of benzyl 3-(2-(tert-butoxycarbonyl)hydrazinyl)piperidine-1-carboxylate (50 g, 0.143 mol) in methanol (180 mL) was added a solution of 4N hydrochloric acid in dioxane (180 mL) drop wise, ensuring that the temperature did not exceed 10° C. The reaction was allowed to stir at ambient temperature over 16 h, after which a white precipitate had formed. The precipitate was filtered, then allowed to stir in ethyl acetate (700 mL) at ambient temperature for an additional 16 h, filtered, then dried under vacuum to afford the title compound as a white powder. MS (M+H) m/z 250.2. ¹H-NMR (DMSO-d₆) δ 7.28-7.41 (m, 5H), 5.08 (s, 2H), 4.10 (d, 1H), 3.72 (d, 1H), 2.95 (bs, 3H), 1.98 (m, 1H), 1.70 (m, 1H), 1.29-1.37 (m, 2H).

Step 9: preparation of benzyl 3-[5-amino-4-cyano-3-(4-phenoxy-phenyl)-pyrazol-1-yl]-piperidine-1-carboxylate.
To a solution of 2-[(4-phenoxy-phenyl)-methoxy-methylene]-malononitrile (step 3; 146 g, 0.53 mol) in ethanol (500 mL) was added benzyl 3-hydrazino-piperidine-1-carboxylate (step 8; 150.6 g, 0.53 mol) and triethylamine (107 g, 1.05 mol), causing the temperature of the solution to reach 55° C. The reaction was then allowed to cool to ambient temperature over 16 h, after which a precipitate had formed. The precipitate was filtered off and added to 2-methyl tetrahydrofuran (3.5 L), which dissolved the desired product, leaving behind triethyl amine-hydrochloric acid, which was then removed by vacuum filtration. The filtrate was then washed with brine (1 L) and concentrated in vacuo to afford the title compound as a white solid. MS (M+H) m/z 494.

Step 10: preparation of 5-amino-3-(4-phenoxy-phenyl)-1-piperidin-3-yl-1H-pyrazole-4-carbonitrile. A solution of benzyl 3-[5-amino-4-cyano-3-(4-phenoxy-phenyl)-pyrazol-1-yl]-piperidine-1-carboxylate (260 g, 527 mmol) in 2-methyl tetrahydrofuran (5 L) was passed through a Midi apparatus at 65° C., 7 mL/min, under full hydrogen, using a 10% Pd/C cartridge over a period of 16 h. Solvent was removed in vacuo to afford the title compound as a tan solid. MS (M+H) m/z 360.

Step 11: preparation of 5-amino-3-(4-phenoxyphenyl)-1-piperidin-3-yl-1H-pyrazole-4-carboxylic acid amide. To a 2 L SS Parr autoclave was added a solution of 5-amino-3-(4-phenoxy-phenyl)-1-piperidin-3-yl-1H-pyrazole-4-carbonitrile (189 g, 527 mmol) and ethanol (550 mL). A 2N sodium hydroxide solution (880 mL) was then added and the autoclave was sealed and heated at 150° C. for 30 min, after which the reaction was judged complete. The solution was cooled to ambient temperature and added to ethyl acetate (500 mL). The organic layer was separated, washed with brine, and concentrated in vacuo to afford a gummy solid, which was triturated with acetonitrile (500 mL), then purified further by silica gel column chromatography (15-40% methanol/dichloromethane solvent gradient) to afford the title compound as a white solid (135 g, 70%). MS (M+H) m/z 360.

Step 12: preparation of (S)-5-amino-3-(4-phenoxyphenyl)-1-piperidin-3-yl-1H-pyrazole-4-carboxylic acid amide. rac-5-amino-3-(4-phenoxyphenyl)-1-piperidin-3-yl-1H-pyrazole-4-carboxylic acid amide was chirally separated by supercritical fluid chromatography (Chiralpak IC, 30×250 mm col, 50/50, CO₂/1% triethylamine in ethanol, 100 mL/min). Isolation of the first eluting isomer afforded the title compound.

Step 13: preparation of 1-[(3S)-1-acryloylpiperidine-3-yl]-5-amino-3-(4-phenoxyphenyl)-1H-pyrazole-4-carboxamide. To a solution of (S)-5-amino-3-(4-phenoxyphenyl)-1-piperidin-3-yl-1H-pyrazole-4-carboxylic acid amide (377 mg, 1.0 mmol) in N,N-dimethylformamide (4.00 mL) was added 2-(1H-Benzotriazol-1-yl)tris(dimethylamino)phosphonium hexafluorophosphate (486 mg, 1.1 mmol) and N,N-diisopropylethylamine (323 mg, 2.5 mmol). The reaction mixture was cooled to 0° C. and a solution of acrylic acid (79.3 mg, 1.1 mmol) in N,N-dimethylformamide (1.0 mL) was added drop wise over few minutes. The reaction was gradually warmed up to room temperature and stirred for 10 min, after which water was added, and extracted into ethyl acetate. The combined organic layers were dried over sodium sulfate, concentrated in vacuo and purified by silica gel column chromatography (ethyl acetate/10% methanol) to afford the title compound. MS (M+H) m/z 432.3. ¹H NMR (400 MHz, DMSO-d₆) δ ppm 7.55-7.47 (m, 4H), 7.27 (m, 1H), 7.2-7.0 (m, 4H), 6.91-6.77 (m, 1H), 6.41 (br. s., 2H), 6.19-6.04 (m, 1H), 5.77-5.61 (m, 1H), 4.53-4.03 (m, 3H), 3.53-3.43 (m, 1H), 3.13-2.97 (m, 1H), 2.85-2.65 (m, 1H), 2.08-1.92 (m, 1H), 1.90-1.78 (m, 1H), 1.55-1.45 (m, 1H).

Example 127

1-[(3R)-1-acryloylpiperidin-3-yl]-5-amino-3-(4-phenoxyphenyl)-1H-pyrazole-4-carboxamide

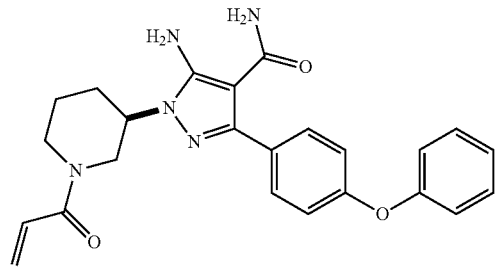 [SMILES: C=CC(=O)N1CCC[C@@H](n2nc(-c3ccc(Oc4ccccc4)cc3)c(C(N)=O)c2N)C1]

Step 1: preparation of (R)-5-amino-3-(4-phenoxyphenyl)-1-piperidin-3-yl-1H-pyrazole-4-carboxylic acid amide. rac-5-amino-3-(4-phenoxyphenyl)-1-piperidin-3-yl-1H-pyrazole-4-carboxylic acid amide was chirally separated by supercritical fluid chromatography (Chiralpak IC, 30×250 mm col, 50/50, CO₂/1% triethylamine in ethanol, 100 mL/min). Isolation of the second eluting isomer afforded the title compound.

Step 2: preparation of 1-[(3R)-1-acryloylpiperidin-3-yl]-5-amino-3-(4-phenoxyphenyl)-1H-pyrazole-4-carboxamide. To a solution of (R)-5-amino-3-(4-phenoxyphenyl)-1-piperidin-3-yl-1H-pyrazole-4-carboxylic acid amide (377 mg, 1.0 mmol) in N,N-dimethylformamide (4.00 mL) was added 2-(1H-benzotriazol-1-yl)tris(dimethylamino)phosphonium hexafluorophosphate (486 mg, 1.1 mmol) and N,N-diisopropylethylamine (323 mg, 2.5 mmol). The reaction mixture was cooled to 0° C. and a solution of acrylic acid (79.3 mg, 1.1 mmol) in N,N-dimethylformamide (1.0 mL) was added drop wise over few minutes. The reaction was gradually warmed to room temperature and stirred for 10 min, after which water was added, and extracted into ethyl acetate. The combined organic layers were dried over sodium sulfate, concentrated in vacuo and purified by silica gel column chromatography (ethyl acetate/10% methanol)

to afford the title compound. MS (M+H) m/z 432.3. ¹H NMR (400 MHz, DMSO-d) δ ppm 7.55-7.47 (m, 4H), 7.27 (m, 1H), 7.2-7.0 (m, 4H), 6.91-6.77 (m, 1H), 6.41 (br. s., 2H), 6.19-6.04 (m, 1H), 5.77-5.61 (m, 1H), 4.53-4.03 (m, 3H), 3.53-3.43 (m, 1H), 3.13-2.97 (m, 1H), 2.85-2.65 (m, 1H), 2.08-1.92 (m, 1H), 1.90-1.78 (m, 1H), 1.55-1.45 (m, 1H).

Example 128

5-amino-1-{1-[(2E)-but-2-enoyl]piperidin-3-yl}-3-(4-phenoxyphenyl)-1H-pyrazole-4-carboxamide

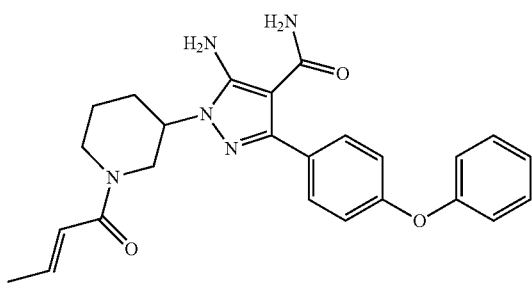 [SMILES: C/C=C/C(=O)N1CCCC(n2nc(-c3ccc(Oc4ccccc4)cc3)c(C(N)=O)c2N)C1]

A mixture of rac-5-amino-3-(4-phenoxyphenyl)-1-piperidin-3-yl-1H-pyrazole-4-carboxylic acid amide (prepared as described in Example 1) (200 mg, 0.53 mmol), crotonic acid (50 mg, 0.58 mmol), O-(benzotriazol-1-yl)-N,N,N',N'-tetramethyluronium hexafluorophosphate (221 mg, 0.58 mmol) and N,N-diisopropylethylamine (0.37 mL, 2.1 mmol) in tetrahydrofuran (20 mL) was stirred at room temperature for 24 h. The suspension was partitioned between water and ethyl acetate and the aqueous layer was further extracted with ethyl acetate (25 mL). The combined organic layers were dried (MgSO₄), filtered and concentrated. The crude product was purified by reverse phase HPLC to provide the title compound. MS (M+H) m/z 446. ¹H NMR (400 MHz, DMSO-d₆) δ ppm 7.48 (d, J=8.79 Hz, 2H), 7.38-7.44 (m, 2H), 7.16 (s, 1H), 7.06 (t, J=8.42 Hz, 4H), 6.59-6.77 (m, 1H), 6.50-6.58 (m, 1H), 6.34-6.47 (m, 2H), 4.27-4.52 (m, 1H), 4.02-4.24 (m, 2H), 3.40-3.52 (m, 1H), 3.00 (m, 1H), 2.60-2.73 (m, 1H), 1.89-2.02 (m, 2H), 1.82 (d, J=9.52 Hz, 4H), 1.37-1.51 (m, 1H).

Example 129

5-amino-1-{(3R)-1-[(2E)-4-hydroxybut-2-enoyl]piperidin-3-yl}-3-(4-phenoxyphenyl)-1H-pyrazole-4-carboxamide

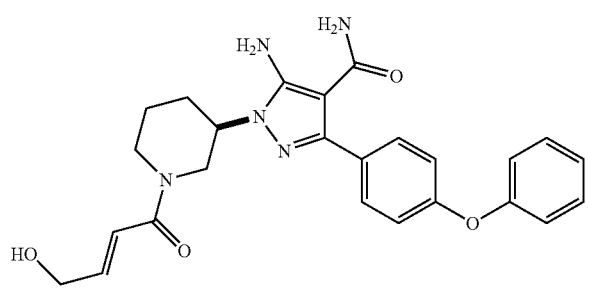 [SMILES: NC(=O)c1c(-c2ccc(Oc3ccccc3)cc2)nn([C@@H]2CCCN(C(=O)/C=C/CO)C2)c1N]

A mixture of (R)-5-amino-3-(4-phenoxyphenyl)-1-piperidin-3-yl-1H-pyrazole-4-carboxylic acid amide (prepared as described in Example 2 Step 1) (500 mg, 1.3 mmol), (E)-4-hydroxybut-2-enoic acid (149 mg, 1.5 mmol), O-(benzotriazol-1-yl)-N,N,N',N'-tetramethyluronium hexafluorophosphate (554 mg, 1.5 mmol) and triethylamine (335 mg, 3.3 mmol) in N,N-dimethylformamide (6 mL) was stirred at room temperature for 1 h. The suspension was partitioned between water and ethyl acetate. The organic layer was washed with water, 1N hydrochloric acid solution and brine. The combined organic layers were dried (Na₂SO₄), filtered and concentrated. The crude product was purified by column chromatography (methanol/ethyl acetate) to provide 234 mg of the title compound. MS (M+H) m/z 462. ¹H NMR (400 MHz, DMSO-d₆) δ ppm 7.50 (d, J=8.6 Hz, 2H), 7.44-7.40 (m, 2H), 7.19-7.15 (m, 1H), 7.09-7.05 (m, 4H), 6.80-6.55 (m, 2H), 6.41 (d, J=8.3 Hz, 2H), 5.07-4.95 (m, 2H), 4.55-4.47 (m, 1H), 4.44-4.27 (m, 1H), 4.02-4.24 (m, 2H), 3.40-3.52 (m, 1H), 3.05 (m, 1H), 2.60-2.73 (m, 1H), 2.00-1.80 (m, 4H), 1.37-1.51 (m, 1H).

Example 130

1-[(3R)-1-acryloyl piperidin-3-yl]-5-amino-3-[4-(4-chlorophenoxy)phenyl]-1H-pyrazole-4-carboxamide

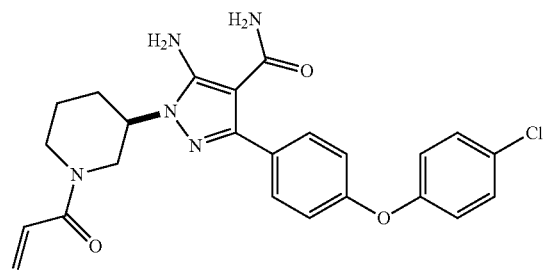 [SMILES: C=CC(=O)N1CCC[C@@H](n2nc(-c3ccc(Oc4ccc(Cl)cc4)cc3)c(C(N)=O)c2N)C1]

Step 1: preparation of methyl 4-(4-chlorophenoxy)benzoate. (4-Chlorophenyl)boronic acid (25.4 g, 162.82 mmol), 4 Å molecular sieves powder (16 g), 4-dimethylaminopyridine (39.5 g, 325.65 mmol) and anhydrous copper (II) acetate (39.0 g, 217.11 mmol) were added to a solution of methyl 4-hydroxybenzoate (16.5 g, 108.55 mmol) in dry dichloromethane (1000 mL) at room temperature, and the resulting mixture was stirred for 48 h. The reaction mixture was then filtered through a Celite pad. The filtrate was concentrated and the residue was purified by column chromatography on silica (8% EtOAc in petroleum ether) to afford the title compound (14 g, 48% yield) as off white solid. MS (M+H) m/z 263. ¹H NMR (CDCl₃, 400 MHz) δ 8.02 (d, 2H), 7.35 (d, 2H), 7.02 (d, 2H), 6.97 (d, 2H), 3.88 (s, 3H).

Step 2: preparation of 4-(4-chlorophenoxy)benzoic acid. To a suspension of methyl 4-(4-chlorophenoxy)benzoate (14.0 g, 53.43 mmol) in methanol-water (5:1, 360 mL), NaOH (10.68 g, 267.11 mmol) was added at 0° C., the cooling batch was then removed and the reaction mixture was stirred at 60° C. for 3 h. Methanol was distilled off, water (500 mL) was added to the residue and washed with diethyl ether (3×100 mL). The aqueous layer was acidified with 2N HCl and then extracted with ethyl acetate (3×100 mL). The combined organic layer was dried over sodium sulfate, filtered and concentrated to afford the title compound (10.5 g, 79% yield) as off white solid. MS (M+H) m/z 247. ¹H NMR (DMSO-de, 300 MHz) δ 12.83 (bs, 1H), 7.95 (d, 2H), 7.51 (d, 2H), 7.17 (d, 2H), 7.07 (d, 2H).

Step 3: preparation of 4-(4-chlorophenoxy)benzoyl chloride. 4-(4-chlorophenoxy)benzoic acid (10.5 g, 42.33 mmol) in thionyl chloride (110 mL) was refluxed for 4 h. The volatiles were evaporated and the crude title compound was taken to the next step.

Step 4: preparation of 2-((4-(4-chlorophenoxy)phenyl)(methoxy)methylene)-malononitrile. A solution of malononitrile (3.54 g, 53.66 mmol) in tetrahydrofuran (25 mL) was added drop wise to a stirred suspension of sodium hydride (3.96 g, 60% in mineral oil, 158.4 mmol) in tetrahydrofuran (50 mL) at 0° C. under nitrogen atmosphere. After stirring for 30 min, 4-(4-chlorophenoxy)benzoyl chloride (11.0 g, 41.35 mmol) in tetrahydrofuran (35 mL) was added drop wise. Cooling bath was removed and the reaction mixture was stirred at room temperature for 3 h. The reaction mixture was heated to reflux and dimethyl sulfate (28 mL, 288.89 mmol) was added drop wise, and the resulting mixture was refluxed for 18 h. After cooling to room temperature, water (100 mL) was added and extracted with ethyl acetate (3×100 mL). The combined organic layer was dried over sodium acetate, concentrated and purified by flash chromatography on silica (5-8% EtOAc in petroleum ether) to afford the title compound (6.0 g, 47% yield) as pale yellow oil. ¹H NMR (DMSO-de, 400 MHz) δ 7.73 (d, 2H), 7.52 (d, 2H), 7.2 (d, 2H), 7.18 (d, 2H), 3.92 (s, 3H).

Step 5: preparation of benzyl 3-(5-amino-3-(4-(4-chlorophenoxy)phenyl)-4-cyano-1H-pyrazol-1-yl)piperidine-1-carboxylate. Triethylamine (8.6 mL 19.35 mmol) was added to a stirred mixture of 2-((4-(4-chlorophenoxy)phenyl)(methoxy)methylene)malononitrile (6.0 g, 19.35 mmol) and 3-hydrazino-piperidine-1-carboxylic acid benzylester hydrochloride (Example 1, Step 8) (5.5 g, 57.89 mmol) in ethanol (6 0 mL) at room temperature. After stirring for 3 h the precipitated solid was filtered off. The solid was washed with ethanol and dried under vacuum to afford the title compound (7.2 g, 70% yield). MS (M+H) m/z 526. ¹H NMR (DMSO-d₆, 400 MHz) δ 8.0 (d, 2H), 7.45 (d, 2H), 7.37 (m, 5H), 7.12 (d, 2H), 7.08 (d, 2H), 6.77 (s, 2H), 5.06 (bs, 2H), 4.23 (m, 1H), 4.0 (m, 2H), 2.97 (m, 2H), 1.87 (m, 3H), 1.50 (m, 1H).

Step 6: preparation of 5-amino-3-(4-(4-chlorophenoxy)phenyl)-1-(piperidin-3-yl)-1H-pyrazole-4-carboxamide. A cold 2.5M aq. NaOH solution (70 mL) was added to a solution of benzyl 3-(5-amino-3-(4-(4-chlorophenoxy)phenyl)-4-cyano-1H-pyrazol-1-yl)piperidine-1-carboxylate (7.2 g, 13.66 mmol) in ethanol (70 mL) in a 250 mL sealed tube and the resulting mixture was heated with stirring at 140° C. for 48 h. After cooling to room temperature water was added to the reaction mixture and extracted with ethyl acetate (3×100 mL). The combined organic layer was dried over sodium sulfate, filtered, concentrated to afford the title compound (2.6 g). ¹H NMR (DMSO-d₆, 400 MHz) δ 8.21 (s, 1H), 7.49 (m, 4H), 7.45 (d, 2H), 7.10 (m, 4H), 6.36 (s, 2H), 4.20 (m, 1H), 3.11 (m, 1H), 2.97 (m, 2H), 2.50 (m, 1H), 1.93 (m, 2H), 1.76 (m, 1H), 1.60 (m, 1H).

Step 7: preparation of (R)-5-amino-3-(4-(4-chlorophenoxy)phenyl)-1-(piperidin-3-yl)-1H-pyrazole-4-carboxamide. rac-5-amino-3-(4-(4-chlorophenoxy)phenyl)-1-(piperidin-3-yl)-1H-pyrazole-4-carboxamide was chirally separated by supercritical fluid chromatography (Chiralpak OJ-H, 30×250 mm col, 50/50, CO₂/1% triethylamine in ethanol, 70 mL/min). Isolation of the second eluting isomer afforded the title compound.

Step 8: preparation of 1-[(3R)-1-acryloylpiperidin-3-yl]-5-amino-3-[4-(4-chlorophenoxy)phenyl]-1H-pyrazole-4-carboxamide. N,N-diisopropylethylamine (0.72 mL, 4.1 mmol) and acrylic acid (131 mg, 1.8 mmol) was added to a mixture of (R)-5-amino-3-(4-(4-chlorophenoxy)phenyl)-1-(piperidin-3-yl)-1H-pyrazole-4-carboxamide (675 mg, 1.6 mmol) and (benzotriazol-1-yloxy)tris(dimethylamino)phosphonium hexafluorophosphate (740 mg, 1.6 mmol) in N,N-dimethylformamide (5 mL). The mixture was stirred at room temperature and then purified by reverse phase HPLC to provide 250 mg of the title compound. MS (M+H) m/z 466. ¹H NMR (400 MHz, DMSO-de) δ ppm 7.51 (d, J=5.77 Hz, 2H), 7.48-7.40 (m, 2H), 7.15-7.04 (m, 4H), 6.93-6.74 (m, 1H), 6.41 (br. s., 2H), 6.19-6.01 (m, 1H), 5.74-5.55 (m, 1H), 4.59-4.01 (m, 3H), 3.54-3.39 (m, 0.5H), 3.12-2.97 (m, 1H), 2.76-2.71 (m, 0.5H), 2.05-1.90 (m, 2H), 1.89-1.77 (m, 1H), 1.56-1.37 (m, 1H).

Example 131

5-amino-3-[4-(4-chlorophenoxy)phenyl]-1-{(3R)-1-[(2E)-4-hydroxybut-2-enoyl]piperidin-3-yl}-1H-pyrazole-4-carboxamide

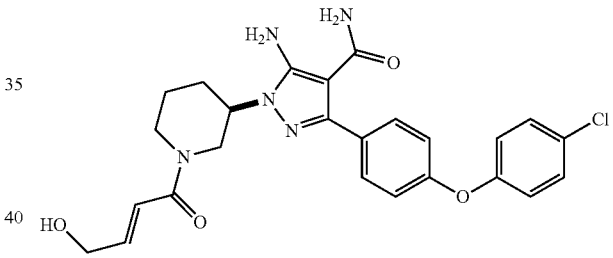

To a solution of 5-amino-3-(4-(4-chlorophenoxy)phenyl)-1-(piperidin-3-yl)-1H-pyrazole-4-carboxamide (prepared as described in Example 13, Step 6) (844 mg, 2.05 mmol), (E)-4-hydroxybut-2-enoic acid (251 mg, 2.46 mmol) and O-(7-azabenzotriazole-1-yl)-1,1,3,3-tetramethyluronium hexafluorophosphate (1.07 g, 2.66 mmol) in N,N-dimethylformamide (10 mL) was added triethylamine (0.71 mL, 5.12 mmol). After 2.5 h the reaction was diluted into ethyl acetate (100 mL), washed three times with 1N HCl (15 mL) and three times with 10% Na₂CO₃ (15 mL). After drying over MgSO₄, filtration and removal of the volatiles, the crude product was purified by reverse phase HPLC. The resulting solid was chirally separated by preparative HPLC (3.0×25.0 cm ChiralPak OD-H, 45/55, CO₂/isopropanol with 1% isopropyl amine at 70 mL/min flow rate). Isolation of the second eluting isomer afforded the title compound. MS (M+H) m/z 496. ¹H NMR (DMSO-d6, 400 MHz) δ 7.52 (m, 2H), 7.46 (m, 2H), 7.10 (m, 4H), 6.74 (m, 1H), 6.60 (m, 1H), 6.41 (m, 1H), 4.44 (m, 1H), 4.12 (m, 4H), 3.06 (m, 1H).

Example 132

5-amino-3-[4-(4-chlorophenoxy)phenyl]-1-{(3R)-1-[(2E)-4-fluorobut-2-enoyl]piperidin-3-yl}-1H-pyrazole-4-carboxamide

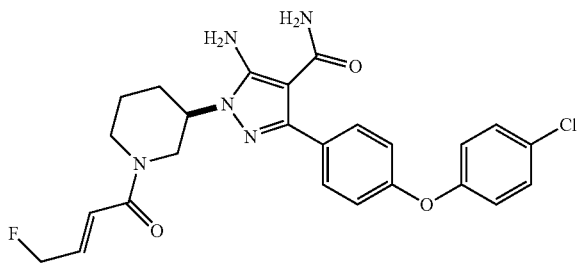 [SMILES: NC(=O)c1c(-c2ccc(Oc3ccc(Cl)cc3)cc2)nn([C@@H]2CCCN(C(=O)/C=C/CF)C2)c1N]

Step 1: preparation of (E)-ethyl 4-fluorobut-2-enoate. To the suspension of AgF (19.71 g, 155.40 mmol) in MeCN (70 mL) was added a solution of (E)-ethyl 4-bromobut-2-enoate (10 g, 51.80 mmol) in MeCN (50 ml) under nitrogen atmosphere in the dark. The reaction mixture was stirred at room temperature for 24 h. The reaction mixture was filtered through a short pad of celite and washed with dichloromethane. The filtrate was concentrated under reduced pressure and low temperature to afford the title compound (6.83 g, 100%) as a brown liquid. $^1$H NMR (400 MHz, CDCl$_3$) δ 1.29 (t, 3H, J=7.1 Hz), 4.21 (q, 2H, J=4.1 Hz), 5.04 (d, 2H, J=46.1 Hz), 6.10 (d, 1H, J=15.8 Hz), 6.90-7.00 (m, 1H).

Step 2: preparation of (E)-4-fluorobut-2-enoic acid. To the stirred solution of (E)-ethyl 4-fluorobut-2-enoate (4.4 g, 33.33 mmol) in tetrahydrofuran (30 ml), a solution of LiOH.H$_2$O (4.2 g, 99.99 mmol) in water (30 ml) was added and stirred at room temperature for 2.5 h. The reaction mixture was acidified with HCl (2N, aq, 10 ml) and extracted with 10% MeOH-dichloromethane. The combined organic phase was washed with brine, dried over Na$_2$SO$_4$ and concentrated to provide the title compound (1.7 g, 49%) as a yellow solid. $^1$H NMR (400 MHz, DMSO-d$_6$) δ 5.13 (d, J=46.3 Hz, 2H), 5.96 (d, J=15.9 Hz, 1H), 6.82-6.94 (m, 1H), 12.54 (br s, 1H).

Step 3: preparation of 5-amino-3-[4-(4-chlorophenoxy) phenyl]-1-{(3R)-1-[(2E)-4-fluorobut-2-enoyl]piperidin-3-yl}-1H-pyrazole-4-carboxamide. To a solution of (R)-5-amino-3-(4-(4-chlorophenoxy)phenyl)-1-(piperidin-3-yl)-1H-pyrazole-4-carboxamide (prepared as described in Example 13, step 7) (150 mg, 0.36 mmol) in N,N-dimethylformamide (2.00 mL) was cooled to 0° C. 2-(1H-Benzotriazol-1-yl)tris(dimethylamino)phosphonium hexafluorophosphate (177 mg, 0.40 mmol), N,N-diisopropylethylamine (0.16 mL, 0.91 mmol) and (E)-4-fluorobut-2-enoic acid (41.69 mg, 0.4 mmol) were added at 0° C. The reaction mixture was stirred for 15 min at 0° C. and quenched with ice water (10 mL). The resulting mixture was extracted using ethyl acetate. The combined organic layers were washed with brine and dried over sodium sulfate, concentrated in vacuo and purified by silica gel column chromatography (10% methanol/ethyl acetate) followed by trituration with dichloromethane:hexane (1:5, 12 mL) to afford the title compound. MS (M+H) m/z 498. $^1$H NMR (400 MHz, DMSO-d$_6$) δ ppm 7.50 (b,s, 2H), 7.45 (d, 2H), 7.15-7.05 (d, 4H), 6.8-6.70 (m, 2H), 6.40 (d, 2H), 5.15 (d, 1H), 5.02 (d, 1H), 4.55-3.95 (m, 3H), 3.49 (t, 0.5H), 3.12 (q, 1H), 2.76 (t, 0.5 H), 1.99 (bs, 2H), 1.80-1.90 (m, 1H), 1.47 (bs, 1H).

Example 133

5-amino-3-[4-(4-chlorophenoxy)phenyl]-1-{(3R)-1-[(2E)-4,4-difluorobut-2-enoyl]piperidin-3-yl}-1H-pyrazole-4-carboxamide

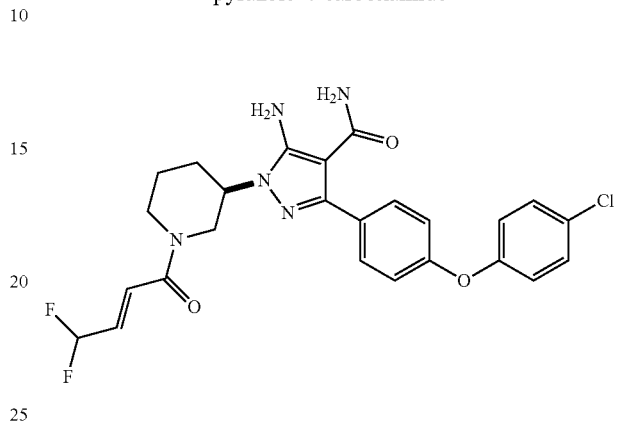

Step 1: preparation of ethyl 4,4-difluoro-3-hydroxybutanoate. To a stirred solution of ethyl 4,4-difluoro-3-oxobutanoate (10 g, 60.19 mmol) in toluene (300 mL) was added sodium borohydride (2.4 g, 63.2 mmol) portionwise at 0° C. The resulting mixture was stirred at room temperature for 4 h. The reaction mixture was diluted with water and extracted with ethyl acetate. The combined organic phase was washed with water followed by brine, dried over Na$_2$SO$_4$ and concentrated to provide the title compound as a colorless liquid (9 g, 89%). $^1$H NMR (400 MHz, DMSO-d$_6$) δ 5.89 (dt, J=3.6 Hz, 55.7 Hz, 1H), 5.81 (br s, 1H), 4.11-4.02 (m, 3H), 2.57 (dd, J=3.9 Hz, 16 Hz, 1H), 2.39 (dd, J=9 Hz, 15.6 Hz, 1H), 1.19 (t, J=7 Hz, 3H).

Step 2: preparation of (E)-ethyl 4,4-difluorobut-2-enoate. Phosphorous pentoxide (1.68 g, 11.89 mmol) was added to ethyl 4,4-difluoro-3-hydroxybutanoate (4 g, 23.78 mmol) under a nitrogen atmosphere. The mixture was stirred at 60° C. for 1 h and then distilled (at 120° C. under 0.05 mm-Hg pressure) to afford the title compound (1.4 g, 39%). $^1$H NMR (400 MHz, DMSO-d$_6$) δ 6.84-6.37 (m, 3H), 4.19 (q, 2H), 1.24 (t, 3H).

Step 3: Prep of (E)-4,4-difluorobut-2-enoic acid. A solution of (E)-ethyl 4,4-difluorobut-2-enoate (1.3 g, 8.66 mmol) in 10% aqueous sodium hydroxide solution (13 ml) was heated to 50° C. for 1 h. The reaction mixture was cooled to room temperature and diluted with water. The aqueous fraction was extracted with ethyl acetate and organic extract was discarded. The aqueous fraction was acidified with 1N HCl solution to pH ~4 and then extracted with ethyl acetate. The combined organic extracts were washed with water, brine, dried over sodium sulphate and concentrated the title compound as an off white solid (650 mg, 62%). $^1$H NMR (400 MHz, DMSO-d$_6$) δ12.82 (br s, 1H), 6.76-6.67 (m, 1H), 6.56 (dd, 1H, J=4.96 Hz, 54.7 Hz), 6.37-6.33 (m, 1H). MS (M−H) m/z 121.

Step 4: Prep of 5-amino-3-[4-(4-chlorophenoxy)phenyl]-1-{(3R)-1-[(2E)-4,4-difluorobut-2-enoyl]piperidin-3-yl}-1H-pyrazole-4-carboxamide. To a solution of (R)-5-amino-3-(4-(4-chlorophenoxy)phenyl)-1-(piperidin-3-yl)-1H-pyrazole-4-carboxamide (prepared as described in Example 13, step 7) (150 mg, 0.36 mmol) in N,N-dimethylformamide (2.00 mL) was cooled to 0° C. 2-(1H-benzotriazol-1-yl)tris (dimethylamino)phosphonium hexafluorophosphate (177 mg, 0.40 mmol), N,N-diisopropylethylamine (0.16 mL, 0.91 mmol) and (E)-4,4-difluorobut-2-enoic acid (41.69 mg, 0.4 mmol) were added at 0° C. The reaction mixture was stirred for 15 min at 0° C. and quenched with Ice water (10 mL). The resulting mixture was extracted using ethyl acetate. The combined organic layers were washed with brine and dried over sodium sulfate, concentrated in vacuo and purified by silica gel column chromatography (10% methanol/ethyl acetate) followed by trituration with dichloromethane: hexane (1:5, 12 mL) to afford the title compound. MS (M+H) m/z 516. $^1$H NMR (400 MHz, DMSO-$d_6$) δ ppm 7.55-7.45 (m, 4H), 7.25-7.05 (m, 5H), 6.7-6.35 (m, 4H), 4.5-3.95 (m, 3H), 3.53 (t, 0.5H), 3.15 (q, 1H), 2.82 (t, 0.5H), 1.98 (b,s, 2H), 1.95-1.80 (m, 1H), 1.47 (bs, 1H).

Example 134

5-amino-3-[4-(4-chlorophenoxy)phenyl]-1-[(3R)-1-(2-fluoroacryloyl)piperidin-3-yl]-1H-pyrazole-4-carboxamide

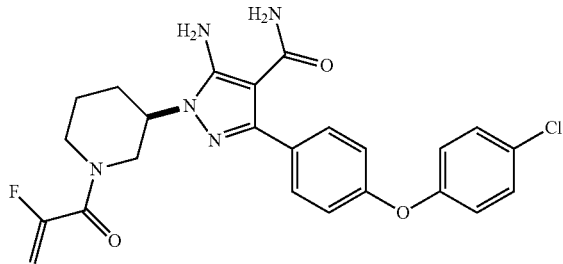

To a solution of (R)-5-amino-3-(4-(4-chlorophenoxy)phenyl)-1-(piperidin-3-yl)-1H-pyrazole-4-carboxamide (prepared as described in Example 13, step 7) (79.1 mg, 0.192 mmol) in N,N-dimethylformamide (2.00 mL) was cooled to 0° C. 2-(1H-Benzotriazol-1-yl)tris(dimethylamino)phosphonium hexafluorophosphate (106 mg, 0.24 mmol), N,N-diisopropylethylamine (65.3 mg, 0.48 mmol) and 2-fluoroacrylic acid (21.69 mg, 0.24 mmol) were added at 0° C. The reaction mixture was stirred for 15 min at 0° C. and then quenched by pouring over ice water. The solid was filtered and purified by reverse phase HPLC to afford the title compound. MS (M+H) m/z 484.1.

Example 135

5-amino-3-[4-(4-chlorophenoxy)phenyl]-1-{(3R)-1-[(2E)-3-cyanoprop-2-enoyl]piperidin-3-yl}-1H-pyrazole-4-carboxamide

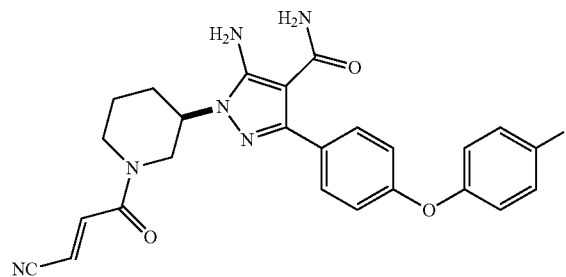

Step 1: preparation of (E)-ethyl 3-cyanoacrylate. To a stirred solution of (Z)-ethyl 3-cyanoacrylate (2 g, 16 mmol) in acetonitrile (16 ml) was added triphenyl phosphine (4.2 g, 16 mmol) and heated to reflux for 5 days. The reaction mixture was cooled to room temperature and volatiles were removed under reduced pressure. The residue was purified by silica gel column chromatography in hexane to afford the title compound as colorless liquid (370 mg, 19%). $^1$H NMR (400 MHz, CDCl$_3$) δ 6.69 (d, 1H), 6.48 (d, 1H), 4.28 (q, 2H), 1.32 (t, 3H). GCMS: Rt=6.71 min; m/z 125

Step 2: preparation of (E)-3-cyanoacrylic acid. A solution of (E)-ethyl 3-cyanoacrylate (1.3 g, 10.38 mmol) in hydrochloric acid (6N, aq, 20 ml) was heated to 100° C. for 4 h. The reaction mixture was cooled to room temperature and evaporated to dryness. The residue was triturated with ether to afford the title compound as a white solid (900 mg, 89%). $^1$H NMR (400 MHz, CDCl$_3$) δ 7.99 (br s, 1H), 6.72 (d, 1H), 6.57 (d, 1H). MS (M+H) m/z 98.

Step 3: preparation of 5-amino-3-[4-(4-chlorophenoxy)phenyl]-1-{(3R)-1-[(2E)-3-cyanoprop-2-enoyl]piperidin-3-yl}-1H-pyrazole-4-carboxamide. The title compound was prepared analogous to 1-[(3R)-1-acryloylpiperidin-3-yl]-5-amino-3-[4-(4-chlorophenoxy)phenyl]-1H-pyrazole-4-carboxamide (Example 13) employing (E)-3-cyanoacrylic acid. $^1$H NMR (400 MHz, DMSO-$d_6$) δ 1.50 (m, 1H), 1.85-2.07 (m, 3H), 2.91 (t, 0.5H), 3.14 (t, 1H), 3.55 (dd, 0.5H), 4.07-4.45 (m, 3H), 6.38-6.42 (m, 2H), 6.52 (dd, 1H), 7.08-7.12 (m, 4H), 7.44-7.52 (m, 4H), 7.83 (dd, 1H). MS (M+H) m/z 491.

Example 136

1-[(3S)-1-acryloyl piperidin-3-yl]-5-amino-3-[4-(2,4-difluorophenoxy)phenyl]-1H-pyrazole-4-carboxamide

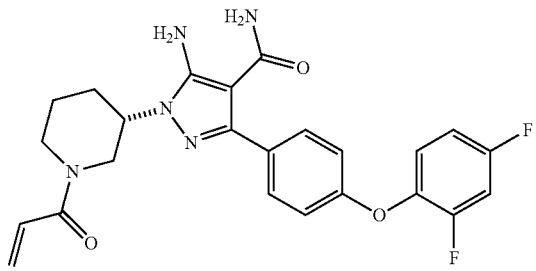

Step 1: preparation of methyl 4-(2,4-difluorophenoxy)benzoate. 4 Å molecular sieves powder (17 g), (4-(methoxycarbonyl)phenyl)boronic acid (17.34 g, 133.33 mmol), 4-dimethylaminopyridine (27.13 g, 222.22 mmol) and anhydrous copper (II) acetate (30.3 g, 166.7 mmol) were added to a solution of 2,4-difluorophenol (20.0 g, 111.11 mmol) in dry dichloromethane (800 mL) at room temperature, and the resulting mixture was stirred for 48 h. The reaction mixture was then filtered through celite pad, the filtrate was concentrated and purified by column chromatography on silica (100-200 mesh), eluting with 8% EtOAc in petroleum ether to give compd-2×10 (15 g, 51.2%) as solid. MS (M+H) m/z 265. $^1$H NMR (DMSO-de, 300 MHz) δ 7.97 (d, 2H), 7.56 (m, 1H), 7.45 (m, 1H), 7.20 (t, 1H), 7.05 (d, 2H), 3.83 (s, 3H).

Step 2: preparation of 4-(2,4-difluorophenoxy)benzoic acid. To a suspension of methyl 4-(2,4-difluorophenoxy)

benzoate (15.0 g, 56.82 mmol) in methanol (525 mL) were added water (63 mL) and NaOH pellets (12.22 g, 284.11 mmol) at 0° C., the cooling batch was then removed and the reaction mixture was stirred at 50° C. for 3 h. Methanol was distilled off and water was added. The residue was acidified with 1N HCl and then extracted with EtOAc. The combined organic layer was dried over sodium sulfate, filtered and concentrated to afford the title compound (12.0 g, 91.5%) as white solid. MS (M+H) m/z 249. $^1$H NMR (DMSO-d$_6$, 300 MHz) δ 12.85 (bs, 1H), 7.92 (d, 2H), 7.52 (m, 1H), 7.40 (m, 1H), 7.20 (t, 1H), 7.00 (d, 2H).

Step 3: preparation of 4-(2,4-difluorophenoxy)benzoyl chloride. 4-(2,4-difluorophenoxy)benzoic acid (3.0 g, 30 mmol) in thionyl chloride (80 mL) was refluxed overnight. The volatiles were evaporated to afford the title compound.

Step 4: preparation of 2-((4-(2,4-difluorophenoxy)phenyl)(methoxy)methylene)-malononitrile. A solution of malononitrile (1.0 g, 15.52 mmol) in tetrahydrofuran (10 mL) was added drop wise to a stirred suspension of NaH (574 mg, 23.9 mmol) in tetrahydrofuran (50 mL) at 0° C. in N$_2$ atmosphere. After stirring for 30 min, 4-(2,4-difluorophenoxy)benzoyl chloride (3.2 g, 11.94 mmol) in tetrahydrofuran (15 mL) was added dropwise. The reaction mixture was brought to room temperature and stirred (~3 h). The reaction mixture was then heated to reflux and dimethyl sulfate (7.7 mL, 83.6 mmol) was added drop wise. The mixture was refluxed for 18 h. After cooling to room temperature, the mixture was quenched with ice water (100 mL) and extracted with EtOAc (2×). The combined organic layers were dried over sodium sulfate, concentrated and purified by flash chromatography on silica gel (100-200 mesh) eluting with 12% EtOAc in petroleum ether to afford the title compound (1.8 g) as liquid. MS (M+H) m/z 297. $^1$H NMR (DMSO-de, 400 MHz) δ 7.71 (d, 2H), 7.52 (m, 1H), 7.43 (m, 1H), 7.20 (t, 1H), 7.16 (d, 2H), 3.93 (s, 3H).

Step 5: preparation of benzyl 3-(5-amino-4-cyano-3-(4-(2,4-difluorophenoxy)phenyl)-1H-pyrazol-1-yl)piperidine-1-carboxylate. Triethylamine (2.2 mL 14.4 mmol) was added to a stirred mixture of 2-((4-(2,4-difluorophenoxy)phenyl)methoxy)methylene)malononitrile (1.5 g, 4.8 mmol) and 3-hydrazino-piperidine-1-carboxylic acid benzylester hydrochloride (Example 1, Step 8) (1.4 g, 4.8 mmol) in ethanol (30 mL) at room temperature. After stirring for 3 h the precipitate was filtered. The resulting solid was washed with ethanol and dried under vacuum to afford the title compound (1.8 g, 40%). MS (M+H) m/z 530. $^1$H NMR (DMSO-d$_6$, 300 MHz) δ 7.78 (d, 2H), 7.50 (m, 1H), 7.33 (m, 6H), 7.18 (m, 1H), 7.05 (d, 2H), 6.78 (s, 2H), 5.06 (bs, 2H), 4.26 (m, 1H), 3.99 (m, 2H), 3.30 (m, 1H), 2.97 (t, 1H), 2.21 (s, 3H), 1.90 (m, 3H), 1.48 (m, 1H).

Step 6: preparation of 5-amino-3-(4-(2,4-difluorophenoxy)phenyl)-1-(piperidin-3-yl)-1H-pyrazole-4-carboxamide. A cold 2.5M aq. NaOH solution (20 mL) was added to a mixture of benzyl 3-(5-amino-4-cyano-3-(4-(2,4-difluorophenoxy)phenyl)-1H-pyrazol-1-yl)piperidine-1-carboxylate (1.8 g, 3.39 mmol) in ethanol (20 mL) charged to a 100 mL sealed tube. The mixture was heated with stirring at 140° C. for 24 h. After cooling to room temperature, the reaction mixture was diluted with water and extracted with EtOAc (2×). The combined organic layers were dried over Na$_2$SO$_4$, filtered, and concentrated to afford the title compound (1.4 g). MS (M+H) m/z 414. $^1$H NMR (DMSO-d, 300 MHz) δ 7.45 (d, 2H), 7.32 (m, 1H), 7.23 (m, 1H), 7.18 (m, 1H), 7.01 (d, 2H), 6.30 (s, 2H), 5.17 (t, 1H), 4.07 (m, 1H), 3.0 (d, 1H), 2.7-2.90 (m, 3H), 1.90 (m, 2H), 1.70 (m, 1H), 1.48 (m, 1H).

Step 7: preparation of (S)-5-amino-3-(4-(2,4-difluorophenoxy)phenyl)-1-(piperidin-3-yl)-1H-pyrazole-4-carboxamide. rac-5-amino-3-(4-(2,4-difluorophenoxy)phenyl)-1-(piperidin-3-yl)-1H-pyrazole-4-carboxamide was chirally separated by supercritical fluid chromatography (ChiralPak OJ-H, 4.6×250 mm, 15/85, CO$_2$/ethanol with 0.2% isopropylamine, 2.5 mL/min flow rate). Isolation of the second eluting isomer afforded the title compound.

Step 8: preparation of 1-[(3S)-1-acryloylpiperidin-3-yl]-5-amino-3-[4-(2,4-difluorophenoxy)-phenyl]-1H-pyrazole-4-carboxamide. Triethylamine (1.69 mL, 12.1 mmol) and N-[(dimethylamino)-1H-1,2,3-triazolo-[4,5-b]pyridin-1-yl-methylene]-N-methylmethanaminium hexafluorophosphate N-oxide (2.02 g (5.3 mmol) were added to a solution of (S)-5-amino-3-(4-(2,4-difluorophenoxy)phenyl)-1-(piperidin-3-yl)-1H-pyrazole-4-carboxamide (2.0 g, 4.8 mmol) and acrylic acid (0.38 g, 5.3 mmol) in N,N-dimethylformamide (20 mL). After stirring at room temperature for 3 h, mixture was poured into water and extracted with ethyl acetate. The organic layer was washed with water, 1N hydrochloric acid solution and brine and then dried (Na$_2$SO$_4$), filtered and concentrated. The crude product was purified by column chromatography (methano/ethyl acetate) to afford the title compound. MS (M+H) m/z 468. $^1$H NMR (400 MHz, DMSO-d$_6$) δ ppm 7.42-7.59 (m, 3H), 7.30-7.41 (m, 1H), 7.11-7.21 (m, 1H), 7.02 (d, J=8.20 Hz, 2H), 6.74-6.92 (m, 1H), 6.40 (br. s., 2H), 6.10 (t, J=18.70 Hz, 1H), 5.67 (dd, J=25.37, 10.54 Hz, 1H), 4.01-4.55 (m, 2H), 3.39-3.52 (m, 1H), 2.96-3.11 (m, 1H), 2.73 (t, J=11.51 Hz, 1H), 1.78-2.07 (m, 3H), 1.47 (br. s., 1H)

Example 137

1-[(3R)-1-acryloyl piperidin-3-yl]-5-amino-3-[4-(2,4-difluorophenoxy)phenyl]-1H-pyrazole-4-carboxamide

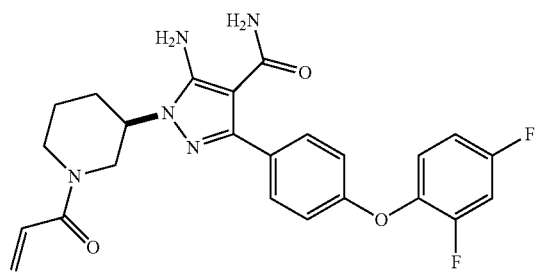

Step 1: preparation of (R)-5-amino-3-(4-(2,4-difluorophenoxy)phenyl)-1-(piperidin-3-yl)-1H-pyrazole-4-carboxamide. rac-5-amino-3-(4-(2,4-difluorophenoxy)phenyl)-1-(piperidin-3-yl)-1H-pyrazole-4-carboxamide (prepared as described in Example 25, Step 6) was chirally separated by supercritical fluid chromatography (ChiralPak OJ-H, 4.6×250 mm, 15/85, CO$_2$/ethanol with 0.2% isopropylamine, 2.5 mL/min flow rate). Isolation of the first eluting isomer afforded the title compound.

Step 2: preparation of 1-[(3R)-1-acryloylpiperidin-3-yl]-5-amino-3-[4-(2,4-difluorophenoxy)-phenyl]-1H-pyrazole-4-carboxamide. The title compound was prepared analogous to 1-[(3S)-1-acryloylpiperidin-3-yl]-5-amino-3-[4-(2,4-difluorophenoxy)-phenyl]-1H-pyrazole-4-carboxamide (Example 25, Step 8). MS (M+H) m/z 468. $^1$H NMR (400 MHz, DMSO-d$_6$) δ ppm 7.42-7.59 (m, 3H), 7.30-7.41 (m, 1H), 7.11-7.21 (m, 1H), 7.02 (d, J=8.20 Hz, 2H), 6.74-6.92 (m, 1H), 6.40 (br. s., 2H), 6.10 (t, J=18.70 Hz, 1H), 5.67 (dd, J=25.37, 10.54 Hz, 1H), 4.01-4.55 (m, 2H), 3.39-3.52 (m, 1H), 2.96-3.11 (m, 1H), 2.73 (t, J=11.51 Hz, 1H), 1.78-2.07 (m, 3H), 1.47 (br. s., 1H)

Example 138

5-amino-3-[4-(2,4-difluorophenoxy)phenyl]-1-{(3R)-1-[(2E)-4-methoxybut-2-enoyl]piperidin-3-yl}-1H-pyrazole-4-carboxamide

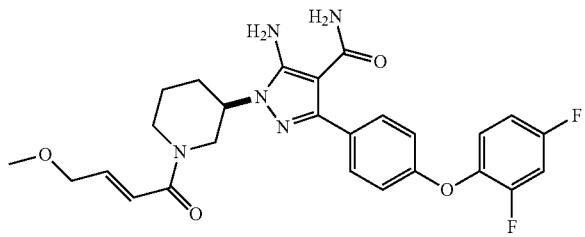

To a solution of (R)-5-amino-3-(4-(2,4-difluorophenoxy)phenyl)-1-(piperidin-3-yl)-1H-pyrazole-4-carboxamide (prepared as described in Example 26, Step 1) (50 mg, 0.12 mmol), (E)-4-methoxybut-2-enoic acid (15 mg, 0.13 mmol, prepared according to J. Org. Chem. 1981, 46, 940-948) and O-(7-azabenzotriazole-1-yl)-1,1,3,3-tetramethyluronium hexafluorophosphate (53 mg, 0.13 mmol) in N,N-dimethylformamide (1 mL) was added triethylamine (25 mg, 0.24 mmol). After 3 h the reaction was diluted into ethyl acetate (10 mL), washed three times with aqueous 1N hydrochloric acid (2 mL) and three times with 10% $Na_2CO_3$ (2 mL). After drying over magnesium sulfate, filtration and concentration, the crude product was purified by reverse phase HPLC to afford the title compound. MS (M+H) m/z 512. $^1$H NMR (DMSO-$d_6$, 400 MHz) δ 7.49 (m, 3H), 7.36 (m, 1H), 7.16 (m, 1H), 7.03 (m, 2H), 6.65 (m, 2H), 4.40 (m, 1H), 4.20 (m, 1H), 4.04 (m, 3H), 3.28 (m, 3H), 3.06 (m, 1H), 1.92 (m, 3H), 1.47 (m, 1H).

Example 139

5-amino-3-[4-(2,4-difluorophenoxy)phenyl]-1-[(3R)-1-(2-methylacryloyl)piperidin-3-yl]-1H-pyrazole-4-carboxamide

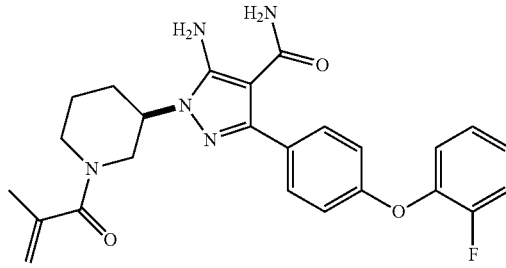

To a solution of (R)-5-amino-3-(4-(2,4-difluorophenoxy)phenyl)-1-(piperidin-3-yl)-1H-pyrazole-4-carboxamide (prepared as described in Example 26, Step 1) (69 mg, 0.17 mmol), methacrylic acid (15 mg, 0.17 mmol) and O-(benzotriazol-1-yl)-N,N,N',N'-tetramethyluronium hexafluorophosphate (67 mg, 0.17 mmol) in N,N-dimethylformamide (2 mL) was added N,N-diisopropylethylamine (0.1 mL). After 18 h the crude reaction mixture was purified by reverse phase HPLC to afford the title compound. MS (M+H) m/z 482. $^1$H NMR (DMSO-$d_6$, 400 MHz) δ 7.54-7.46 (m, 3H), 7.35 (td, J=9.1, 5.6 Hz, 1H), 7.16 (t, J=8.5 Hz, 1H), 7.03 (d, J=8.5 Hz, 2H), 6.4 (br s, 2H), 5.17 (br s, 1H), 5.01 (s, 1H), 4.40 (m, 1H), 4.23 (m, 1H), 3.90 (m, 1H), 3.3 (m, 1H), 3.10 (m, 1H), 2.05-1.80 (m, 6H), 1.49 (m, 1H).

Example 140

5-amino-3-[4-(2,4-difluorophenoxy)phenyl]-1-{(3R)-1-[(2E)-4-(dimethylamino)but-2-enoyl]piperidin-3-yl}-1H-pyrazole-4-carboxamide The title compound was prepared analogous to 5-amino-3-[4-(2,4-difluorophenoxy)phenyl]-1-[(3R)-1-(2-methylacryloyl)piperidin-3-yl]-1H-pyrazole-4-carboxamide (Example) employing (E)-4-(dimethylamino)but-2-enoic acid. MS (M+H) m/z 526. $^1$H NMR (400 MHz, methanol-$d_4$) δ ppm 7.47-7.53 (m, 2H), 7.24 (td, J=9.1, 5.4 Hz, 1H), 7.16 (ddd, J=11.0, 8.4, 3.0 Hz, 1H), 6.97-7.07 (m, 3H), 6.55-6.83 (m, 2H), 4.63 (d, J=12.0 Hz, 1H), 4.34 (d, J=13.0 Hz, 1H), 4.09-4.27 (m, 4H), 3.65 (dd, J=13.1, 10.0 Hz, 1H), 2.27 (s, 3H), 2.24 (s, 2H), 1.93-2.18 (m, 3H), 1.56-1.70 (m, 1H).

Example 141

5-amino-3-[4-(2,4-difluorophenoxy)phenyl]-1-{(3R)-1-[(2E)-5-hydroxypent-2-enoyl]piperidin-3-yl}-1H-pyrazole-4-carboxamide Step 1: Preparation of (E)-ethyl 5-hydroxypent-2-enoate. To a solution of propane-1,3-diol (9.0 g, 118.42 mmol) in dichloromethane (1.2 L), was added ethyl 2-(triphenylphosphoranylidene)acetate (99.03 g, 284.21 mmol) and manganese dioxide (206.5 g, 2368.42 mmol) at room temperature. Resulting mixture was stirred at room temperature for 48 h. After completion of reaction (monitored by TLC) the mixture was filtered through a short pad of celite bed and washed with dichloromethane. The filtrate was concentrated under reduced pressure. The crude material was purified by column chromatography (13% ethyl acetate/hexane) to afford the title compound (12 g, 70.5) as colorless liquid. $^1$H NMR (400 MHz, CDCl$_3$) δ 6.97-6.87 (m, 1H), 5.90 (d, J=15.6 Hz, 1 H), 4.16 (q, J=7.1 Hz, 2H), 3.75 (m, 2H) 2.45 (q, J=6.2 Hz, 2H), 1.89 (br s, 1H), 1.26 (t, J=7.2 Hz, 3H).

Step 2: Preparation of (E)-ethyl 5-hydroxypent-2-enoic acid. To a solution of (E)-ethyl 5-hydroxypent-2-enoate (1.5 g, 10.41 mmol) in tetrahydrofuran (6 mL), a solution of lithium hydroxide-hydrate (1.31 g, 31.24 mmol) in water (6 mL) was added at room temperature. The resulting reaction mixture was stirred at room temperature for 2 h. The mixture was acidified with 1N-HCl (15 mL) and extracted with ethyl acetate (3×50 mL).

The combined organic portion was dried over sodium sulfate, filtered and concentrated to afford the title compound (0.6 g, 50%) as a colorless liquid. $^1$H NMR (400 MHz, CDCl$_3$) δ 12.1 (br s, 1H), 6.97-6.87 (m, 1H), 5.79 (d, J=15.6 Hz, 1H), 3.50 (t, J=6.2 Hz, 2H) 2.31 (q, J=6.2 Hz, 2H), Step 3: Preparation of 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide. A solution of (R)-5-amino-3-(4-(2,4-difluorophenoxy)phenyl)-1-(piperidin-3-yl)-1H-pyrazole-4-carboxamide (prepared as described in Example 26, Step 1) (100 mg, 0.24 mmol) in N,N-dimethylformamide (0.5 mL) was cooled to 0° C. (Benzotriazol-1-yloxy)tris-(dimethylamino)phosphonium hexafluorophosphate (118 mg, 0.27 mmol) and N,N-diisopropylethylamine (0.1 mL, 0.61 mmol) were added followed by (E)-5-hydroxypent-2-enoic acid (30.89 mg, 0.27 mmol). The mixture was stirred at same temperature for 15 min. The reaction mixture was quenched with ice water (10 mL) and was extracted with ethyl acetate (2×50 mL). The combined organic layer was washed with water (2×10 mL), brine (2×10 mL), dried over sodium sulfate and concentrated under vacuo. The crude residue was purified by silica gel column chromatography (1% MeOH in EtOAc) followed by trituration with (1:5 dichloromethane:Hexane, 12 mL) to afford the title compound as off white solid. MS (M+H) m/z 512. $^1$H NMR (400 MHz, DMSO-d$_6$) δ 7.55-7.45 (m, 3H), 7.40-7.30 (m, 1H), 7.15 (t, 1H), 7.01 (d, 2H), 6.75-6.60 (m, 1H), 6.60-6.50 (m, 1H), 6.39 (bs, 2H), 4.70-4.00 (m, 5H), 3.49 (bs, 2H), 3.10-2.95 (m, 1H), 2.32 (bs, 2H), 2.01 (bs, 2H), 1.90-1.75 (m, 1H), 1.45 (bs, 1H).

Example 142

5-amino-1-{(3R)-1-[(2E)-but-2-enoyl]piperidin-3-yl}-3-[4-(2,4-difluorophenoxy)phenyl]-1H-pyrazole-4-carboxamide

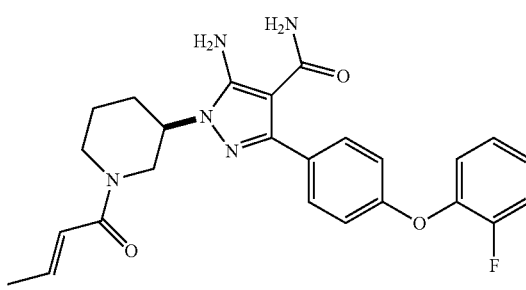

The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (E)-but-2-enoic acid. MS (M+H) m/z 482. $^1$H NMR (400 MHz, DMSO-d) δ ppm 7.55-7.45 (m, 3H), 7.40-7.30 (m, 1H), 7.15 (t, 1H), 7.02 (d, 2H), 6.75-6.60 (m, 1H), 6.60-6.50 (m, 1H), 6.39 (bs, 2H), 4.50-4.00 (m, 3H), 3.55-3.35 (m, 1H), 3.10-2.90 (m, 1H), 1.97 (bs, 2H), 1.82 (bs, 4H), 1.45 (bs, 1H).

Example 143

5-amino-3-[4-(2,4-difluorophenoxy)phenyl]-1-{(3R)-1-[(2E)-pent-2-enoyl]piperidin-3-yl}-1H-pyrazole-4-carboxamide

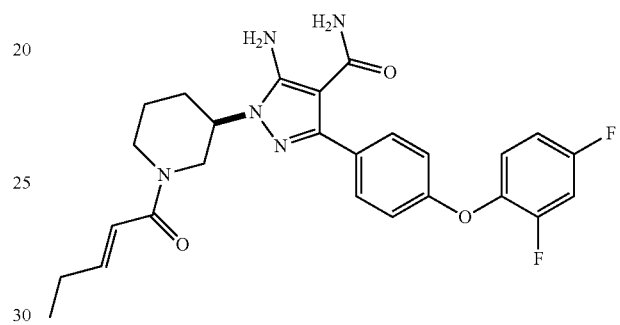

The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (E)-pent-2-enoic acid. MS (M+H) m/z 496. $^1$H NMR (400 MHz, DMSO-d$_6$) δ ppm 7.55-7.45 (m, 3H), 7.40-7.30 (m, 1H), 7.15 (t, 1H), 7.02 (d, 2H), 6.75-6.60 (m, 1H), 6.60-6.50 (m, 1H), 6.39 (bs, 2H), 4.50-4.05 (m, 3H), 3.55-3.40 (m, 0.5H), 3.10-2.95 (m, 1H), 2.80-2.65 (m, 0.5H), 2.55-2.10 (m, 2H), 1.97 (bs, 2H), 1.90-1.80 (m, 1H), 1.45 (bs, 1H), 0.99 (bs, 3H).

Example 144

5-amino-1-{(3R)-1-[(2E)-4,4-difluorobut-2-enoyl]piperidin-3-yl}-3-[4-(2,4-difluorophenoxy)phenyl]-1H-pyrazole-4-carboxamide

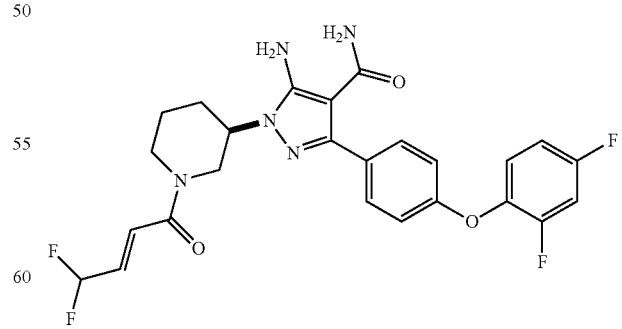

The title compound was prepared analogous to 5-amino-3-[4-(2,4-difluorophenoxy)-phenyl]-1-{(3R)-1-[(2E)-5-hydroxypent-2-enoyl]piperidin-3-yl}-1H-pyrazole-4-carboxamide (Example) employing (E)-4,4-difluorobut-2-enoic acid (prepared as described in Example 133, step 3). MS (M+H) m/z 518. $^1$H NMR (400 MHz, DMSO-$d_6$) δ 7.55-7.45 (m, 3H), 7.40-7.30 (m, 1H), 7.23-7.11 (m, 2H), 7.02 (d, 2H), 6.70-6.35 (m, 4H), 4.50-3.95 (m, 3H), 3.53 (t, 0.5H), 3.12 (q, 1H), 2.81 (t, 0.5H), 1.98 (bs, 2H), 1.95-1.80 (m, 1H), 1.48 (bs, 1H).

Example 145

5-amino-3-[4-(2,4-difluorophenoxy)phenyl]-1-{(3R)-1-[(2E)-4-fluorobut-2-enoyl]piperidin-3-yl}-1H-pyrazole-4-carboxamide

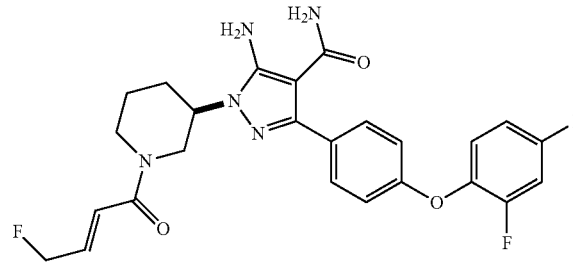

The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (E)-4-fluorobut-2-enoic acid (Example, step 2). MS (M+H) m/z 500. $^1$H NMR (400 MHz, DMSO-$d_6$) δ 7.55-7.45 (m, 3H), 7.40-7.30 (m, 1H), 7.15 (t, 1H), 7.02 (d, 2H), 6.80-6.70 (m, 2H), 6.39 (d, 2H), 5.15 (d, 1H), 5.02 (d, 1H), 4.60-4.00 (m, 3H), 3.48 (t, 0.5H), 3.07 (q, 1H), 2.76 (t, 0.5H), 1.98 (bs, 2H), 1.80-1.90 (m, 1H), 1.47 (bs, 1H).

Example 146

5-amino-3-[4-(2,4-difluorophenoxy)phenyl]-1-{(3R)-1-[(2Z)-2-fluoro-4-hydroxybut-2-enoyl]piperidin-3-yl}-1H-pyrazole-4-carboxamide

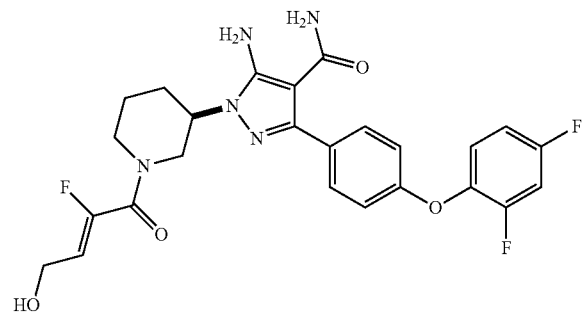

Step 1: preparation of (Z-ethyl 2-fluorobut-2-enoate. To a stirred suspension of sodium hydride (50% in mineral oil, 11.3 g, 235.6 mmol) in tetrahydrofuran (125 mL) were added diethyl oxalate (35.4 mL, 259.2 mmol) and ethyl 2-fluoroacetate (5 g, 47.1 mmol). When the reaction was initiated (reaction mixture observed to be refluxing), the balance of ethyl 2-fluoroacetate (20 g, 188.5 mmol) was slowly added (to maintain 40-45° C.) and the whole reaction mixture was heated for 3 h at 60° C. The reaction mixture was allowed to attain room temperature and cooled to 0° C. Acetaldehyde (13.6 mL, 240.35 mmol) was added and resulting mixture was brought slowly to the boiling point (80° C.) and continued for additional 1 h. After cooling, it was poured into water and extracted with dichloromethane. The combined organic layer was washed with 5% aqueous sodium carbonate solution, water, dried over sodium sulfate and concentrated to afford the title compound (21 g, 68%) as a brown liquid. GCMS m/z 132. $^1$H NMR (400 MHz, CDCl$_3$): 6.23-6.09 (m, 1H). 4.35 (q, 2H), 1.79 (dd, 3H), 1.37 (t, 3H).

Step 2: preparation of (Z)-ethyl 4-bromo-2-fluorobut-2-enoate. To a stirred solution of (Z)-ethyl 2-fluorobut-2-enoate (2 g, 15.15 mmol) in carbon tetrachloride (20 mL) was added N-bromosuccinimide (2.98 g, 16.66 mmol) and benzoyl peroxide (2.5 mg). The mixture was heated to reflux and continued for 6 h. The reaction mixture was filtered and the filtrate was concentrated. The crude material thus obtained was purified by column chromatography (1% ethyl acetate/hexane) to afford the title compound (0.4 g, 13%) as a yellow liquid. $^1$H NMR (400 MHz, CDCl$_3$): 6.41-6.30 (m, 1H). 4.30 (q, 2H), 4.05 (dd, 2H), 1.34 (t, 3H).

Step 3: preparation of (Z)-ethyl 4-acetoxy-2-fluorobut-2-enoate. To a stirred solution of (Z)-ethyl 4-bromo-2-fluorobut-2-enoate (2.5 g, 11.84 mmol) in N,N-dimethylformamide (25 mL) was added sodium acetate (1.94 g, 23.69 mmol) and resulting solution heated at 70° C. for 6 h. The reaction mixture was allowed to attain room temperature, diluted with water and extracted with diethyl ether. The combined organic phase was washed with brine, dried over sodium sulfate and concentrated. The crude product was purified by column chromatography (2.5% ethyl acetate/hexane) to afford the title compound (0.75 g, 33%) as a yellow liquid. $^1$H NMR (400 MHz, CDCl$_3$) δ 6.26-6.14 (m, 1H). 4.79 (dd, 2H), 4.29 (q, 2H), 2.07 (s, 3H), 1.34 (t, 3H).

Step 4: preparation of (Z)-2-fluoro-4-hydroxybut-2-enoic acid. To a solution of lithium hydroxide-hydrate (0.99 g, 23.68 mmol) in water (12 mL) was added solution of (Z)-ethyl 4-acetoxy-2-fluorobut-2-enoate (1.5 g, 7.89 mmol) in tetrahydrofuran (12 mL) and stirred at room temperature for 2.5 h. The reaction mixture was acidified with 2N-HCl and extracted with ethyl acetate. The combined organic phase was washed with brine, dried over sodium sulfate and concentrated to afford the title compound (0.45 g, 48%) as a yellow solid. $^1$H NMR (400 MHz, CDCl$_3$) δ 13.45 (b,s, 1H), 6.18-6.06 (m, 1H), 5.06 (bs, 1H), 4.15 (m, 2H).

Step 5: preparation of 5-amino-3-[4-(2,4-difluorophenoxy)phenyl]-1-{(3R)-1-[(2Z)-2-fluoro-4-hydroxybut-2-enoyl]piperidin-3-yl}-1H-pyrazole-4-carboxamide. The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (Z)-2-fluoro-4-hydroxybut-2-enoic acid. MS (M+H) m/z 516. $^1$H NMR (400 MHz, DMSO-$d_6$) δ 7.55-7.45 (m, 3H), 7.40-7.34 (m, 1H), 7.15 (t, 1H), 7.01 (d, 2H), 6.40 (bs, 2H), 5.66-5.50 (m, 1H), 4.97 (t, 1H), 4.27 (bs, 1H), 4.10 (bs, 2H), 4.00 (br, 1H), 3.55 (br, 1H), 3.00 (br, 1H), 1.98 (bs, 2H), 1.95-1.80 (m, 1H), 1.52 (bs, 1H).

Example 147

5-amino-3-[4-(2,4-difluorophenoxy)phenyl]-1-{(3R)-1-[(2E)-4-hydroxy-4-methyl pent-2-enoyl]piperidin-3-yl}-1H-pyrazole-4-carboxamide

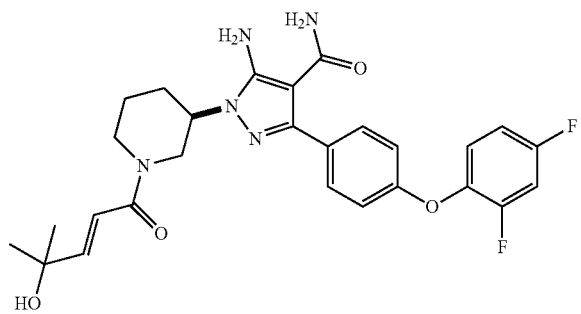

Step 1: preparation of 1,1,1-trichloro-4-methylpent-3-en-2-ol. To a stirred solution of 3-methylbut-2-enal (4 g, 47.55 mmol) in anhydrous N,N-dimethylformamide (80 mL) was added trichloroacetic acid (11.65 g, 71.32 mmol) and sodium trichloroacetate (13.22 g, 71.32 mmol) at room temperature. After 3 h of stirring at room temperature the reaction mixture was diluted with diethyl ether (200 mL) and washed with saturated aqueous sodium bicarbonate (50 mL). The precipitated solids were filtered and washed with diethyl ether (3×50 mL). The combined organics were again washed with saturated aqueous sodium bicarbonate (2×50 mL), brine, dried over sodium sulfate and filtered. The solvent was evaporated to afford the title compound as light yellow solid. $^1$H NMR (400 MHz, CDCl$_3$) δ 5.45-5.35 (m, 1H), 4.11 (bs, 2H), 1.73 (s, 3H), 1.67 (s, 3H).

Step 2: preparation of (E)-4-hydroxy-4-methylpent-2-enoic acid. To a stirred solution of compound 1,1,1-trichloro-4-methylpent-3-en-2-ol (7 g, 34.39 mmol) in dimethoxyethane:water (4:3, 140 mL) was added powdered NaOH (8.25 g, 206.38 mmol) and the resulting mixture was stirred at room temperature for 5 mins and then heated at 55° C. for 12 h. The mixture was allowed to attain room temperature and excess dimethoxyethane was evaporated under reduced pressure. The remaining aqueous phase was acidified to pH=1 by slow addition of 2N aqueous HCl and extracted with ethylacetate (2×200 mL). Evaporation of solvent followed by purification by silica gel column chromatography (15% EtOAc-Hexane) afforded the title compound as light yellow solid. $^1$H NMR (400 MHz, CDCl$_3$) δ 7.12 (d, 1H), 6.03 (d, 1H), 1.38 (s, 6H).

Step 3: preparation of 5-amino-3-[4-(2,4-difluorophenoxy)phenyl]-1-{(3R)-1-[(2E)-4-hydroxy-4-methylpent-2-enoyl]piperidin-3-yl}-1H-pyrazole-4-carboxamide. The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (E)-4-hydroxy-4-methylpent-2-enoic acid. MS (M+H) m/z 526. $^1$H NMR (400 MHz, DMSO-d$_6$) δ 7.55-7.45 (m, 3H), 7.40-7.30 (m, 1H), 7.15 (t, 1H), 7.02 (d, 2H), 6.80-6.65 (m, 1H), 6.55-6.37 (m, 3H), 4.83 (d, 1H), 4.55-4.00 (m, 3H), 3.42 (t, 0.5H), 3.15-2.95 (m, 1H), 2.75-2.65 (m, 0.5H), 2.05-1.80 (m, 3H), 1.47 (bs, 1H), 1.20 (d, 6H).

Example 148

5-amino-3-[4-(2,4-difluorophenoxy)phenyl]-1-{(3R)-1-[(2E,4S)-4-hydroxypent-2-enoyl]piperidin-3-yl}-1H-pyrazole-4-carboxamide

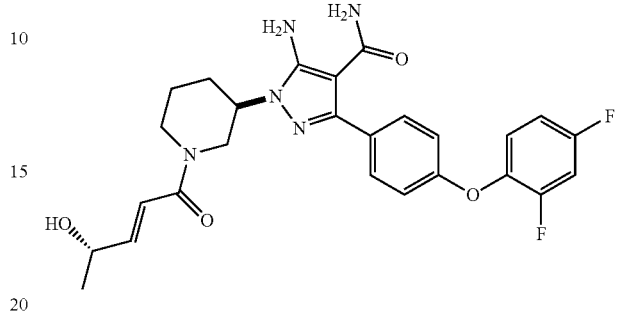

Step 1: Preparation of (E-4-oxopent-2-enoic acid. To a mixture of 2-oxoacetic add (11.17 g, 121.45 mmol) and ground morpholinium hydrochloride (15 g, 121.45 mmol) was stirred in acetone (120 mL) at room temperature for 1 h and then heated at reflux for another 16 h. The reaction mixture was cooled and concentrated under vacuo to remove excess acetone. The crude residue thus obtained was dissolved in water (100 mL) and the aqueous phase was extracted with 10% IPA in dichloromethane (5×100 mL). The combined organic layer was dried over sodium sulfate and filtered. Evaporation of solvent afforded title as off white solid. This material was used for next step without further purification. $^1$H NMR (400 MHz, DMSO-d$_6$) δ ppm 13.06 (bs, 1H), 6.79 (d, 1H), 6.67 (d, 1H), 2.33 (s, 3H).

Step 2: Preparation of (E)-4-hydroxypent-2-enoic acid. To a stirred solution of (E)-4-oxopent-2-enoic acid (7.6 g, 66.61 mmol) in 10% aqueous potassium hydrogen carbonate (133 mL) was added potassium borohydride (4.02 g, 74.60 mmol) at 4-5° C. in portions and the resulting reaction mixture was allowed to stir at room temperature for 4 h. The reaction mixture was cooled to 0° C. and acidified with 6N aqueous HCl to pH=5-6. The aqueous phase was extracted with 10% IPA in dichloromethane (8×100 mL). The combined organic layer was dried over sodium sulfate and filtered. Evaporation of solvent followed by purification using column chromatography (1.5% methanol-dichloromethane) afforded the title compound (5 g, 65%) as light yellow solid. $^1$H NMR (400 MHz, DMSO-d$_6$) δ ppm 12.20 (bs, 1H), 6.80 (dd, 1H), 5.84 (dd, 1H), 5.04 (bs, 1H), 4.25-4.35 (m, 1H), 1.15 (d, 3H).

Step 3: preparation of rac-5-amino-3-[4-(2,4-difluorophenoxy)phenyl]-1-{(3R)-1-[(2E,4S)-4-hydroxypent-2-enoyl]piperidin-3-yl}-1H-pyrazole-4-carboxamide. The title compound was prepared analogous to 5-amino-3-[4-(2,4-difluorophenoxy)phenyl]-1-{(3R)-1-[(2E)-5-hydroxypent-2-enoyl]piperidin-3-yl}-1H-pyrazole-4-carboxamide (Example) employing (E)-4-hydroxypent-2-enoic acid. MS (M+H) m/z 512. $^1$H NMR (400 MHz, DMSO-d$_6$) δ ppm 7.55-7.45 (m, 3H), 7.40-7.30 (m, 1H), 7.15 (t, 1H), 7.02 (d, 2H), 6.70-6.60 (m, 1H), 6.60-6.50 (m, 1H), 6.39 (bs, 2H), 4.96 (d, 1H), 4.55-4.00 (m, 4H), 3.43 (t, 0.5H), 3.10-3.05 (m, 1H), 2.75-2.60 (m, 0.5H), 2.00-1.75 (m, 3H), 1.47 (bs, 1H), 1.15 (bs, 3H).

Step 4: preparation of 5-amino-3-[4-(2,4-difluorophenoxy)phenyl]-1-{(3R)-1-[(2E,4S)-4-hydroxypent-2-enoyl]piperidin-3-yl}-1H-pyrazole-4-carboxamide. rac-5-amino-3-(4-(2,4-difluorophenoxy)phenyl)-1-((3R)-1-((E)-4- hydroxypent-2-enoyl)piperidin-3-yl)-1H-pyrazole-4-carboxamide was chirally separated by supercritical fluid chromatography (Chiralcel OD-H, 20×250 mm, 5, hexane, ethanol, methanol, N, N-diisopropylethylamine (70:20:10:0.1), 18 mL/min). Isolation of the first eluting isomer afforded the title compound. MS (M+H) m/z 512. ¹H NMR (400 MHz, DMSO-d₆) δ ppm 7.55-7.45 (m, 3H), 7.40-7.30 (m, 1H), 7.15 (t, 1H), 7.02 (d, 2H), 6.70-6.60 (m, 1H), 6.60-6.50 (m, 1H), 6.39 (d, 2H), 4.96 (d, 1H), 4.55-4.00 (m, 4H), 3.43 (t, 0.5H), 3.10-3.05 (m, 1H), 2.75-2.60 (m, 0.5H), 2.00-1.75 (m, 3H), 1.47 (bs, 1H), 1.15 (bs, 3H).

Example 149

5-amino-3-(4-(2,4-difluorophenoxy)phenyl)-1-((R)-1-((R,E)-4-hydroxypent-2-enoyl)piperidin-3-yl)-1H-pyrazole-4-carboxamide

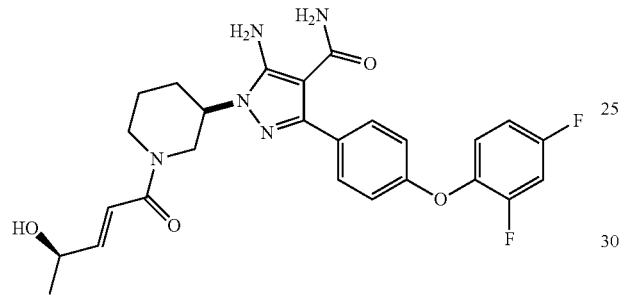

rac-5-amino-3-(4-(2,4-difluorophenoxy)phenyl)-1-((3R)-1-((E)-4-hydroxypent-2-enoyl)piperidin-3-yl)-1H-pyrazole-4-carboxamide (prepared as described in Example, step 3) was chirally separated by supercritical fluid chromatography (Chiralcel OD-H, 20×250 mm, 5, hexane, ethanol, methanol, N,N-diisopropylethylamine (70:20:10:0.1), 18 mL/min). Isolation of the second eluting isomer afforded the title compound. MS (M+H) m/z 512. ¹H NMR (400 MHz, DMSO-d₆) δ 7.55-7.45 (m, 3H), 7.40-7.30 (m, 1H), 7.15 (t, 1H), 7.02 (d, 2H), 6.70-6.60 (m, 1H), 6.60-6.50 (m, 1H), 6.39 (bs, 2H), 4.96 (d, 1H), 4.55-4.00 (m, 4H), 3.43 (t, 0.5H), 3.10-3.05 (m, 1H), 2.75-2.60 (m, 0.5H), 2.00-1.75 (m, 3H), 1.47 (bs, 1H), 1.15 (bs, 3H).

Example 150

5-amino-3-[4-(2,4-difluorophenoxy)phenyl]-1-[(3R)-1-(2-fluoroacryloyl)piperidin-3-yl]-1H-pyrazole-4-carboxamide

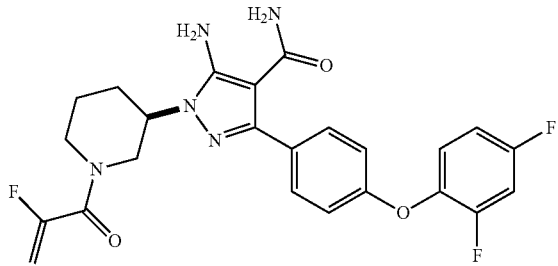

To a solution of (R)-5-amino-3-(4-(2,4-difluorophenoxy)phenyl)-1-(piperidin-3-yl)-1H-pyrazole-4-carboxamide (prepared as described in Example 26, step 1) (200 mg, 0.48 mmol) in N,N-dimethylformamide (3 mL) at 0° C. was added (benzotriazol-1-yloxy)tris(dimethylamino)phosphonium hexafluorophosphate (235 mg, 0.53 mmol), N,N-diisopropylethylamine (0.22 mL, 1.21 mmol) and 2-fluoroacrylic acid (43.6 mg, 0.48 mmol). After 30 min, the mixture was poured into water/ethyl acetate and the layers separated. The organic layer was dried (Na₂SO₄) and concentrated. The crude product was purified by reverse-phase HPLC to afford the title compound. ¹H NMR (600 MHz, DMSO-d₆) δ ppm 1.57 (m, 1H), 1.89-2.09 (m, 3H), 2.97 (m, 0.5H), 3.22 (m, 1H), 3.61 (m, 0.5H), 3.97 (m, 1H), 4.13-4.42 (m, 2H), 5.11-5.38 (m, 2H), 6.45 (br. s., 2H), 7.00-7.09 (m, 2H), 7.15-7.24 (m, 1H), 7.42-7.38 (m, 1H), 7.51-7.59 (m, 3H). MS (M+H) m/z 486.1.

Example 151

5-am no-3-[4-(2,4-difluorophenoxy)phenyl]-1-{(3R)-1-[(2E)-4-hydroxybut-2-enoyl]-piperidin-3-yl}-1H-pyrazole-4-carboxamide

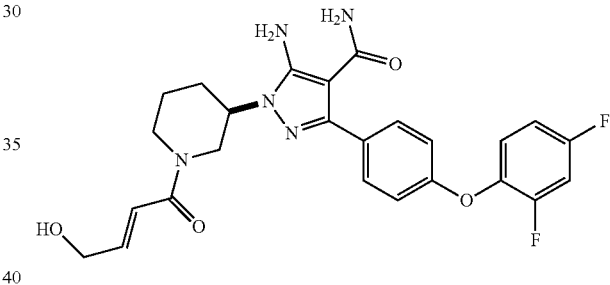

To a solution of (R)-5-amino-3-(4-(2,4-difluorophenoxy)phenyl)-1-(piperidin-3-yl)-1H-pyrazole-4-carboxamide (prepared as described in Example 26, step 1) (100 mg, 0.24 mmol), O-(benzotriazol-1-yl)-N,N,N',N'-tetramethyluronium hexafluorophosphate (112 mg, 0.29 mmol), (E)-4-hydroxybut-2-enoic acid (98 mg, 0.97 mmol) in 2 mL of N,N-dimethylformamide was added N,N-diisopropylethylamine (0.13 mL, 0.73 mmol) dropwise. The solution was stirred overnight at room temperature. The reaction mixture was poured into water/ethyl acetate and the layers separated. The organic extract was dried (Na₂SO₄), filtered and concentrated. The crude product was purified by reverse-phase HPLC to afford the title compound. ¹H NMR (400 MHz, methanol-d₄) δ ppm 1.64 (d, J=12.88 Hz, 1H) 1.97 (dt, J=13.64, 3.03 Hz, 1H) 2.06-2.25 (m, 2H) 2.76-2.95 (m, 0.5H) 3.07-3.24 (m, 1H) 3.52-3.71 (m, 0.5H) 4.05-4.30 (m, 4H) 4.37-4.72 (m, 1H) 6.56-6.72 (m, 1H) 6.75-6.93 (m, 1H) 6.96-7.08 (m, 3H) 7.10-7.32 (m, 2H) 7.50 (d, J=8.34 Hz, 2H). MS (M+H) m/z 498.2.

Example 152

5-amino-1-{(3R)-1-[(2E)-3-cyanoprop-2-enoyl]piperidin-3-yl}-3-[4-(2,4-difluorophenoxy)phenyl]-1H-pyrazole-4-carboxamide

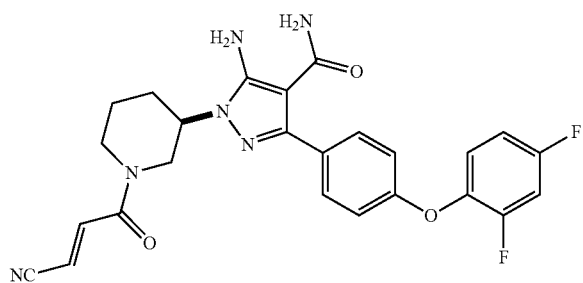

A solution of (R)-5-amino-3-(4-(2,4-difluorophenoxy)phenyl)-1-(piperidin-3-yl)-1H-pyrazole-4-carboxamide (prepared as described in Example 26, step 1) (0.19 g, 0.468 mmol) in N,N-dimethylformamide (4 mL) was cooled to −10° C. (ice-salt). Benzotriazol-1-yloxy)tris (dimethylamino) phosphonium hexafluorophosphate (228 mg, 0.515 mmol) and N,N-diisopropylethylamine (0.2 mL, 1.17 mmol) were added followed by (E)-3-cyanoacrylic acid (prepared as described in Example, step 2) (50 mg, 0.515 mmol) and the mixture was stirred at −10° C. for additional 30 min. The reaction mixture was diluted with water and extracted with ethyl acetate. The organic layer was washed with brine, dried over sodium sulfate and concentrated. The crude product was purified by preparative TLC (5% MeOH-dichloromethane) to afford the title compound (80 mg, 35%) as off white solid. MS (M+H) m/z 493.4. $^1$H NMR (400 MHz, DMSO-d$_6$) δ 1.46 (m, 1H), 1.82 (m, 1H), 1.96 (m, 2H), 2.86 (m, 0.5H), 3.07-3.13 (m, 1H), 3.48-3.53 (m, 0.5H), 3.98-4.42 (m, 3H), 6.37 (m, 2H), 6.49 (dd, 1H), 6.98-7.00 (m, 2H), 7.12 (t, 1H), 7.29-7.34 (m, 1H), 7.42-7.48 (m, 3H), 7.75-7.84 (m, 1H).

Example 153

1-[(3R)-1-acryloyl piperidin-3-yl]-5-amino-3-{4-[(5-chloro-3-fluoropyridin-2-yl)oxy]phenyl}-1H-pyrazole-4-carboxamide

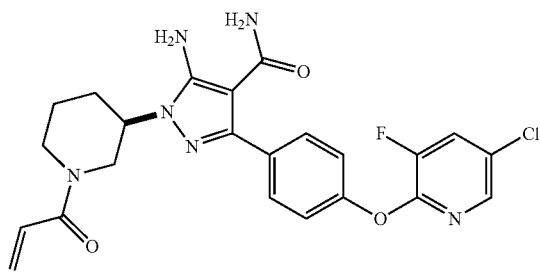

Step 1: preparation of 4-((tert-butyldimethylsilyl)oxy) benzoic acid. To a stirred solution of 4-hydroxybenzoic acid (200 g, 1.45 mol) in N,N-dimethylformamide (3.25 L), was added imidazole (595 g, 8.67 mol) followed by addition of tert-butyl dimethylsilyl chloride (327 g, 2.17 mol) at 0° C. The resulting reaction mixture was stirred at room temperature for 16 h. The reaction mixture was poured onto crushed ice and extracted with ethyl acetate (2×2 L). The combined organic layers were washed with water (2×1 L) followed by brine, dried over sodium sulfate and concentrated under reduced pressure. The crude product was purified by column chromatography in hexanes to afford the title compound (170 g, 47%) as white solid. $^1$H NMR (400 MHz, CDCl$_3$): 7.96-7.98 (d, J=8.68 Hz, 2H), 6.86-6.88 (d, J=8.68 Hz, 2H), 0.98 (s, 9H), 0.23 (s, 6H).

Step 2: preparation of 2-((4-((tert-butyldimethylsilyl)oxy)phenyl)(methoxy)methylene)malononitrile. To a stirred suspension of sodium hydride (60%, 22.8 g, 0.95 mol) in 600 mL tetrahydrofuran, was added malononitrile (31.4 g, 0.47 mol, dissolved in 600 mL of tetrahydrofuran) at 0° C. The resulting suspension was stirred at 0° C. for 1 h. To another 3 necked round bottom flask was charged 4-((tert-butyldimethylsilyl)oxy)benzoic acid (120 g, 0.47 mol dissolved in 1200 mL of tetrahydrofuran) followed by N-methylmorpholine (52.9 mL, 0.47 mol) and isobutyl-chloroformate (61.94 mL, 0.47 mol, dissolved in 600 mL tetrahydrofuran) at −30° C. The resulting white suspension was stirred at −30° C. for 1 h. This acid chloride suspension was slowly added (through cannula) at 0° C. to the stirred suspension of NaH. The resulting suspension was stirred at room temperature for 3 h. Dimethyl sulfate (135.9 mL, 1.4 mol) was added to the suspension at room temperature and the resulting reaction mixture was heated at reflux for 16 h. The reaction mixture was poured onto crushed ice and extracted with ethyl acetate (2×2 L). The combined organic layers were washed with water (2×1 L) followed by brine, dried over sodium sulfate and concentrated under reduced pressure. The crude product was purified by silica gel column chromatography to afford the title compound (76 g, 61%) as light yellow solid. MS (M+H) m/z 315.6. $^1$H NMR (400 MHz, CDCl$_3$) δ 7.43 (d, J=8.68 Hz, 2H), 6.95 (d, J=11.4 Hz, 2H), 3.95 (s, 3H), 0.98 (s, 9H), 0.24 (s, 6H).

Step 3: preparation of benzyl 3-(5-amino-3-(4-((tert-butyldimethylsilyl)oxy)phenyl)-4-cyano-1H-pyrazol-1-yl)piperidine-1-carboxylate. To a stirred solution of 2-((4-((tert-butyldimethylsilyl)oxy)phenyl)(methoxy)methylene)-malononitrile (76 g, 0.24 mol) in ethanol (760 mL) was added benzyl 3-hydrazinylpiperidine-1-carboxylate (Example 1, Step 8) (68.9 g, 0.24 mol) followed by addition of triethylamine (37 mL, 0.26 mol) at room temperature. The resulting reaction mixture was heated to reflux for 16 h and then concentrated under reduced pressure. The residue was diluted with water (500 mL) and extracted with ethyl acetate (2×500 mL). The combined organic layers were washed with water (500 mL) followed by brine, dried over sodium sulfate and concentrated under reduced pressure to afford the title compound (102 g, 89%) as an off white solid. MS (M+H) m/z 532. $^1$H NMR (400 MHz, CDCl$_3$) δ 7.76 (d, J=8.48 Hz, 2H), 7.31-7.38 (m, 5H), 6.86 (d, J=8.48 Hz, 2H), 5.10-5.18 (m, 2H), 4.44 (m, 1H), 4.28 (m, 1H), 4.16 (m, 1H), 3.82 (m, 1H), 3.2 (m, 1H), 2.83-2.90 (t, J=12 Hz, 1H), 2.25 (m, 1H), 2.09-2.12 (m, 1H), 1.88 (m, 1H), 0.97 (s, 9H), 0.20 (s, 6H).

Step 4: preparation of benzyl 3-(5-acetamido-3-(4-((tert-butyldimethylsilyl)oxy)phenyl)-4-cyano-1H-pyrazol-1-yl) piperidine-1-carboxylate. To a stirred solution of benzyl 3-(5-amino-3-(4-((tert-butyldimethylsilyl)oxy)phenyl)-4-cyano-1H-pyrazol-1-yl)piperidine-1-carboxylate (120 g, 0.19 mol) in dichloromethane (1.2 L) was added triethylamine (133 mL, 0.96 mol) followed by drop-wise addition of acetyl chloride (78.5 mL, 1.9 mol) at 0° C. The resulting reaction mixture was stirred at 0° C. for 30 minutes and then at room temperature for 16 h. The reaction mixture was diluted with cold water (500 mL). The resulting aqueous layer was extracted with dichloromethane (2×500 mL). The combined organic layers were washed with water (500 mL) followed by brine, dried over sodium sulfate and concentrated under reduced pressure. The crude product was purified by silica gel column chromatography (30% ethyl acetate/hexanes) to afford the title compound (100 g). MS (M+H) m/z 574. $^1$H NMR (400 MHz, CDCl$_3$) δ 7.79 (d, J=8.48 Hz, 2H), 7.33 (m, 5H), 6.88 (d, J=8.48 Hz, 2H), 5.11 (s, 2H), 4.03-4.24 (m, 3H), 3.31-3.32 (m, 2H), 2.90 (t, J=12 Hz, 1H), 2.21 (m, 5H), 1.88 (m, 1H), 0.97 (s, 9H), 0.20 (s, 6H).

Step 5: preparation of benzyl 3-(5-acetamido-4-cyano-3-(4-hydroxyphenyl)-1H-pyrazol-1-yl)piperidine-1-carboxylate. To a stirred solution of benzyl 3-(5-acetamido-3-(4-((tert-butyldimethylsilyl)oxy)phenyl)-4-cyano-1H-pyrazol-1-yl)piperidine-1-carboxylate (165 g, 0.35 mol) in methanol:water (4:1, 2.8 L) was added LiOH.H$_2$O (43.8 g, 1.04 mol) at 0° C. The resulting reaction mixture was stirred at 0° C. for 2 h. The reaction mixture was concentrated under reduced pressure and the residue was dissolved in water (1 L) and neutralized with 1N HCl (1.8 L) to pH 6.5. The precipitated solid was filtered, washed with water (500 mL×2) followed by hexanes and dried under vacuum. The solid was dissolved in ethyl acetate (1 L) and washed with water (2×500 mL). The organic layer was dried over sodium sulfate and concentrated under reduced pressure to afford the title compound (104 g) as off white solid. MS (M+H) m/z 460. $^1$H NMR (400 MHz, CDCl$_3$) δ 10.48 (s, 1H), 9.83 (s, 1H), 7.67 (d, J=8.48 Hz, 2H), 7.33 (m, 5H), 6.87 (d, J=8.48 Hz, 2H), 5.06 (s, 2H), 4.23 (bs, 1H), 4.05 (m, 1H), 3.90 (m, 1H), 3.00 (t, J=11.0 Hz, 1H), 2.17 (s, 3H), 2.0 (m, 1H), 1.87 (m, 1H), 1.51 (m, 1H).

Step 6: preparation of (R)-benzyl 3-(5-acetamido-4-cyano-3-(4-hydroxyphenyl)-1H-pyrazol-1-yl)piperidine-1-carboxylate. rac-benzyl 3-(5-acetamido-4-cyano-3-(4-hydroxyphenyl)-1H-pyrazol-1-yl)piperidine-1-carboxylate was chirally separated by supercritical fluid chromatography (ChiralPak AS-H, 50×250 mm, 86/14, CO$_2$/methanol, 235 mL/min flow rate). Isolation of the first eluting isomer afforded the title compound.

Step 7: preparation of (R)-benzyl 3-(5-acetamido-3-(4-((5-chloro-3-fluoropyridin-2-yl)oxy)phenyl)-4-cyano-1H-pyrazol-1-yl)piperidine-1-carboxylate. A solution of (R)-benzyl 3-(5-acetamido-4-cyano-3-(4-hydroxyphenyl)-1H-pyrazol-1-yl)piperidine-1-carboxylate (1 g, 2.2 mmol), cesium carbonate (1.06 g, 3.3. mol), 5-chloro-2,3-difluoropyridine (369 mg, 2.4 mmol) in DMSO (7.25 mL) was heated to 80° C. for 3 h. The reaction mixture was partitioned between water and ethyl acetate. The organic layer was dried (Na$_2$SO$_4$), filtered and concentrated. The crude product was purified by silica gel column chromatography (ethyl acetate/dichloromethane) to afford 0.86 g of the title compound. $^1$H NMR (400 MHz, DMSO-d$_6$) δ ppm 10.57 (br. s., 1H), 8.26 (dd, J=9.85, 2.20 Hz, 1H), 8.10 (d, J=2.26 Hz, 1H), 7.84-7.91 (m, 2H), 7.25-7.42 (m, 7H), 5.07 (br. s., 2H), 4.30 (br. s., 1H), 4.04-4.15 (m, 1H), 3.90 (br. s., 1H), 3.04 (t, J=11.04 Hz, 1H), 2.15 (br. s., 3H), 2.04 (d, J=5.02 Hz, 2H), 1.89 (br. s., 1H), 1.46-1.61 (m, 1H)

Step 8: preparation of (R)-5-amino-3-(4-((5-chloro-3-fluoropyridin-2-yl)oxy)phenyl)-1-(piperidin-3-yl)-1H-pyrazole-4-carboxamide. (R)-benzyl 3-(5-acetamido-3-(4-((5-chloro-3-fluoropyridin-2-yl)oxy)phenyl-4-cyano-1H-pyrazol-1-yl)piperidine-1-carboxylate (860 mg, 1.46 mmol) was dissolved in 80% sulfuric acid (20 mL) and stirred at room temperature for 18 h. The reaction mixture was poured into ice and concentrated ammonium hydroxide was added slowly until the pH reached 10. The mixture was extracted with ethyl acetate. The organic layer was dried (Na$_2$SO$_4$), filtered and concentrated to afford the title compound. $^1$H NMR (400 MHz, DMSO-d) δ ppm 8.25 (dd, J=9.9, 2.1 Hz, 1H), 8.08 (d, J=2.3 Hz, 1H), 7.51-7.56 (m, 2H), 7.24-7.29 (m, 2H), 7.06 (m, 2H), 6.31 (s, 2H), 4.03-4.13 (m, 2H), 3.00 (dd, J=11.7, 3.5 Hz, 1H), 2.87 (d, J=12.1 Hz, 1H), 2.74-2.83 (m, 1H), 2.36-2.47 (m, 1H), 1.85-1.95 (m, 2H), 1.70 (m, 1H), 1.43-1.57 (m, 1H)

Step 9: preparation of 1-[(3R)-1-acryloylpiperidin-3-yl]-5-amino-3-{4-[(5-chloro-3-fluoropyridin-2-yl)oxy]phenyl}-1H-pyrazole-4-carboxamide. Diisopropylamine (0.61 mL, 3.5 mmol) was added to a solution of (R)-5-amino-3-(4-((5-chloro-3-fluoropyridin-2-yl)oxy)phenyl)-1-(piperidin-3-yl)-1H-pyrazole-4-carboxamide (600 mg, 1.4 mmol), (benzotriazol-1-yloxy)tris(dimethylamino)phosphonium hexafluorophosphate (691 mg, 1.5 mmol) and acrylic acid (0.11 mL, 1.5 mmol) in N,N-dimethylformamide (10 mL). The reaction mixture was stirred at room temperature for 30 min and then purified by reverse-phase HPLC to afford the title compound. MS (M+H) m/z 485. $^1$H NMR (400 MHz, DMSO-d$_6$) δ ppm 8.25 (dd, J=9.91, 2.26 Hz, 1H), 8.09 (d, J=2.26 Hz, 1H), 7.55 (d, J=6.27 Hz, 2H), 7.24-7.29 (m, 2H), 6.77-6.91 (m, 1H), 6.40 (br. s., 2H), 6.05-6.18 (m, 1H), 5.61-5.74 (m, 1H), 4.52 (d, J=10.04 Hz, 1H), 4.01-4.38 (m, 2H), 3.43-3.53 (m, 1H), 3.01-3.13 (m, 1H), 2.72-2.79 (m, 1H), 1.81-2.05 (m, 3H), 1.47 (br. s., 1H).

Example 154

5-amino-3-{4-[(5-chloro-3-fluoropyridin-2-yl)oxy]phenyl}-1-{(3R)-1-[(2E)-4-hydroxybut-2-enoyl]piperidin-3-yl}-1H-pyrazole-4-carboxamide

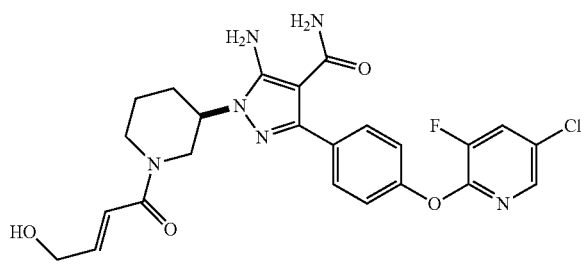

A solution of (R)-5-amino-3-(4-((5-chloro-3-fluoropyridin-2-yl)oxy)phenyl)-1-(piperidin-3-yl)-1H-pyrazole-4-carboxamide in N,N-dimethylformamide (2 mL) was cooled to 0° C. and (benzotriazol-1-yloxy)tris(dimethylamino)phosphonium hexafluorophosphate (265 mg, 0.6 mmol), N,N-diisopropylethylamine (0.21 mL, 1.2 mmol) and (E)-4-hydroxybut-2-enoic acid (61.3 mg, 0.6 mmol) were added. After 30 min, the reaction was poured into water/ethyl acetate and the layers separated. The organic layer was dried (Na$_2$SO$_4$) and the solvent removed. The crude product was purified by reverse-phase-HPLC to afford the title compound (50 mg). MS (M+H) m/z 515.

Example 155

5-amino-3-{4-[(5-chloro-3-fluoropyridin-2-yl)oxy]phenyl}-1-{(3R)-1-[(2E)-4,4-difluorobut-2-enoyl]piperidin-3-yl}-1H-pyrazole-4-carboxamide

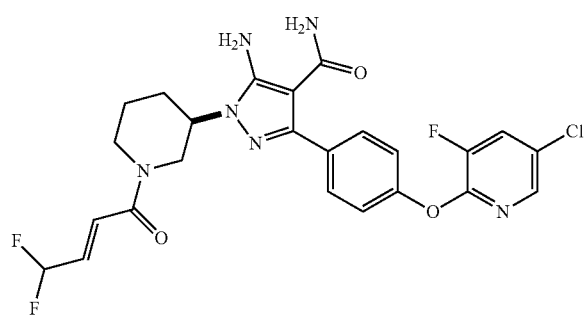

(Benzotriazol-1-yloxy)tris(dimethylamino)phosphonium hexafluorophosphate (274 mg, 0.62 mmol), N,N-diisopropylethylamine (0.24 mL, 1.4 mmol) and (E)-4,4-difluorobut-2-enoic (prepared as described in Example 133, step 3) (100 mg, 0.82 mmol) were added to a solution of (R)-5-amino-3-(4-((5-chloro-3-fluoropyridin-2-yl)oxy)phenyl)-1-(piperidin-3-yl)-1H-pyrazole-4-carboxamide (0.32 g, 0.745 mmol) in N,N-dimethylformamide (4 mL) at −10° C. After 15 min, the reaction was diluted with water/ethyl acetate. The layers were separated and the organic extract washed with brine, dried ($Na_2SO_4$) and concentrated. The crude product was purified by silica gel column chromatography (3.5% MeOH/dichloromethane) to afford the title compound (120 mg, 30%). $^1$H NMR (400 MHz, DMSO-$d_6$) δ 1.49 (m, 1H), 1.87-2.32 (m, 3H), 2.83 (t, 0.5H), 3.09-3.17 (m, 1H), 3.52-3.58 (m, 0.5H), 3.99-4.49 (m, 3H), 6.39-6.68 (m, 4H), 7.13-7.21 (m, 1H), 7.27 (d, 2H), 7.53-7.56 (m, 2H), 8.08 (d, 1H), 8.25 (dd, 1H). MS (M+H) m/z 535.

Example 156

5-amino-3-{4-[(5-chloro-3-fluoropyridin-2-yl)oxy]phenyl}-1-{(3R)-1-[(2E)-4-fluorobut-2-enoyl]piperidin-3-yl}-1H-pyrazole-4-carboxamide

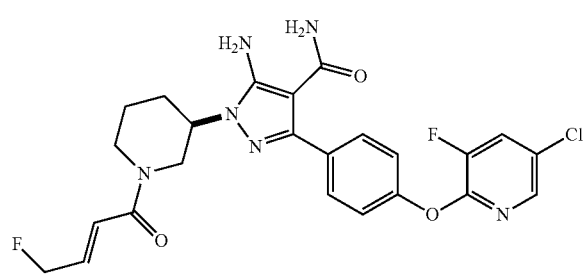

The title compound was prepared analogous to 5-amino-3-{4-[(5-chloro-3-fluoropyridin-2-yl)oxy]phenyl}-1-{(3R)-1-[(2E)-4,4-difluorobut-2-enoyl]piperidin-3-yl}-1H-pyrazole-4-carboxamide (Example) employing (E)-4-fluorobut-2-enoic acid (prepared as described in Example, step 2). $^1$H NMR (400 MHz, DMSO-$d_6$) δ 8.24 (dd, 1H), 8.08 (d, 1H), 7.55 (d, 2H), 7.27 (d, 2H), 6.67-6.77 (m, 2H), 6.38 (br s, 2H), 5.10 (dd, 2H), 4.18-4.52 (m, 2H), 4.05 (m, 1H), 3.52 (t, 0.5H), 3.04-3.12 (m, 1H), 2.79 (t, 0.5H), 1.84-1.99 (m, 2H), 1.48 (m, 1H). MS (M+H) m/z 517.

Example 157

1-[(3R)-1-acryloyl piperidin-3-yl]-5-amino-3-{4-[(5-chloropyridin-2-yl)oxy]phenyl}-1H-pyrazole-4-carboxamide

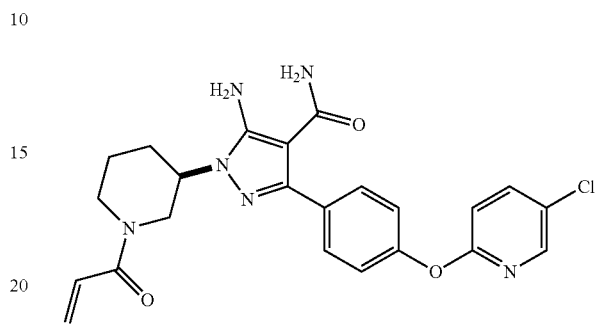

Step 1: preparation of (R)-benzyl 3-(5-acetamido-3-(4-((5-chloropyridin-2-yl)oxy)phenyl)-4-cyano-1H-pyrazol-1-yl)piperidine-1-carboxylate. 5-Chloro-2-fluoropyridine (237 mg, 1.80 mmol) and $Cs_2CO_3$ (1.95 g, 5.99 mmol) were added to a solution of (R)-benzyl 3-(5-acetamido-4-cyano-3-(4-hydroxyphenyl)-1H-pyrazol-1-yl)piperidine-1-carboxylate (prepared as described in Example, step 6) (500 mg, 1.20 mmol) in N,N-dimethylformamide (1 mL) was added. The reaction mixture was then heated to 100° C. for 30 minutes under microwave conditions, after which it was diluted with water and extracted into ethyl acetate (3×5 mL). The combined organic layers were dried over sodium sulfate, concentrated in vacuo, and purified by silica gel column chromatography to afford the title compound (300 mg, 44%). $^1$H NMR (400 MHz, CDCl$_3$) δ ppm 8.10-8.18 (m, 1H), 7.93 (d, J=8.78 Hz, 2H), 7.66 (dd, J=8.66, 2.64 Hz, 1H), 7.33 (s, 5H), 7.11-7.20 (m, 2H), 6.90 (d, J=8.78 Hz, 1H), 5.12 (s, 2H), 4.27 (d, J=11.04 Hz, 1H), 4.08-4.20 (m, 2H), 3.18-3.43 (m, 1H), 2.91 (t, J=11.92 Hz, 1H), 2.21 (s, 2H), 1.83-1.95 (m, 1H), 1.48-1.68 (m, 1H).

Step 2: preparation of (R)-5-amino-3-(4-((5-chloropyridin-2-yl)oxy)phenyl)-1-(piperidin-3-yl)-1H-pyrazole-4-carboxamide. (R)-benzyl 3-(5-acetamido-3-(4-((5-chloropyridin-2-yl)oxy)phenyl)-4-cyano-1H-pyrazol-1-yl)piperidine-1-carboxylate (300 mg, 0.53 mmol) was added portion wise over 10 min to a stirred solution of concentrated sulfuric acid (6 mL) at 0° C. The reaction mixture was then allowed to stir at 30° C. over 16 h, after which it was cooled to 0° C. Concentrated ammonium hydroxide was carefully added until pH=7, ensuring that the temperature did not exceed 5° C. The mixture was then extracted with ethyl acetate (3×5 mL), and the combined organic layers were dried over sodium sulfate, and concentrated in vacuo to afford the title compound. $^1$H NMR (400 MHz, DMSO-$d_6$) δ ppm: 8.19-8.27 (m, 1H), 7.91-8.02 (m, 1H), 7.48-7.56 (m, 2H), 7.19-7.22 (m, 2H), 7.16 (s, 1H), 6.32 (s, 2H), 4.03-4.16 (m, 1H), 3.31 (br. s., 1H), 3.01 (dd, J=11.8, 3.5 Hz, 1H), 2.87 (d, J=12.3 Hz, 1H), 2.79 (dd, J=11.5, 10.3 Hz, 1H), 2.38-2.48 (m, 1H), 1.81-1.96 (m, 2H), 1.71 (d, J=13.1 Hz, 1H), 1.42-1.57 (m, 1H).

Step 3: preparation of 1-[(3R)-1-acryloylpiperidin-3-yl]-5-amino-3-{4-[(5-chloropyridin-2-yl)oxy]phenyl}-1H-pyrazole-4-carboxamide. The title compound was prepared analogous to 1-[(3R)-1-acryloylpiperidin-3-yl]-5-amino-3-

{4-[(5-chloro-3-fluoropyridin-2-yl)oxy]phenyl}-1H-pyrazole-4-carboxamide (Example) employing (R)-5-amino-3-(4-((5-chloropyridin-2-yl)oxy)phenyl)-1-(piperidin-3-yl)-1H-pyrazole-4-carboxamide to afford the title compound. ¹H NMR (400 MHz, DMSO-d₆) δ ppm 8.30 (d, J=2.34 Hz, 1H), 8.04 (dd, J=8.59, 2.73 Hz, 1H), 7.53-7.65 (m, 2H), 7.28 (d, J=8.20 Hz, 2H), 7.21 (d, J=8.59 Hz, 1H), 6.79-6.98 (m, 1H), 6.41-6.49 (m, 2H), 6.06-6.26 (m, 1H), 5.60-5.80 (m, 1H), 4.05-4.61 (m, 3H), 3.47-3.60 (m, 0.5H), 3.05-3.20 (m, 1H), 2.71-2.87 (m, 0.5H), 1.83-2.12 (m, 3H), 1.54 (br. s., 1H). MS (M+H) m/z 467.

Example 158

5-amino-3-{4-[(5-chloropyridin-2-yl)oxy]phenyl}-1-{(3R)-1-[(2E)-4-hydroxybut-2-enoyl]piperidin-3-yl}-1H-pyrazole-4-carboxamide

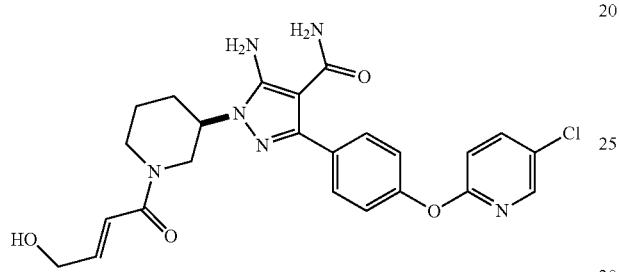

The title compound was prepared analogous to 5-amino-3-{4-[(5-chloro-3-fluoropyridin-2-yl)oxy]phenyl}-1-{(3R)-1-[(2E)-4-hydroxybut-2-enoyl]piperidin-3-yl}-1H-pyrazole-4-carboxamide (Example) employing (R)-5-amino-3-(4-((5-chloropyridin-2-yl)oxy)phenyl)-1-(piperidin-3-yl)-1H-pyrazole-4-carboxamide (prepared as described in Example, Step 2) to afford the title compound. ¹H NMR (400 MHz, DMSO-d₆) δ ppm 8.30 (d, J=2.34 Hz, 1H), 8.04 (dd, J=8.59, 2.73 Hz, 1H), 7.53-7.65 (m, 2H), 7.28 (d, J=8.20 Hz, 2H), 7.21 (d, J=8.59 Hz, 1H), 6.79-6.98 (m, 1H), 6.41-6.49 (m, 2H), 6.06-6.26 (m, 1H), 5.60-5.80 (m, 1H), 4.05-4.61 (m, 3H), 3.47-3.60 (m, 0.5H), 3.05-3.20 (m, 1H), 2.71-2.87 (m, 0.5H), 1.83-2.12 (m, 3H), 1.54 (br. s., 1H). MS (M+H) m/z 467.

Example 159

5-amino-3-{4-[(5-chloropyridin-2-yl)oxy]phenyl}-1-{(3R)-1-[(2E)-4,4-difluorobut-2-enoyl]piperidin-3-yl}-1H-pyrazole-4-carboxamide

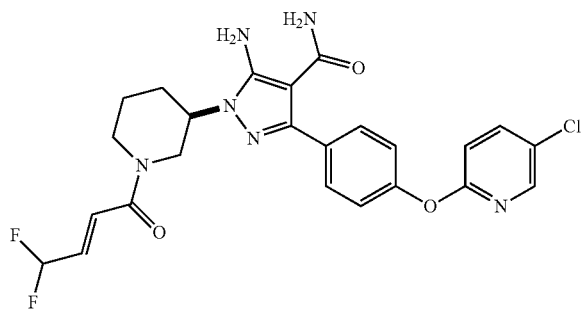

The title compound was prepared analogous to 5-amino-3-{4-[(5-chloro-3-fluoropyridin-2-yl)oxy]phenyl}-1-{(3R)-1-[(2E)-4,4-difluorobut-2-enoyl]piperidin-3-yl}-1H-pyrazole-4-carboxamide (Example) employing (R)-5-amino-3-(4-((5-chloropyridin-2-yl)oxy)phenyl)-1-(piperidin-3-yl)-1H-pyrazole-4-carboxamide (prepared as described in Example, Step 2) to afford the title compound. ¹H NMR (400 MHz, DMSO-d₆) δ 8.23 (d, 1H), 7.99 (dd, 1H), 7.53 (t, 2H), 7.21 (d, 2H), 7.18 (m, 1H), 7.15 (d, 1H), 6.52-6.60 (m, 2H), 6.37-6.42 (m, 2H), 4.19-4.49 (m, 2H), 3.99-4.08 (m, 1H), 3.55 (dd, 0.5H), 3.05-3.17 (m, 1H), 2.86 (m, 0.5H), 1.99 (m, 2H), 1.86-1.90 (m, 1H), 1.50 (m, 1H). MS (M+H) m/z 517.

Example 160

5-amino-3-{4-[(5-chloropyridin-2-yl)oxy]phenyl}-1-{(3R)-1-[(2E)-4,4-difluorobut-2-enoyl]piperidin-3-yl}-1H-pyrazole-4-carboxamide

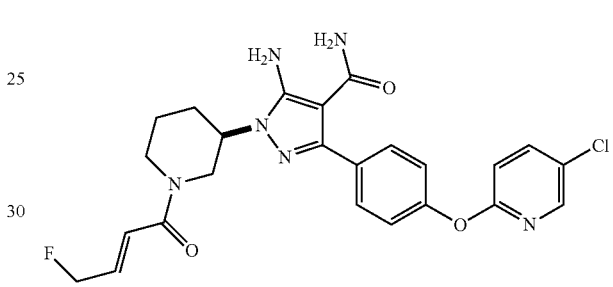

The title compound was prepared analogous to 5-amino-3-{4-[(5-chloro-3-fluoropyridin-2-yl)oxy]phenyl}-1-{(3R)-1-[(2E)-4-fluorobut-2-enoyl]piperidin-3-yl}-1H-pyrazole-4-carboxamide (Example) employing (R)-5-amino-3-(4-((5-chloropyridin-2-yl)oxy)phenyl)-1-(piperidin-3-yl)-1H-pyrazole-4-carboxamide (prepared as described in Example, Step 2) to afford the title compound. ¹H NMR (400 MHz, DMSO-d₆) δ 8.23 (d, 1H), 7.98 (dd, 1H), 7.54 (d, 2H), 7.21 (d, 2H), 7.15 (d, 1H), 6.74 (d, 2H), 6.40 (d, 2H), 5.10 (dd, 2H), 4.18-4.52 (m, 2H), 4.06 (m, 1H), 3.51 (t, 0.5H), 3.08 (q, 1H), 2.79 (t, 0.5H), 1.99 (m, 2H), 1.86 (d, 1H), 1.48 (m, 1H). MS (M+H) m/z 499.

Example 161

1-[(3R)-1-acryloyl piperidin-3-yl]-5-amino-3-(4-{[6-(trifluoromethyl)pyridin-2-yl]oxy}phenyl)-1H-pyrazole-4-carboxamide

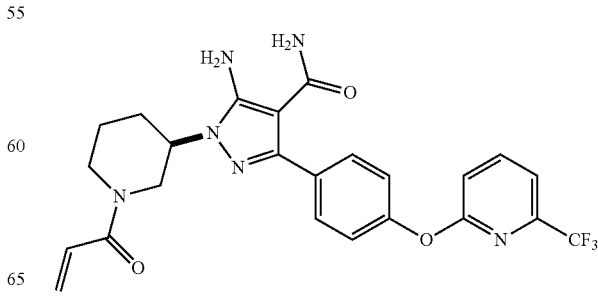

Step 1: preparation of (R)-benzyl 3-(5-acetamido-4-cyano-3-(4-((6-(trifluoromethyl)pyridin-2-yl)oxy)phenyl)-1H-pyrazol-1-yl)piperidine-1-carboxylate. 2-Chloro-6-(trifluoromethyl)pyridine (11.4 g, 62.6 mmol) and Cs$_2$CO$_3$ (55.6 g, 171 mmol) were added to a solution of (R)-benzyl 3-(5-acetamido-4-cyano-3-(4-hydroxyphenyl)-1H-pyrazol-1-yl)piperidine-1-carboxylate (prepared as described Example, step 6) (26.2 g, 56.9 mmol) in DMSO (60 mL). The reaction mixture was heated to 110° C. for 3 hours and then allowed to cool to room temperature. The mixture was poured into water/ethyl acetate and the layers separated. The organic layer was dried (Na$_2$SO$_4$) and the solvent evaporated to afford the title compound. $^1$H NMR (400 MHz, DMSO-d$_6$) δ ppm 8.16 (t, J=7.91 Hz, 1H), 7.85-7.95 (m, 2H), 7.68 (d, J=7.28 Hz, 1H), 7.23-7.44 (m, 8H), 5.07 (br. s., 2H), 4.30 (br. s., 1H), 4.09 (d, J=12.05 Hz, 1H), 3.91 (br. s., 1H), 3.41 (s, 1H), 3.04 (t, J=10.67 Hz, 1H), 1.82-2.19 (m, 7H), 1.54 (br. s., 1H). MS (M+H) m/z 605.4.

Step 2: preparation of (R)-5-amino-1-(piperidin-3-yl)-3-(4-((6-(trifluoromethyl)pyridin-2-yl)oxy)phenyl)-1H-pyrazole-4-carboxamide. To a round bottom flask containing (R)-benzyl 3-(5-acetamido-4-cyano-3-(4-((6-(trifluoromethyl)pyridin-2-yl)oxy)phenyl)-1H-pyrazol-1-yl)piperidine-1-carboxylate (26 g, 43 mmol) was added dropwise 80% sulfuric acid (160 mL) slowly at room temperature. After addition was complete the reaction was warmed to 40° C. for 3 h. The mixture was then cooled to 0° C. and ice added to the mixture. The solution was then neutralized by slow addition of concentrated ammonium hydroxide. The resulting suspension was extracted with ethyl acetate. The combined organic layers were washed with water, dried (Na$_2$SO$_4$) and concentrated to afford the title compound. $^1$H NMR (400 MHz, DMSO-d$_6$) δ ppm 8.15 (t, J=8.00 Hz, 1H), 7.68 (d, J=7.41 Hz, 1H), 7.54-7.61 (m, 2H), 7.34-7.40 (m, 1H), 7.25-7.31 (m, 2H), 7.03-7.20 (m, 2H), 6.35 (s, 2H), 4.09-4.18 (m, 1H), 3.72-3.90 (m, 1H), 3.03 (dd, J=11.71, 3.90 Hz, 1H), 2.77-2.93 (m, 2H), 2.37-2.50 (m, 1H), 1.88-1.98 (m, 2H), 1.68-1.77 (m, 1H), 1.45-1.58 (m, 1H). MS (M+H) m/z 447.3.

Step 3: preparation of 1-[(3R)-1-acryloylpiperidin-3-yl]-5-amino-3-(4-{[6-(trifluoromethyl)pyridin-2-yl]oxy}phenyl)-1H-pyrazole-4-carboxamide. (Benzotriazol-1-yloxy)tris(dimethylamino)phosphonium hexafluorophosphate (5.45 g, 12.3 mmol), N,N-diisopropylethylamine (5.10 mL, 28.0 mmol) and then acrylic acid (0.85 mL, 12.3 mmol) were added to a solution of (R)-5-amino-1-(piperidin-3-yl)-3-(4-((6-(trifluoromethyl)pyridin-2-yl)oxy)phenyl)-1H-pyrazole-4-carboxamide (5.0 g, 11.2 mmol) in N,N-dimethylformamide (35 mL) at 0° C. After 15 min, the reaction mixture was poured into water/ethyl acetate and the layers separated. The organic layer was dried (Na$_2$SO$_4$) and concentrated. The crude product was purified by reverse phase HPLC to afford the title compound. $^1$H NMR (400 MHz, DMSO-d$_6$) δ ppm 8.15 (t, J=8.00 Hz, 1H), 7.49-7.77 (m, 3H), 7.19-7.44 (m, 3H), 6.73-7.02 (m, 1H), 6.42 (br. s., 2H), 6.13 (t, J=19.51 Hz, 1H), 5.55-5.80 (m, 1H), 3.90-4.69 (m, 3H), 3.50 (d, J=11.32 Hz, 1H), 2.98-3.21 (m, 1H), 2.76 (br. s., 1H), 2.02 (br. s., 1H), 1.87 (d, J=12.10 Hz, 1H), 1.23-1.60 (m, 1H). MS (M+H) m/z 501.3.

Example 162

5-amino-1-{(3R)-1-[(2E)-4-hydroxybut-2-enoyl]piperidin-3-yl}-3-(4-{[6-(trifluoromethyl)pyridin-2-yl]oxy}phenyl)-1H-pyrazole-4-carboxamide

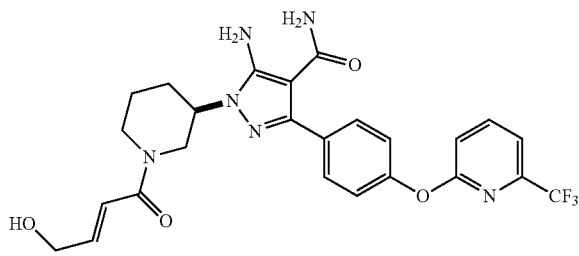

N,N-diisopropylethylamine (0.13 mL, 0.72 mmol) was added dropwise to a solution of (R)-5-amino-1-(piperidin-3-yl)-3-(4-((6-(trifluoromethyl)pyridin-2-yl)oxy)phenyl)-1H-pyrazole-4-carboxamide (prepared as described in Example, step 2) (108 mg, 0.24 mmol), O-(benzotriazol-1-yl)-N,N,N',N'-tetramethyluronium hexafluorophosphate (112 mg, 0.29 mmol), and (E)-4-hydroxybut-2-enoic acid (98.7 mg, 0.96 mmol) in DMF (2 mL). After 14 hrs, the reaction was poured into water/ethyl acetate and the layers separated. The organic layer was dried (Na$_2$SO$_4$) and concentrated. The crude product was purified by reverse phase HPLC to afford the title compound. $^1$H NMR (600 MHz, DMSO-d$_6$) δ ppm 7.71 (d, J=7.47 Hz, 1H), 7.63 (d, J=8.35 Hz, 2H), 7.41 (d, J=8.35 Hz, 1H), 7.28-7.35 (m, 2H), 6.71-6.85 (m, 2H), 6.65 (t, J=13.62 Hz, 1H), 6.46 (d, J=14.50 Hz, 2H), 4.97-5.10 (m, 1H), 4.59 (br. s., 1H), 4.44 (br. s., 1H), 4.04-4.32 (m, 4H), 3.56 (br. s., 1H), 3.12 (d, J=12.74 Hz, 1H), 2.73 (br. s., 1H), 1.96-2.11 (m, 1H), 1.90 (br. s., 1H), 1.53 (br. s., 1H). MS (M+H) m/z 531.1.

Example 163

5-amino-1-{(3R)-1-[(2E)-4,4-difluorobut-2-enoyl]piperidin-3-yl}-3-(4-{[6-(trifluoromethyl)pyridin-2-yl]oxy}phenyl)-1H-pyrazole-4-carboxamide

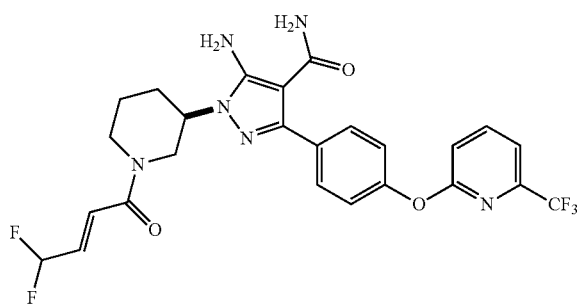

(Benzotriazol-1-yloxy)tris(dimethylamino)phosphonium hexafluorophosphate (163.4 mg, 0.37 mmol), N,N-diisopropylethylamine (0.15 mL, 0.85 mmol) and (E)-4,4-difluorobut-2-enoic acid (prepared as described in Example 133, step 3) (45 mg, 0.37 mmol) were added to a solution of (R)-5-amino-1-(piperidin-3-yl)-3-(4-((6-(trifluoromethyl)pyridin-2-yl)oxy)phenyl)-1H-pyrazole-4-carboxamide (prepared as described in Example, step 2) (150 mg, 0.34 mmol) in N,N-dimethylformamide (3 mL). After 30 min, the reaction was poured into water/ethyl acetate. The layers were separated and the organic layer was washed with brine, dried ($Na_2SO_4$) and concentrated. The crude product was purified by silica gel column chromatography (3% MeOH/dichloromethane) to afford the title compound (70 mg, 38%). $^1$H NMR (400 MHz, DMSO-$d_6$) δ ppm 8.13 (t, 1H), 7.66 (d, 1H), 7.56 (t, 2H), 7.36 (d, 1H), 7.27 (d, 2H), 7.13-7.25 (m, 1H), 6.30-6.80 (m, 4H), 3.95-4.55 (m, 3H), 3.57 (dd, 0.5H), 3.14 (t, 1H), 2.78 (m, 0.5H), 2.07 (bs, 2H), 1.75-1.95 (m, 1H), 1.49 (bs, 1H). MS (M+H) m/z 551.

Example 164

5-amino-1-{(3R)-1-[(2E)-4-fluorobut-2-enoyl]piperidin-3-yl}-3-(4-{[6-(trifluoromethyl)pyridin-2-yl]oxy}phenyl)-1H-pyrazole-4-carboxamide

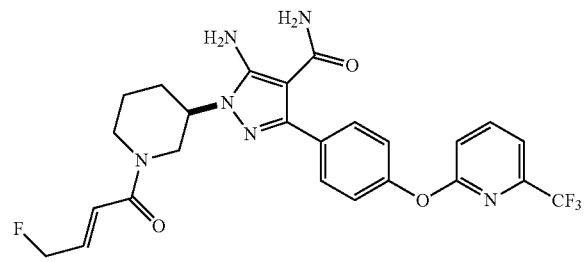

The title compound was prepared analogous to 5-amino-1-{(3R)-1-[(2E)-4,4-difluorobut-2-enoyl]piperidin-3-yl}-3-(4-{[6-(trifluoromethyl)-pyridin-2-yl]oxy}phenyl)-1H-pyrazole-4-carboxamide (Example) employing (E)-4-fluorobut-2-enoic acid (prepared as described in Example, Step 2) to afford the title compound. $^1$H NMR (400 MHz, DMSO-$d_6$) δ ppm 1.48 (bs, 1H), 1.80-1.90 (m, 1H), 1.99 (bs, 2H), 2.76 (t, 0.5H), 3.08 (t, 1H), 3.52 (t, 0.5H), 4.00-4.60 (m, 3H), 5.04 (d, 1H), 5.15 (d, 1H), 6.40 (bs, 2H), 6.65-6.80 (m, 2H), 7.27 (d, 2H), 7.36 (d, 1H), 7.57 (d, 2H), 7.66 (d, 1H), 8.13 (t, 1H). MS (M+H) m/z 533.

Example 165

5-amino-1-[(3R)-1-(2-fluoroacryloyl)piperidin-3-yl]-3-(4-{[6-(trifluoromethyl))-pyridin-2-yl]oxy}phenyl)-1H-pyrazole-4-carboxamide

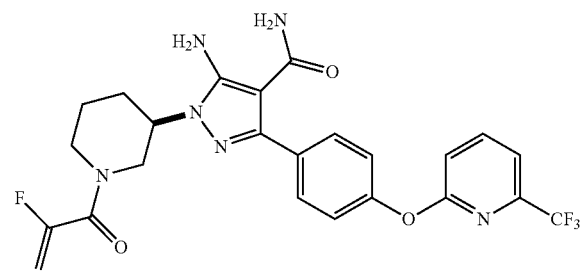

(Benzotriazol-1-yloxy)tris(dimethylamino)phosphonium hexafluorophosphate (218 mg, 0.49 mmol), diisopropylamine (0.2 mL, 1.12 mmol) and 2-fluoroacrylic acid (40.3 mg, 0.45 mmol) were added to a solution of (R)-5-amino-1-(piperidin-3-yl)-3-(4-((6-(trifluoromethyl)pyridin-2-yl)oxy)phenyl)-1H-pyrazole-4-carboxamide (prepared as described in Example, step 2) (200 mg, 0.45 mmol) in N,N-dimethylformamide (3 mL) at 0° C. After 30 min, the mixture was poured into water/ethyl acetate and the layers separated. The organic layer was dried ($Na_2SO_4$) and concentrated. The crude product was purified by reverse phase HPLC to afford the title compound. $^1$H NMR (600 MHz, DMSO-$d_6$) δ ppm 8.18 (t, J=7.69 Hz, 1H), 7.70 (d, J=7.47 Hz, 1H), 7.62 (d, J=8.35 Hz, 2H), 7.41 (d, J=8.35 Hz, 1H), 7.27-7.34 (m, 2H), 6.45 (s, 2H), 5.31 (br. s., 1H), 5.11-5.26 (m, 2H), 4.10-4.44 (m, 3H), 3.79-4.06 (m, 1H), 3.66 (m, 1H), 3.26 (m, 1H), 2.96 (m, 1H), 2.07 (m, 1H), 1.95 (d, J=12.30 Hz, 1H), 1.58 (m, 1H). MS (M+H) m/z 519.1.

Example 166

5-amino-1-{(3R)-1-[(2E)-3-cyanoprop-2-enoyl]piperidin-3-yl}-3-(4-{[6-(trifluoromethyl)pyridin-2-yl]oxy}phenyl)-1H-pyrazole-4-carboxamide

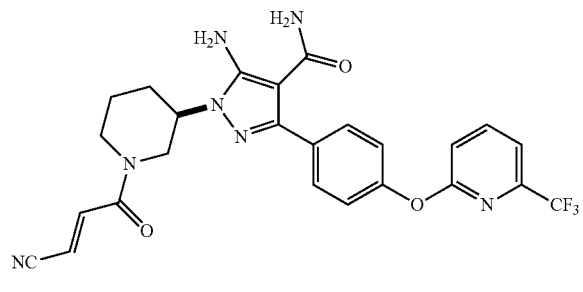

The title compound was prepared analogous to 5-amino-1-{(3R)-1-[(2E)-4,4-difluorobut-2-enoyl]piperidin-3-yl}-3-(4-{[6-(trifluoromethyl)-pyridin-2-yl]oxy}phenyl)-1H-pyrazole-4-carboxamide (Example) employing (E)-3-Cyanoacrylic acid (prepared as described in Example, Step 2) to afford the title compound. $^1$H NMR (400 MHz, DMSO-$d_6$) δ ppm 8.14 (t, 1H), 7.83 (t, 1H), 7.66 (d, 1H), 7.55-7.58 (m, 2H), 7.36 (d, 1H), 7.26-7.29 (m, 2H), 6.52 (dd, 1H), 6.37-6.41 (m, 2H), 4.07-4.48 (m, 3H), 3.58 (dd, 0.5H), 3.14-3.20 (m, 1H), 2.90 (t, 0.5H), 2.01 (m, 2H), 1.85 (m, 1H), 1.49 (m, 1H). MS (M+H) m/z 526.4.

Example 167

In Vitro Pharmacology
Human BTK LanthaScreen Assay

TR-FRET LanthaScreen assays were performed by incubating a dilution series of inhibitor concentrations with 50 µM ATP, 100 nM FAM-Srctide peptide substrate (5FAM-GEEPLYWSFPAKKK-NH2, SEQ ID NO: 1, Molecular Devices, RP7595) and 70 µM of human full-length BTK Kinase (expressed in Sf9 insect cells and purified in-house). The assays were performed with and without pre-incubating the inhibitors with the enzyme for 60 minutes before starting the kinase reaction by adding ATP and the peptide substrate. Samples containing enzyme but no inhibitor were included to determine the maximal extent of reaction. Samples containing no enzyme served as the negative control. The kinase reaction mixtures were incubated at room temperature for 60 minutes before stopping the kinase activity by the addition of 15 mM EDTA. The extent of peptide phosphorylation by BTK was detected using a Terbium-conjugated anti-phospho-Tyrosine antibody (Tb-PT66 antibody, invitrogen # PV3557). Phosphorylation of peptide substrate was measured by determining the ratio of 520/495 nm on an Envision Multi-label Reader (Perkin Elmer) and $IC_{50}$ values were calculated by fitting the data to a four-parameter equation using XLFit4 (IDBS).

TABLE 1

BTK Inhibition

| EX | $IC_{50}$ (nM) |
|---|---|
| 1 | 1.4 |
| 2 | 0.37 |
| 3 | 3.3 |
| 4 | 35.0 |
| 5 | 32.1 |
| 6 | 11.7 |
| 7 | 16.2 |
| 8 | 16.5 |
| 9 | 23.3 |
| 10 | 13.5 |
| 11 | 5.9 |
| 12 | 54.2 |
| 13 | 2.6 |
| 14 | 12.5 |
| 15 | 0.64 |
| 16 | 1.28 |
| 17 | 0.4 |
| 18 | 3 |
| 19 | 1.0 |
| 20 | 3.4 |
| 21 | 22.5 |
| 22 | 1.0 |
| 23 | 9.2 |
| 24 | 5.0 |
| 25 | 2.18 |
| 26 | 17.3 |
| 27 | 1.3 |
| 28 | 1.0 |
| 29 | 2.9 |
| 30 | 0.43 |
| 31 | 2.8 |
| 32 | 4.1 |
| 33 | 24.1 |
| 34 | 3.8 |
| 35 | 1.7 |
| 36 | 25.3 |
| 37 | 0.79 |
| 38 | 2.5 |
| 39 | 1.1 |
| 40 | 1.5 |
| 41 | 6.3 |
| 42 | 1.2 |
| 43 | 0.77 |
| 44 | 24.4 |
| 45 | 0.81 |
| 46 | 6.4 |
| 47 | 1.6 |
| 48 | 0.44 |
| 49 | 2.2 |
| 50 | 1.8 |
| 51 | 1.9 |
| 52 | 2.9 |
| 53 | 1.7 |
| 54 | 1.2 |
| 55 | 2.2 |
| 56 | 1.3 |
| 57 | 3.1 |
| 58 | 1.8 |
| 59 | 8.5 |
| 60 | 4.8 |
| 61 | 5.1 |
| 62 | 3.3 |
| 63 | 4.9 |
| 64 | 8.7 |
| 65 | 10.6 |
| 66 | 7.2 |
| 67 | 2.4 |
| 68 | 1.9 |
| 69 | 0.6 |
| 70 | 21.9 |
| 71 | 2.7 |
| 72 | 0.54 |
| 73 | 6.1 |
| 74 | 1.0 |
| 75 | 0.81 |
| 76 | 12.0 |
| 77 | 2.3 |
| 78 | 1.4 |
| 79 | 31.0 |
| 80 | 15.6 |
| 81 | 5.7 |
| 82 | 126 |
| 83 | 15.3 |
| 84 | 5.6 |
| 85 | 212 |
| 86 | 26.8 |
| 87 | 1.3 |
| 88 | 5.7 |
| 89 | 7.7 |
| 90 | 3.2 |
| 91 | 154 |
| 92 | 73.4 |
| 93 | 35 |
| 94 | 50.2 |
| 95 | 79.2 |
| 96 | 21.9 |
| 97 | 52.8 |
| 98 | 27.3 |
| 99 | 15.6 |
| 100 | 16.3 |
| 101 | 5.3 |
| 102 | 7.6 |
| 103 | 13.4 |
| 104 | 53.1 |
| 105 | 55.5 |
| 106 | 58 |
| 107 | 171 |
| 108 | 7.8 |
| 109 | 128 |
| 110 | 9.2 |
| 111 | 119 |
| 112 | 16.5 |
| 113 | 264 |
| 114 | 10.1 |
| 115 | 3.7 |
| 116 | 2.6 |
| 117 | 18.9 |
| 118 | 7.6 |
| 119 | 60.5 |
| 120 | 141 |
| 121 | 9.9 |
| 122 | 0.46 |
| 123 | 396 |
| 124 | 0.74 |
| 125 | 0.40 |
| 126 | 1.3 |
| 127 | 0.18 |
| 128 | 4.5 |
| 129 | 1.0 |
| 130 | 0.17 |
| 131 | 2.3 |
| 132 | 1.1 |
| 133 | 0.38 |
| 134 | 5.0 |
| 135 | 1.2 |
| 136 | 7.8 |
| 137 | 0.25 |
| 138 | 21.8 |
| 139 | 247 |
| 140 | 3.7 |
| 141 | 58 |

TABLE 1-continued

BTK Inhibition

| EX | IC$_{50}$ (nM) |
|---|---|
| 142 | 61 |
| 143 | 125 |
| 144 | 0.41 |
| 145 | 2.8 |
| 146 | 48 |
| 147 | 241 |
| 148 | 39 |
| 149 | 52 |
| 150 | 5.3 |
| 151 | 2.3 |
| 152 | 1.5 |
| 153 | 0.48 |
| 154 | 49 |
| 155 | 0.7 |
| 156 | 1.4 |
| 157 | 1.3 |
| 158 | 71 |
| 159 | 1.3 |
| 160 | 5.5 |
| 161 | 1.2 |
| 162 | 9.8 |
| 163 | 1.3 |
| 164 | 3.2 |
| 165 | 4.4 |
| 166 | 2.2 |

Human Primary B Cell Proliferation Assay

Human B cells were purified from buffy coats using the human B cell RosetteSep kit per manufacturer's instructions. Purified cells were resuspended in RPMI-10% HIFCS, 2 mM L-glutamine, 100 U/mL penicillin, 100 µg/ml streptomycin, incubated with compounds for 1 hour at 37° C. and then stimulated with 50 µg/mL anti-human IgM F(ab')2 for 72 hours. ³H-thymidine was included in the culture media for the final 8-16 hours. Cells were harvested and ³H-thymidine incorporation was measured. Inhibition was calculated using DMSO+50 µg/ml anti-human IgM F(ab')2 stimulated B cells as the 0% inhibition control, and DMSO+assay buffer stimulated B cells as the 100% inhibition control.

Human Primary T cell Proliferation Assay

Human CD4⁺ T cells were purified from buffy coats using the human cell RosetteSep CD4⁺ T cells kit per manufacturer's instructions. Purified cells were resuspended in RPMI-10% HIFCS, 2 mM L-glutamine, 100 U/mL penicillin, 100 µg/ml streptomycin, plated at 200,000 cells/well in 96-well round-bolltom plates, incubated with compounds for 1 hour at 37° C. and then stimulated with an equal number of anti-CD3/anti-CD28-coated beads (Invitrogen) for 72 hours. ³H-thymidine was included in the culture media for the final 8-16 hours. Cells were harvested and ³H-thymidine incorporation was measured. Inhibition was calculated using DMSO+bead-stimulated CD4⁺ T cells as the 0% inhibition control, and DMSO+assay buffer stimulated CD4⁺ T cells as the 100% inhibition control.

Human B cell Proliferation Assay

Human B cells were purified from buffy coats using the human B cell RosetteSep kit per manufacturer's instructions. Purified cells were resuspended in RPMI-10% HIFCS, 2 mM L-glutamine, 100 U/mL penicillin, 100 µg/ml streptomycin, incubated with compounds for 1 hour at 37° C. and then stimulated with 50 µg/mL anti-human IgM F(ab')2 for 72 hours. ³H-thymidine was included in the culture media for the final 8-16 hours. Cells were harvested and ³H-thymidine incorporation was measured. Inhibition was calculated using DMSO+50 µg/ml anti-human IgM F(ab')2 stimulated B cells as the 0% inhibition control, and DMSO+assay buffer stimulated B cells as the 100% inhibition control.

Human Whole Blood Histamine Assay

Heparinized human whole blood (200 µl) was plated in 96-well V-bottom assay plates (VWR). Compounds diluted in 100% DMSO (1 µl) were added and incubated at 37° C. for 120 minutes. Anti-human-IgE antibody (KPL) was added to a final concentration of 2 µg/ml and assay plates incubated for 30 minutes at 37° C. Plates were spun at 2000 rpm for 8 minutes and the analyzed for histamine release by ELISA kits (Beckman Coulter).

For each inhibitor tested, inhibition of histamine release is normalized as a percentage of control histamine based on the formula: % of Control=100×(A−B)/(C−B) where A is the histamine from wells containing inhibitor and anti-IgE antibody, B is the histamine from wells without anti-IgE antibody (minimum histamine) and C is the histamine from wells containing anti-IgE antibody but no inhibitor (maximum). Inhibition curves and IC$_{50}$ values are determined using Excel-fit.

Human EGFR LanthaScreen Selectivity Assay

TR-FRET LanthaScreen assays were performed by incubating a dilution series of inhibitor concentrations with 20 µM ATP, 100 nM peptide substrate (FITC-C6-KKAEEEEY-FELVAKK-NH2 (SEQ ID NO.: 2, American Peptide, #333778) and 600 µM of human EGFR kinase domain (Invitrogen). The assays were performed with and without pre-incubating the inhibitors with the enzyme for 60 minutes before starting the kinase reaction by adding ATP and the peptide substrate. Samples containing enzyme but no inhibitor were included to determine the maximal extent of reaction. Samples containing no enzyme served as the negative control. The kinase reaction mixtures were incubated at room temperature for 60 minutes before stopping the kinase activity by the addition of 15 mM EDTA. The extent of peptide phosphorylation by EGFR was detected using a Terbium-conjugated anti-phospho-Tyrosine antibody (Tb-PT66 antibody, invitrogen # PV3557). Phosphorylation of peptide substrate was measured by determining the ratio of 520/495 nm on an Envision Multi-label Reader (Perkin Elmer) and IC$_{50}$ values were calculated by fitting the data to a four-parameter equation using XLFIt4 (IDBS).

TABLE 2

| Example | B Cell IC$_{50}$ (nM) | HWB IC$_{50}$ (nM) | EGFR IC$_{50}$ (nM) |
|---|---|---|---|
| 2 | 0.5 | 33.3 | 1,710 |
| 15 | 1.7 | 20.6 | 3,890 |
| 27 | 2.7 | 64.3 | 16,800 |
| 110 | 1.6 | 94.7 | >15,400 |
| 116 | 14.9 | 41.8 | >26,800 |
| 118 | 29.6 | 50 | >50,000 |
| 126 | 20.9 | 201 | 802 |
| 130 | 0.15 | 133 | 7.9 |
| 131 | 1.6 | 259 | 2200 |
| 136 | 0.44 | 570 | 214 |
| 137 | 0.63 | 31.4 | 25.6 |
| 144 | 0.84 | | 274 |
| 145 | 11.8 | 126 | 2180 |
| 151 | 0.22 | 258 | 12100 |
| 153 | 0.56 | | 2.9 |
| 155 | 2.0 | | 106 |
| 156 | 2.5 | | 381 |
| 157 | 24.2 | 98.7 | 29.7 |
| 159 | 2.8 | | 311 |
| 160 | 2.9 | | 890 |
| 161 | 3.0 | 52.7 | 89.8 |
| 162 | 103 | 343 | 14100 |
| 163 | 0.92 | | 1190 |
| 164 | 11.4 | | 3360 |

Example 168

In Vivo Pharmacology
NP Ficoll Model

Type 2 T cell independent antibody responses were induced by immunizing 8 to 10 week old C57BV6 female mice i.p. with 100 μg of NP-Ficoll in PBS (day 0). BTK inhibitors were prepared in methylcellulose tween and mice were dosed QD with compounds starting on day −1. Mice were euthanized and serum collected 6 days post-NP-Ficoll immunization. Sera from immunized mice were then tested in an ELISA to measure NP-specific IgM and IgG3 titers. Briefly, to assess NP-specific antibody titers Nunc Maxi-Sorp plates (VWR International) were coated overnight at room temperature with 20 μg/mL of BSA:NP (Biosearch Technologies). Plates were washed with PBS Tween 0.05% buffer (PBS-T) and blocked with PBS containing 0.5% gelatin for 2 hours. Serum samples were then diluted in PBS-T and incubated for 1 hour. Bound antibody was detected using goat anti-mouse IgM-HRP or IgG3-HRP antibodies (Southern Biotech) diluted in PBS-T. ELISA plates were developed using TMB Sure Blue reagent (Kirkegaard & Perry Labs), reactions were stopped by adding 1.0M sulfuric acid to sample wells and absorbances assessed at 450 nm on a Spectramax Plus 384 microplate reader (Molecular Devices).

Mouse Collage-Induced Arthritis (CIA) Model of Arthritis

Arthritis was induced by immunizing DBA/1 mice with bovine type II collagen (CII) emulsified in complete Freund's adjuvant and by a boost 21 days later with CII emulsified in incomplete Freund's adjuvant. Efficacy was assessed in a semi-therapeutic dosing regimen, which involved assignment to treatment groups when 10% of the mice showed disease symptoms. Mice were dosed orally one a day. Disease severity was evaluated by scoring all four paws for each animal, with a maximum possible score being 16 according to the following classification: 0, no arthritis; 1, one or two swollen digits; 2, three or more swollen digits or mild to moderate swelling of the entire paw; 3, extensive swelling of the entire paw; 4, resolution of swelling, ankylosis of the paw. At the end of the study, all four paws from each animal were collected for microscopic analysis. Tissue samples were decalcified and embedded in paraffin, sectioned at 6 μm, stained with hematoxylin and eosin (H&E), and examined microscopically. Each section from each paw was examined for the presence of arthritis, and the severity of arthritis, when present, was subjectively scored according to the following criteria: Grade 0, normal synovial membrane (1-3 synoviocytes thick) and absence of Inflammatory cells; Grade 1, synoviocyte hypertrophy, slight synovial membrane fibrosis, and slight to mild inflammatory cell infiltrates into the synovial membrane/articular capsule and/or synovial fluid; Grade 2, grade 1 plus mild to moderate inflammatory cell infiltrates, absence or minimal pannus formation, and superficial cartilage erosion; Grade 3: grade 2 plus marked inflammatory cell infiltrates, fibrosis, and mild to severe erosion of cartilage extending into subchondral bone; Grade 4, loss of joint integrity through erosion or destruction with bone remodeling, fibrosis, and ankylosis.

K/BxN Serum Transfer Model of Arthritis

In the K/BxN serum transfer model, 6 week old male BTKxid, CBA/CaJ, and C57BL/6 mice, from Jackson Laboratory, were injected with pooled serum from 8-week-old arthritic K/BxN mice (150 μL serum i.p. on days 0 and 2). Hind ankle width was measured with a pocket thickness gauge and the average change in ankle thickness in both ankles was calculated for each animal. Animals were measured Monday through Friday for 14 days. At the end of the study, all four paws from each animal were collected for microscopic analysis.

For treatment studies, 6 week old male C57BL/6 mice, from Jackson Laboratory, were injected with pooled serum from 8-week-old arthritic K/BxN mice (150 μL serum i.p. on days 0 and 2). Mice were dosed orally once a day starting on day 0. Hind ankle width was measured with a pocket thickness gauge and the average change in ankle thickness in both ankles was calculated for each animal. Animals were measured Monday through Friday for 14 days. At the end of the study, all four paws from each animal were collected for microscopic analysis as described above.

INCORPORATION BY REFERENCE

All publications and patent applications mentioned in this specification are herein incorporated by reference to the same extent as if each individual publication or patent application was specifically and individually indicated to be incorporated by reference.

We claim:
1. A compound having Formula (I)

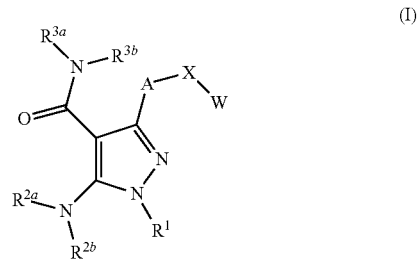

or a pharmaceutically acceptable salt thereof, wherein
A is phenyl;
X is O;
W is phenyl optionally substituted with one or two $R^7$, wherein $R^7$ is independently selected from the group consisting of F, Cl, Br, and I;
$R^1$ is pyrrolidin-3-yl substituted on nitrogen with R;
R is cyano or cyano($C_1$-$C_3$)alkyl; and
$R^{2a}$, $R^{2b}$, $R^{3a}$, and $R^{3b}$ are hydrogen.

2. The compound of claim 1, wherein W is

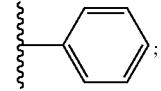

or a pharmaceutically acceptable salt thereof.

3. The compound of claim 2, wherein $R^1$ is

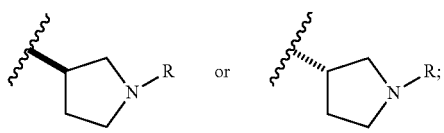

or a pharmaceutically acceptable salt thereof.

4. A pharmaceutical composition comprising a compound according to claim 1 or a pharmaceutically acceptable salt thereof, admixed with a pharmaceutically acceptable carrier, excipient or dilutant.
5. A compound of structure
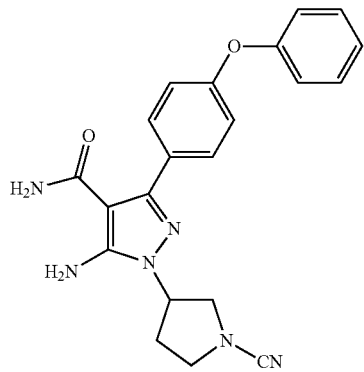 [SMILES: N#CN1CCC(n2nc(-c3ccc(Oc4ccccc4)cc3)c(C(N)=O)c2N)C1]
or a pharmaceutically acceptable salt thereof.
6. A compound of structure
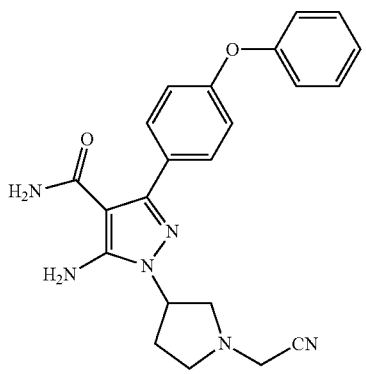 [SMILES: N#CCN1CCC(n2nc(-c3ccc(Oc4ccccc4)cc3)c(C(N)=O)c2N)C1]
or a pharmaceutically acceptable salt thereof.
* * * * *